(12) United States Patent
Roberts et al.

(10) Patent No.: US 8,796,318 B2
(45) Date of Patent: *Aug. 5, 2014

(54) MODULATORS OF SPHINGOSINE PHOSPHATE RECEPTORS

(75) Inventors: Edward Roberts, La Jolla, CA (US); Hugh Rosen, La Jolla, CA (US); Steven Brown, La Jolla, CA (US); Miguel A. Guerrero, La Jolla, CA (US); Xuemei Peng, La Jolla, CA (US); Ramulu Poddutoori, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/465,767

(22) Filed: May 14, 2009

(65) Prior Publication Data

US 2010/0010001 A1    Jan. 14, 2010

Related U.S. Application Data

(60) Provisional application No. 61/127,603, filed on May 14, 2008.

(51) Int. Cl.
*A61K 31/4245* (2006.01)
*C07D 271/06* (2006.01)

(52) U.S. Cl.
CPC .......... *A61K 31/4245* (2013.01); *C07D 271/06* (2013.01)
USPC .......................................... 514/364; 548/131

(58) Field of Classification Search
CPC ........................... A61K 31/4245; C07D 271/06
USPC .......................................... 514/364; 548/131
See application file for complete search history.

(56) References Cited

U.S. PATENT DOCUMENTS

| | | | |
|---|---|---|---|
| 6,511,975 B1 | 1/2003 | Nishi et al. | |
| 7,105,538 B2 | 9/2006 | Hennies et al. | |
| 7,220,734 B2 | 5/2007 | Doherty | |
| 7,541,372 B2 | 6/2009 | Buettelmann et al. | |
| 7,605,171 B2 | 10/2009 | Colandrea et al. | |
| 7,678,820 B2 | 3/2010 | Harada et al. | |
| 7,951,825 B2 | 5/2011 | Harada et al. | |
| 8,466,183 B2 * | 6/2013 | Roberts et al. | 514/364 |
| 8,481,573 B2 * | 7/2013 | Roberts et al. | 514/364 |
| 8,530,503 B2 | 9/2013 | Roberts et al. | |
| 2006/0161005 A1 * | 7/2006 | Doherty et al. | 546/202 |
| 2007/0043014 A1 | 2/2007 | Doherty et al. | |
| 2007/0293545 A1 | 12/2007 | Edwards et al. | |
| 2008/0009534 A1 | 1/2008 | Cheng et al. | |
| 2008/0249093 A1 | 10/2008 | Colandrea et al. | |
| 2008/0280876 A1 | 11/2008 | Hobson et al. | |
| 2012/0329838 A1 | 12/2012 | Roberts et al. | |
| 2012/0329839 A1 | 12/2012 | Roberts et al. | |
| 2012/0329840 A1 | 12/2012 | Roberts et al. | |

FOREIGN PATENT DOCUMENTS

| | | |
|---|---|---|
| EP | 2003132 A1 | 12/2008 |
| JP | 2006-511579 A | 4/2006 |
| JP | 2007-515432 A | 6/2007 |
| JP | 2007-528872 A | 10/2007 |
| NZ | 589617 | 8/2012 |
| WO | WO-2004024725 A1 | 3/2004 |
| WO | WO-2004/058149 A2 | 7/2004 |
| WO | WO-2004058149 A2 | 7/2004 |
| WO | WO-2004096220 A1 | 11/2004 |
| WO | WO-2005/032465 A2 | 4/2005 |
| WO | WO-2005/058848 A1 | 6/2005 |
| WO | WO-2006043149 A2 | 4/2006 |
| WO | WO-2006/120577 A1 | 11/2006 |
| WO | WO-2006/131336 A1 | 12/2006 |
| WO | WO-2007003604 A3 | 1/2007 |
| WO | WO-2007/116866 A1 | 10/2007 |
| WO | WO-2007116866 A1 | 10/2007 |
| WO | WO-2007/149395 A2 | 12/2007 |
| WO | WO-2008/064320 A2 | 5/2008 |
| WO | WO-2008/076356 A1 | 6/2008 |
| WO | WO-2009/151529 A1 | 12/2009 |
| WO | WO-2009/151529 A9 | 12/2010 |

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*
Gonzalez-Cabrera et al. Molecular Pharmacology, 2008, 74, 1308-1318 (published online Aug. 15, 2008).*
WebMD entry for Multiple Sclerosis (http://www.webmd.com/multiple-sclerosis/tc/multiple-sclerosis-ms-prevention, accessed Jun. 15, 2010).*

(Continued)

*Primary Examiner* — Joseph Kosack
*Assistant Examiner* — Matthew Coughlin
(74) *Attorney, Agent, or Firm* — Schwegman Lundberg & Wossner, P.A.

(57) ABSTRACT

Compounds that activate a sphingosine-1-phosphate receptor of the subtype 1 are provided. Certain compounds selectively activate the receptor subtype 1 in relation to the sphinogosine-1-phosphate receptor subtype 3. Uses and methods of inventive compounds for treatment of malconditions wherein activation, agonism, inhibition or antagonism of the S1P1 is medically indicated are provided.

9 Claims, 8 Drawing Sheets

(2 of 8 Drawing Sheet(s) Filed in Color)

(56) References Cited

OTHER PUBLICATIONS

Registry entry for registry No. 388575-59-5, which entered STN on Jan. 31, 2002.*
Registry entry for registry No. 713089-00-0, which entered STN on Jul. 20, 2004.*
Registry entry for registry No. 333322-82-0, which entered STN on Apr. 27, 2001.*
Registry entry for registry No. 433702-30-8, which entered STN on Jun. 26, 2002.*
Koshland, D. E. Proc. Nat. Acad. Sci. 1958, 44, 98-104.*
"International Application Serial No. PCT/US2009/003014, Search Report mailed Nov. 19, 2009", 5 pgs.
"International Application Serial No. PCT/US2009/003014, Written Opinion mailed Nov. 19, 2009", 15 pgs.
Fujiwara, et al., "Identification of the Hydrophobic Ligand Binding Pocket of the S1 P1 Receptor", *The Journal of Biological Chemistry*, 2007, vol. 282(4), pp. 2374-2385, 2007.
"Japanese Application Serial No. 2011-509488, Voluntary Amendments filed May 11, 2012", (English Translation of Amendments), 39 pgs.
"New Zealand Application Serial No. 589617, Response filed May 9, 2012 to Office Action mailed Apr. 29, 2011", 45 pgs.
"Singapore Application Serial No. 201008314-5, Response filed Apr. 16, 2012 to Written Opinion", 7 pgs.
"Chinese Application Serial No. 200980127478.8, Office Action mailed Nov. 21, 2012", (w/English Translation), 98 pgs.
"Singapore Application Serial No. 201008314-5, Written Opinion mailed Oct. 10, 2011", 6 pgs.
"International Application No. PCT/US2010/056757, International Search Report dated Jan. 14, 2011", 3 pgs.
"International Application No. PCT/US2010/056759, International Search Report dated Jan. 12, 2011", 3 pgs.
"International Application No. PCT/US2010/056760, International Search Report dated Jan. 19, 2011", 3 pgs.
Wu, Kuei-Meng, et al., "Regulatory perspectives of Type II prodrug development and time-dependent toxicity management: Nonclinical Pharm/Tox analysis and the role of comparative toxicology", Toxicology 236 (2007) 1-6, (Apr. 21, 2007), 1-6.
Zanotti-Gerosa, Antonio, et al., "Ruthenium-Catalysed Asymmetric Reduction of Ketones: Diphosphine Ligands in Hydrogenations for Pharmaceutical Synthesis", Platinum Metals Rev., 2005, 49(4), 158-165.
"U.S. Appl. No. 13/605,358, Notice of Allowance mailed Mar. 1, 2013", 8 pgs.
"U.S. Appl. No. 13/605,561, Notice of Allowance mailed Mar. 19, 2013", 8 pgs.
"Eurasian Application Serial No. 201001785/28, Response filed Mar. 5, 2013 to Office Action mailed Oct. 5, 2012", (w/ English Claims), 132 pgs.
"U.S. Appl. No. 13/605,358, Non Final Office Action mailed Oct. 12, 2012", 15 pgs.
"U.S. Appl. No. 13/605,358, Non Final Office Action mailed Nov. 6, 2012", 15 pgs.
"U.S. Appl. No. 13/605,358, Notice of Allowance mailed Dec. 14, 2012", 7 pgs.
"U.S. Appl. No. 13/605,358, Response filedd Nov. 16, 2012 to Non Final Office Action mailed Nov. 6, 2012", 10 pgs.
"U.S. Appl. No. 13/605,427, Non Final Office Action mailed Nov. 6, 2012", 13 pgs.
"U.S. Appl. No. 13/605,427, Notice of Allowance mailed Dec. 18, 2012", 7 pgs.
"U.S. Appl. No. 13/605,427, Response filed Nov. 16, 2012 to Non Final Office Action mailed Nov. 6, 2012", 10 pgs.

"U.S. Appl. No. 13/605,561, Non Final Office Action mailed Nov. 6, 2012", 13 pgs.
"U.S. Appl. No. 13/605,561, Notice of Allowance mailed Dec. 19, 2012", 7 pgs.
"U.S. Appl. No. 13/605,561, Response filed Nov. 16, 2012 to Non Final Office Action mailed Oct. 6, 2012", 9 pgs.
"Eurasian Application Serial No. 201001785/28, Office Action mailed Oct. 5, 2012", 5 pgs.
Alewignse, Astrid E, et al., "Sphingolipid signalling in the cardiovascular system: Good, bad or both?", *European Journal of Pharmacology*, (2008), 11 pgs.
Wang, Lichun, et al,, "Regulation of vascular permeability by sphingosine 1-phosphate", *Microvascular Research*, (2009), 7 pgs.
"New Zealand Application Serial No. 589617, First Examiner Report mailed Apr. 1911", 5 pgs.
"Brazilian Application Serial No. 0912545-0, Voluntary Amendment filed Apr. 26, 2013", (w/ English Translation of Claims), 276 pgs.
"Chinese Application Serial No. 200980127478.8, Response filed Oct. 25, 2013 to Office Action mailed Aug. 16, 2013", (w/ English Translation of Amended Claims), 27 pgs.
"Philippines Application Serial No. 1-2010-502486, Voluntary Amendment filed Sep. 20, 2013", 91 pgs.
"Eurasian Application Serial No. 201001785/28, Amendment and Response filed Oct. 18, 2013 to Office Action mailed Jun. 19, 2013", (w/ English Translation of Claims), 114 pgs.
"Canadian Application Serial No. 2,723,904, Voluntary Amendment dated Dec. 10, 2010", 40 pgs.
"European Application Serial No. 097628267, Invitation pursuant to Rule 63(1) EPC mailed Jul. 9, 2012", 4 pgs.
"European Application Serial No. 09762826.7, Response filed Sep. 6, 2012 to Communication issued under Rule 63(1) EPC mailed Jul. 9, 2012", 1 pg.
"Japanese Application Serial No. 2011-509488, Office Action mailed Nov. 16, 2013", (w/ English Translation), 9 pgs.
"Mexican Application Serial No. MX/a/2010/012461, Voluntary Amendment filed Sep. 9, 2013", 49 pgs.
"U.S. Appl. No. 13/605,427, Notice of Allowance mailed May 3, 2013", 8 pgs.
"Australian Application Serial No. 2009258242, Voluntary Amendment filed Apr. 9, 2013", 134 pgs.
"Chinese Application Serial No. 200980107871.0, Response filed Apr. 7, 2013 to Office Action mailed Nov. 21, 2012", (w/ English Translation of Claims), 95 pgs.
"Chinese Application Serial No. 200980127478.8, Office Action mailed Aug. 16, 2013", 12 pgs.
"Eurasian Application Serial No. 201001785/28, Office Action mailed Jun. 19, 2013",(w/ English Translation), 6 pgs.
"European Application Serial No. 09762826.7, Extended European Search Report mailed Aug. 8, 2013", 10 pgs.
"Israel Application Serial No. 209306, Office Action mailed Apr. 4, 2013", 2 pgs.
"Israel Application Serial No. 209306, Office Action mailed Aug. 18, 2013", 3 pgs.
"Korean Application Serial No. 10-2010-7028062, Amendment filed Jun. 5, 2013", (w/ Partial Translation), 61 pgs.
Gonzalez-Cabrera, P. J. et al., "Full pharmacological efficacy of a novel S1P1 agonist that does not require S1P-like headgroup interactions", Mol Pharmacol., 74(5), (Nov. 2008), 1308-18.
"Eurasian Application Serial No. 201001785/28, Office Action mailed Jan. 10, 2014", (w/ English Translation), 31 pgs.
"Chinese Application Serial No. 200980127478.8, Office Action mailed Feb. 25, 2014", (w/ English Translation), 13 pgs.
"Mexican Application Serial No. MX/a/2010/012461, Office Action mailed Feb. 11, 2014", (w/ English Summary), 3 pgs.

* cited by examiner

MODULATORS OF SPHINGOSINE PHOSPHATE RECEPTORS

CROSS-REFERENCE TO RELATED APPLICATIONS

This application claims the priority of U.S. Ser. No. 61/127,603, filed May 14, 2008, the disclosure of which is incorporated by reference herein in its entirety.

STATEMENT OF GOVERNMENT SUPPORT

This invention was made with government support under Grant Nos. MH074404 and MH084512 awarded by the National Institutes of Health. The government has certain rights in the invention.

BACKGROUND

Sphingosine-1-phosphate (S1P), the structure of which is shown below, is a phospholipid with a wide range of biological activities, notably, involved in cellular signaling.

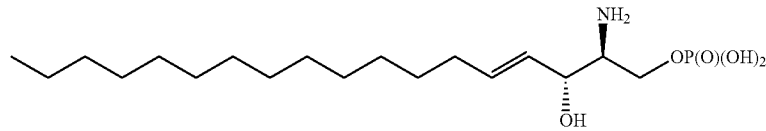

For example, S1P modulates cellular proliferation, such as of epidermal cells. The bioactivity of S1P is mediated by multiple receptor subtypes. For example, receptors subtypes 1 and 3, (S1P1 and S1P3 respectively) are both expressed in endothelial cells, and play a role in lung and lymphoid endothelial functions. Thus, agonists of receptors, such as agonists of S1P1, could be of value in the treatment of malconditions such as multiple sclerosis, transplant rejection, and adult respiratory distress syndrome. Agonist stimulation of the S1P1 receptor is modulated by receptor degradation. Ligand stimulation induces receptor phosphorylation, internalization, polyubiquination and degradation (Gonzalez-Cabrera, Hla et al. 2007).

Oxadiazoles and oxazoles have been described for use as sphingosine-1-phosphate receptor ligands, see for examples PCT patent application publication numbers WO2006/131336, WO2008/037476 and WO2008/074821.

SUMMARY

The present invention is directed to heterocyclic compounds adapted to act as agonists of S1P receptor subtype 1, S1P1; methods of preparation and methods of use, such as in treatment of a malcondition mediated by S1P1 activation, or when activation of S1P1 is medically indicated.

Accordingly, various embodiments of the present invention provide a compound of formula (I) or a pharmaceutically acceptable salt, prodrug, tautomer, stereoisomer, hydrate, or solvate thereof:

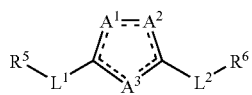

(I)

wherein
a dashed line signifies that a single bond or a double bond can be present, provided that there are two double bonds and three single bonds in the ring comprising $A^1$, $A^2$, and $A^3$;

$A^1$, $A^2$, and $A^3$ each independently is C or O or is N when the N is bonded to two adjacent ring atoms by a double bond and a single bond or is NR wherein R is H or $(C_1-C_6)$alkyl when the N is bonded to two adjacent ring atoms by two single bonds; provided that no more than one of $A^1$, $A^2$, and $A^3$ is C and that at least one of $A^1$, $A^2$, and $A^3$ is N or NR; provided that only one of $A^1$, $A^2$, and $A^3$ is O;

$L^1$ and $L^2$ are each independently a bond; $(CHR')_n$ wherein R' is H or $(C_1-C_6)$alkyl and n is 1, 2, or 3; or a heteroaryl selected from the group consisting of thiophenyl, phenyl, furanyl, or benzothiophenyl and wherein such heteroaryl is substituted with 0-3 J;

J independently at each occurrence is F, Cl, Br, I, OR', OC(O)N(R')$_2$, CN, CF$_3$, OCF$_3$, CHF$_2$, NO$_2$, R', O, S, C(O), S(O), methylenedioxy, ethylenedioxy, N(R')$_2$, N(R')CH$_2$CH$_2$OR', SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')N(R'), N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J; or wherein two R' groups together with a nitrogen atom or with two adjacent nitrogen atoms to which they are bonded can together form a $(C_3-C_8)$ heterocyclyl substituted with 0-3 J; optionally further comprising 1-3 additional heteroatoms selected from the group consisting of O, N, S, S(O) and S(O)$_2$;

$R^5$ is a mono- or bicyclic cycloalkyl, aryl, heterocyclyl, or heteroaryl; each of which is substituted with 0-5 J, wherein any cycloalkyl, aryl, heterocyclyl, or heteroaryl can be fused, bridged, or in a spiro configuration with one or more additional cycloalkyl, aryl, heterocyclyl, heteroaryl rings, any of which can be monocyclic, bicyclic or polycyclic, saturated, partially unsaturated, or aromatic, and any of which is substituted with 0-5 J;

$R^6$ is cycloalkyl, aryl, heterocyclyl, or heteroaryl, wherein any cycloalkyl, aryl, heterocyclyl, or heteroaryl is independently mono- or pluri-substituted with J, $(C_1-C_6)$alkyl, $(C_2-C_6)$alkenyl, $(C_2-C_6)$alkynyl, $(C_1-C_6)$haloalkyl, hydroxyl, halo, $(C_1-C_6)$haloalkoxy, cycloalkyl$(C_1-C_6)$alkyl, heterocyclyl$(C_1-C_6)$alkyl, aryl$(C_1-C_6)$alkyl, heteroaryl$(C_1-C_6)$alkyl, OR$^3$ wherein R$^3$ comprises H or $(C_1-C_6)$alkyl or NR$^4_2$ wherein each R$^4$ independently comprises H or $(C_1-C_6)$alkyl or where two R$^4$ groups together with a nitrogen atom to which they are bonded form a $(C_3-C_8)$heterocyclyl which optionally further comprises 1-3 heteroatoms selected from the group consisting of N, O, S, S(O) and S(O)$_2$; or R$^4$ is optionally substituted cycloalkyl, optionally substituted aryl, optionally substituted heterocyclyl, or optionally substituted heteroaryl;

wherein any alkyl, alkenyl, alkynyl, haloalkyl, alkoxy, haloalkoxy, $R^3$, $R^4$, cycloalkyl, aryl, heterocyclyl, or heteroaryl can be further substituted with J;

and provided that (i), (ii), (iii) or (iv) applies:

(i) $L^1$ is bond or $(CHR')_n$ and $R^5$ is a bicyclic ring moiety which is optionally substituted with 0-5 J where the bicyclic ring moiety is any one of a-i to a-xxviii wherein a wavy line indicates a point of attachment:

a-xvii 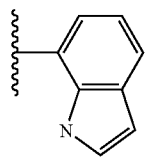

a-xviii 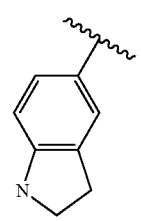

a-xix 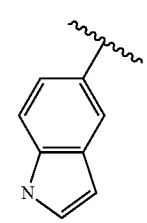

a-xx 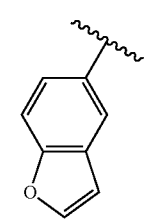

a-xxi 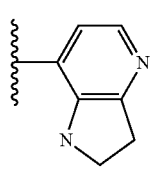

a-xxii 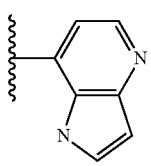

a-xxiii 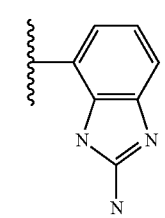

a-xxiv 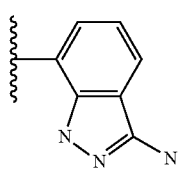

a-xxv 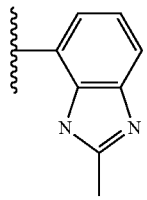

a-xxvi 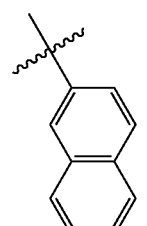

a-xxvii 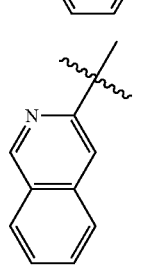

a-xxviii 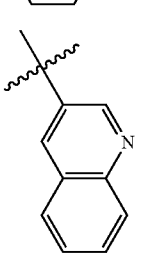

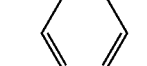

provided that when $R^5$ is either a-xvii or a-xix that $L^2$ is bond or $(CHR')_n$;

(ii) $L^1$ and $L^2$ are each independently a bond or $(CHR')_n$; $R^5$ is a 6-membered heteroaryl ring moiety optionally substituted with 0-3 $J^1$, wherein $J^1$ is OR', $CF_3$, Cl, Br, F, CN, $O(C_1-C_6)$alkoxy, $O(C_1-C_6)$cycloalkoxy, alkyl, or $N(R')_2$ and wherein the 6-membered heteroaryl ring moiety is any one of b-i to b-xiii wherein a wavy line indicates a point of attachment:

b-i 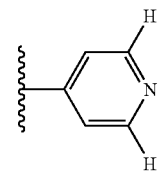

b-ii 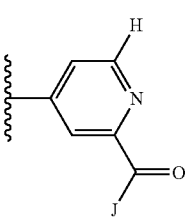

or (iv) $L^1$ is a bond or $(CHR')_n$ and $L^2$ is a bond or $(CHR')_n$ or a phenyl substituted with 0-5 J; and $R^5$ and $R^6$ are independently selected from phenyl or heteroaryl each optionally substituted with 0-5 occurrences of J; provided that if $L^2$ is a bond and $R^5$ and $R^6$ are both phenyl, then $R^5$ is substituted with at least one of 4-CN, 3-alkyl-NHR', 3-alkyl-OR', 4-alkyl-OR', or 2,3-dialkyl and $R^6$ is substituted with at least 4-OR'; provided, that when (ii), (iii), or (iv) applies, that the compound of formula (I) is not one of the following:

(iii) $L^1$ is a bond or $(CHR')_n$, and $L^2$ is a heteroaryl substituted with 0-3 J wherein the heteroaryl is c-i or c-ii wherein a wavy line indicates a point of attachment:

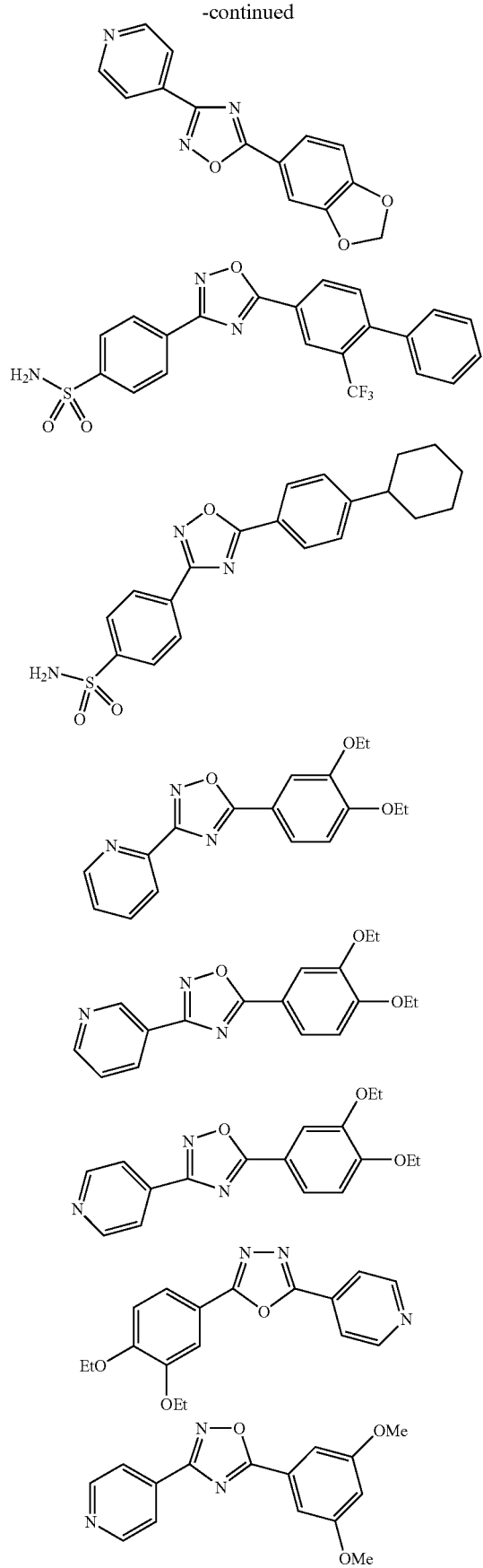

-continued

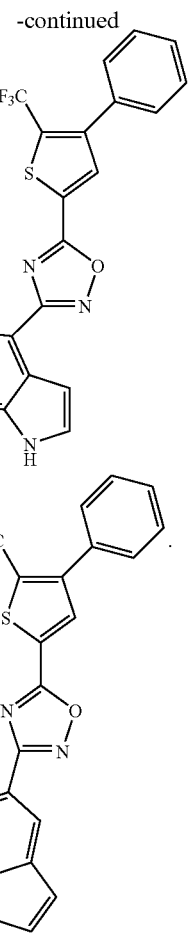

In various embodiments, a pharmaceutical composition comprising a compound of the invention and a suitable excipient is provided.

In various combinations a pharmaceutical combination comprising a compound of the invention and a second medicament is provided. In various embodiments the second medicament is medically indicated for the treatment of multiple sclerosis, transplant rejection, or adult respiratory distress syndrome.

Various embodiments of the invention provide a method of activation, agonism, inhibition, or antagonism of a sphingosine-1-phosphate receptor subtype 1 comprising contacting the receptor subtype 1 with an effective amount of a compound of formula (II) or a pharmaceutically acceptable salt, prodrug, tautomer, stereoisomer, hydrate, or solvate thereof:

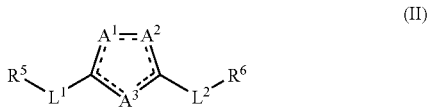
(II)

wherein a dashed line signifies that a single bond or a double bond can be present, provided that there are two double bonds and three single bonds in the ring comprising $A^1$, $A^2$, and $A^3$;

$A^1$, $A^2$, and $A^3$ each independently is C or O or is N when the N is bonded to two adjacent ring atoms by a double bond and a single bond or is NR wherein R is H or $(C_1-C_6)$alkyl when the N is bonded to two adjacent ring atoms by two single bonds; provided that no more than one of $A^1$, $A^2$, and $A^3$ is C and that at least one of $A^1$, $A^2$, and $A^3$ is N or NR; provided that only one of $A^1$, $A^2$, and $A^3$ is O;

$L^1$ and $L^2$ are each independently a bond; $(CHR')_n$ wherein R' is H or $(C_1-C_6)$alkyl and n is 1, 2, or 3; or a heteroaryl selected from the group consisting of thiophenyl, phenyl, furanyl, or benzothiophenyl and wherein such heteroaryl is substituted with 0-3 J;

J independently at each occurrence is F, Cl, Br, I, OR', OC(O)N(R')$_2$, CN, CF$_3$, OCF$_3$, CHF$_2$, NO$_2$, R', O, S, C(O), S(O), methylenedioxy, ethylenedioxy, N(R')$_2$, N(R')CH$_2$CH$_2$OR', SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')N(R'), N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J; or wherein two R' groups together with a nitrogen atom or with two adjacent nitrogen atoms to which they are bonded can together form a $(C_3-C_8)$ heterocyclyl substituted with 0-3 J; optionally further comprising 1-3 additional heteroatoms selected from the group consisting of O, N, S, S(O) and S(O)$_2$;

$R^5$ is a mono- or bicyclic cycloalkyl, aryl, heterocyclyl, or heteroaryl; each of which is substituted with 0-5 J, wherein any cycloalkyl, aryl, heterocyclyl, or heteroaryl can be fused, bridged, or in a spiro configuration with one or more additional cycloalkyl, aryl, heterocyclyl, heteroaryl rings, any of which can be monocyclic, bicyclic or polycyclic, saturated, partially unsaturated, or aromatic, and any of which is substituted with 0-5 J;

$R^6$ is cycloalkyl, aryl, heterocyclyl, or heteroaryl, wherein any cycloalkyl, aryl, heterocyclyl, or heteroaryl is independently mono- or pluri-substituted with J, $(C_1-C_6)$alkyl, $(C_2-C_6)$alkenyl, $(C_2-C_6)$alkynyl, $(C_1-C_6)$haloalkyl, hydroxyl, halo, $(C_1-C_6)$haloalkoxy, cycloalkyl$(C_1-C_6)$alkyl, heterocyclyl$(C_1-C_6)$alkyl, aryl$(C_1-C_6)$alkyl, heteroaryl$(C_1-C_6)$alkyl, $OR^3$ wherein $R^3$ comprises H or $(C_1-C_6)$alkyl or $NR^4_2$ wherein each $R^4$ independently comprises H or $(C_1-C_6)$alkyl or where two $R^4$ groups together with a nitrogen atom to which they are bonded form a $(C_3-C_8)$heterocyclyl which optionally further comprises 1-3 heteroatoms selected from the group consisting of N, O, S, S(O) and S(O)$_2$; or $R^4$ is optionally substituted cycloalkyl, optionally substituted aryl, optionally substituted heterocyclyl, or optionally substituted heteroaryl;

wherein any alkyl, alkenyl, alkynyl, haloalkyl, alkoxy, haloalkoxy, $R^3$, $R^4$, cycloalkyl, aryl, heterocyclyl, or heteroaryl can be further substituted with J;

and provided that (i), (ii), (iii) or (iv) applies:

(i) $L^1$ is bond or $(CHR')_n$ and $R^5$ is a bicyclic ring moiety which is optionally substituted with 0-5 J where the bicyclic ring moiety is any one of a-i to a-xxviii wherein a wavy line indicates a point of attachment:

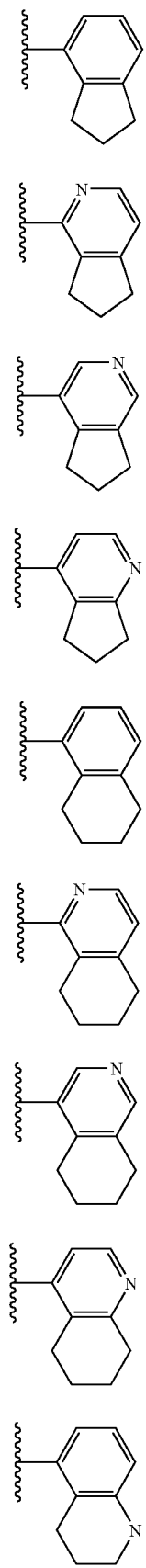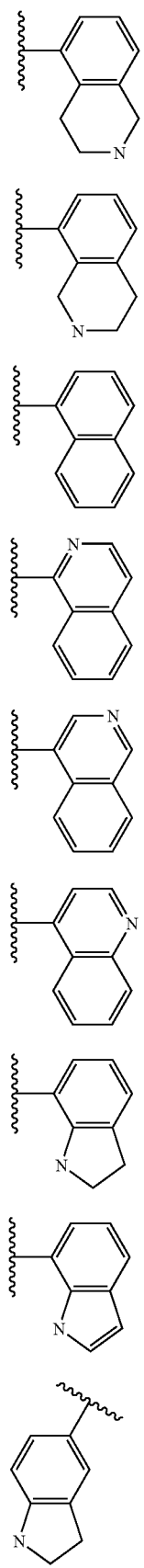

a-xix 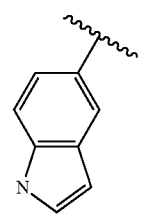

a-xx 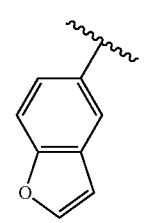

a-xxi 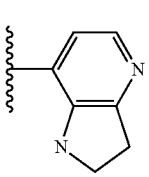

a-xxii 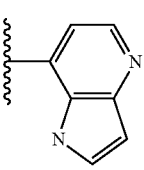

a-xxiii 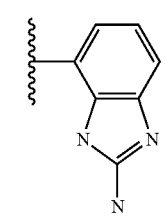

a-xxiv 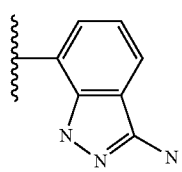

a-xxv 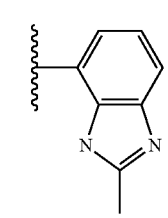

a-xxvi 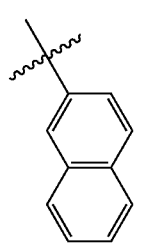

a-xxvii 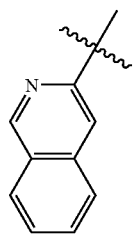

a-xxviii 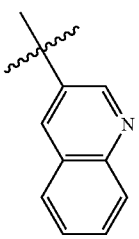

provided that when $R^5$ is either a-xvii or a-xix that $L^2$ is bond or $(CHR')_n$;

(ii) $L^1$ and $L^2$ are each independently a bond or $(CHR')_n$; $R^5$ is a 6-membered heteroaryl ring moiety optionally substituted with 0-3 $J^1$, wherein $J^1$ is OR', $CF_3$, Cl, Br, F, CN, $O(C_1-C_6)$alkoxy, $O(C_1-C_6)$cycloalkoxy, alkyl, or $N(R')_2$ and wherein the 6-membered heteroaryl ring moiety is any one of b-i to b-xiii wherein a wavy line indicates a point of attachment:

b-i 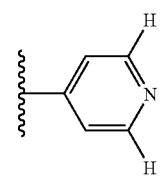

b-ii 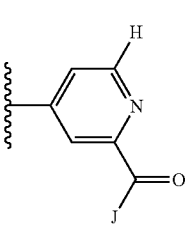

b-iii 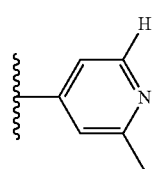

b-iv 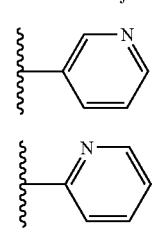

b-v 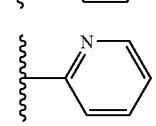

-continued

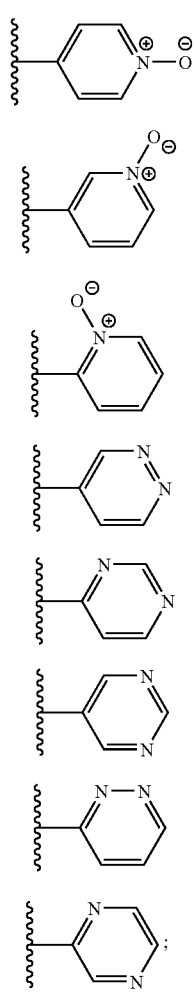

b-vi b-vii b-viii b-ix b-x b-xi b-xii b-xiii (iii) $L^1$ is a bond or $(CHR')_n$, and $L^2$ is a heteroaryl substituted with 0-3 J wherein the heteroaryl is c-i or c-ii wherein a wavy line indicates a point of attachment:

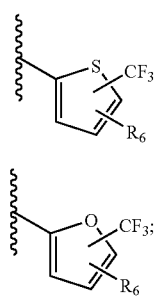

c-i c-ii or (iv) $L^1$ is a bond or $(CHR')_n$ and $L^2$ is a bond or $(CHR')_n$ or a phenyl substituted with 0-5 J; and $R^5$ and $R^6$ are independently selected from phenyl or heteroaryl each optionally substituted with 0-5 occurrences of J; provided that if $L^2$ is a bond and $R^5$ and $R^6$ are both phenyl, then $R^5$ is substituted with at least one of 4-CN, 3-alkyl-NHR', 3-alkyl-OR', 4-alkyl-OR', or 2,3-dialkyl and $R^6$ is substituted with at least 4-OR';

provided, that when (ii), (iii), or (iv) applies, that the compound of formula (I) is not one of the following:

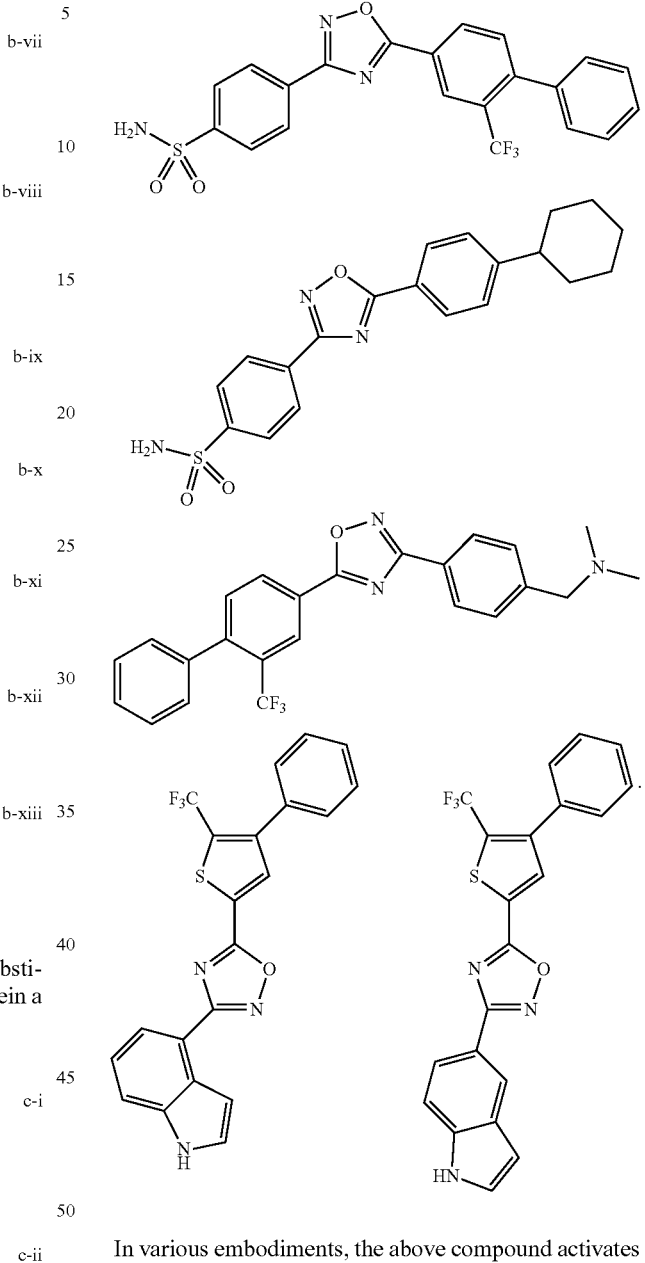

In various embodiments, the above compound activates or agonizes, or inhibits or antagonizes, the sphingosine-1-phosphate receptor subtype 1 to a greater degree than the compound activates or agonizes, or inhibits or antagonizes, another subtype of sphingosine-1-phosphate receptor, for example a sphingosin-1-phosphate receptor subtype 3.

In various embodiments a method of treatment of a malcondition in a patient for which activation or agonism or inhibition or antagonism of an S1P1 receptor is medically indicated, is provided, comprising administering an effective amount of a compound as shown above to the patient to provide a beneficial effect.

In various embodiment, selective activation or agonism of an S1P1 receptor, such as with respect to an S1P3 receptor, is medically indicated. In various embodiments, the malcondition comprises multiple sclerosis, transplant rejection, or adult respiratory distress syndrome. In various embodiments, selective inhibition or antagonism of an S1P1 receptor is medically indicated, for example, with respect to an S1P3 receptor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
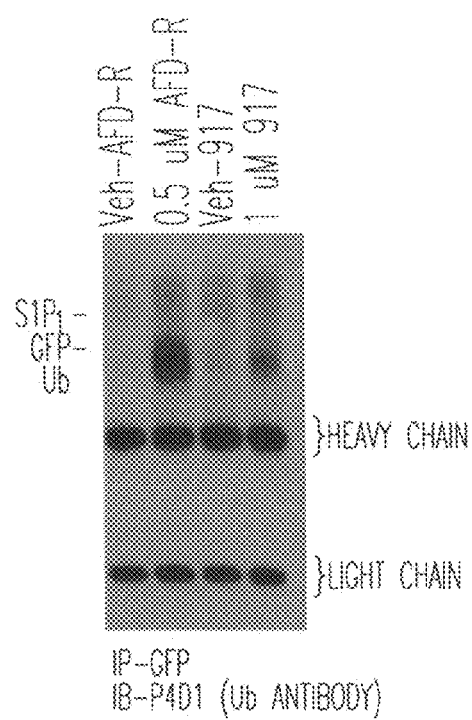
FIG. 1 shows the results of a bioassay, as described in the Examples, for S1P1 activation, involving detection of the ubiquination that is a consequence of S1P1 activation. HEK 293-S1P1-GFP cell lysates were immunoprecipitated (IP) and immunoblotted (IB) with P4D1(anti ubiquitin) antibodies to detect S1P1-ubiquitination. A. S1P1-GFP ubiquination was detected as a band running between 64 and 82 kDa (lane 1 vehicle contro, lane 2 0.5 uM AFD-R, Lane 2 vehicle control for SR-917, lane 4 1 uM SR917). B. Cellular localization of S1P1-GFP with Veh (vehicle control, 0.01, 0.1 and 1 uM of SR-917). C. S1P1-GFP cells were labeled with P32 and stimulated with agonist. S1P1-GFP was immunoprecipitated, resolved by PAGE, transferred to nitrocellulose and exposed to Kodak XAR film overnight. Lane 1 Vehicle control, Lanes 2 and 3, S1P at 0.5 and 0.05 uM, lanes 4 and 5, AFD-R at 0.5 and 0.05 uM, Lanes 6 and 7 SR-917 at 10 and 1 uM. SR-917 is a known agonist of the S1P1 receptor, indexed in the NIH Molecular Libraries Small Molecule Repository (MLMSR). Compound ID is 976135. It is commercially available from ChemBridge Screening Library.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The term "S1P1" as used herein refers to subtype 1 of a sphingosine-1-phosphate receptor, while other sphingosine-1-phosphate receptor subtypes are referred to in a corresponding manner, for example, sphingosine-1-phosphate receptor subtype 3 is referred to as "S1P3".

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell that is coupled with the receptor. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist."

An "S1P1 compound" or "S1P1 agonist" or "S1P1 activator" or "S1P1 inhibitor" or "S1P1 antagonist" as the terms are used herein refer to compounds that interact in some way with the S1P receptor subtype 1. They can be agonist or activators, or they can be antagonists or inhibitors. An "S1P1 compound" of the invention can be selective for action on subtype 1 of the S1P receptor family; for example a compound of the invention can act at a lower concentration on subtype 1 of the S1P receptor family than on other subtypes of the S1P receptor family; more specifically, an "S1P1 compound" of the invention can selectively act on subtype 1 receptors compared to its action on subtype 3, or "S1P3" receptors.

In certain embodiments, compounds of the invention are orthostatic agonists. In certain other embodiments, compounds of the invention are allosteric agonists. Receptor agonists may be classified as orthosteric or allosteric. An orthosteric agonist binds to a site in the receptor that significantly overlaps with the binding of the natural ligand and replicates the key interactions of the natural ligand with the receptor. An orthosteric agonist will activate the receptor by a molecular mechanism similar to that of the natural ligand, will be competitive for the natural ligand, and will be competitively antagonized by pharmacological agents that are competitive antagonists for the natural ligand. An allosteric agonist binds to a site in the receptor that makes some significant interactions that are partly or wholly non-overlapping with the natural ligand. Allosteric agonists are true agonists and not allosteric potentiators. Consequently, they activate receptor signaling alone and without a requirement for a sub-maximal concentration of the natural ligand. Allosteric agonists may be identified when an antagonist known to be competitive for the orthosteric ligand shows non-competitive antagonism. The allosteric agonist site can also be mapped by receptor mutagenesis. The introduction of single point mutations in receptors that retain receptor activation by allosteric agonist, while diminishing or abolishing signaling induced by orthosteric agonist or vice versa provide formal evidence for differences in binding interactions. Orthosteric agonists may destabilize GPCR ("G-protein coupled receptor") structure and conformation, while allosteric agonists may either stabilize or destabilize GPCR structure and conformation. Allosteric agonists, by virtue of their different interactions with receptor, may be pharmaceutically useful because the allosteric site may confer additional opportunities for agonist potency and selectivity within a related family of receptor subtypes that share a similar orthosteric ligand. In addition, the allosteric site may require very different physical and chemical properties of an agonist compared to the orthosteric ligand. These chemico-physical properties, which include hydrophobicity, aromaticity, charge distribution and solubility may also provide advantages in generating agonists of varying pharmacokinetic, oral bioavailability, distributional and metabolism profiles that facilitate the development of effective pharmaceutical substances.

"Substantially" as the term is used herein means completely or almost completely; for example, a composition that is "substantially free" of a component either has none of the component or contains such a trace amount that any relevant functional property of the composition is unaffected by the presence of the trace amount; or a compound that is "substantially pure" has only negligible traces of impurities present.

"Treating" or "treatment" within the meaning herein refers to an alleviation of symptoms associated with a disorder, malcondition, or disease, or inhibition of further progression or worsening of those symptoms, or prevention or prophylaxis of the disorder, malcondition, or disease.

The expression "effective amount", when used to describe use of a compound of the invention in providing therapy to a patient suffering from a disorder or malcondition mediated by a sphingosine-1-phosphate receptor of subtype 1 refers to the amount of a compound of the invention that is effective to bind as an agonist or as an antagonist to an S1P1 receptor in the individual's tissues, wherein the S1P1 receptor is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or malcondition, or halts or slows further progression or worsening of those symptoms, or prevents or provides prophylaxis for the disorder or malcondition. In particular, a "therapeutically effective amount" refers to an amount effective, at dosages and for periods of time necessary, to achieve the desired therapeutic result by acting as an agonist or activator of sphingosine-1-phosphate receptor subtype 1 (S1P1) activity. A therapeutically effective amount is also one in which any toxic or detrimental effects of compounds of the invention are outweighed by the therapeutically beneficial effects. For example, in the context of treating a malcondition mediated by activation of S1P1, a therapeutically effective amount of an S1P1 agonist of the invention is an amount sufficient to control the malcondition, to mitigate the progress of the malcondition, or to relieve the symptoms of the malcondition. Examples of malconditions that can be so treated include multiple sclerosis, transplant rejection, and adult respiratory distress syndrome.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

Isomerism and Tautomerism in Compounds of the Invention
Tautomerism

Within the present invention it is to be understood that a compound of the formula I or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formula drawings within this specification can represent only one of the possible tautomeric forms. However, it is also to be understood that the invention encompasses any tautomeric form which acts on S1P receptors, such as S1P subtype 1 receptors, and is not to be limited merely to any one tautomeric form utilized within the formulae drawings. The formula drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

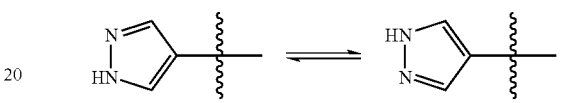

Such tautomerism can also occur with substituted pyrazoles such as 3-methyl, 5-methyl, or 3,5-dimethylpyrazoles, and the like.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention which are biologically active in the treatment of S1P1 mediated diseases.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

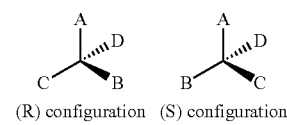

(R) configuration  (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" or "isolated enantiomer" means a compound which has been substantially purified from the corresponding optical isomer (enantiomer) of the same formula. Preferably, the isolated isomer is at least about 80% pure, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below), among other types of bonds, it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of cancer or other proliferative disease states.

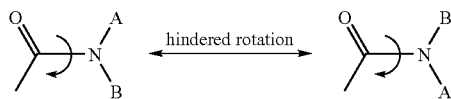

D. Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

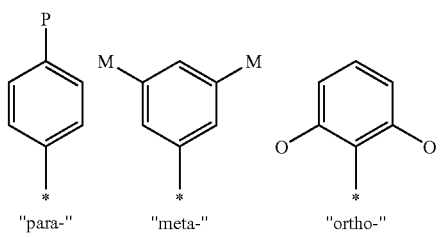

The compounds of the invention may contain one or more stereogenic (chiral) or asymmetric centers, such as one or more asymmetric carbon atoms. Substituents at a double bond may be present in cis-("Z") or trans ("E") form unless indicated otherwise. Substituents on a ring can likewise be disposed cis or trans to each other, or a mixture thereof. The compounds of the invention may thus be present as mixtures of stereoisomers or preferably as substantially pure stereoisomers. Pure stereoisomers may be obtained by separating stereoisomer mixtures or by stereoselective or stereospecific syntheses in manners known to those skilled in the art.

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

When a substituent is specified to be an atom or atoms of specified identity, "or a bond", a configuration is referred to when the substituent is "a bond" that the groups that are immediately adjacent to the specified substituent are directly connected to each other by a chemically feasible bonding configuration.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SW, SOW, SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH(CH3), —CH=C(CH3)2, —C(CH3)=CH2, —C(CH3)=CH(CH3), —C(CH2CH3)=CH2, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R3N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

"Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I compounds, for example in their purification by recrystallization. All of these salts may be prepared by conventional means from the corresponding compound according to Formula I by reacting, for example, the appropriate acid or base with the compound according to Formula I. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, either per se or as are used in practice of embodiments of the inventive methods, can be any one of any of the combinations and/or sub-combinations of the various embodiments recited.

Provisos may apply to any of the disclosed categories or embodiments wherein any one or more of the other above disclosed embodiments or species may be excluded from such categories or embodiments.

More specifically, the inventive compound can be any of the specific examples shown below as exemplary compounds of the invention.

Various embodiments of the invention provide a compound of formula (I) or a pharmaceutically acceptable salt, prodrug, tautomer, stereoisomer, hydrate, or solvate thereof:

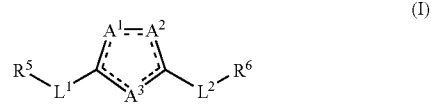

(I)

wherein
a dashed line signifies that a single bond or a double bond can be present, provided that there are two double bonds and three single bonds in the ring comprising $A^1$, $A^2$, and $A^3$;

$A^1$, $A^2$, and $A^3$ each independently is C or O or is N when the N is bonded to two adjacent ring atoms by a double bond and a single bond or is NR wherein R is H or $(C_1$-$C_6)$alkyl when the N is bonded to two adjacent ring atoms by two single bonds; provided that no more than one of $A^1$, $A^2$, and $A^3$ is C and that at least one of $A^1$, $A^2$, and $A^3$ is N or NR; provided that only one of $A^1$, $A^2$, and $A^3$ is O;

$L^1$ and $L^2$ are each independently a bond; $(CHR')_n$, wherein R' is H or $(C_1$-$C_6)$alkyl and n is 1, 2, or 3; or a heteroaryl selected from the group consisting of thiophenyl, phenyl, furanyl, or benzothiophenyl and wherein such heteroaryl is substituted with 0-3 J;

J independently at each occurrence is F, Cl, Br, I, OR', OC(O)N(R')$_2$, CN, CF$_3$, OCF$_3$, CHF$_2$, NO$_2$, R', O, S, C(O), S(O), methylenedioxy, ethylenedioxy, N(R')$_2$, N(R') CH$_2$CH$_2$OR', SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON (R')$_2$, N(R')SO$_2$R', N(R')SO$_2$N(R')$_2$, N(R')C(O)OR', N(R')C (O)R', N(R')N(R'), N(R')C(S)R', N(R')C(O)N(R')$_2$, N(R')C (S)N
(R')$_2$, N(COR')COR', N(OR')R', C(=NH)N(R')$_2$, C(O)N (OR')R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J; or wherein two R' groups together with a nitrogen atom or with two adjacent nitrogen atoms to which they are bonded can together form a $(C_3$-$C_8)$ heterocyclyl substituted with 0-3 J; optionally further comprising 1-3 additional heteroatoms selected from the group consisting of O, N, S, S(O) and S(O)$_2$;

$R^5$ is a mono- or bicyclic cycloalkyl, aryl, heterocyclyl, or heteroaryl; each of which is substituted with 0-5 J, wherein any cycloalkyl, aryl, heterocyclyl, or heteroaryl can be fused, bridged, or in a spiro configuration with one or more additional cycloalkyl, aryl, heterocyclyl, heteroaryl rings, any of which can be monocyclic, bicyclic or polycyclic, saturated, partially unsaturated, or aromatic, and any of which is substituted with 0-5 J;

$R^6$ is cycloalkyl, aryl, heterocyclyl, or heteroaryl, wherein any cycloalkyl, aryl, heterocyclyl, or heteroaryl is independently mono- or pluri-substituted with J, $(C_1-C_6)$alkyl, $(C_2-C_6)$alkenyl, $(C_2-C_6)$alkynyl, $(C_1-C_6)$haloalkyl, hydroxyl, halo, $(C_1-C_6)$haloalkoxy, cycloalkyl$(C_1-C_6)$alkyl, heterocyclyl$(C_1-C_6)$alkyl, aryl$(C_1-C_6)$alkyl, heteroaryl$(C_1-C_6)$alkyl, $OR^3$ wherein $R^3$ comprises H or $(C_1-C_6)$alkyl or $NR^4_2$ wherein each $R^4$ independently comprises H or $(C_1-C_6)$alkyl or where two $R^4$ groups together with a nitrogen atom to which they are bonded form a $(C_3-C_8)$heterocyclyl which optionally further comprises 1-3 heteroatoms selected from the group consisting of N, O, S, S(O) and $S(O)_2$; or $R^4$ is optionally substituted cycloalkyl, optionally substituted aryl, optionally substituted heterocyclyl, or optionally substituted heteroaryl;

wherein any alkyl, alkenyl, alkynyl, haloalkyl, alkoxy, haloalkoxy, $R^3$, $R^4$, cycloalkyl, aryl, heterocyclyl, or heteroaryl can be further substituted with J;

and provided that (i), (ii), (iii) or (iv) applies:

(i) $L^1$ is bond or $(CHR')_n$ and $R^5$ is a bicyclic ring moiety which is optionally substituted with 0-5 J where the bicyclic ring moiety is any one of a-i to a-xxviii wherein a wavy line indicates a point of attachment:

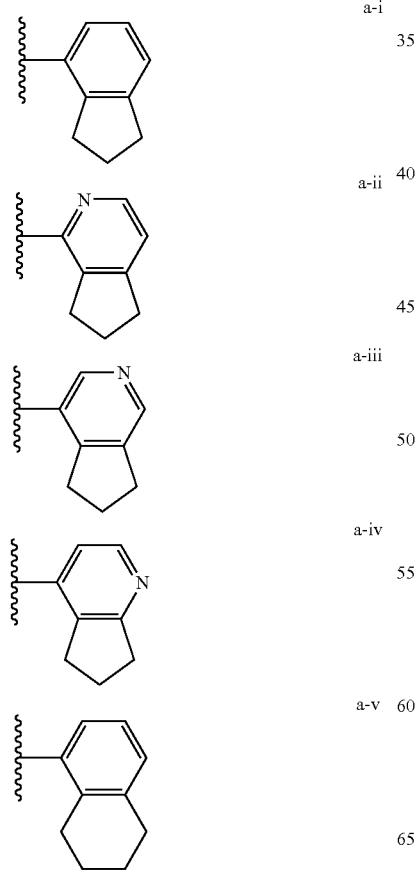

a-i a-ii a-iii a-iv a-v

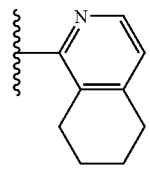

a-vi

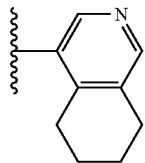

a-vii

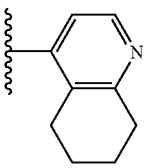

a-viii

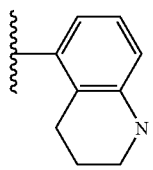

a-ix

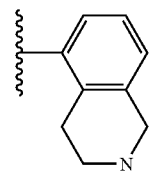

a-x

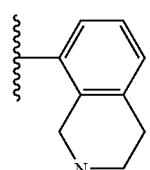

a-xi

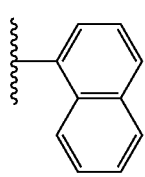

a-xii

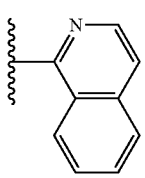

a-xiii

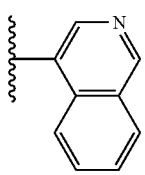

a-xiv a-xv 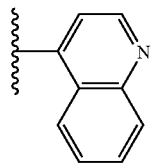

a-xvi 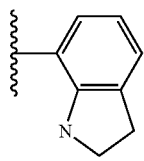

a-xvii 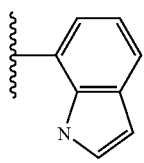

a-xviii 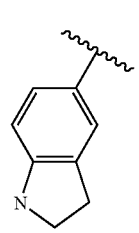

a-xix 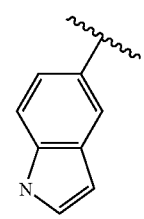

a-xx 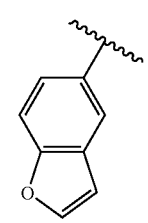

a-xxi 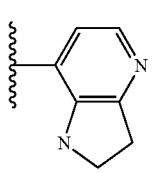

a-xxii 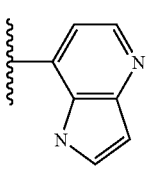

a-xxiii 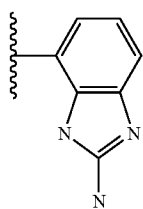

a-xxiv 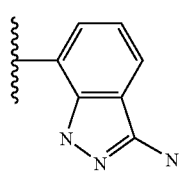

a-xxv 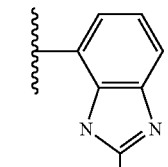

a-xxvi 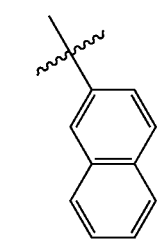

a-xxvii 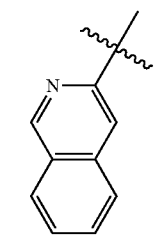

a-xxviii 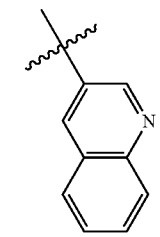

provided that when $R^5$ is either a-xvii or a-xix that $L^2$ is bond or $(CHR')_n$;

(ii) $L^1$ and $L^2$ are each independently a bond or $(CHR')_n$; $R^5$ is a 6-membered heteroaryl ring moiety optionally substituted with 0-3 $J^1$, wherein $J^1$ is OR', $CF_3$, Cl, Br, F, CN, $O(C_1\text{-}C_6)$alkoxy, $O(C_1\text{-}C_6)$cycloalkoxy, alkyl, or $N(R')_2$ and wherein the 6-membered heteroaryl ring moiety is any one of b-i to b-xiii wherein a wavy line indicates a point of attachment:

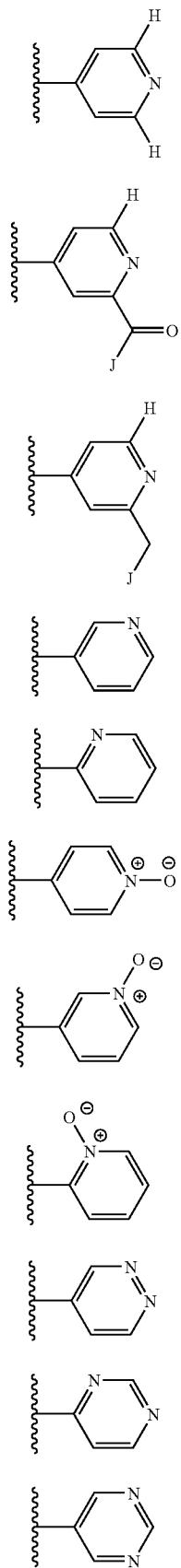
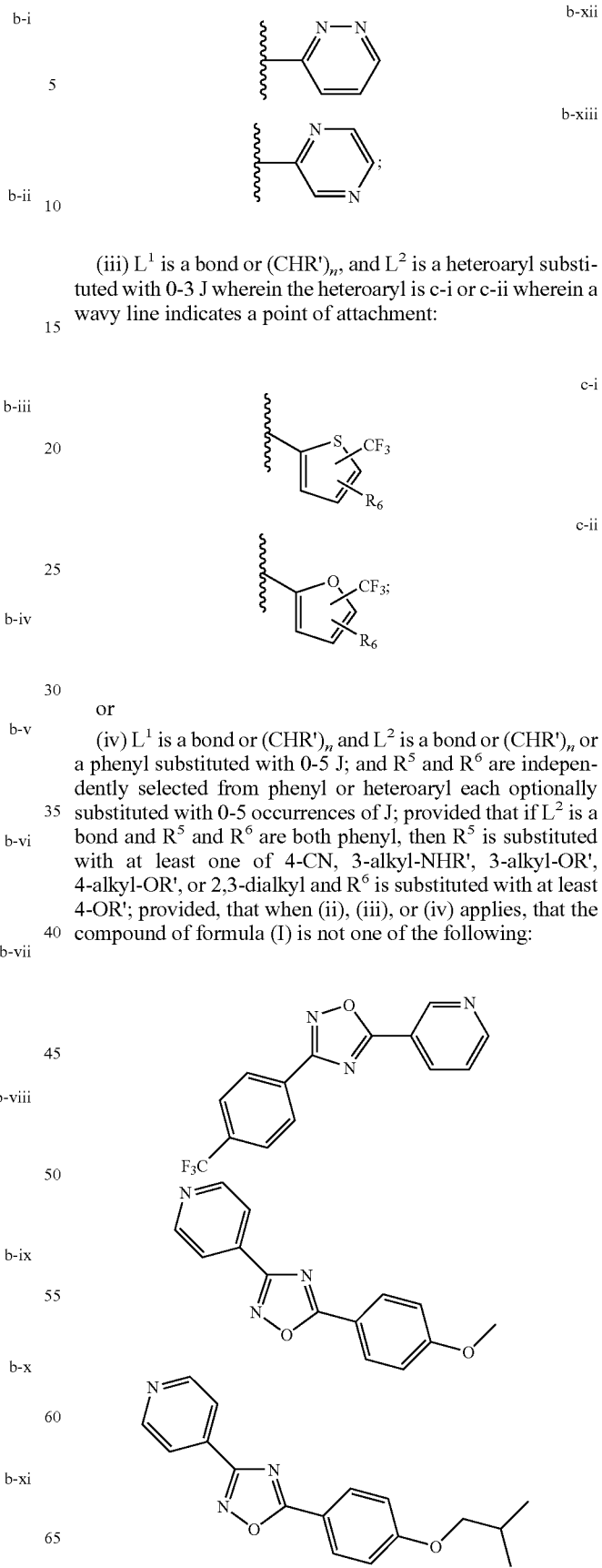

(iii) $L^1$ is a bond or $(CHR')_n$, and $L^2$ is a heteroaryl substituted with 0-3 J wherein the heteroaryl is c-i or c-ii wherein a wavy line indicates a point of attachment:

or (iv) $L^1$ is a bond or $(CHR')_n$ and $L^2$ is a bond or $(CHR')_n$ or a phenyl substituted with 0-5 J; and $R^5$ and $R^6$ are independently selected from phenyl or heteroaryl each optionally substituted with 0-5 occurrences of J; provided that if $L^2$ is a bond and $R^5$ and $R^6$ are both phenyl, then $R^5$ is substituted with at least one of 4-CN, 3-alkyl-NHR', 3-alkyl-OR', 4-alkyl-OR', or 2,3-dialkyl and $R^6$ is substituted with at least 4-OR'; provided, that when (ii), (iii), or (iv) applies, that the compound of formula (I) is not one of the following:

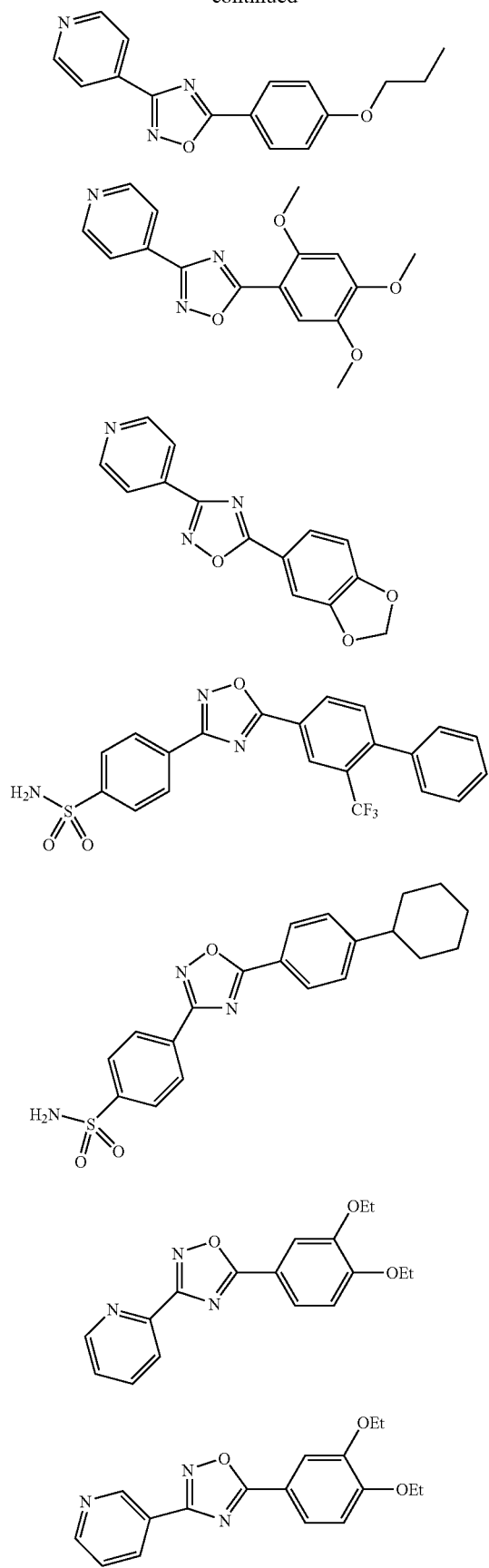
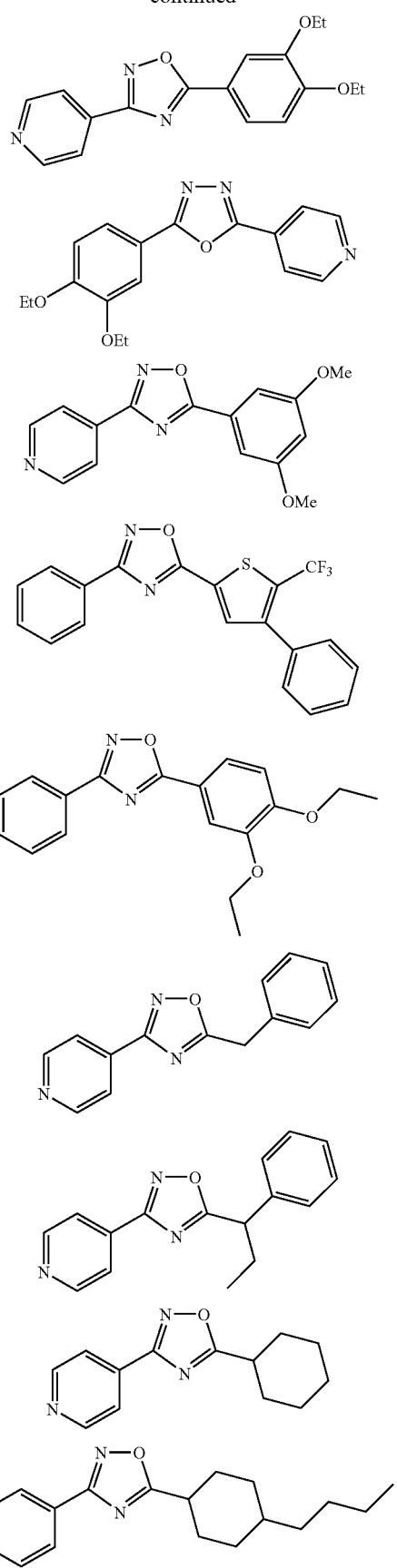

-continued

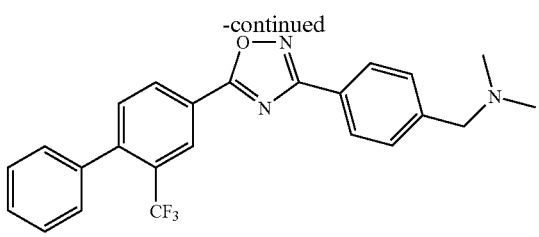

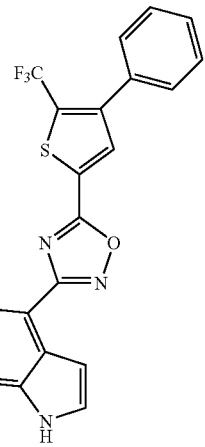

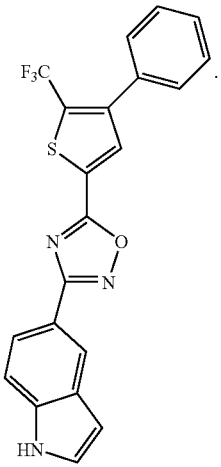 [SMILES: FC(F)(F)c1sc(-c2nc(-c3ccc4[nH]ccc4c3)no2)cc1-c1ccccc1 ; "."]

In various embodiments of a compound of the invention, $L^2$ is bond.

In various embodiments of a compound of the invention, $A^1$ and $A^3$ are N and $A^2$ is O.

In various embodiments of a compound of the invention, $A^2$ and $A^3$ are N and $A^1$ is O, or $A^1$ and $A^2$ are N and $A^3$ is O.

In various embodiments of a compound of the invention, $A^1$ and $A^2$ are N and $A^3$ is NR.

In various embodiments of a compound of the invention, $A^1$ is C, $A^2$ is N and $A^3$ is O.

In various embodiments of a compound of the invention, $A^1$ is O, $A^2$ is N and $A^3$ is C.

In various embodiments of a compound of the invention, $L^1$ and $L^2$ are each independently a bond or $(CHR')_n$, and $R^5$ or $R^6$, or both, comprises a heteroaryl ring. For example, at least one heteroaryl ring of $R^5$ or $R^6$ can be a pyridinyl or a pyridinyl N-oxide, pyrazinyl, pyrrolyl, imidazolyl, benzimidazolyl, thiophenyl, benzothiophenyl, furyl, benzofuryl, indolyl, indolinyl, piperidinyl, quinolyl, or isoquinolyl; wherein any heteroaryl is substituted with 0-5 J. More specifically, any heteroaryl can be substituted with 0-5 R', F, Cl, Br, I, OR', $CF_3$, $OCF_3$, $CHF_2$, or $SO_2N(R')_2$.

In various embodiments of a compound of the invention, $L^1$ and $L^2$ are each independently a bond or $(CHR')_n$, and $R^5$ or $R^6$, or both, comprises a bicyclic carbocyclic ring, wherein the bicyclic carbocyclic ring is substituted with 0-5 J. More specifically, any bicyclic carbocyclic ring can be substituted with 0-5 R', F, Cl, Br, I, OR', $CF_3$, $OCF_3$, $CHF_2$, or $SO_2N(R')_2$.

For example, $L^1$ can be bond and $R^5$ be a bicyclic ring moiety which is substituted with 0-5 J where the bicyclic ring moiety is any one of a-i to a-xxviii, wherein a wavy line indicates a point of attachment:

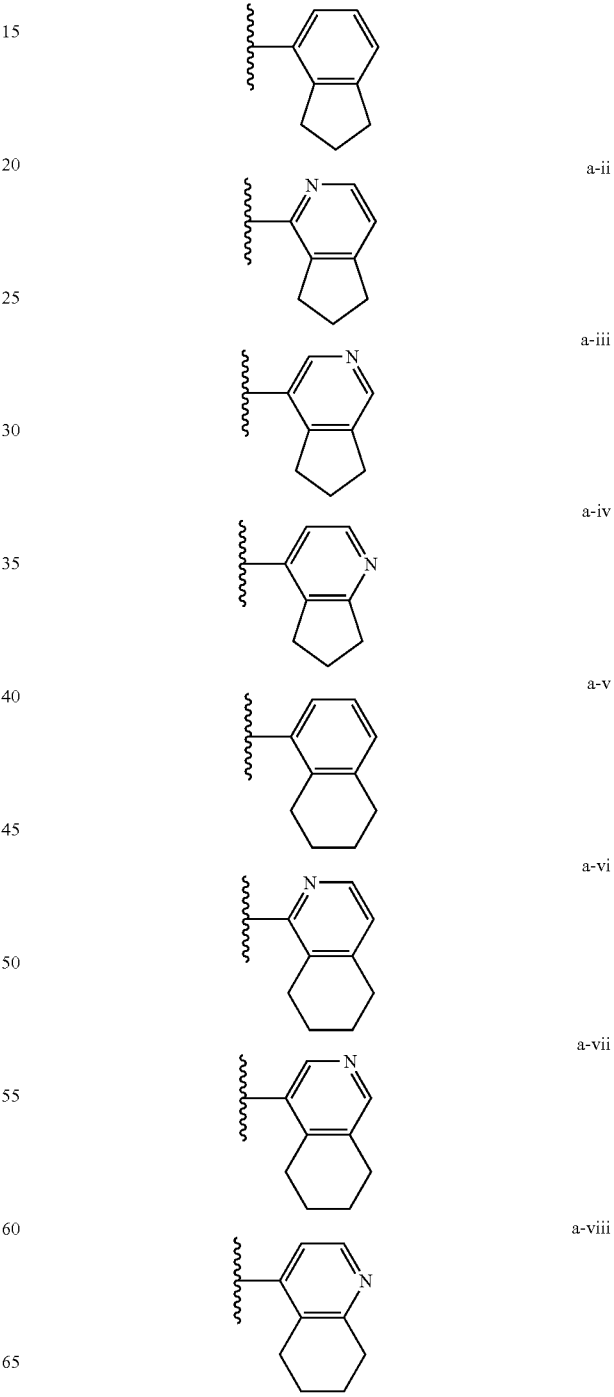

-continued
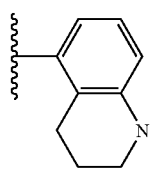
a-ix
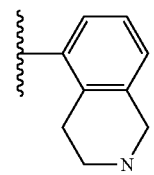
a-x
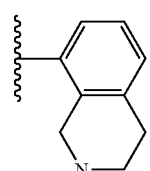
a-xi
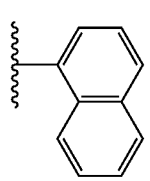
a-xii
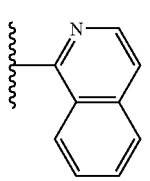
a-xiii
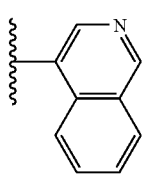
a-xiv
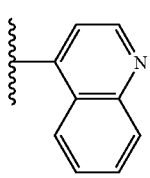
a-xv
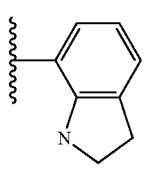
a-xvi
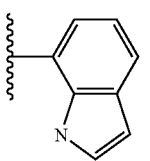
a-xvii
-continued
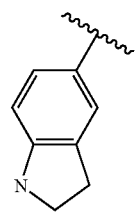
a-xviii
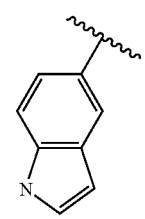
a-xix
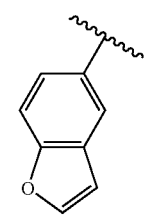
a-xx
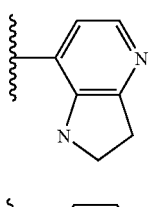
a-xxi
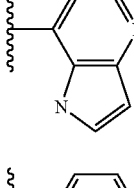
a-xxii
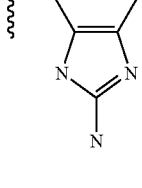
a-xxiii
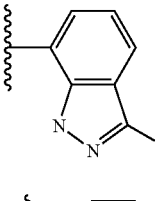
a-xxiv
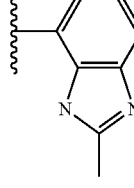
a-xxv -continued a-xxvi
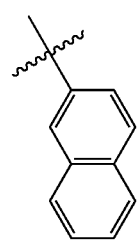

a-xxvii
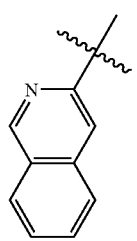

a-xxviii
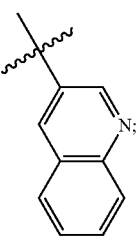

wherein any of the bicyclic ring moieties is substituted with 0-5 J.

For example, $L^1$ and $L^2$ cab each be a bond; and $R^5$ can be a 6-membered heteroaryl ring moiety substituted with 0-3 occurrences of $J^1$; wherein $J^1$ is selected from the group consisting of OR', $CF_3$, Cl, Br, F, CN, $O(C_1-C_6)$alkoxy, $O(C_1-C_6)$cycloalkoxy, alkyl, $N(R')_2$; and wherein the optionally substituted 6-membered heteroaryl ring moiety of $R^5$ is any one of b-i to b-xiii:

b-i
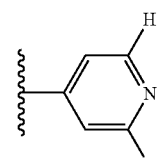

b-ii
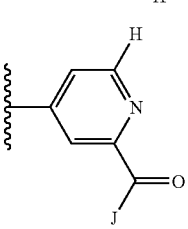

b-iii
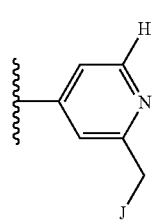

b-iv
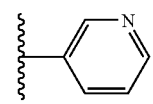

b-v
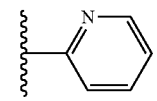

b-vi
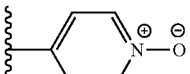

b-vii
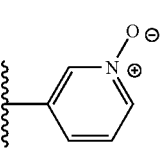

b-viii
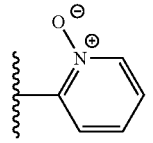

b-ix
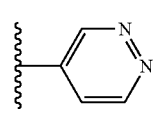

b-x
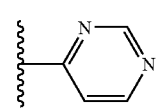

b-xi
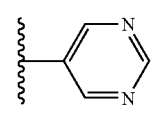

b-xii
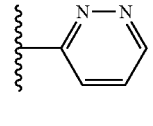

b-xiii
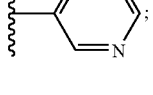

wherein each of the 6-membered heteroaryl ring moieties is substituted with 0-3 $J^1$.

In various embodiments of a compound of the invention, $L^1$ can be a bond, and $L^2$ can be c-i or c-ii, wherein a wavy line indicates a point of attachment:

c-i
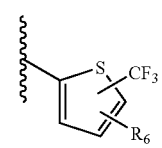

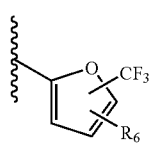
c-ii

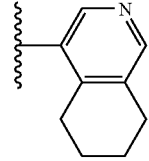
a-vii

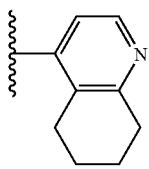
a-viii wherein c-i and c-ii are further substituted with 0-2 J.

In various embodiments of a compound of the invention, $L^1$ can be a bond and $L^2$ can be a bond or a phenyl substituted with 0-5 J; and $R^5$ and $R^6$ can independently be selected from phenyl or heteroaryl each substituted with 0-5 J; provided that if $L^2$ is a bond and $R^5$ and $R^6$ are both phenyl, then $R^5$ is substituted with at least one of 4-CN, 3-alkyl-N(R')$_2$, 3-alkyl-OR', 4-alkyl-OR', or 2,3-dialkyl, and $R^6$ is substituted with at least 4-OR'.

For example, the optionally substituted bicyclic ring moiety can be any one of a-i to a-viii.

wherein any of the bicyclic ring moieties is substituted with 0-5 J.

For example, a compound of the invention can have the formula I-B further substituted with 0-5 J:

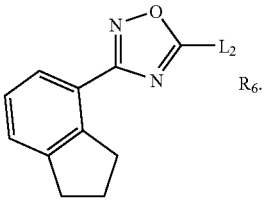
I-B

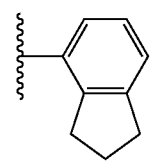
a-i

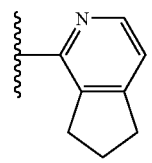
a-ii

For example, a compound of the invention can have the formula I-C further substituted with 0-5 J:

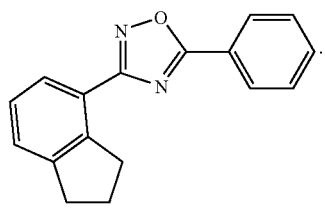
I-C

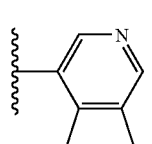
a-iii

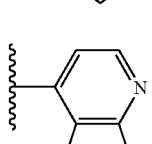
a-iv

For example, a compound of the invention can have the formula I-D and further be substituted with 0-5 J, and wherein $R^7$ and $R^8$ each independently are H, OR', OC(O)N(R')$_2$, N(R')N(R')$_2$, N(R')CH$_2$CH$_2$OR', CN, CHF$_2$, CF$_3$, OCF$_3$, NO$_2$, R', =O, =S, C(O), S(O), N(R')$_2$, SR', SOR', SO$_2$R', SO$_2$N(R')$_2$, SO$_3$R', or C(O)R', or $R^7$ and $R^8$ together are =O, =NR', or =N(R')CH$_2$CH$_2$OR'.

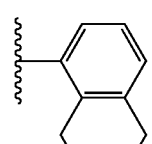
a-v

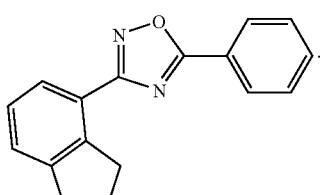
I-D

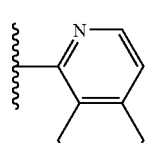
a-vi

For example, a compound of the invention can have a formula I-F

I-F

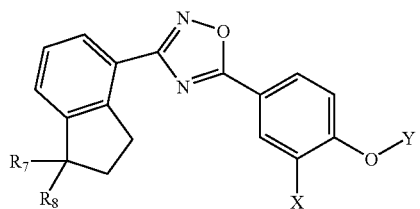

wherein R⁷ and R⁸ are each independently selected from H, OR', N(R")₂, and SR", wherein R" is hydrogen or an alkyl, cycloalkyl, aryl, heterocyclyl, or heteroaryl, wherein any such alkyl, cycloalkyl, aryl, heterocyclyl or heteroaryl is substituted with 0-3 J; X is F, Cl, Br, I, $CHF_2$, CN, $CF_3$, $NO_2$, or OR'; Y is hydrogen or an alkyl, cycloalkyl, aryl, heterocyclyl, or heteroaryl, wherein any such alkyl, cycloalkyl, aryl, heterocyclyl or heteroaryl is substituted with 0-3 J.

In various embodiments of a compound of the invention can be any of:

215

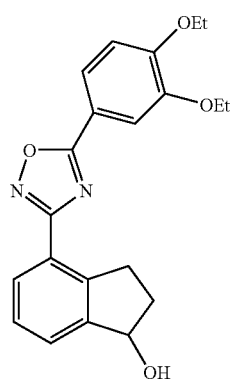

216

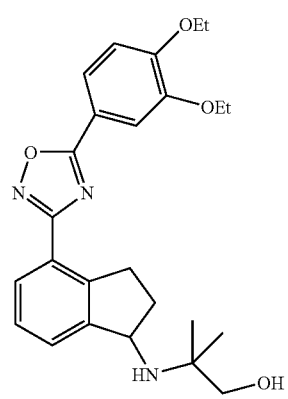

217

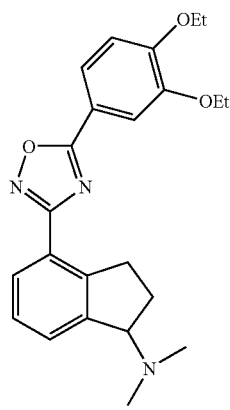

227

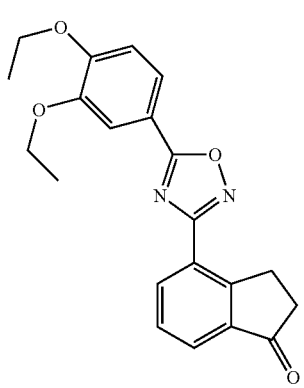

236

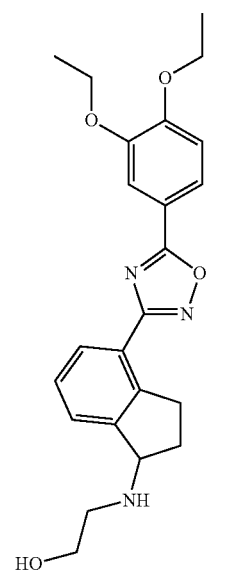

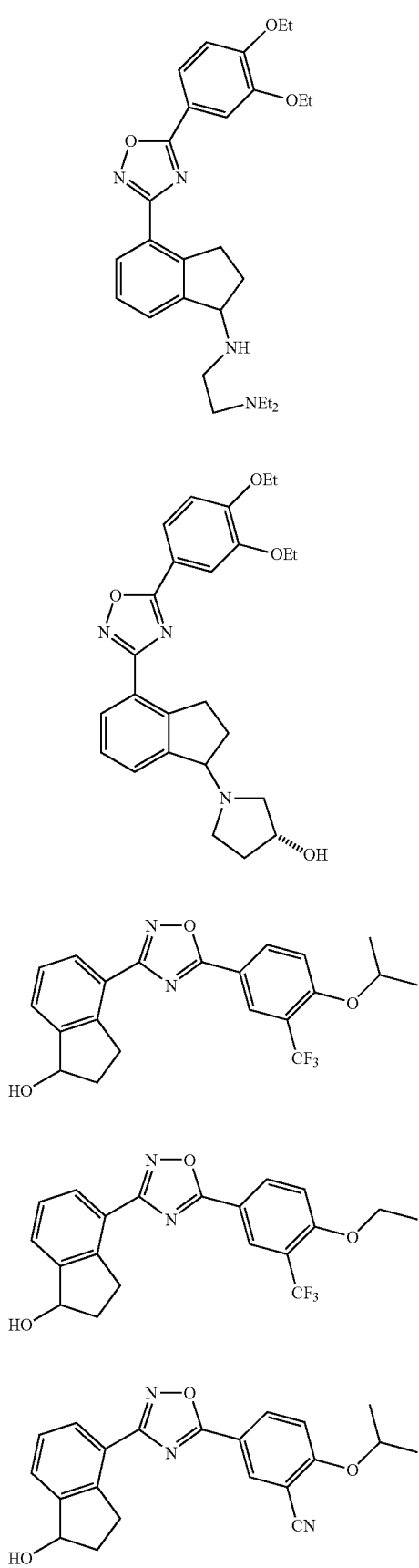
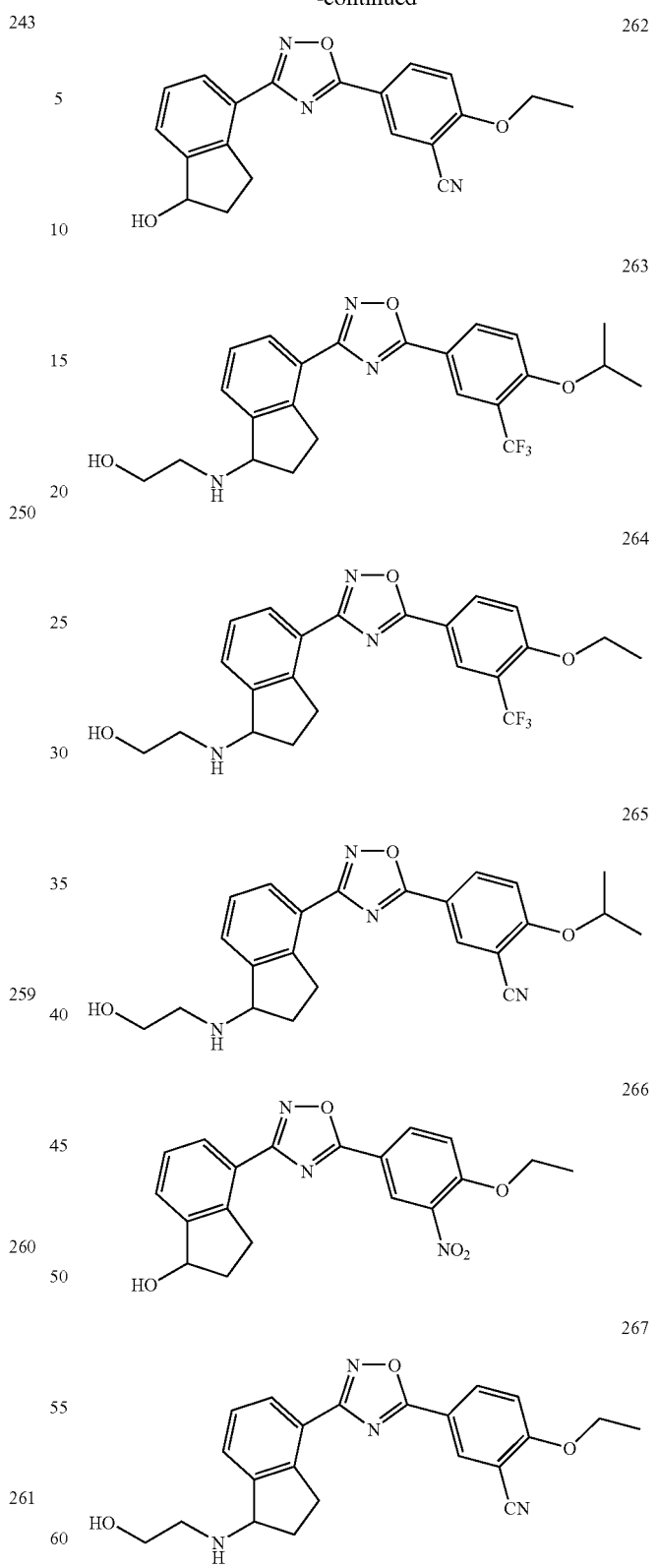
or any pharmaceutically acceptable salt, tautomer, stereoisomer, solvate, hydrate, or prodrug thereof.
In various embodiments of a compound of the invention, the bicyclic ring moiety can be any one of a-ix to a-xv:

a-ix 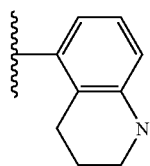
a-x 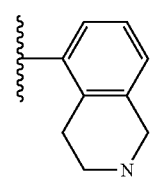
a-xi 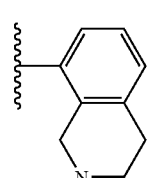
a-xii 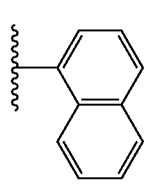
a-xiii 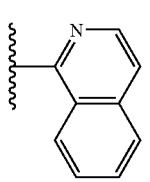
a-xiv 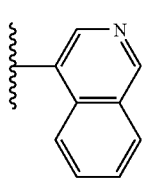
a-xv 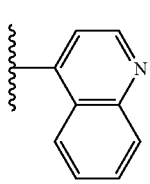
a-xxvi 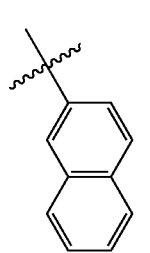
a-xxvii 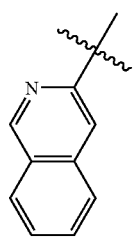
a-xxviii 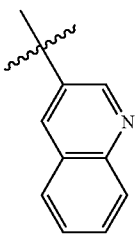
wherein any of the bicyclic ring moieties can be substituted with 0-5 J.
More specifically, in various embodiments of a compound of the invention, the compound can be any of:
208
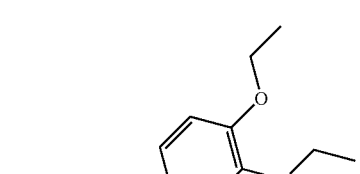
219
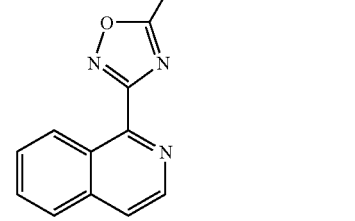

211
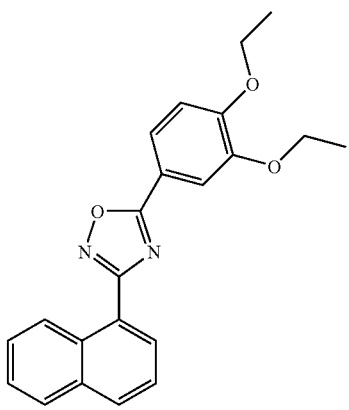
212
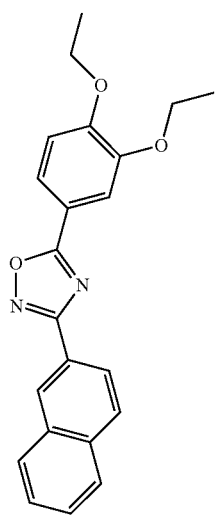
or any pharmaceutically acceptable salt, tautomer, stereoisomer, solvate, hydrate, or prodrug thereof.
In various embodiments of a compound of the invention, the optionally substituted bicyclic ring moiety can be any one of a-xvi to a-xxv:
a-xvi
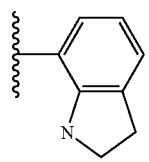
a-xvii
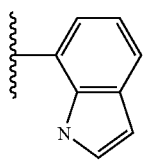
a-xviii
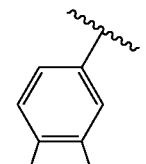
a-xix
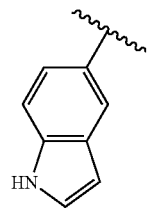
a-xx
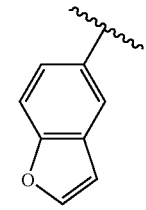
a-xxi
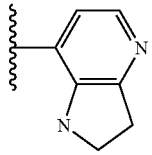
a-xxii
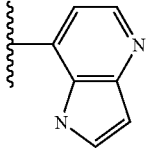
a-xxiii
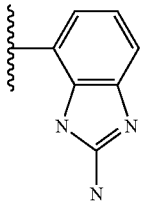
a-xxiv
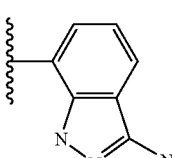
a-xxv
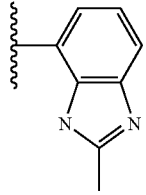
wherein any of the bicyclic ring moieties is substituted with 0-5 J.

In various embodiments of a compound of the invention, the compound can be any of:
153
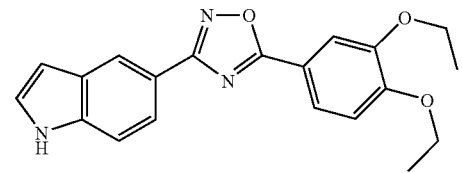
154
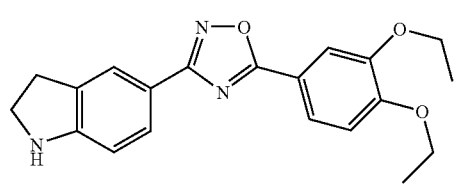
223
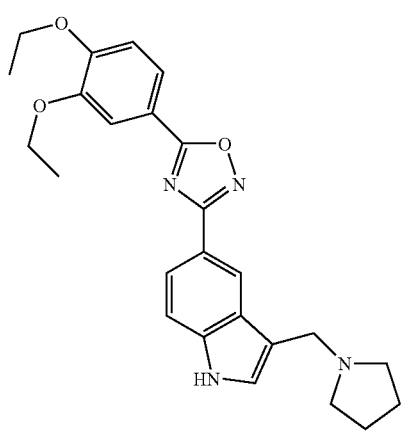
224
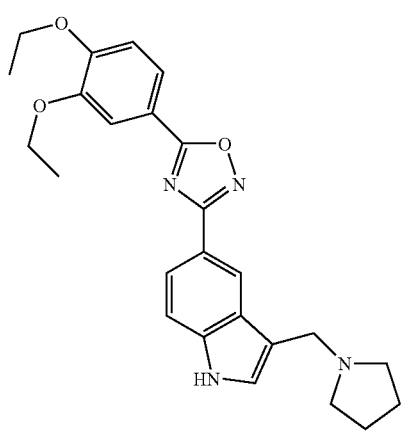
237
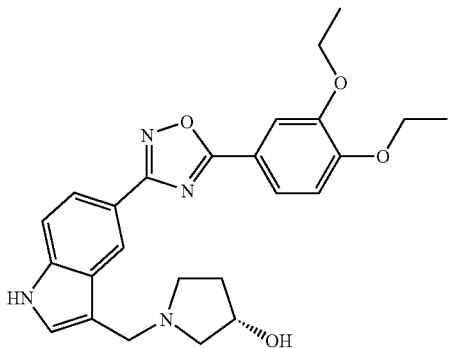
238
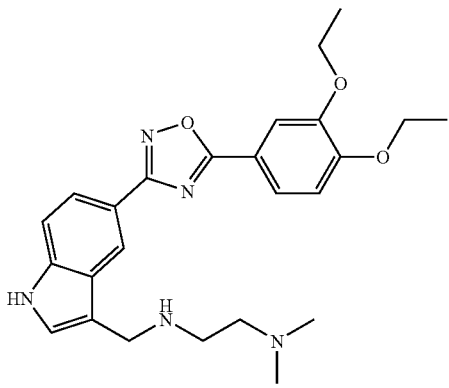
239
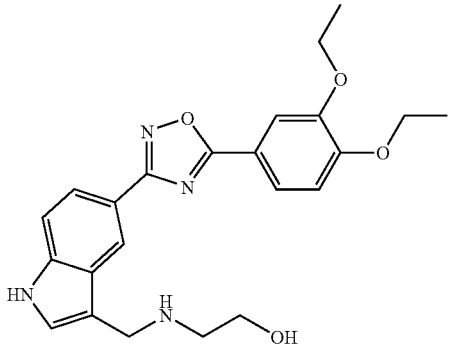
240
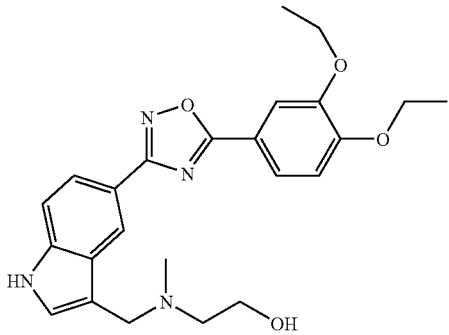
253
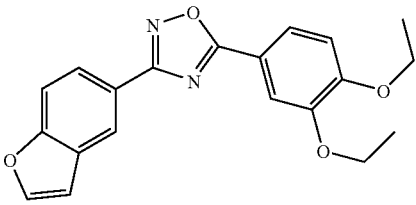

-continued

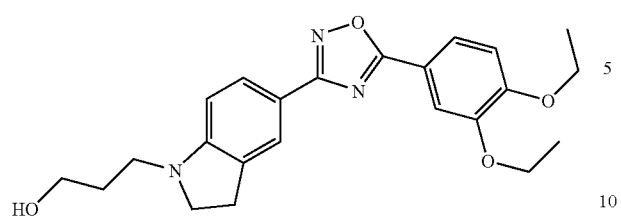
258 or any pharmaceutically acceptable salt, tautomer, stereoisomer, solvate, hydrate, or prodrug thereof.

In various embodiments of a compound of the invention, the optionally substituted 6-membered heteroaryl ring moiety of $R^5$ can be any one of b-i to b-v.

b-i
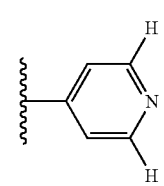

b-ii
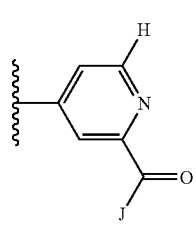

b-iii
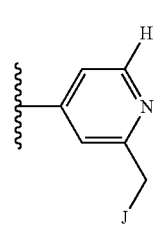

b-iv
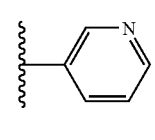

b-v
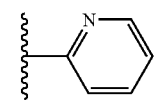

wherein any of the 6-membered heteroaryl ring moieties is substituted with 0-3 $J^1$.

In various embodiments of a compound of the invention, the compound can be any of:

32
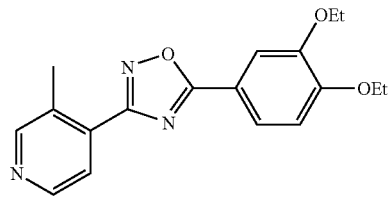

37
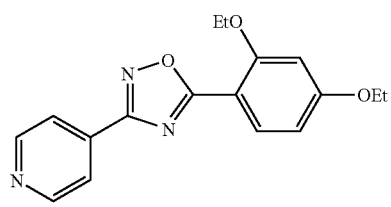

38
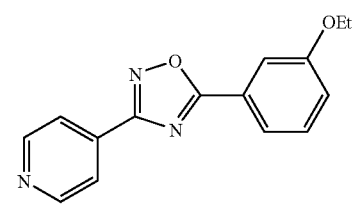

39
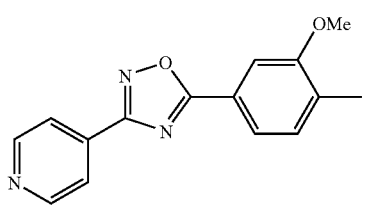

49
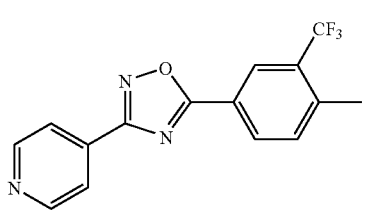

51
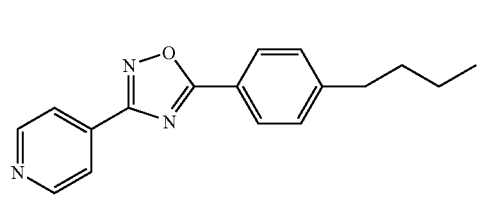

52
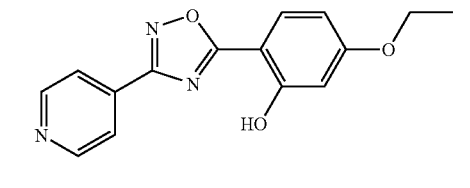

53
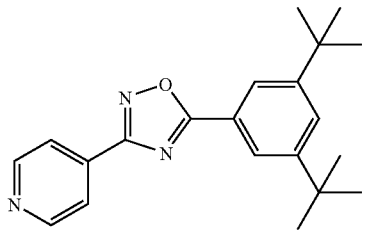

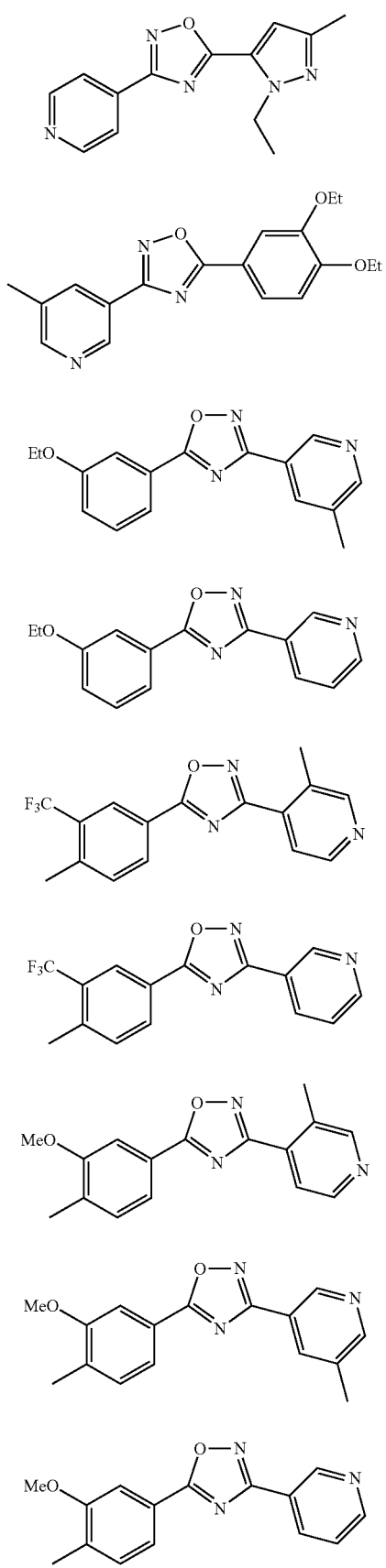

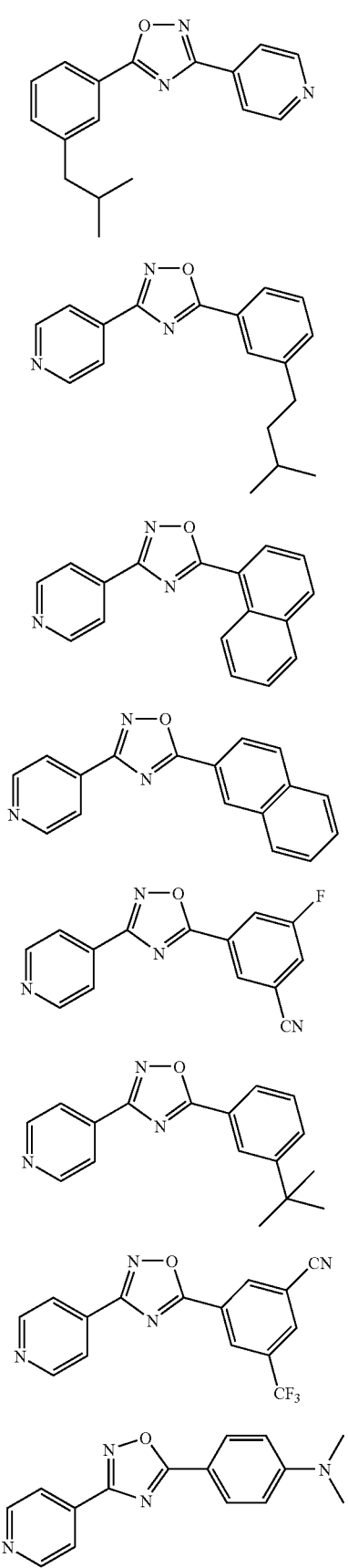
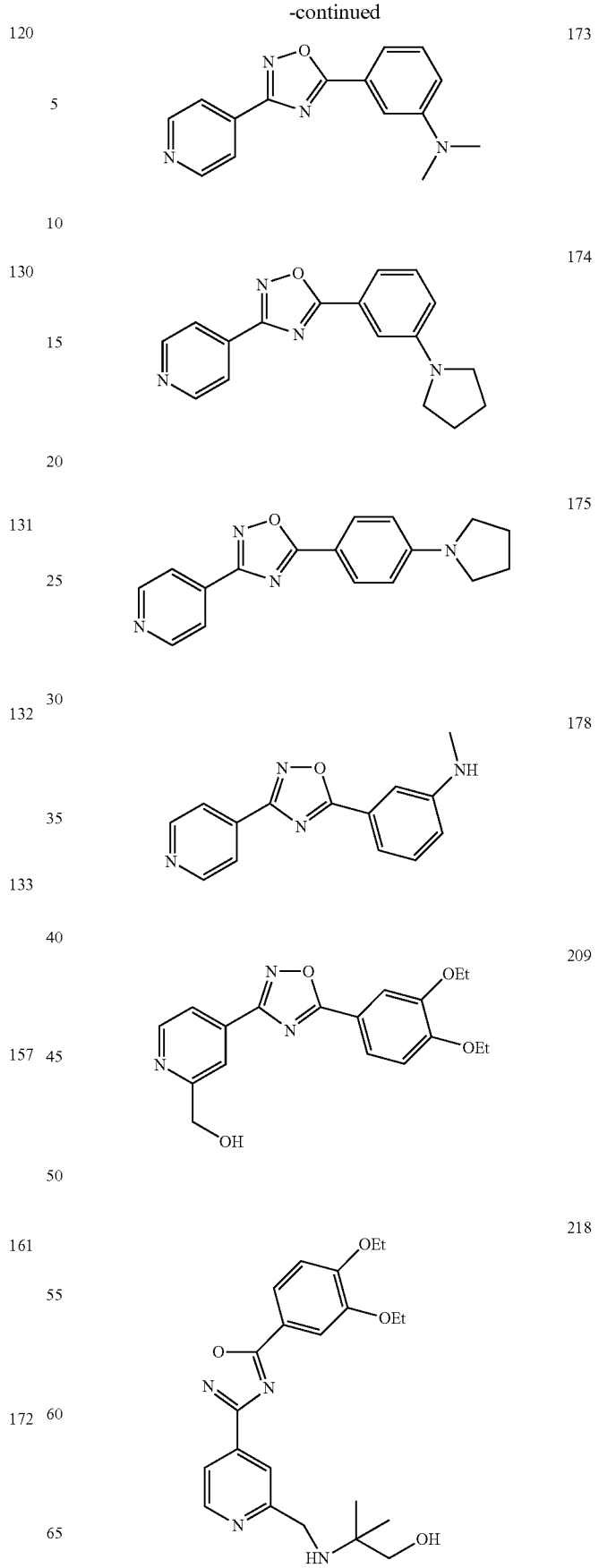

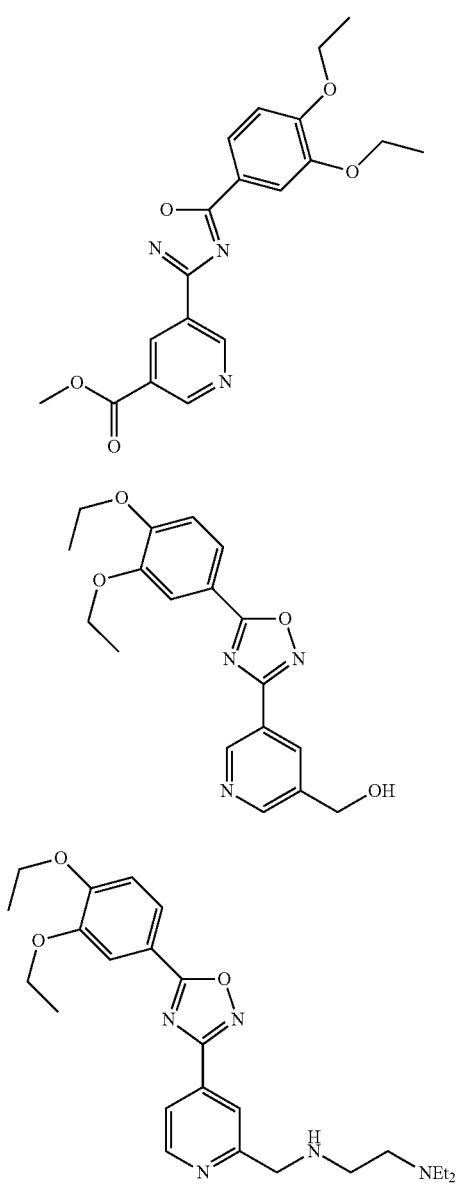
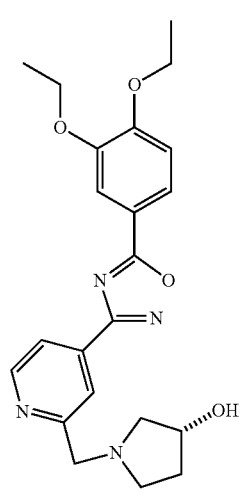
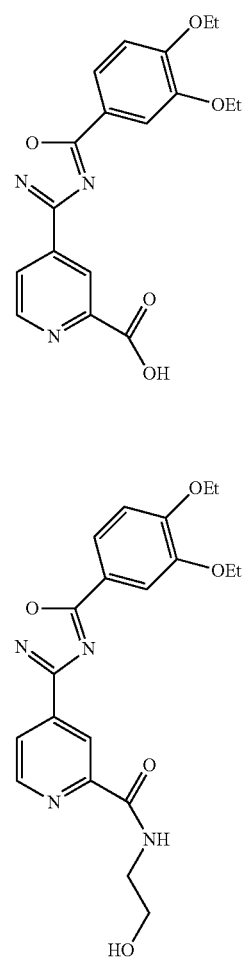
or any pharmaceutically acceptable salt, tautomer, stereoisomer, solvate, hydrate, or prodrug thereof.
More specifically, in various embodiments of a compound of the invention, the compound can be any of:
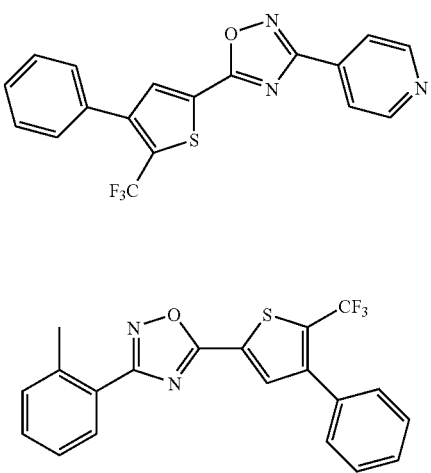

168 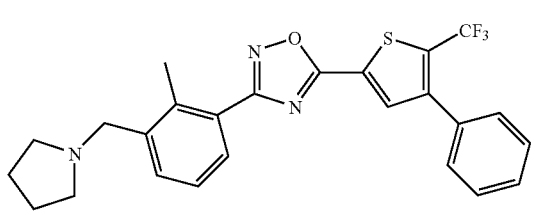
169 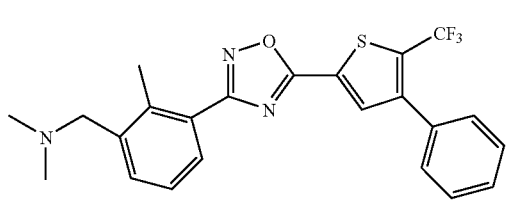
171 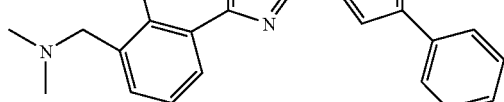
183 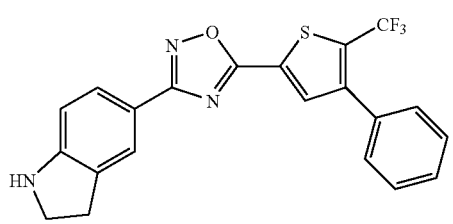
188 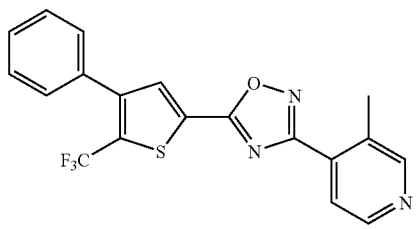
189 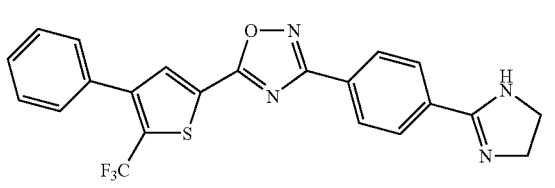
244 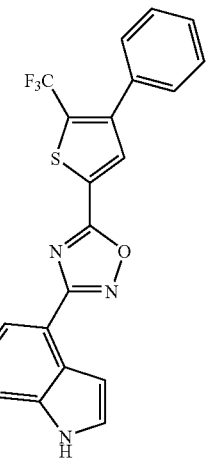
247 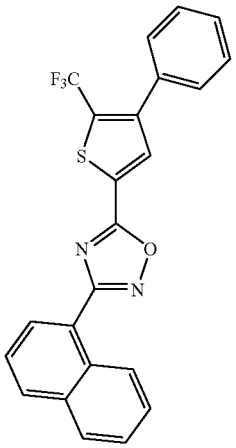
249 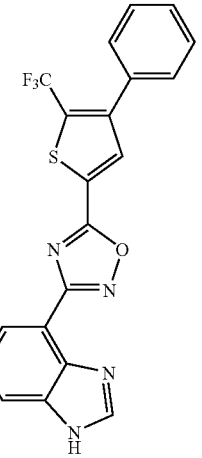
255 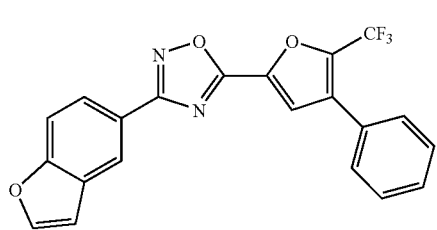

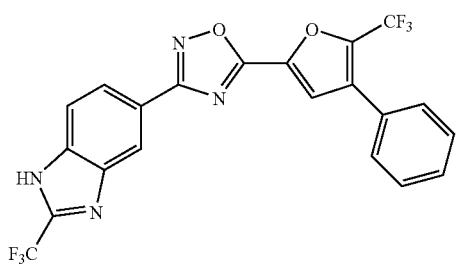
256
or any pharmaceutically acceptable salt, tautomer, stereoisomer, solvate, hydrate, or prodrug thereof.
In various embodiments of a compound of the invention, the compound can be any of:
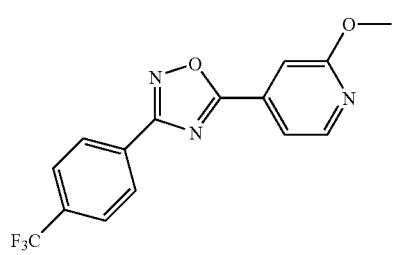
1
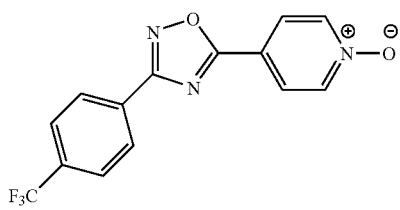
3
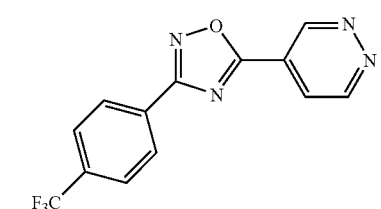
4
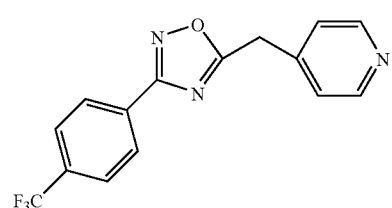
5
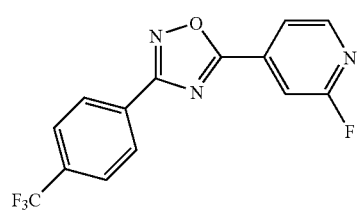
6
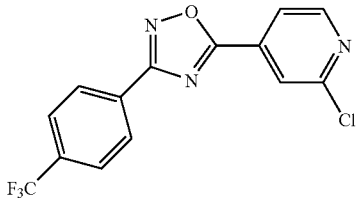
7
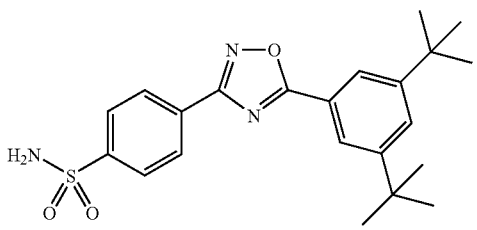
14
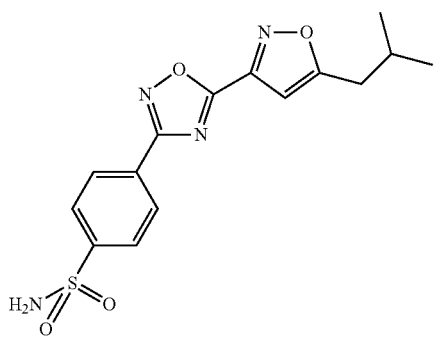
15
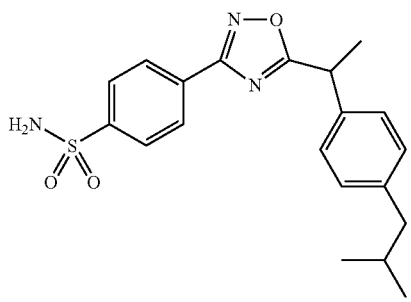
16
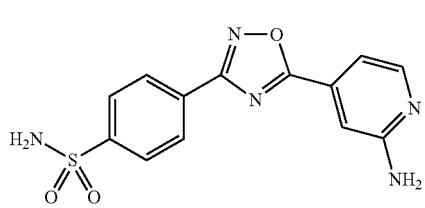
18
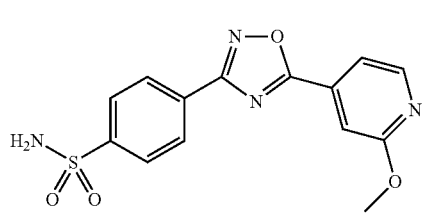
19

71
-continued
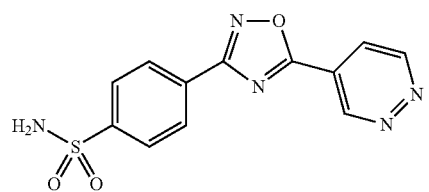
20
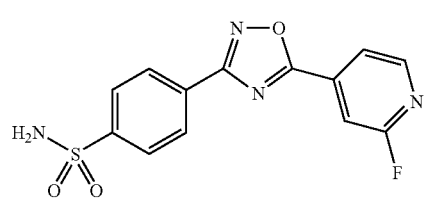
21
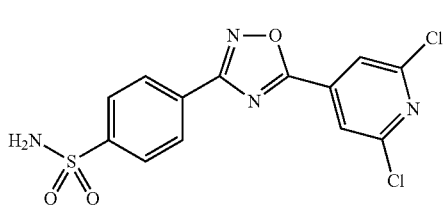
22
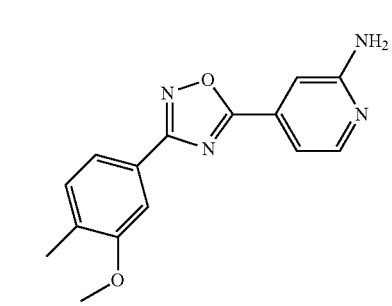
23
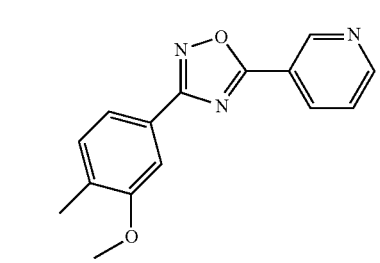
24
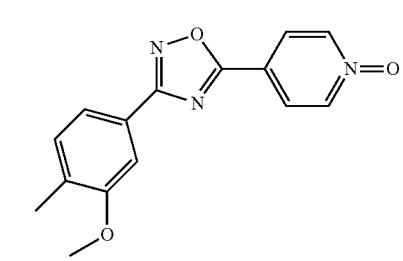
25
72
-continued
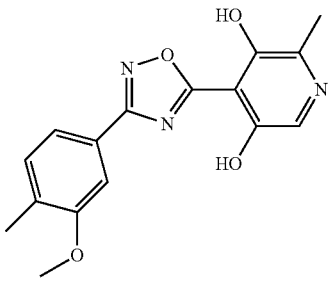
26
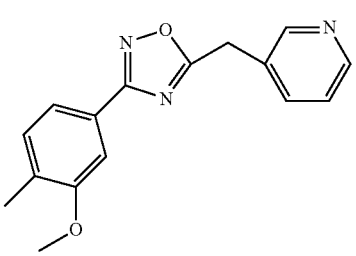
27
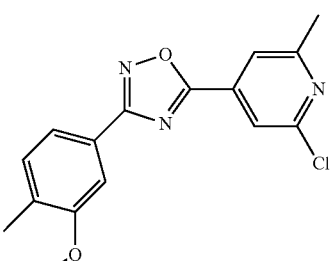
28
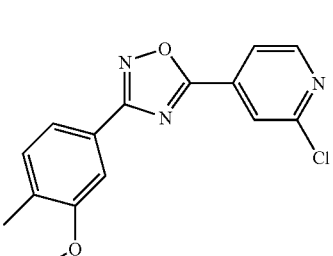
29
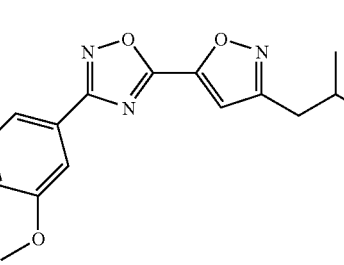
30
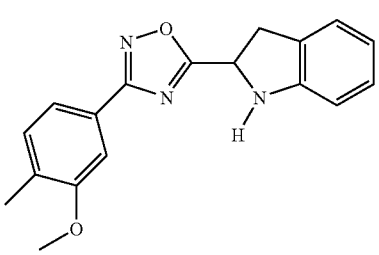
31

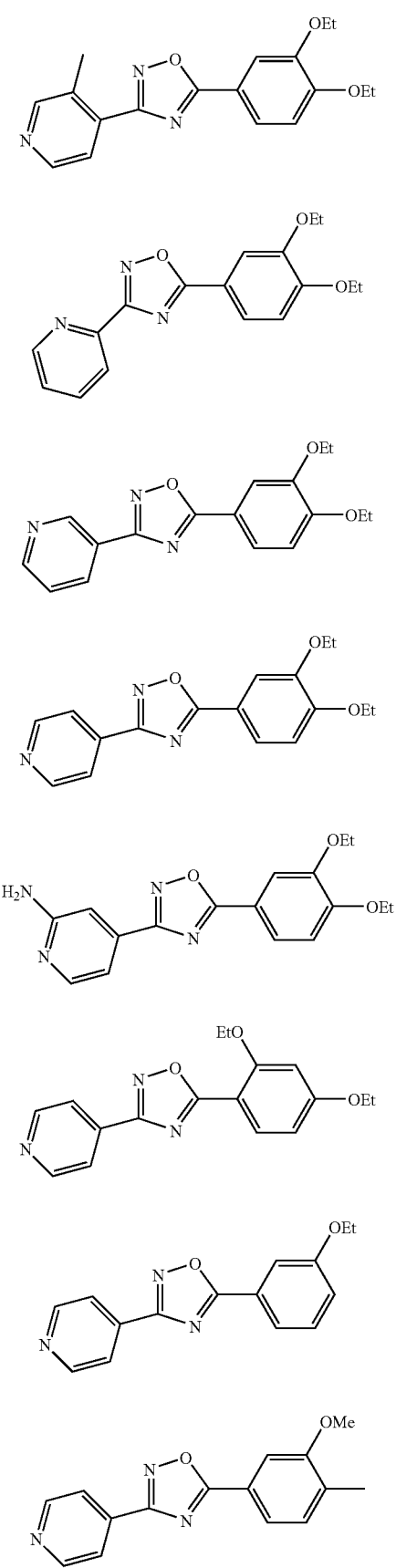
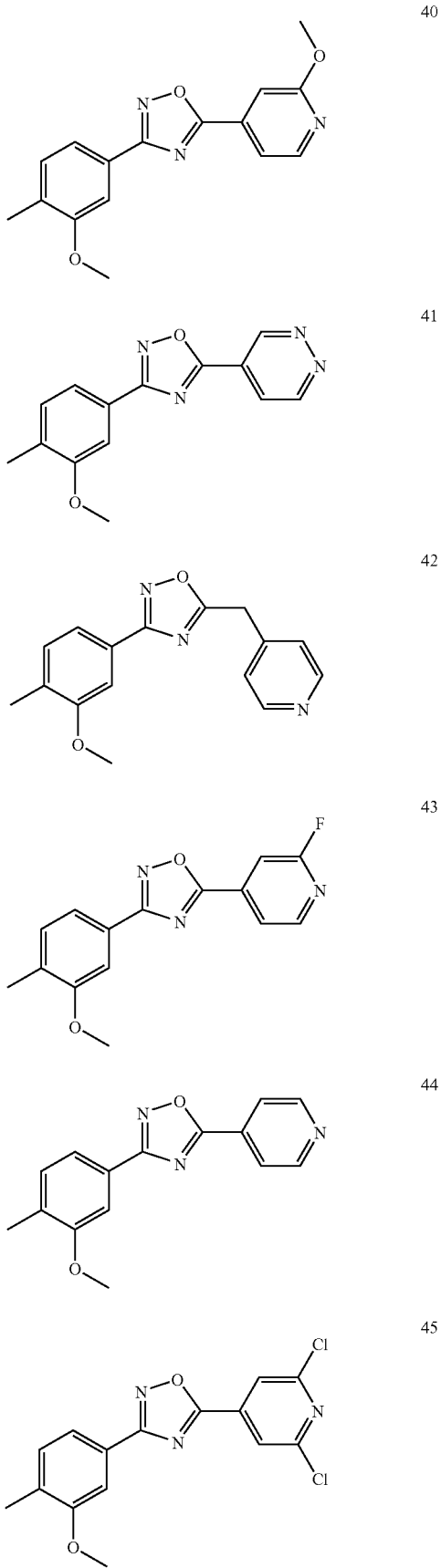

46 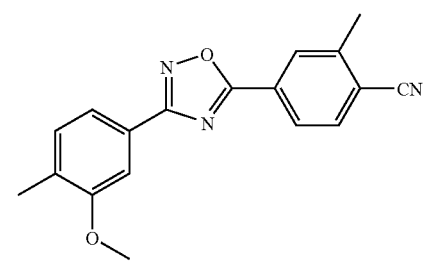
47 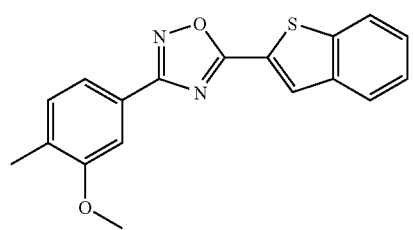
48 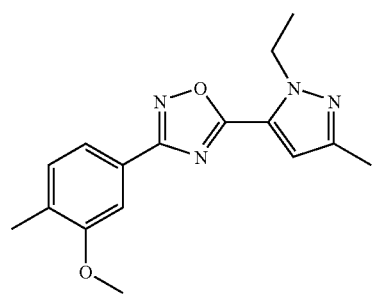
49 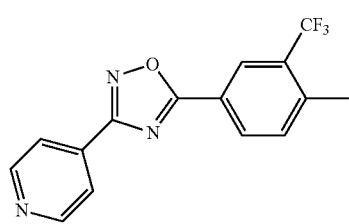
50 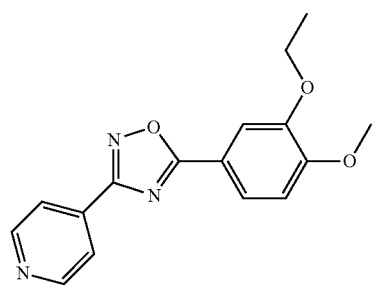
51 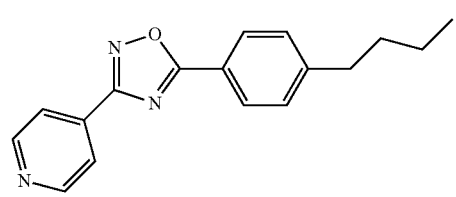
52 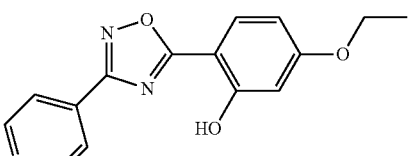
53 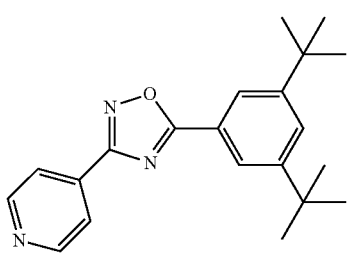
54 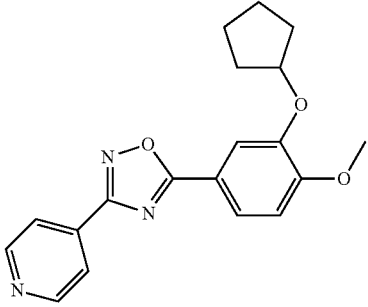
55 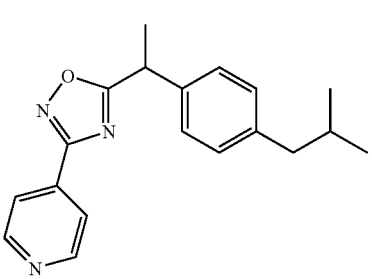
56 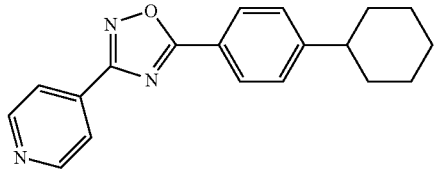
57 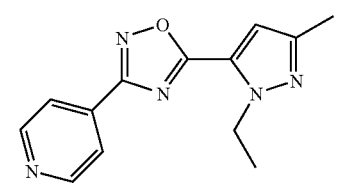
58 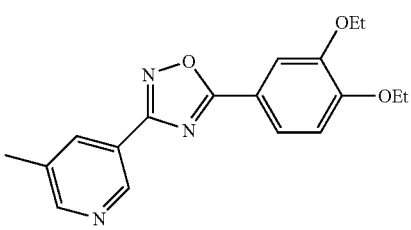

59
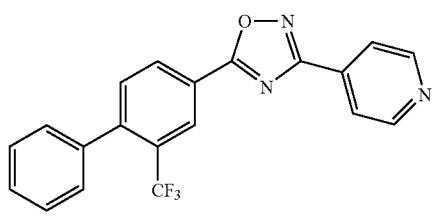
60
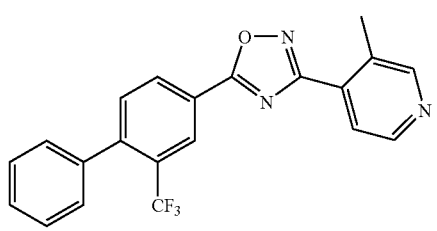
61
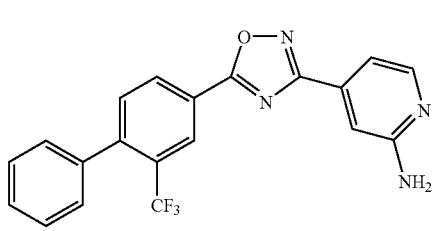
62
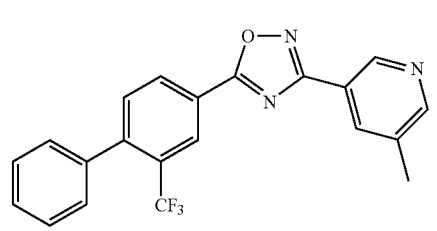
63
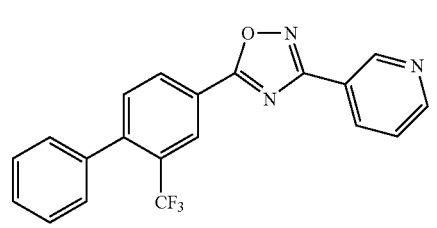
64
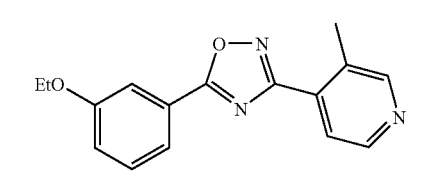
65
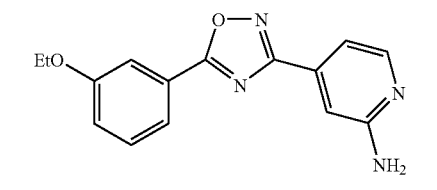
66
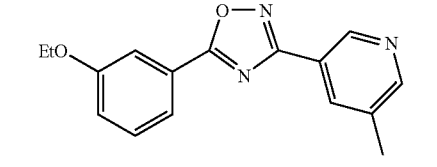
67
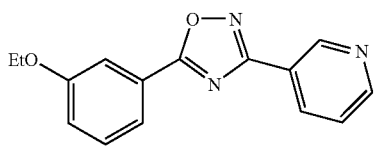
68
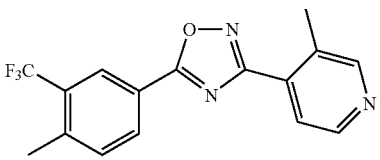
69
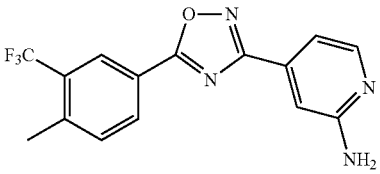
70
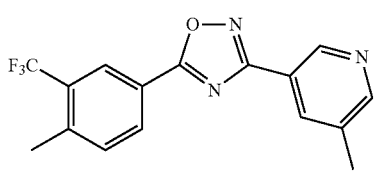
71
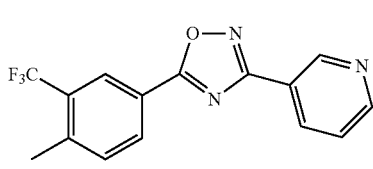
72
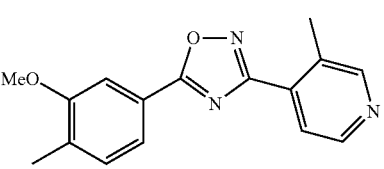
73
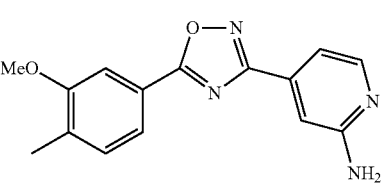
74
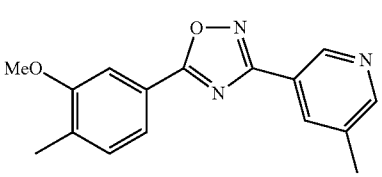
75
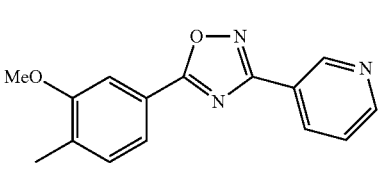

| 76 | 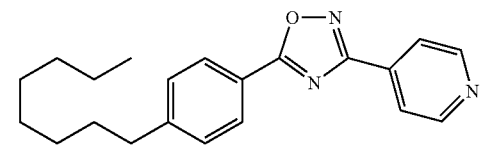 |
| 77 | 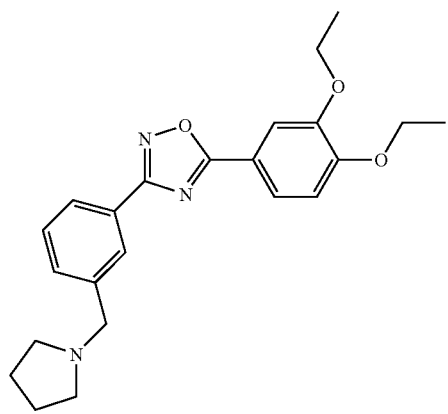 |
| 78 | 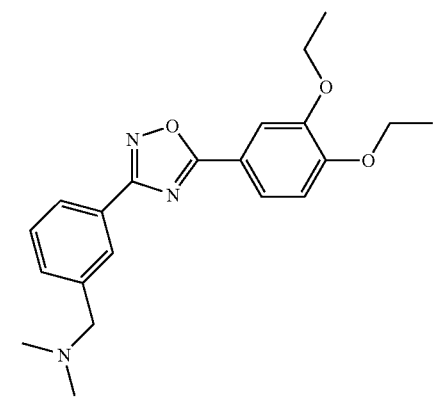 |
| 79 | 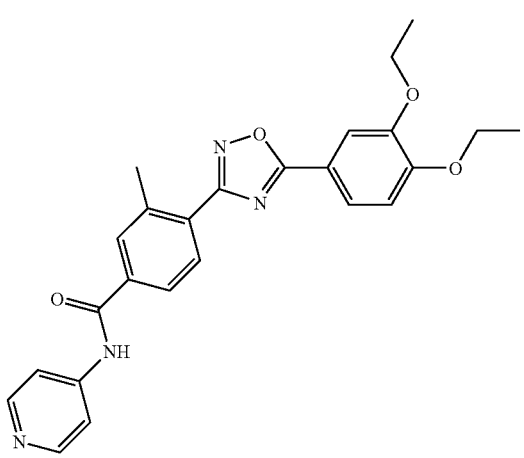 |
| 80 | 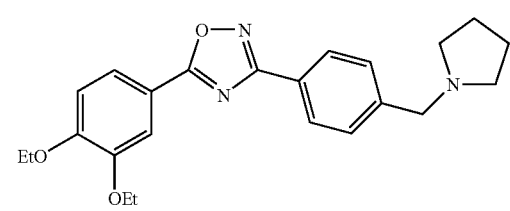 |
| 81 | 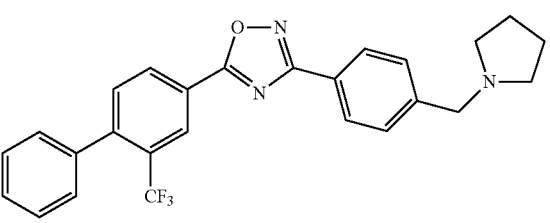 |
| 82 | 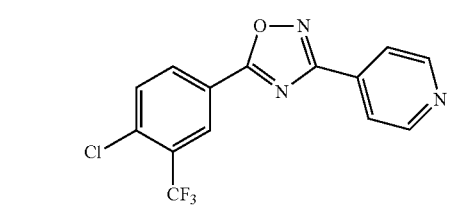 |
| 84 | 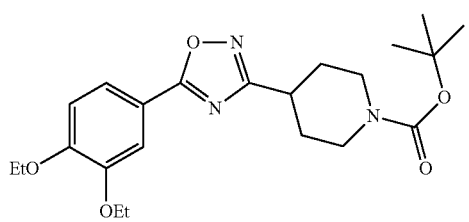 |
| 85 | 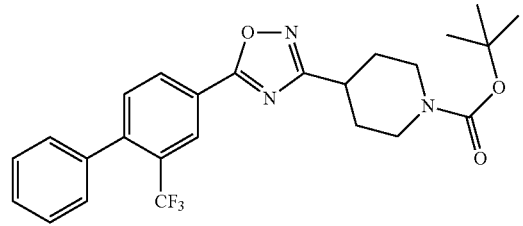 |
| 86 | 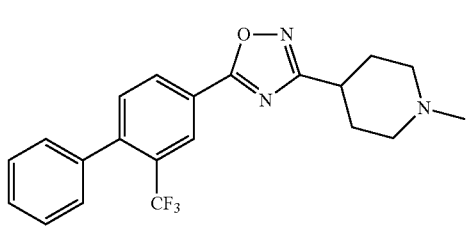 |
| 87 | 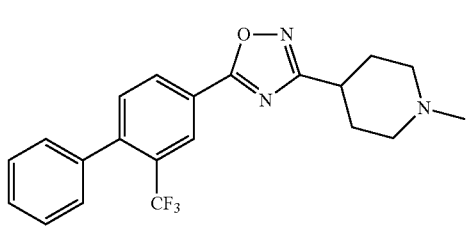 |
| 88 | 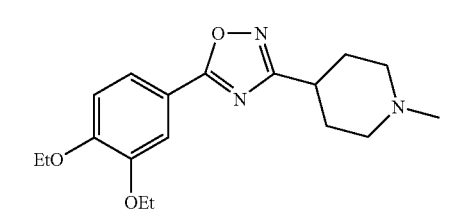 |

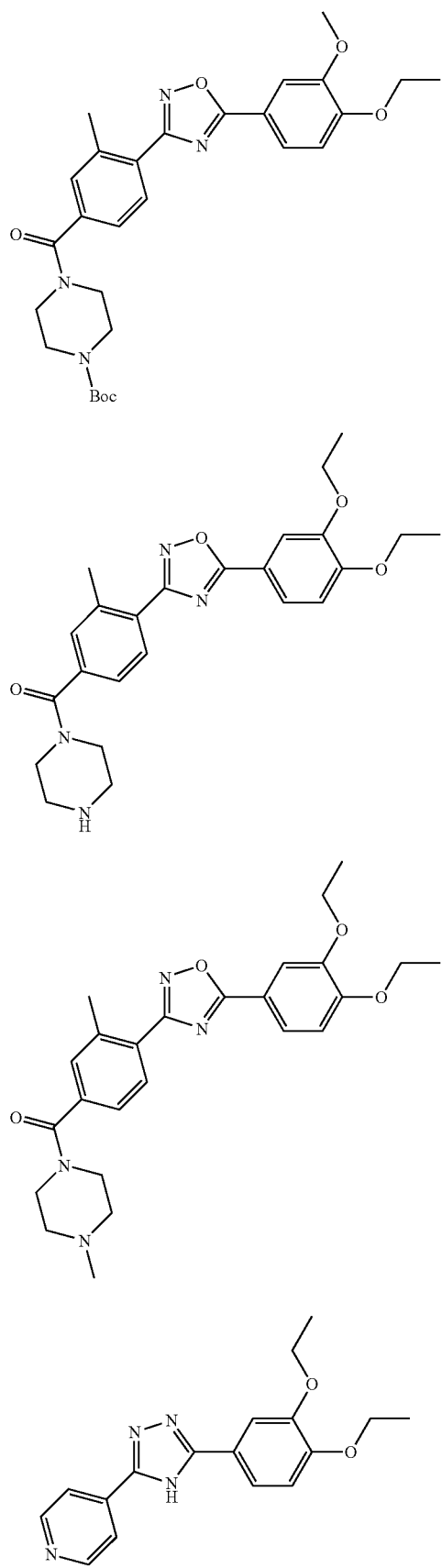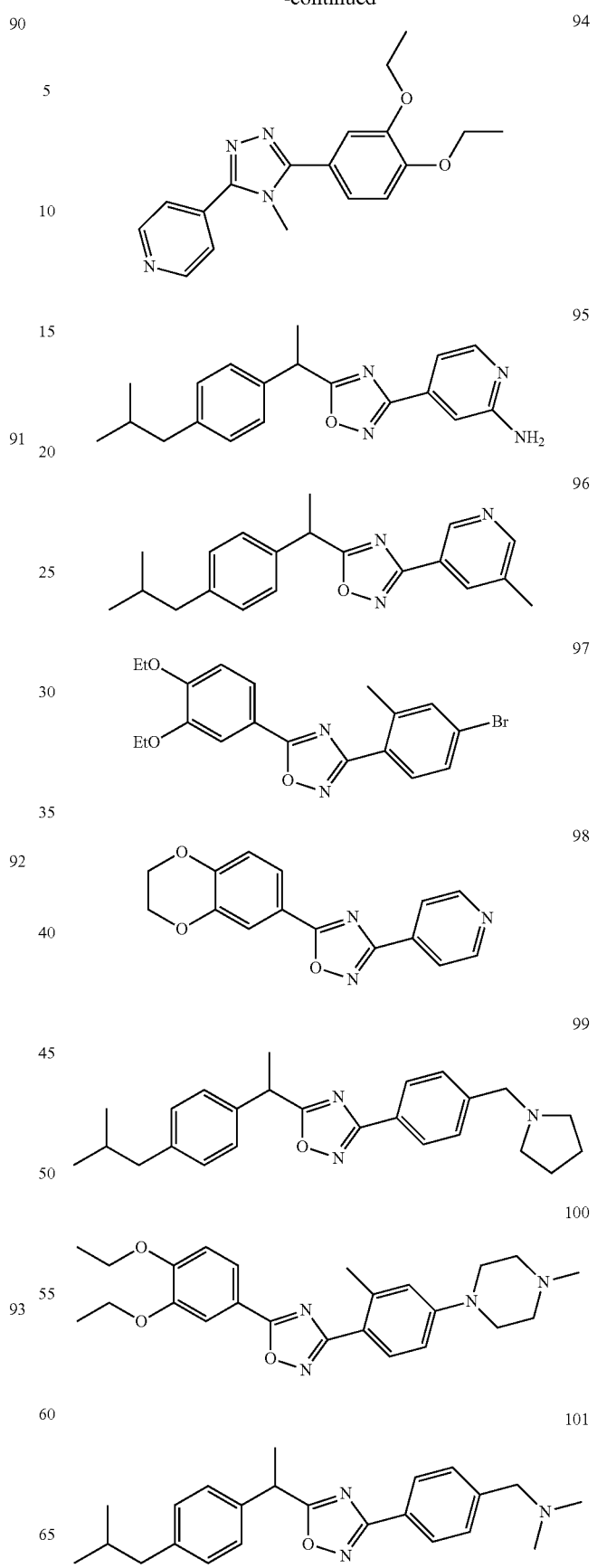

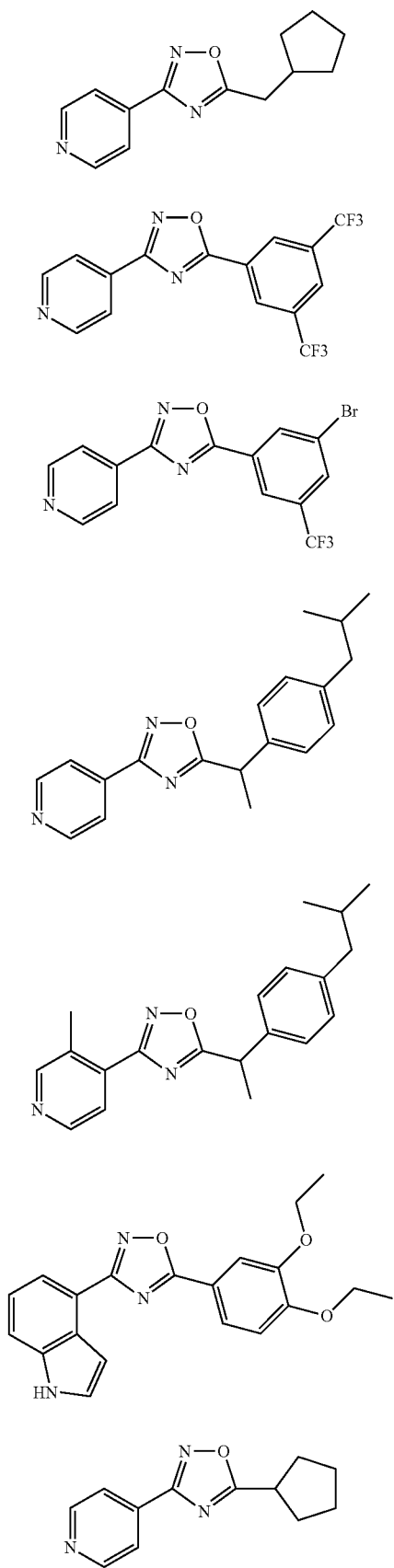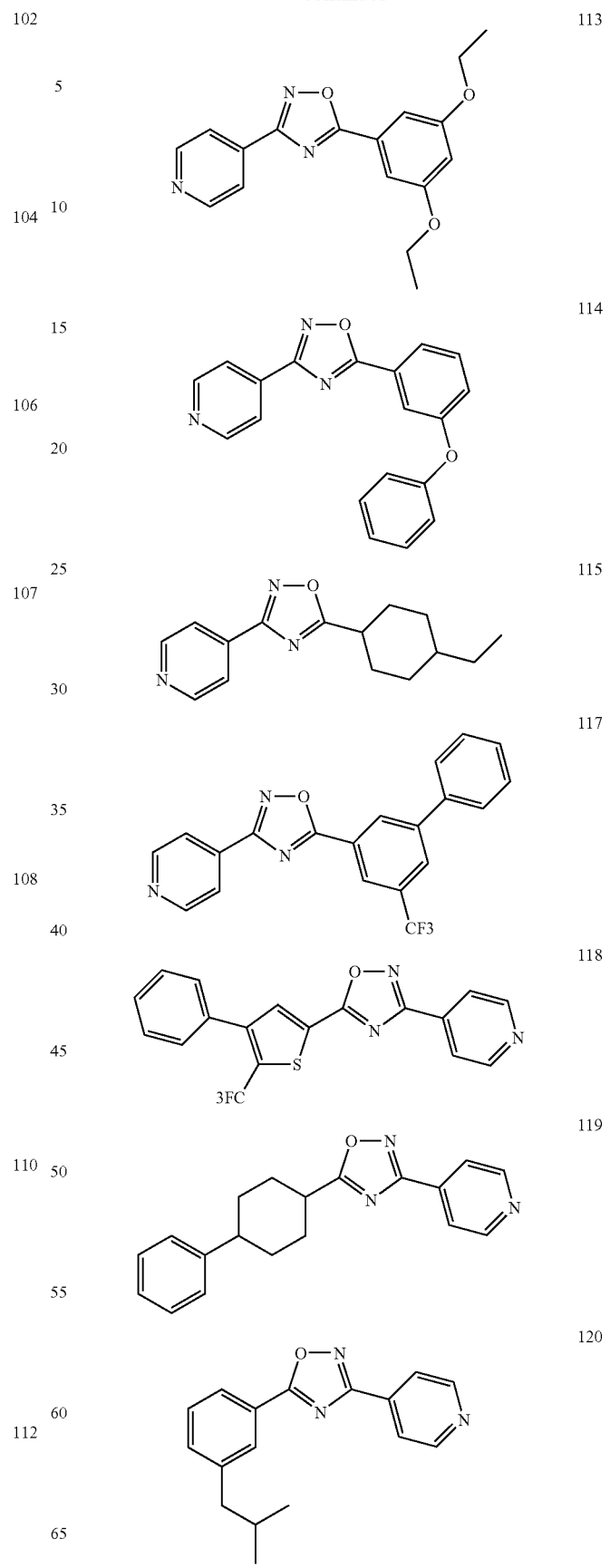

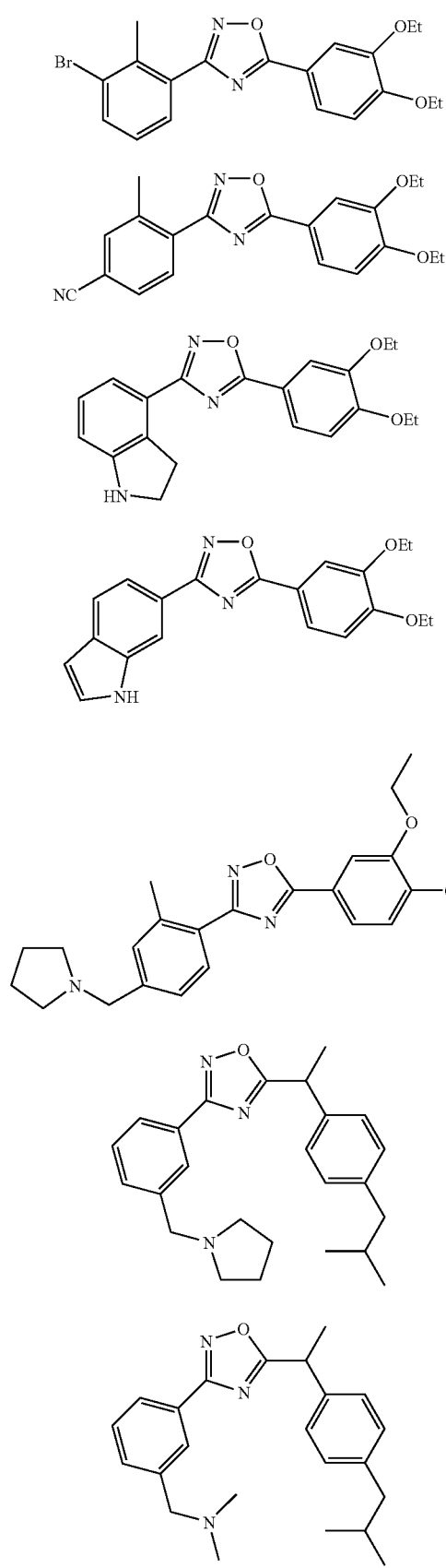
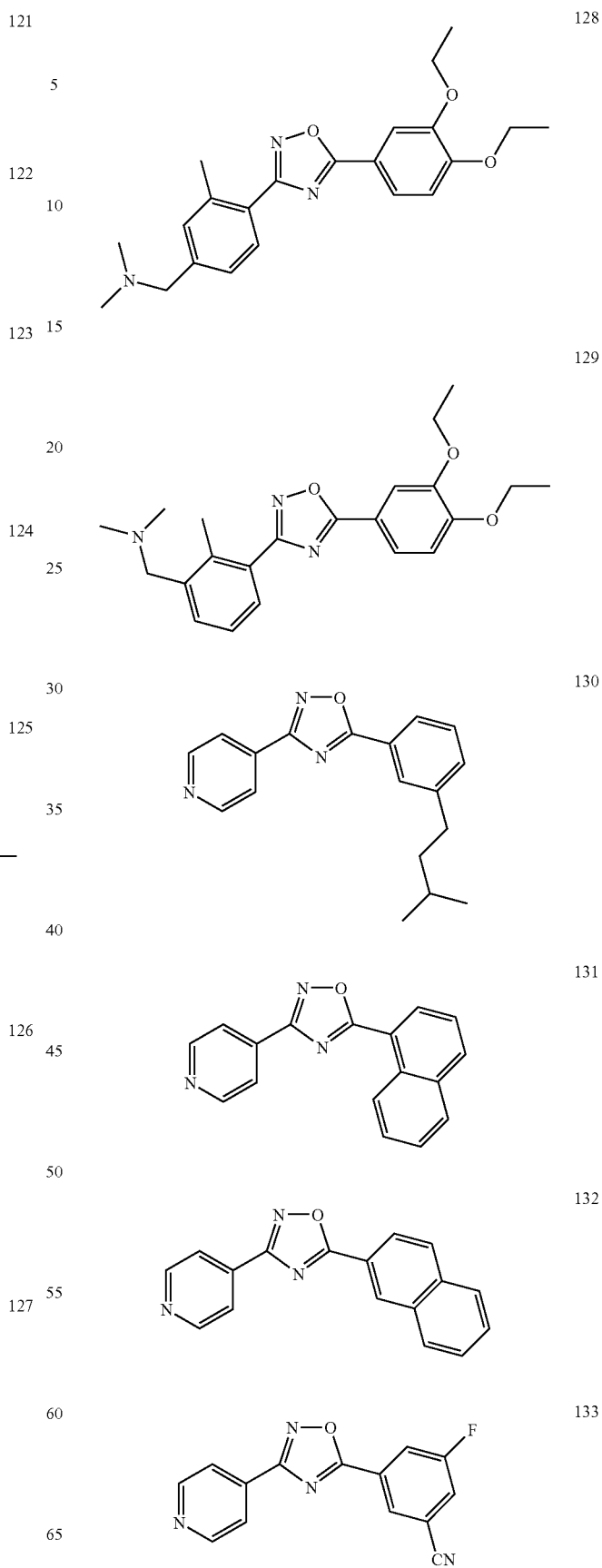

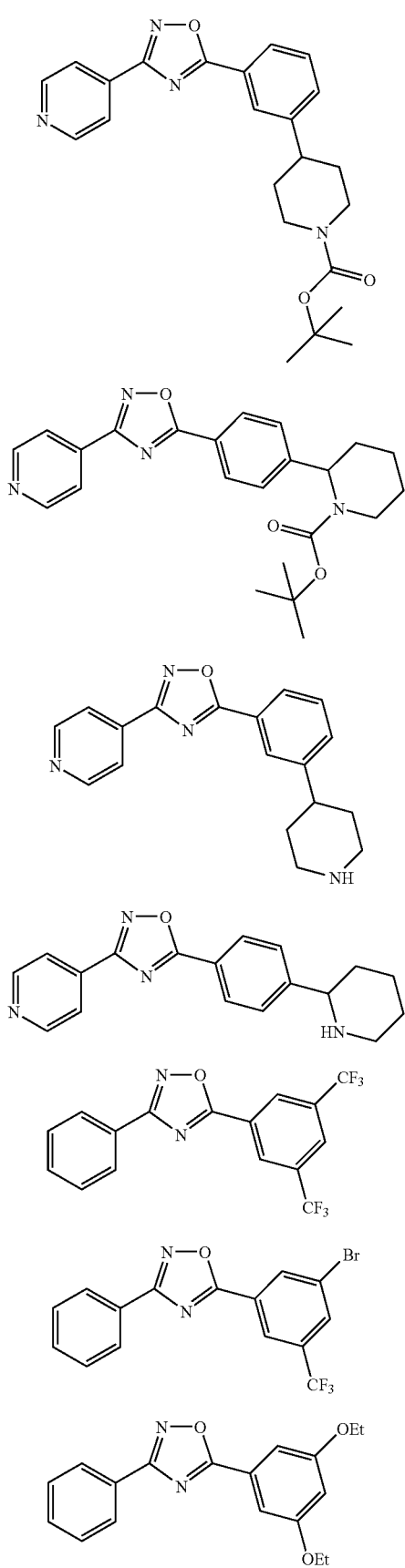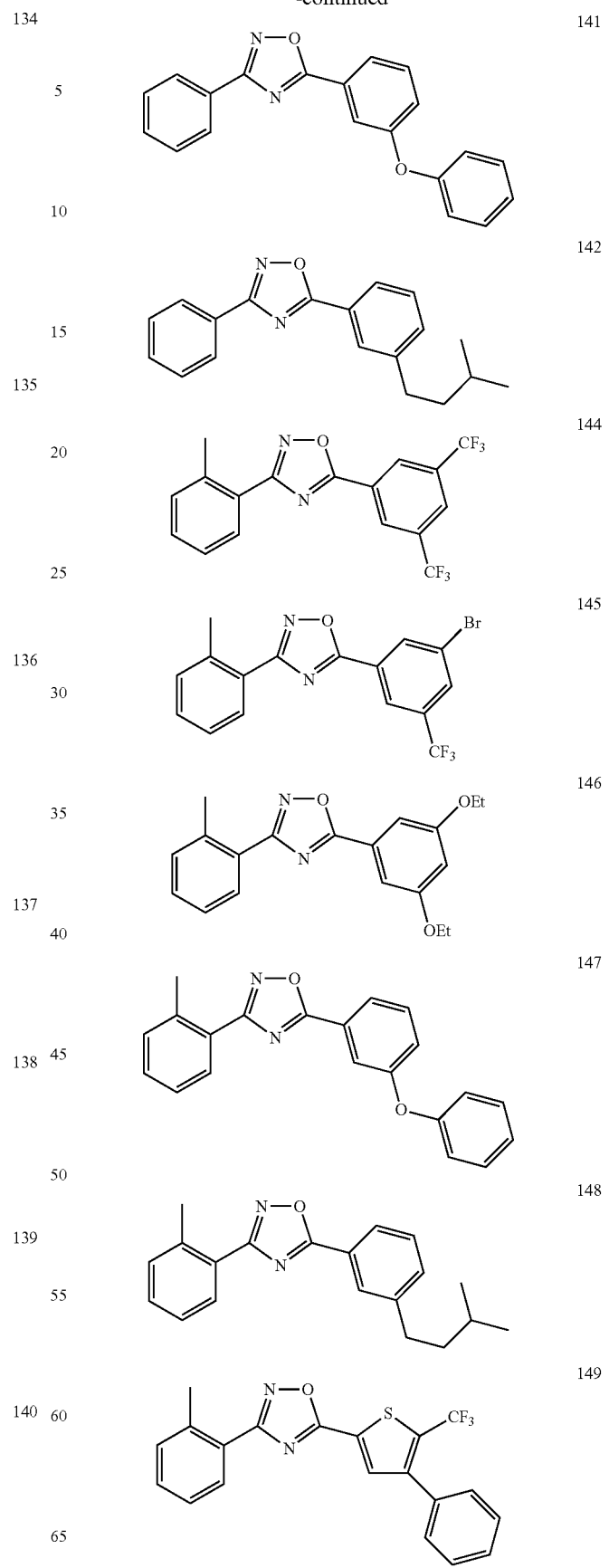

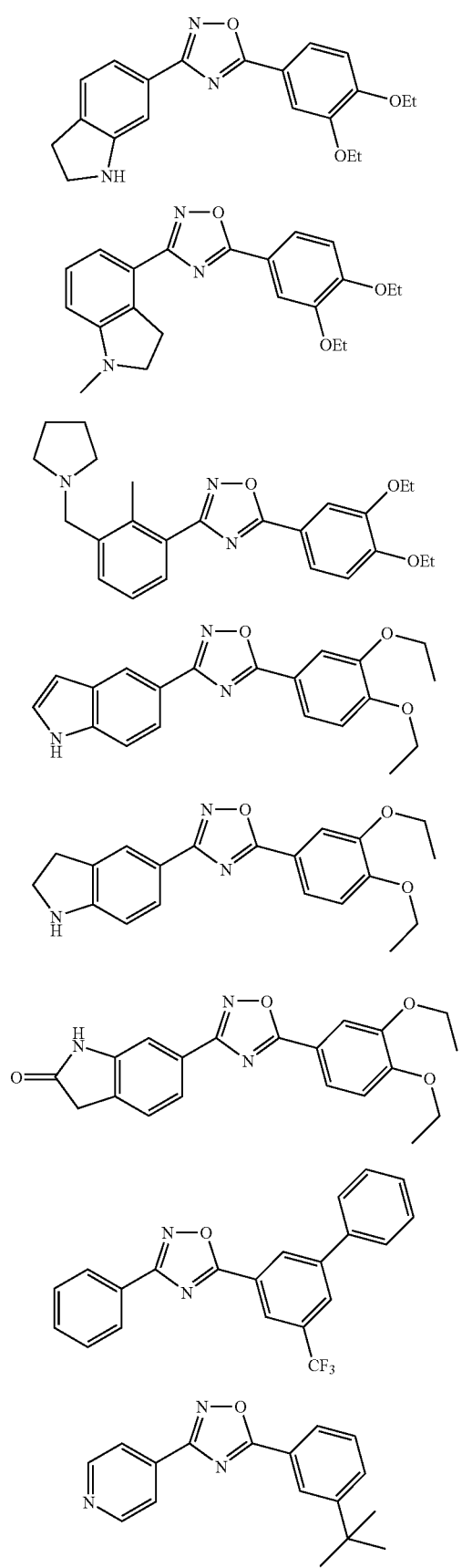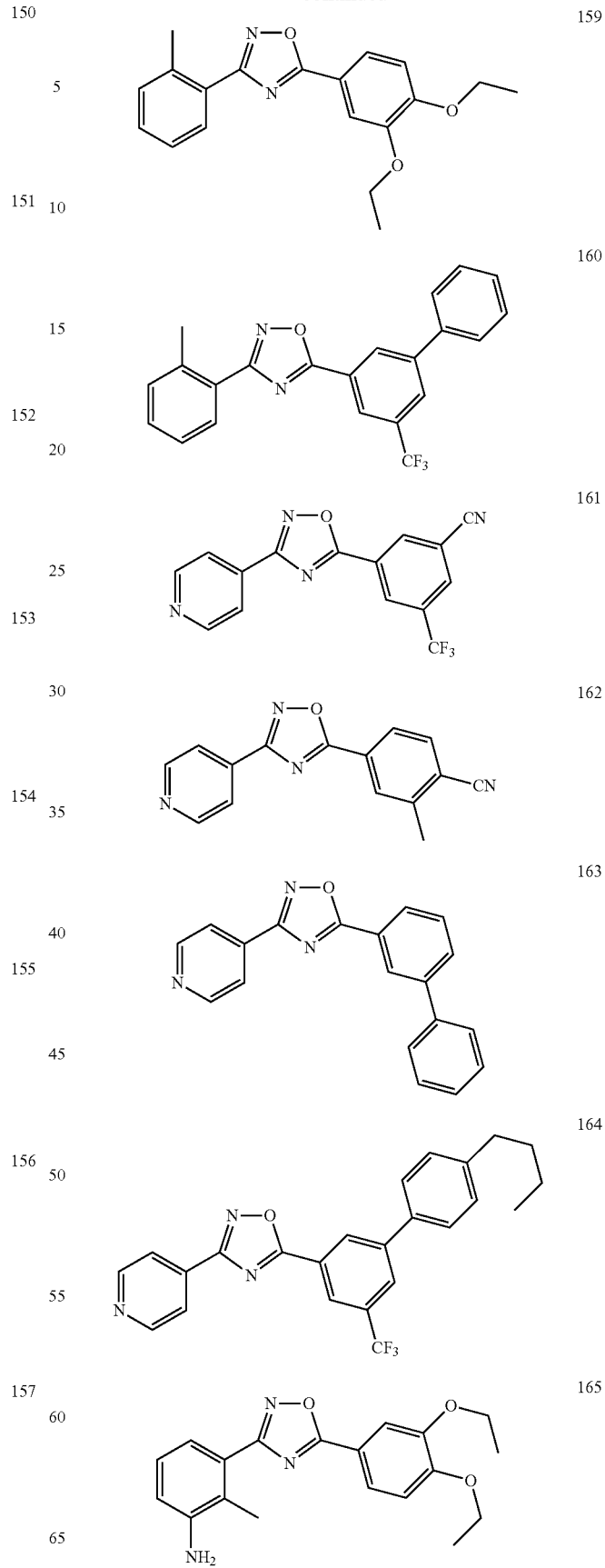

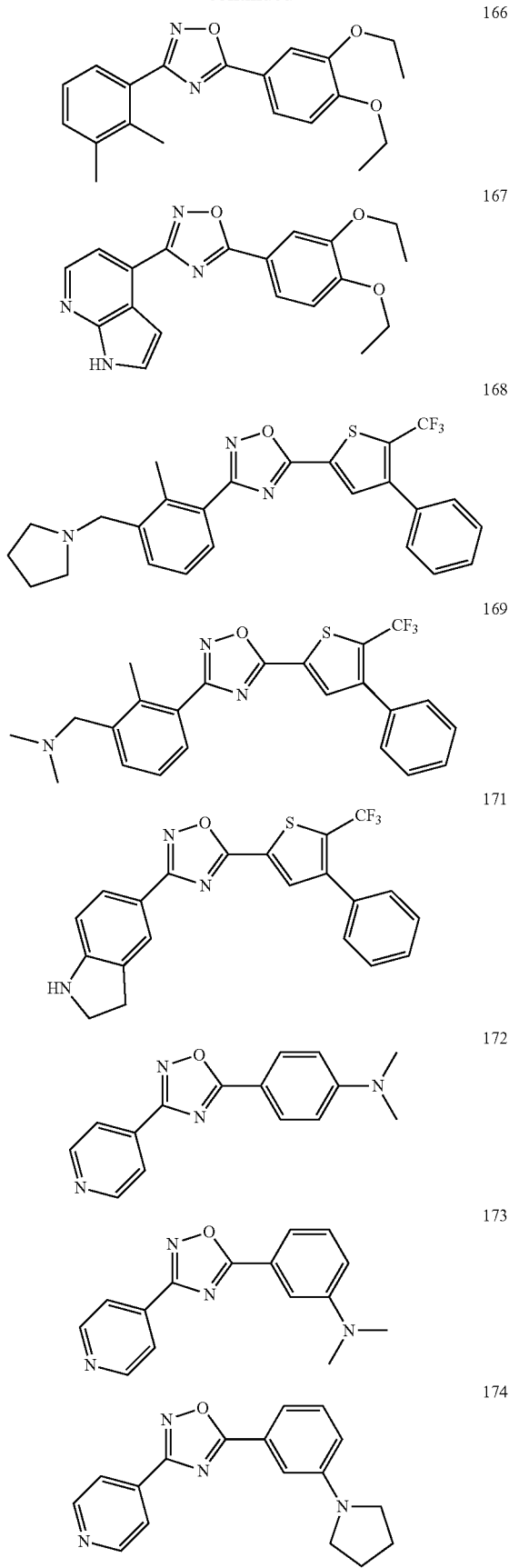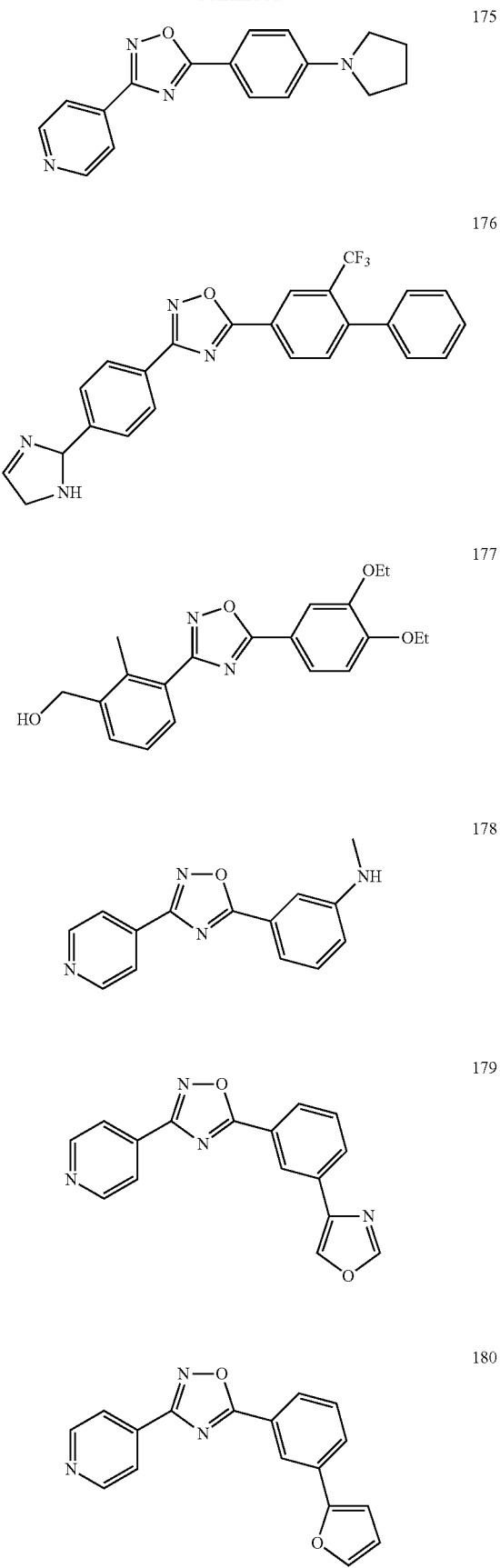

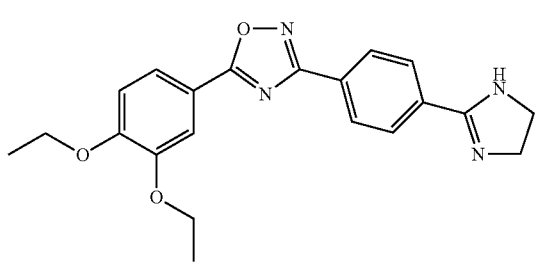
181
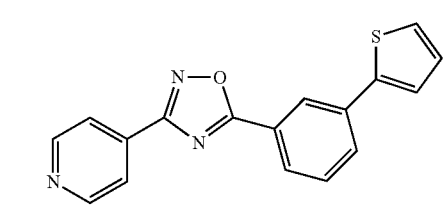
182
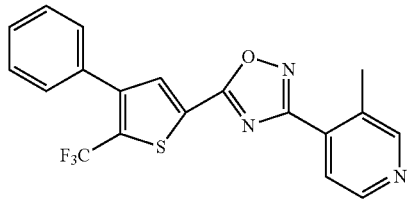
183
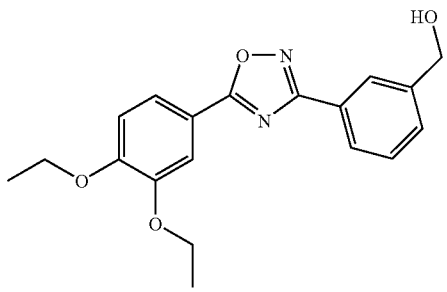
187
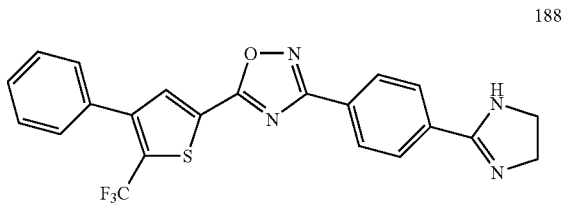
188
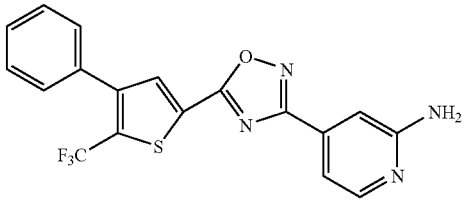
189

193 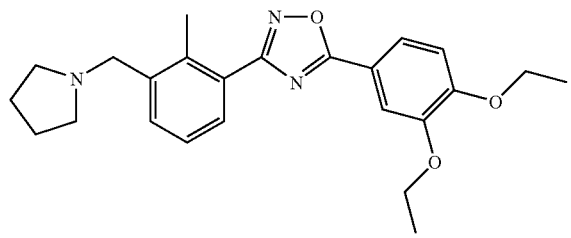
197 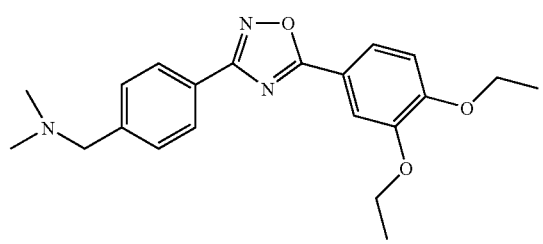
198 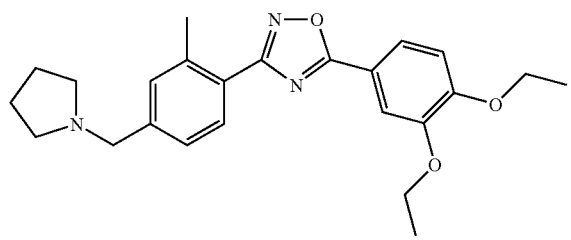
199 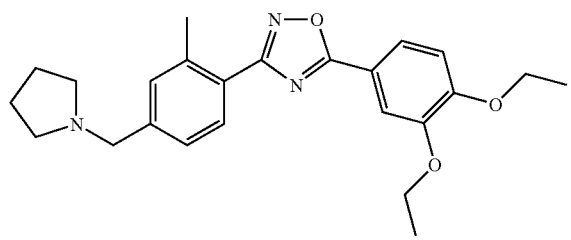
200
201
202 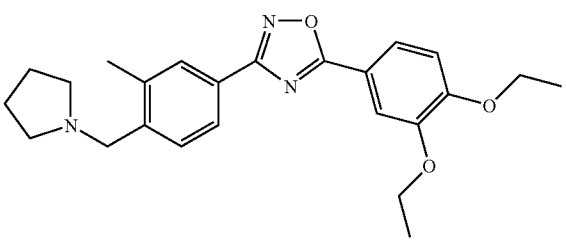
203 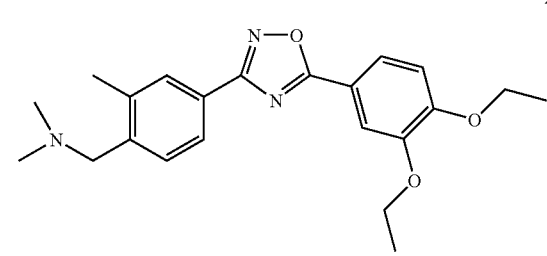
204 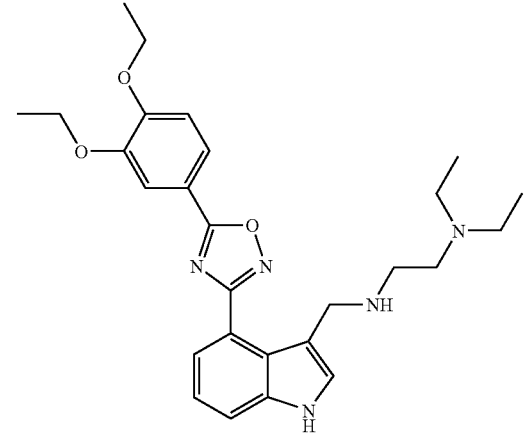
205 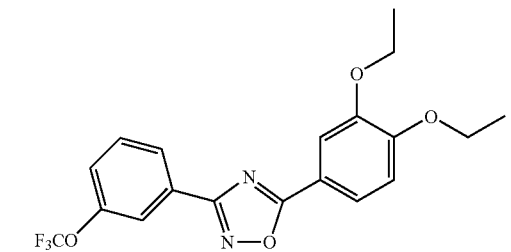
206 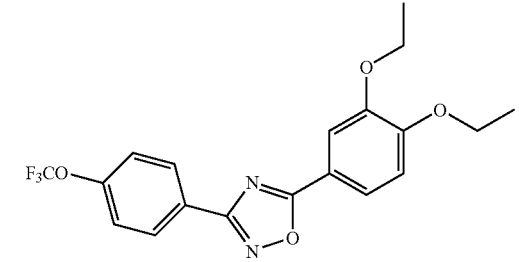

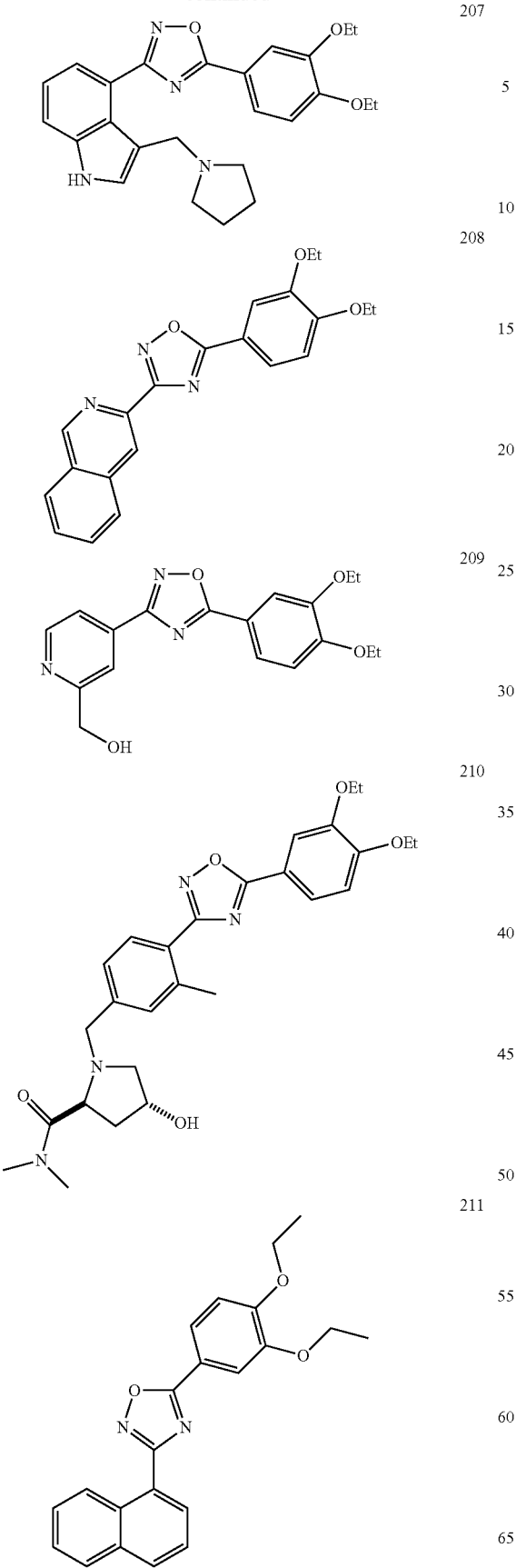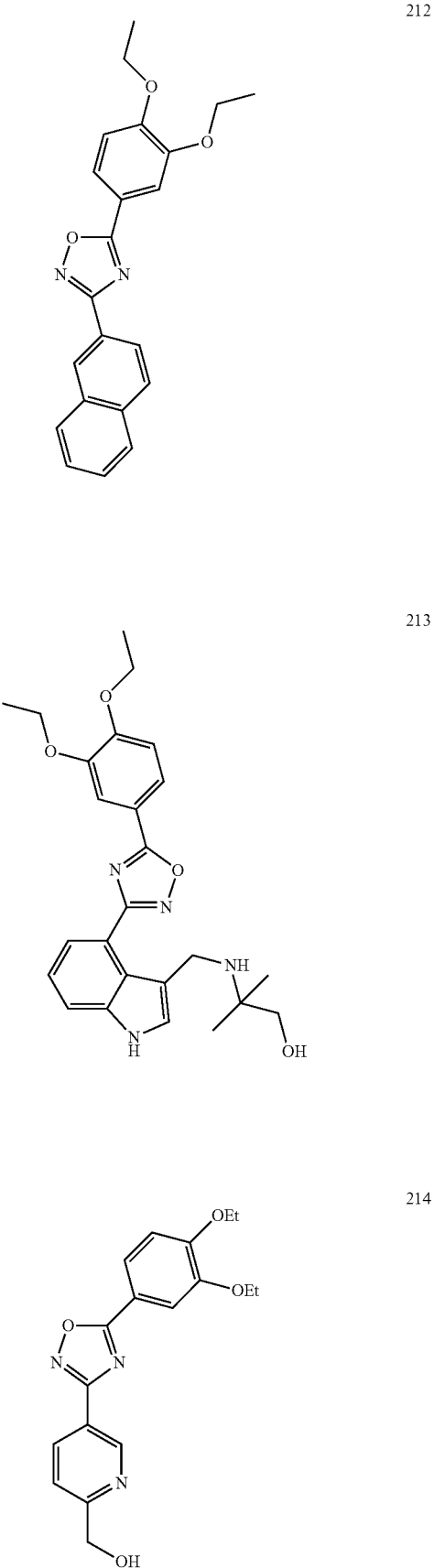

| 215 | 219 |
|---|---|
| 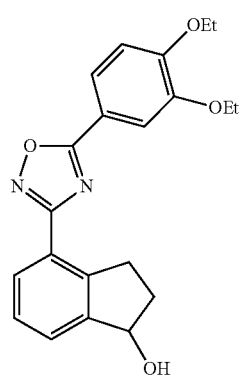 | 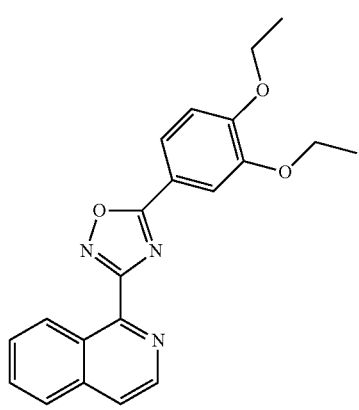 |
| 216 | 220 |
| 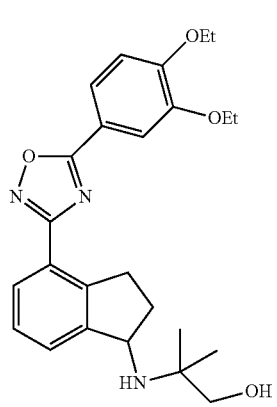 | 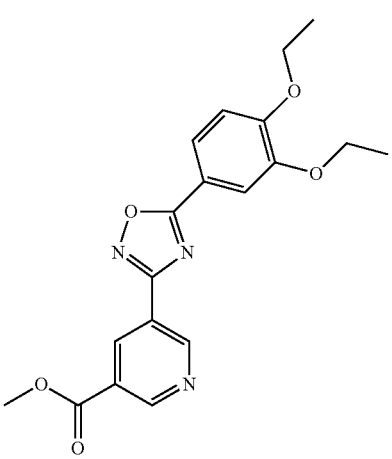 |
| 217 | 221 |
| 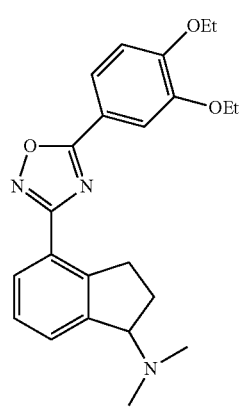 | 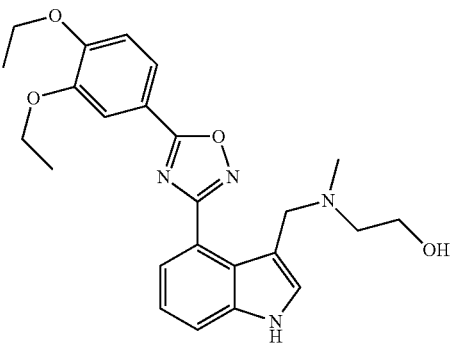 |
| 218 | 222 |
| 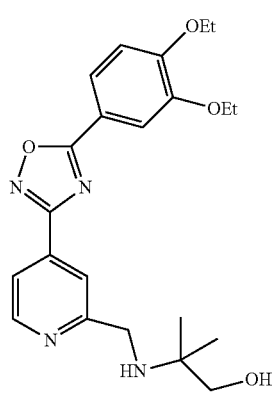 | 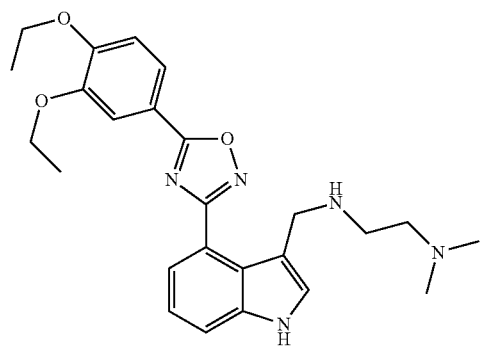 |

101
-continued
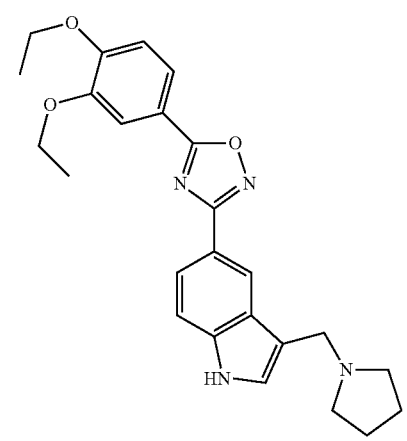
223
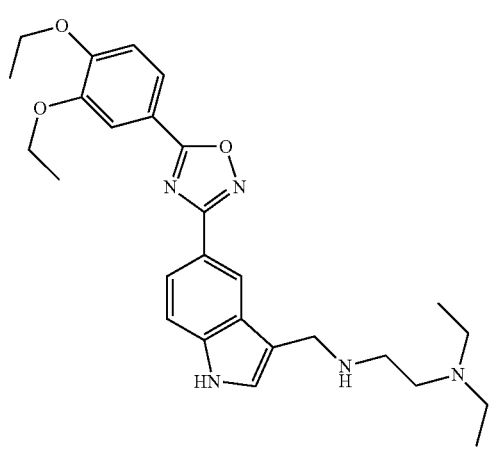
224
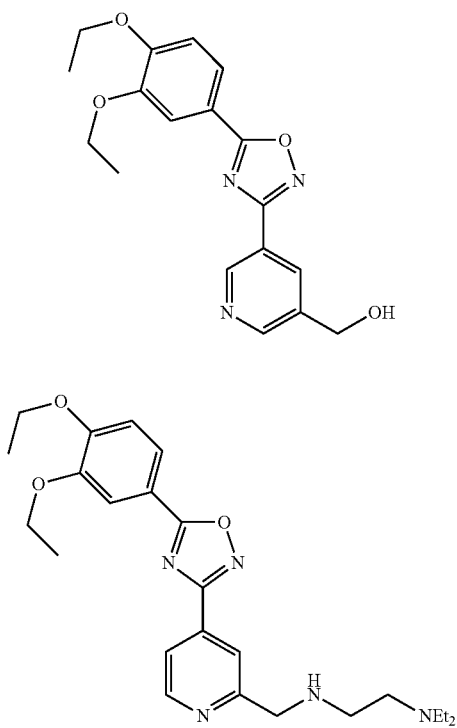
225
226
102
-continued
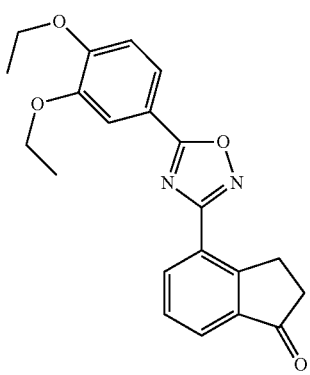
227
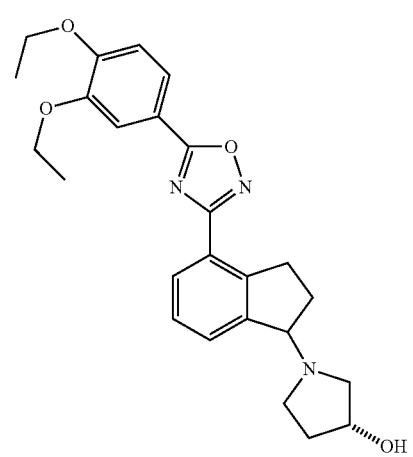
228
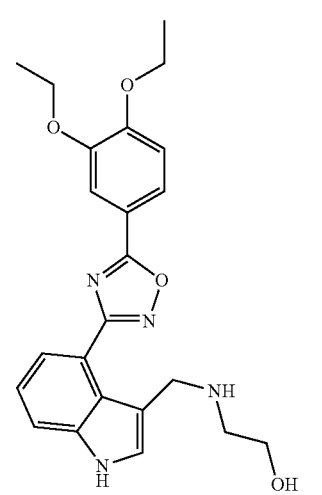
229

| 103 | 104 |
|---|---|
| 230 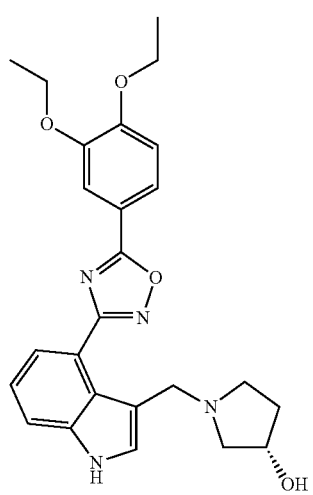 | 233 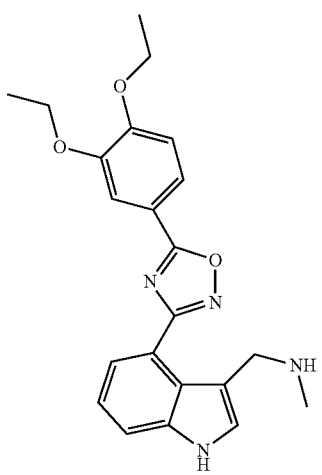 |
| 231 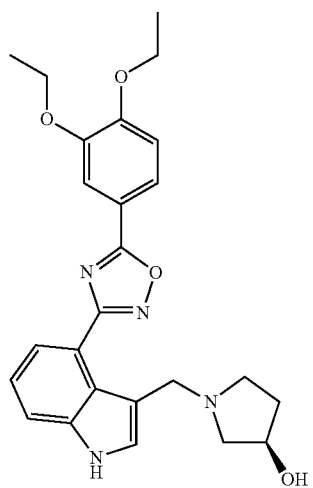 | 234 |
| 232 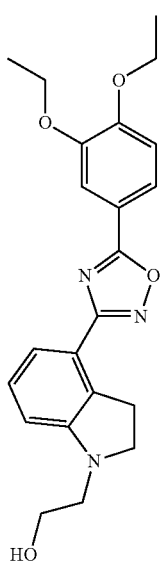 | 235 |
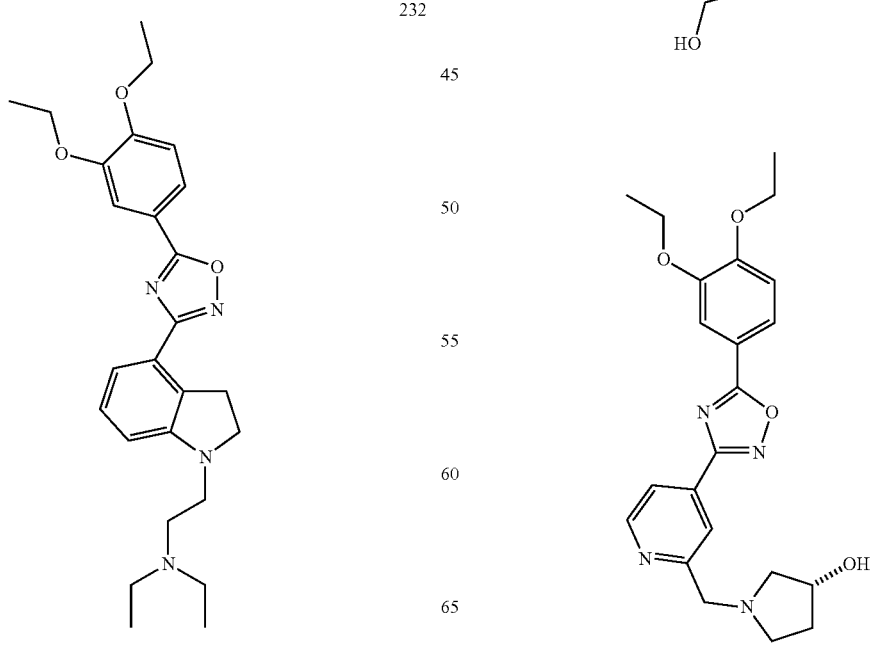

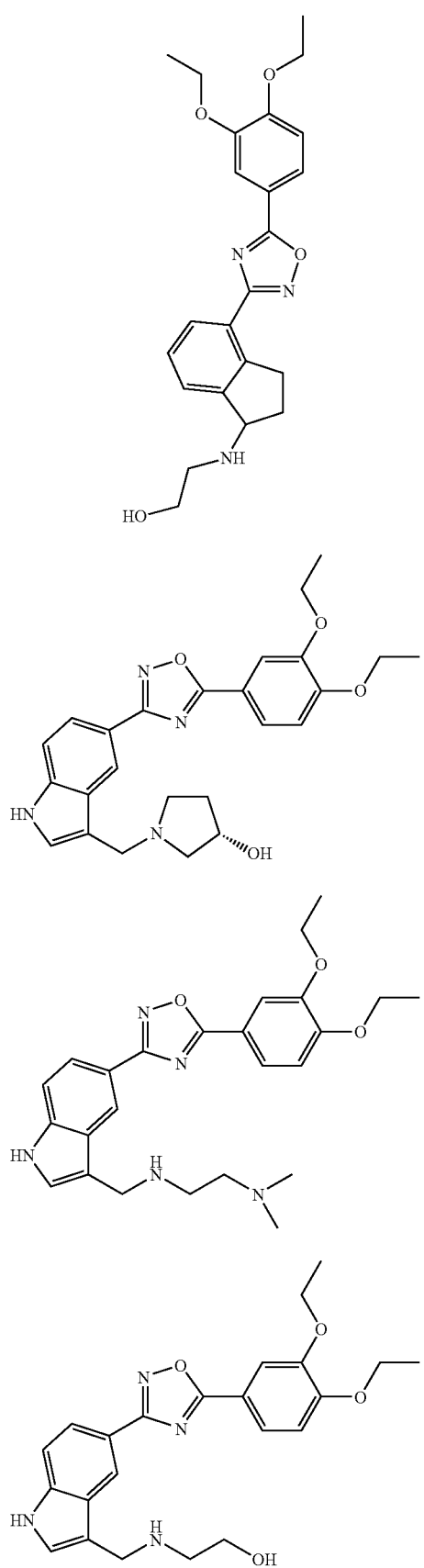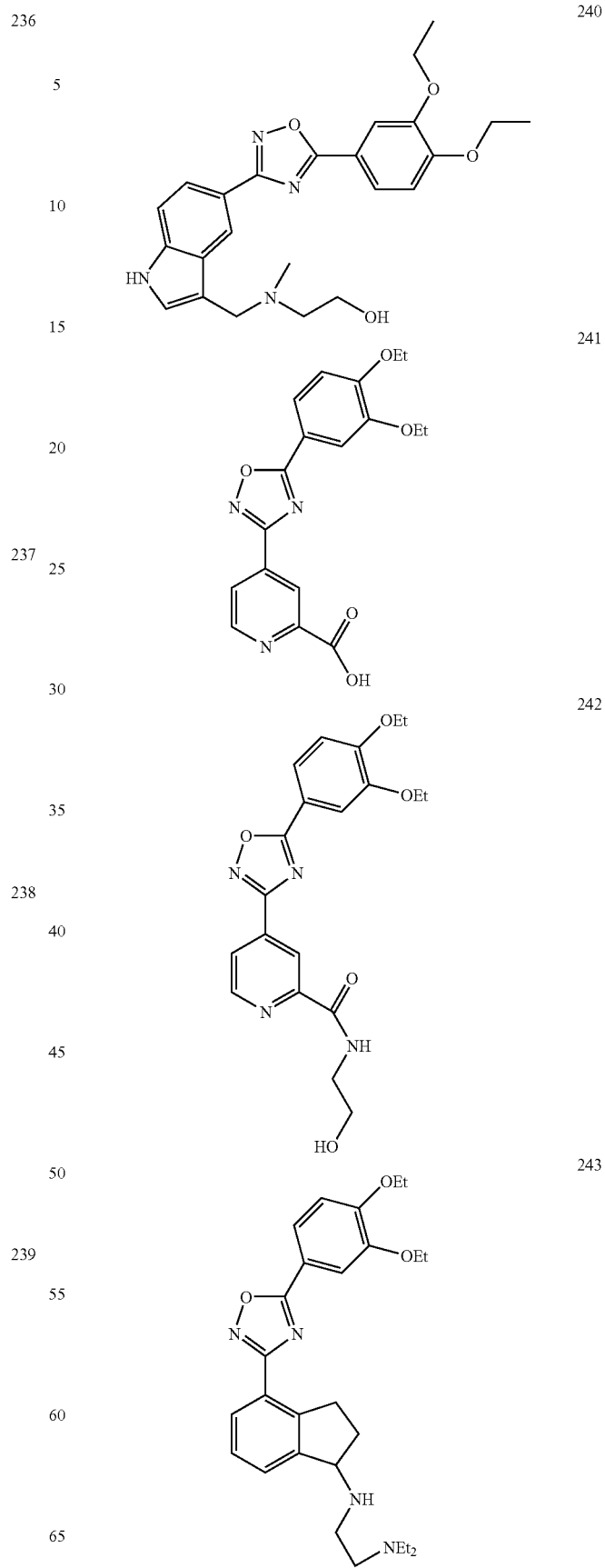

| 246 | 249 |
|---|---|
| 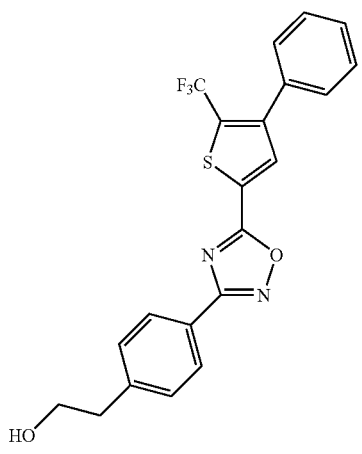 | 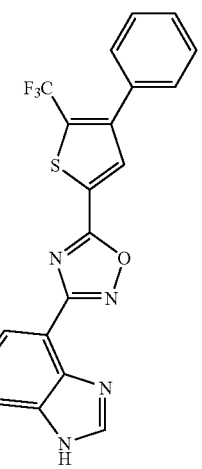 |
| 247 | 250 |
| 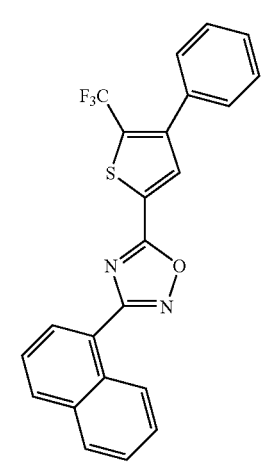 | 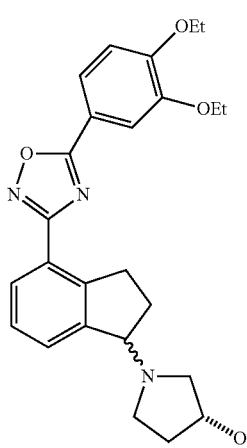 |
| 248 | 251 |
| 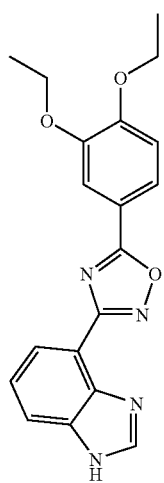 | 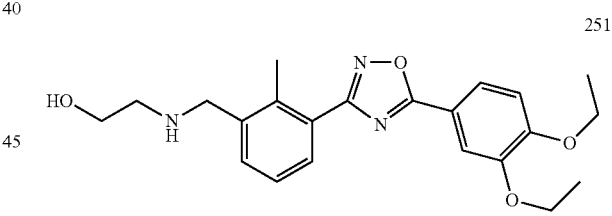 |
| | 252 |
| | 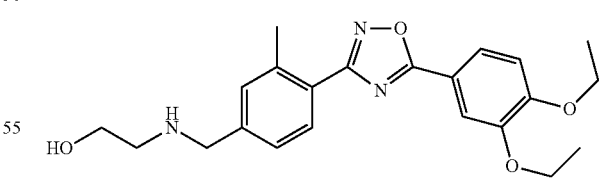 |
| | 253 |
| | 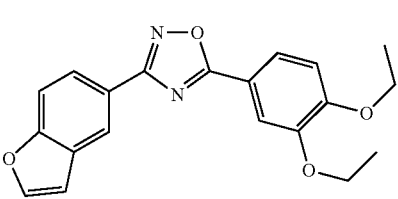 |

| 254 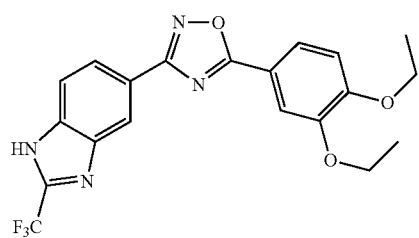 | 261 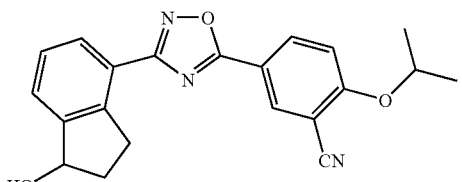 |
| --- | --- |
| 255 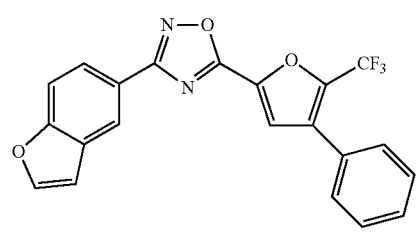 | 262 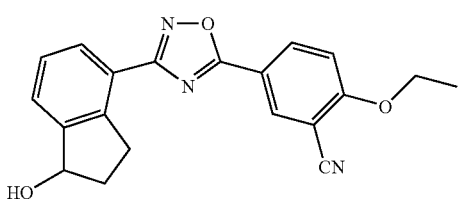 |
| 256 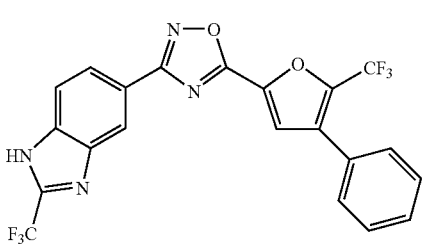 | 263 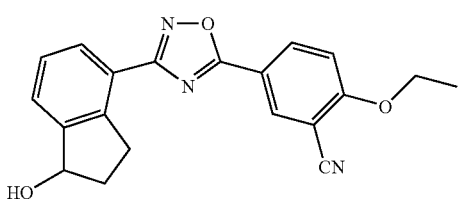 |
| 257  | 264 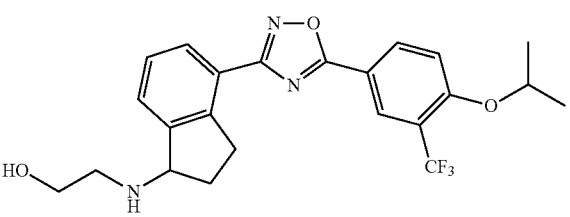 |
| 258 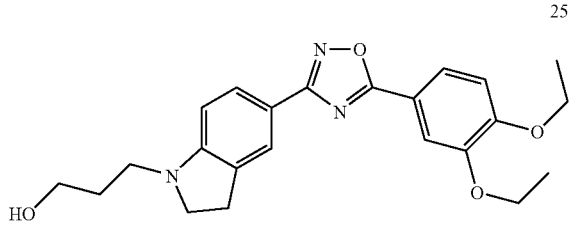 | 265 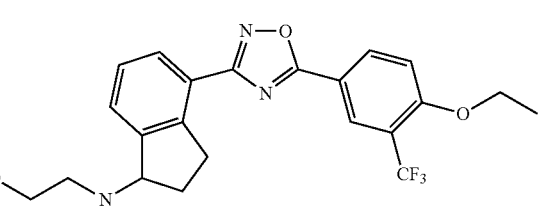 |
| 259 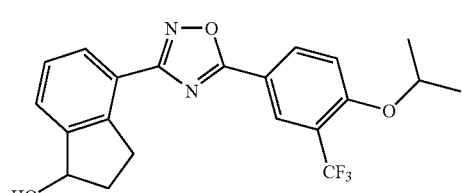 | 266 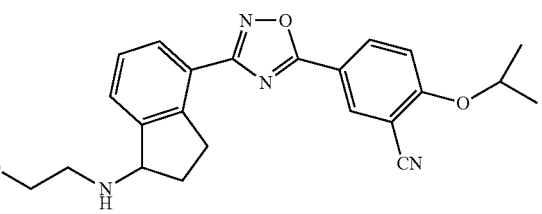 |
| 260 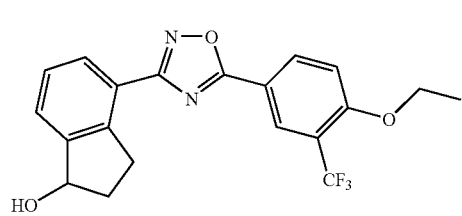 | 267 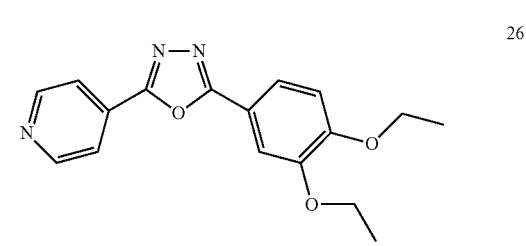 |

268 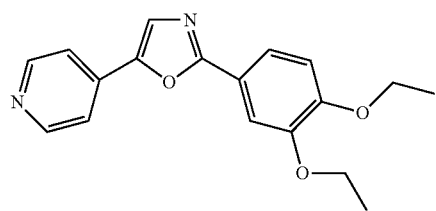
269 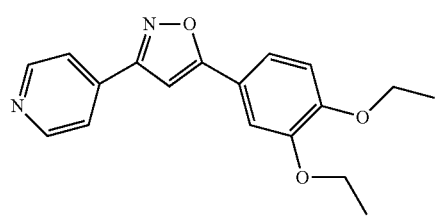
270 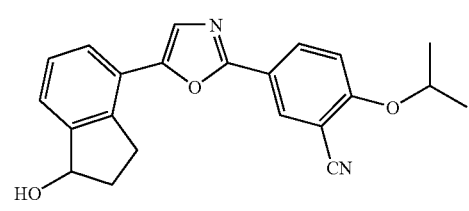
271 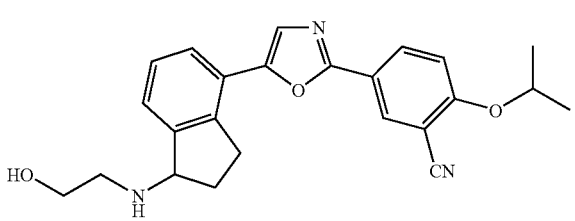
or any pharmaceutically acceptable salt, tautomer, stereoisomer, solvate, hydrate, or prodrug thereof.
More specifically, the compound can be any of the following:
77 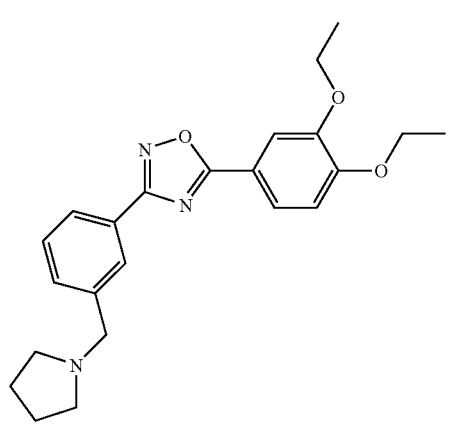
78 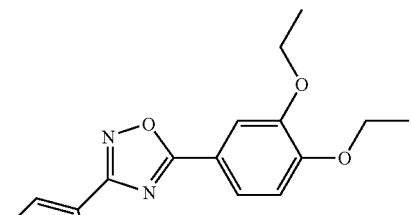
80 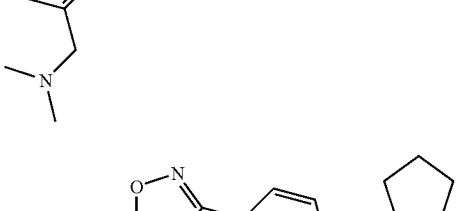
81 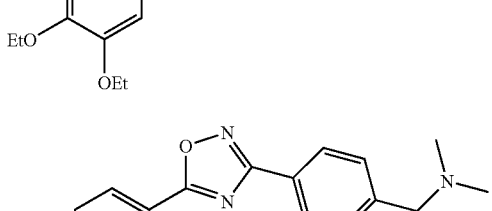
82 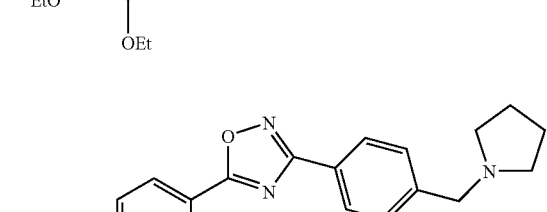
122 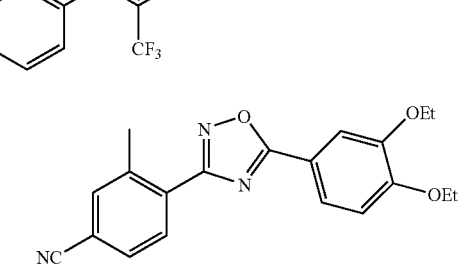
128 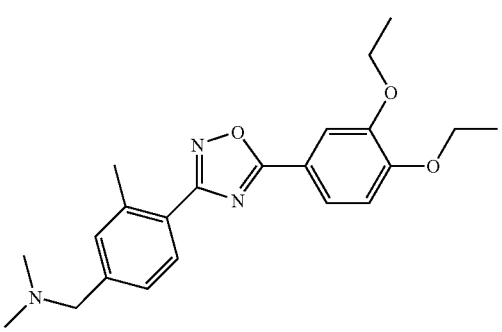

129
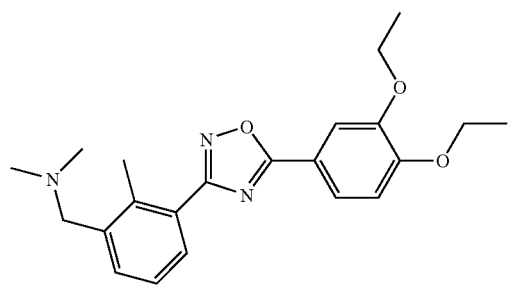
152
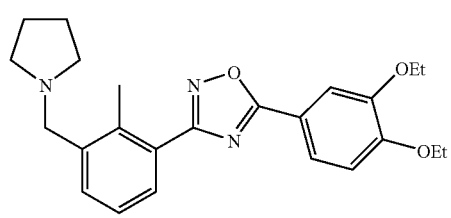
176
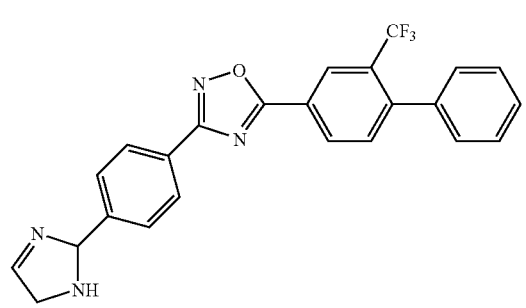
177
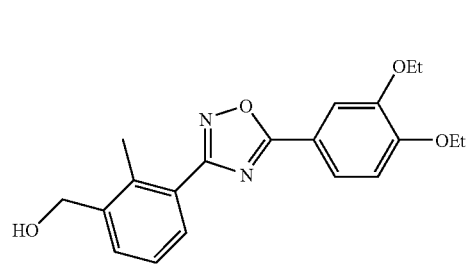
190
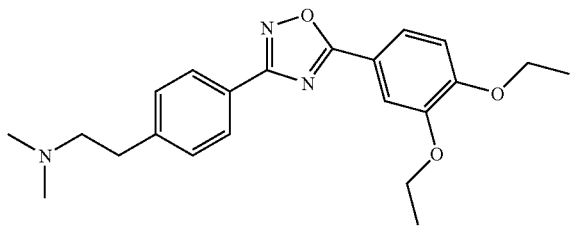
191
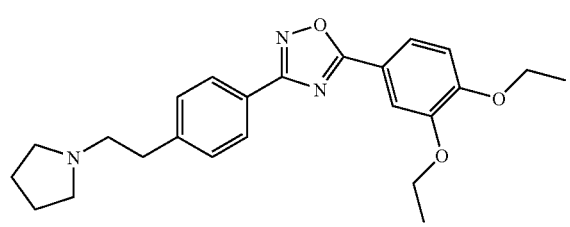
192
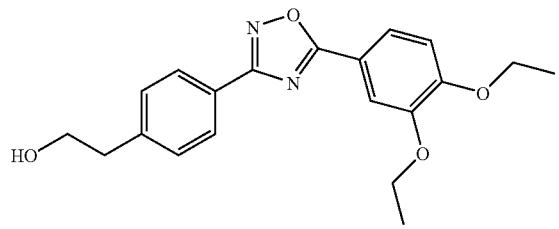
193
194
195
196
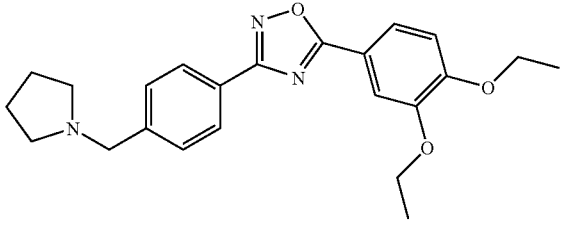
197
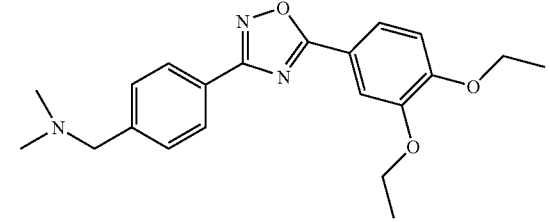

198
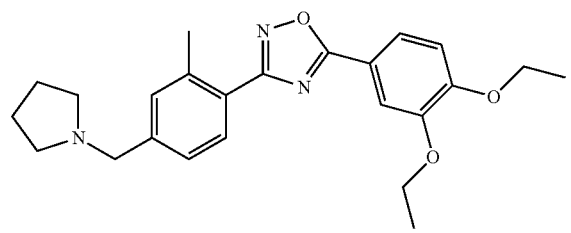
199
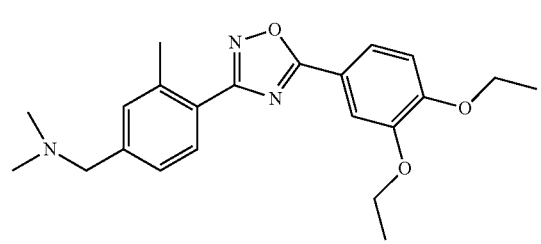
200
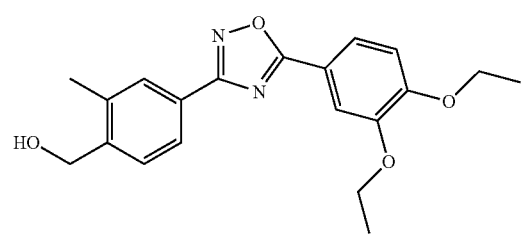
201
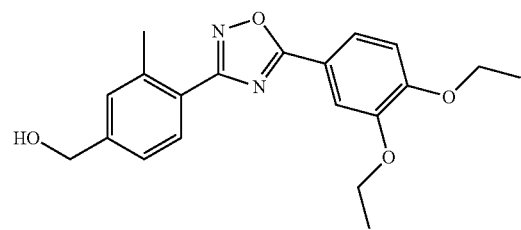
202
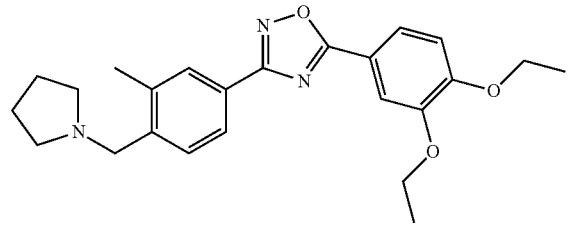
203
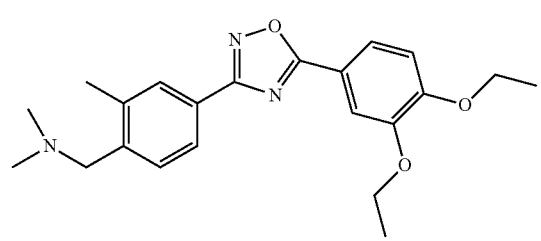
210
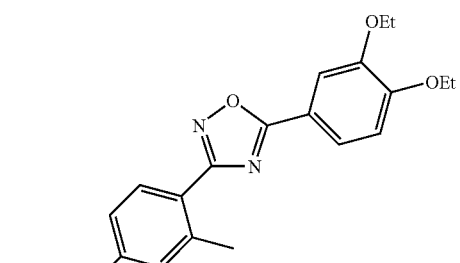
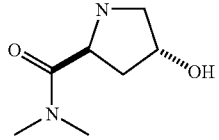
59
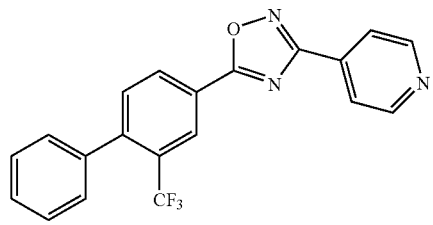
60
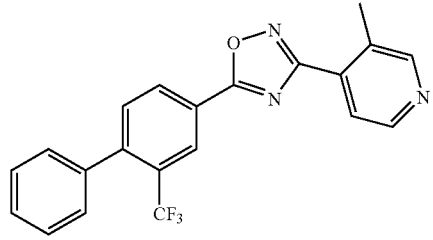
61
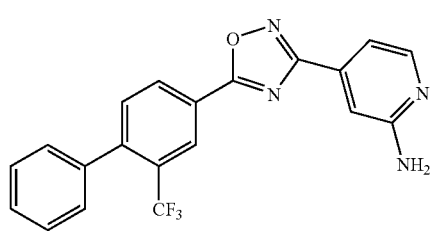
62
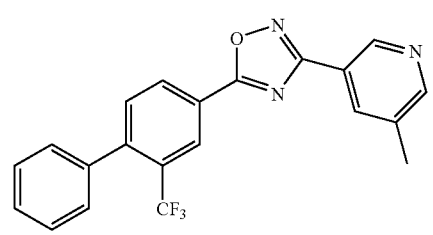
63

-continued

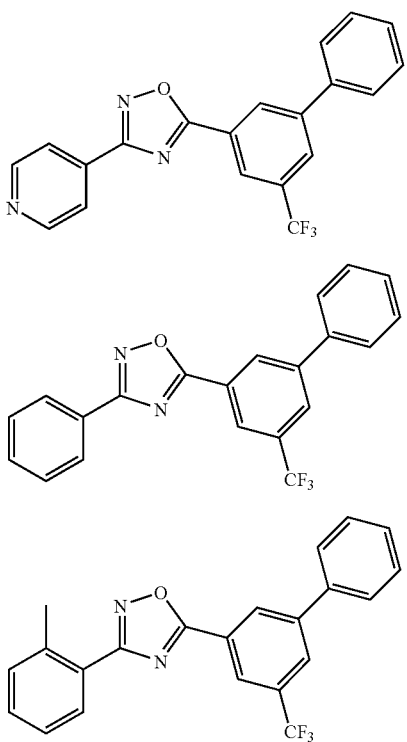

117

156

160 or any pharmaceutically acceptable salt, tautomer, stereoisomer, solvate, hydrate, or prodrug thereof.

More specifically, the compound can be any of:

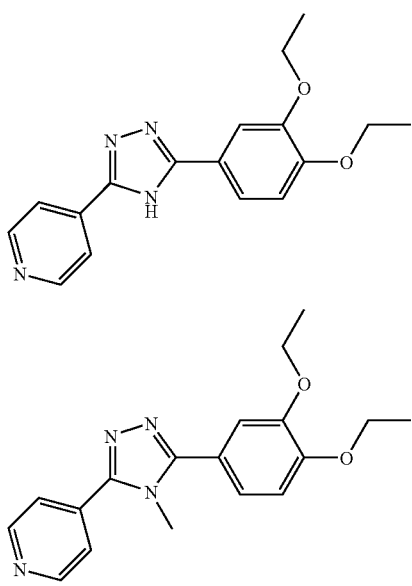

93

94 or any pharmaceutically acceptable salt, tautomer, stereoisomer, solvate, hydrate, or prodrug thereof.

In various embodiments the invention provides a pharmaceutical composition comprising a compound of the invention and a suitable excipient.

In various embodiments the invention provides a pharmaceutical combination comprising the compound of the invention and a second medicament. For example, the second medicament can be medically indicated for the treatment of multiple sclerosis, transplant rejection, or adult respiratory distress syndrome.

Various embodiments of the invention provide a method of activation, agonism, inhibition, or antagonism of a sphingosine-1-phosphate receptor subtype 1 comprising contacting the receptor subtype 1 with an effective amount of a compound of formula (II) or a pharmaceutically acceptable salt, prodrug, tautomer, stereoisomer, hydrate, or solvate thereof:

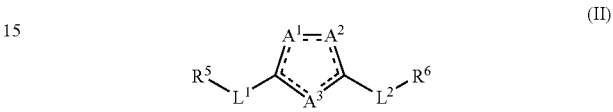

(II)

wherein a dashed line signifies that a single bond or a double bond can be present, provided that there are two double bonds and three single bonds in the ring comprising $A^1$, $A^2$, and $A^3$;

$A^1$, $A^2$, and $A^3$ each independently is C or O or is N when the N is bonded to two adjacent ring atoms by a double bond and a single bond or is NR wherein R is H or $(C_1-C_6)$alkyl when the N is bonded to two adjacent ring atoms by two single bonds; provided that no more than one of $A^1$, $A^2$, and $A^3$ is C and that at least one of $A^1$, $A^2$, and $A^3$ is N or NR; provided that only one of $A^1$, $A^2$, and $A^3$ is O;

$L^1$ and $L^2$ are each independently a bond; (CHR')$_n$ wherein R' is H or $(C_1-C_6)$alkyl and n is 1, 2, or 3; or a heteroaryl selected from the group consisting of thiophenyl, phenyl, furanyl, or benzothiophenyl and wherein such heteroaryl is substituted with 0-3 J;

J independently at each occurrence is F, Cl, Br, I, OR', OC(O)N(R')$_2$, CN, CF$_3$, OCF$_3$, CHF$_2$, NO$_2$, R', O, S, C(O), S(O), methylenedioxy, ethylenedioxy, N(R')$_2$, N(R')CH$_2$CH$_2$OR', SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')N(R'), N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J; or wherein two R' groups together with a nitrogen atom or with two adjacent nitrogen atoms to which they are bonded can together form a $(C_3-C_8)$ heterocyclyl substituted with 0-3 J; optionally further comprising 1-3 additional heteroatoms selected from the group consisting of O, N, S, S(O) and S(O)$_2$;

$R^5$ is a mono- or bicyclic cycloalkyl, aryl, heterocyclyl, or heteroaryl; each of which is substituted with 0-5 J, wherein any cycloalkyl, aryl, heterocyclyl, or heteroaryl can be fused, bridged, or in a spiro configuration with one or more additional cycloalkyl, aryl, heterocyclyl, heteroaryl rings, any of which can be monocyclic, bicyclic or polycyclic, saturated, partially unsaturated, or aromatic, and any of which is substituted with 0-5 J;

$R^6$ is cycloalkyl, aryl, heterocyclyl, or heteroaryl, wherein any cycloalkyl, aryl, heterocyclyl, or heteroaryl is independently mono- or pluri-substituted with J, $(C_1-C_6)$alkyl, $(C_2-$ $C_6$)alkenyl, ($C_2$-$C_6$)alkynyl, ($C_1$-$C_6$)haloalkyl, hydroxyl, halo, ($C_1$-$C_6$)haloalkoxy, cycloalkyl($C_1$-$C_6$)alkyl, heterocyclyl($C_1$-$C_6$)alkyl, aryl($C_1$-$C_6$)alkyl, heteroaryl($C_1$-$C_6$)alkyl, $OR^3$ wherein $R^3$ comprises H or ($C_1$-$C_6$)alkyl or $NR^4_2$ wherein each $R^4$ independently comprises H or ($C_1$-$C_6$)alkyl or where two $R^4$ groups together with a nitrogen atom to which they are bonded form a ($C_3$-$C_8$)heterocyclyl which optionally further comprises 1-3 heteroatoms selected from the group consisting of N, O, S, S(O) and S(O)$_2$; or $R^4$ is optionally substituted cycloalkyl, optionally substituted aryl, optionally substituted heterocyclyl, or optionally substituted heteroaryl;

wherein any alkyl, alkenyl, alkynyl, haloalkyl, alkoxy, haloalkoxy, $R^3$, $R^4$, cycloalkyl, aryl, heterocyclyl, or heteroaryl can be further substituted with J;

and provided that (i), (ii), (iii) or (iv) applies:

(i) $L^1$ is bond or (CHR')$_n$, and $R^5$ is a bicyclic ring moiety which is optionally substituted with 0-5 J where the bicyclic ring moiety is any one of a-i to a-xxviii wherein a wavy line indicates a point of attachment:

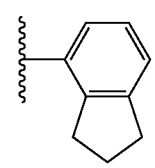
a-i

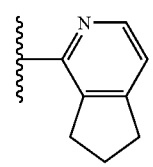
a-ii

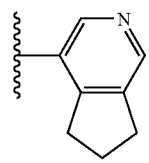
a-iii

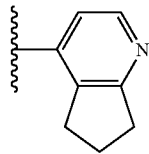
a-iv

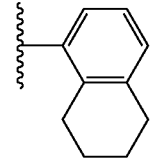
a-v

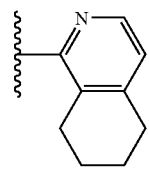
a-vi

-continued

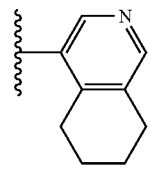
a-vii

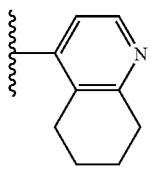
a-viii

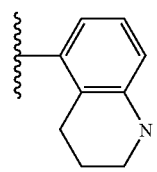
a-ix

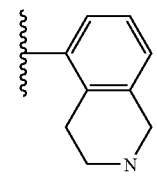
a-x

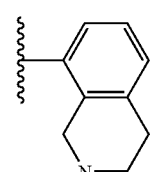
a-xi

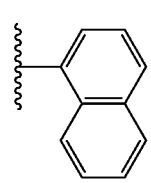
a-xii

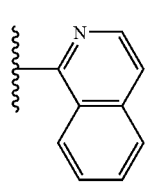
a-xiii

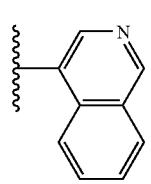
a-xiv

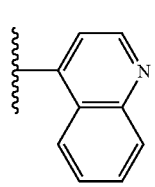
a-xv

-continued a-xvi 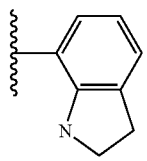

a-xvii 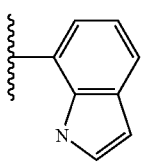

a-xviii 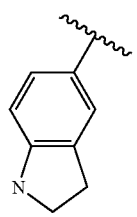

a-xix 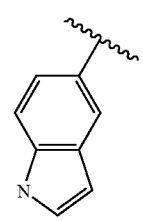

a-xx 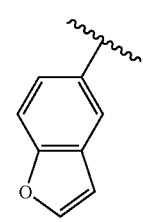

a-xxi 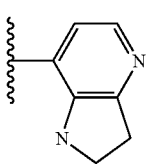

a-xxii 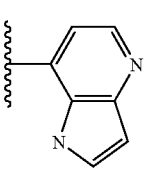

a-xxiii 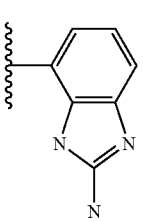

-continued a-xxiv 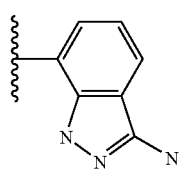

a-xxv 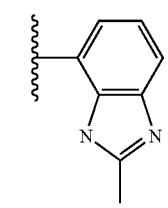

a-xxvi 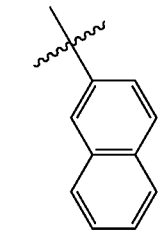

a-xxvii 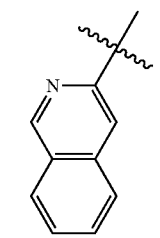

a-xxviii 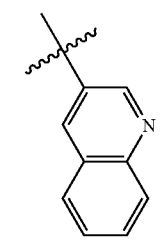

provided that when $R^5$ is either a-xvii or a-xix that $L^2$ is bond or $(CHR')_n$;

(ii) $L^1$ and $L^2$ are each independently a bond or $(CHR')_n$; $R^5$ is a 6-membered heteroaryl ring moiety optionally substituted with 0-3 $J^1$, wherein $J^1$ is OR', $CF_3$, Cl, Br, F, CN, $O(C_1-C_6)$alkoxy, $O(C_1-C_6)$cycloalkoxy, alkyl, or $N(R')_2$ and wherein the 6-membered heteroaryl ring moiety is any one of b-i to b-xiii wherein a wavy line indicates a point of attachment:

b-i 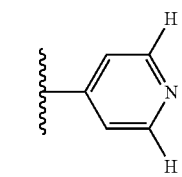

-continued

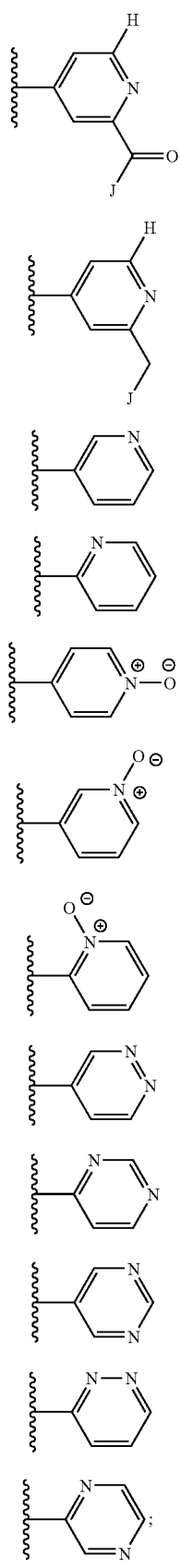

b-ii
b-iii
b-iv
b-v
b-vi
b-vii
b-viii
b-ix
b-x
b-xi
b-xii
b-xiii (iii) $L^1$ is a bond or $(CHR')_n$, and $L^2$ is a heteroaryl substituted with 0-3 J wherein the heteroaryl is c-i or c-ii wherein a wavy line indicates a point of attachment:

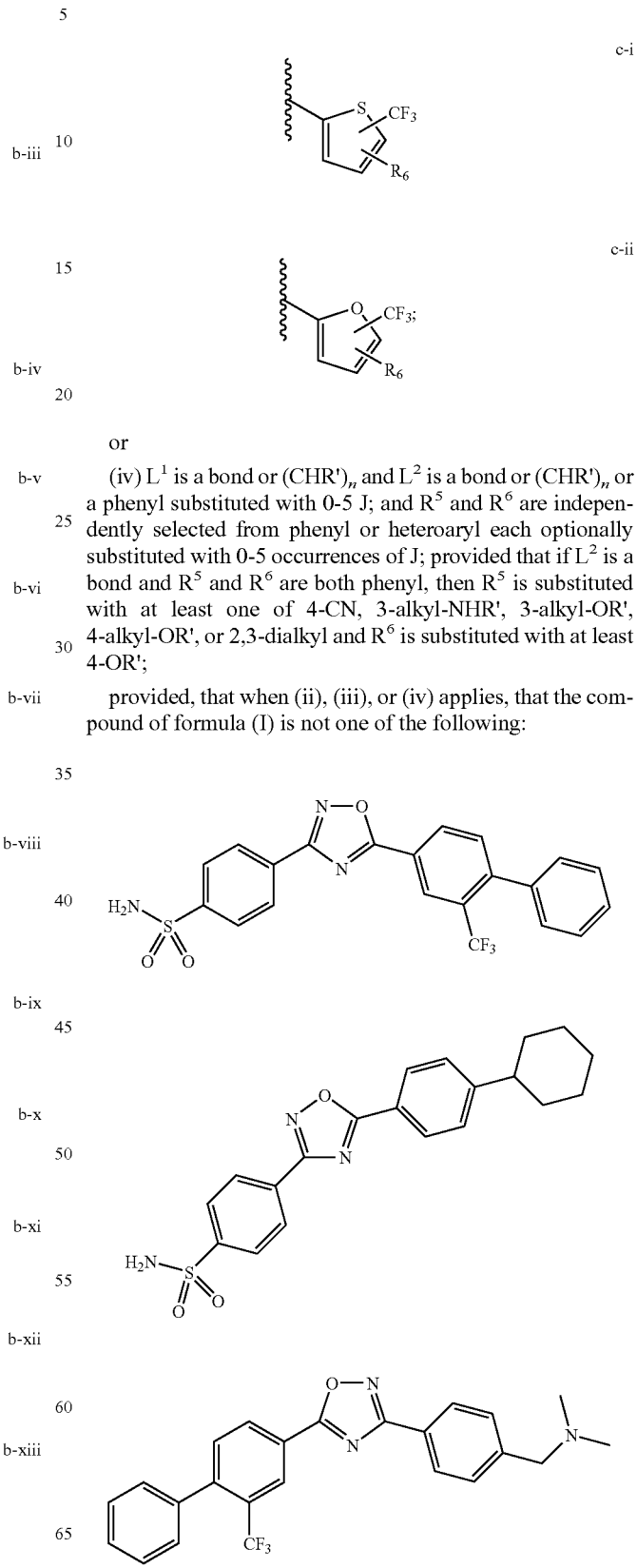

or (iv) $L^1$ is a bond or $(CHR')_n$ and $L^2$ is a bond or $(CHR')_n$ or a phenyl substituted with 0-5 J; and $R^5$ and $R^6$ are independently selected from phenyl or heteroaryl each optionally substituted with 0-5 occurrences of J; provided that if $L^2$ is a bond and $R^5$ and $R^6$ are both phenyl, then $R^5$ is substituted with at least one of 4-CN, 3-alkyl-NHR', 3-alkyl-OR', 4-alkyl-OR', or 2,3-dialkyl and $R^6$ is substituted with at least 4-OR';

provided, that when (ii), (iii), or (iv) applies, that the compound of formula (I) is not one of the following:

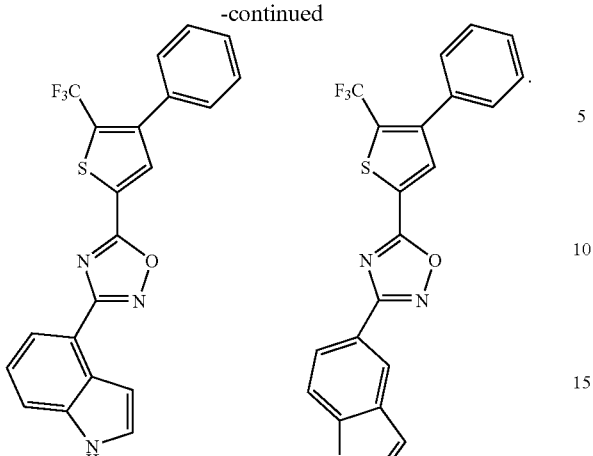

In various embodiments, a method of the invention uses a compound wherein $L^2$ is bond.

In various embodiments, a method of the invention uses a compound wherein $A^1$ and $A^3$ are N and $A^2$ is O, or wherein $A^2$ and $A^3$ are N and $A^1$ is O, or wherein $A^1$ and $A^2$ are N and $A^3$ is O, or wherein $A^1$ and $A^2$ are N and $A^3$ is NR.

In various embodiments, a method of the invention uses a compound wherein $A^1$ is C, A is N and $A^3$ is O, or wherein $A^1$ is O, $A^2$ is N and $A^3$ is C, or wherein $L^1$ and $L^2$ are each independently a bond or $(CHR')_n$, and $R^5$ or $R^6$, or both, comprises a heteroaryl ring. For example, at least one heteroaryl ring of $R^5$ or $R^6$ can be pyridinyl or a pyridinyl N-oxide, pyrazinyl, pyrrolyl, imidazolyl, benzimidazolyl, thiophenyl, benzothiophenyl, furyl, benzofuryl, indolyl, indolinyl, piperidinyl, quinolyl, or isoquinolyl; wherein any heteroaryl can be substituted with 0-5 J. More specifically, any heteroaryl can be substituted with 0-5 R', F, Cl, Br, I, OR', $CF_3$, $OCF_3$, $CHF_2$, or $SO_2N(R')_2$.

In various embodiments, a method of the invention uses a compound wherein $L^1$ and $L^2$ are each independently a bond or $(CHR')_n$, and $R^5$ or $R^6$, or both, comprises a bicyclic carbocyclic ring, wherein the bicyclic carbocyclic ring is substituted with 0-5 J. For example, any bicyclic carbocyclic ring can be substituted with 0-5 R', F, Cl, Br, I, OR', $CF_3$, $OCF_3$, $CHF_2$, or $SO_2N(R')_2$.

In various embodiments, a method of the invention uses a compound wherein $L^1$ is bond and $R^5$ is a bicyclic ring moiety which is substituted with 0-5 J where the bicyclic ring moiety is any one of a-i to a-xxviii, wherein a wavy line indicates a point of attachment:

a-i
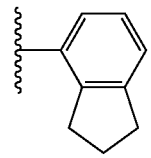

a-ii
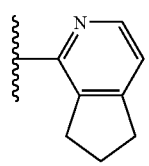

a-iii
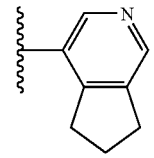

a-iv
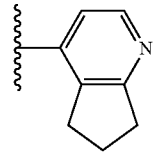

a-v
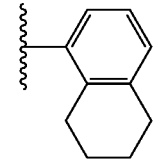

a-vi
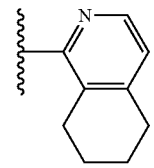

a-vii
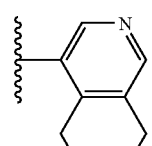

a-viii
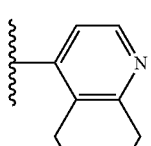

a-ix
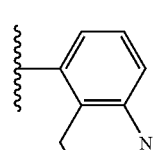

a-x
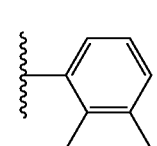

a-xi
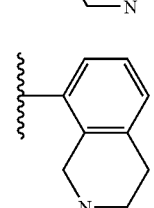

127 128
-continued -continued
a-xii
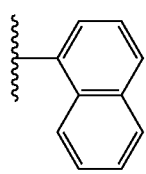
a-xx
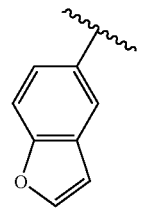
a-xiii
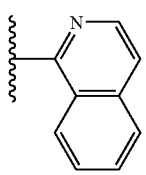
a-xxi
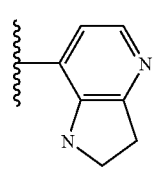
a-xiv
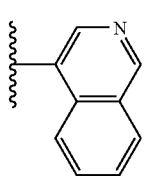
a-xxii
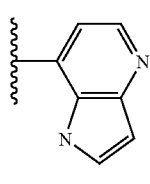
a-xv
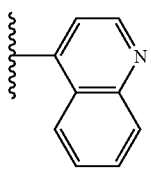
a-xxiii
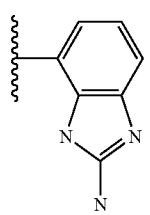
a-xvi
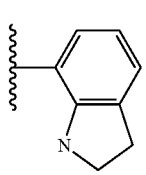
a-xxiv
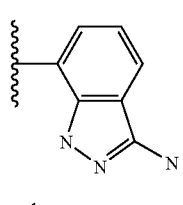
a-xvii
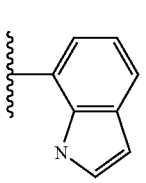
a-xxv
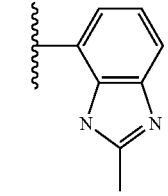
a-xviii
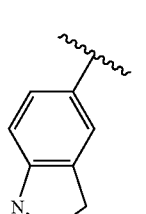
a-xxvi
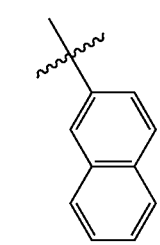
a-xix
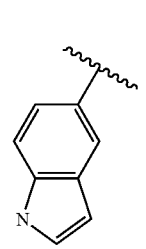
a-xxvii
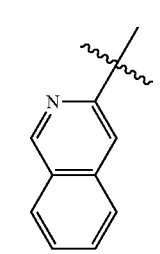

-continued a-xxviii

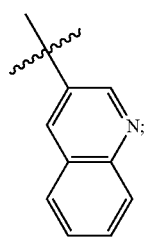

wherein any of the bicyclic ring moieties is substituted with 0-5 J.

In various embodiments, a method of the invention uses a compound wherein $L^1$ and $L^2$ are each a bond; $R^5$ is a 6-membered heteroaryl ring moiety substituted with 0-3 occurrences of $J^1$; wherein $J^1$ is selected from the group consisting of OR', $CF_3$, Cl, Br, F, CN, $O(C_1-C_6)$alkoxy, $O(C_1-C_6)$cycloalkoxy, alkyl, $N(R')_2$; and wherein the optionally substituted 6-membered heteroaryl ring moiety of $R^5$ is any one of b-i to b-xiii:

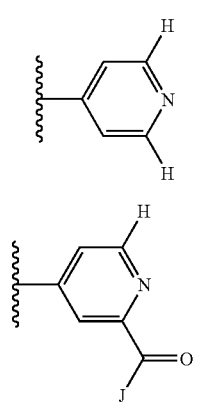

b-i b-ii b-iii

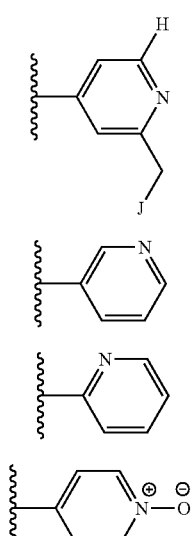

b-iv b-v b-vi

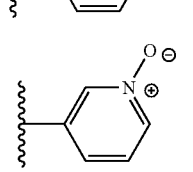

b-vii

-continued

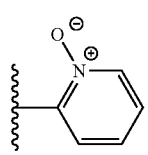

b-viii

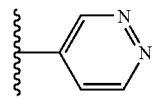

b-ix

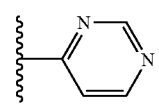

b-x

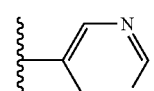

b-xi

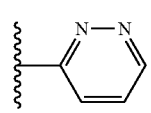

b-xii

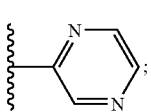

b-xiii wherein each of the 6-membered heteroaryl ring moieties is substituted with 0-3 $J^1$, or wherein $L^1$ is a bond, and $L^2$ is c-i or c-ii, wherein a wavy line indicates a point of attachment:

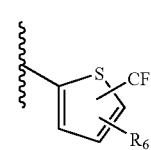

c-i

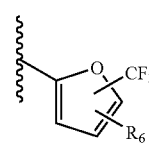

c-ii wherein c-i and c-ii are further substituted with 0-2 J.

In various embodiments, a method of the invention uses a compound wherein $L^1$ is a bond and $L^2$ is a bond or is phenyl substituted with 0-5 J; and $R^5$ and $R^6$ are independently selected from phenyl or heteroaryl each substituted with 0-5 J; provided that if $L^2$ is a bond and $R^5$ and $R^6$ are both phenyl, then $R^5$ is substituted with at least one of 4-CN, 3-alkyl-$N(R')_2$, 3-alkyl-OR', 4-alkyl-OR', or 2,3-dialkyl, and $R^6$ is substituted with at least 4-OR'.

In various embodiments, the optionally substituted bicyclic ring moiety can be any one of a-i to a-viii.

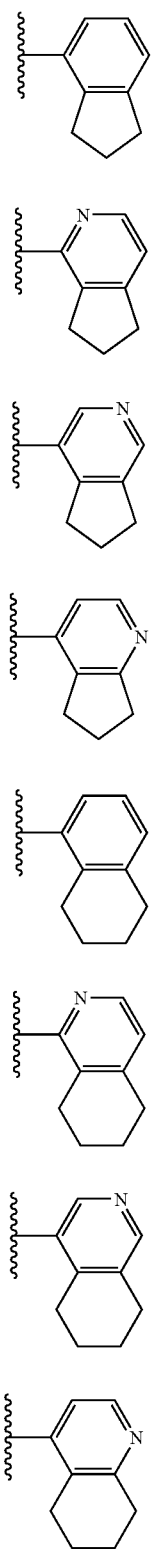

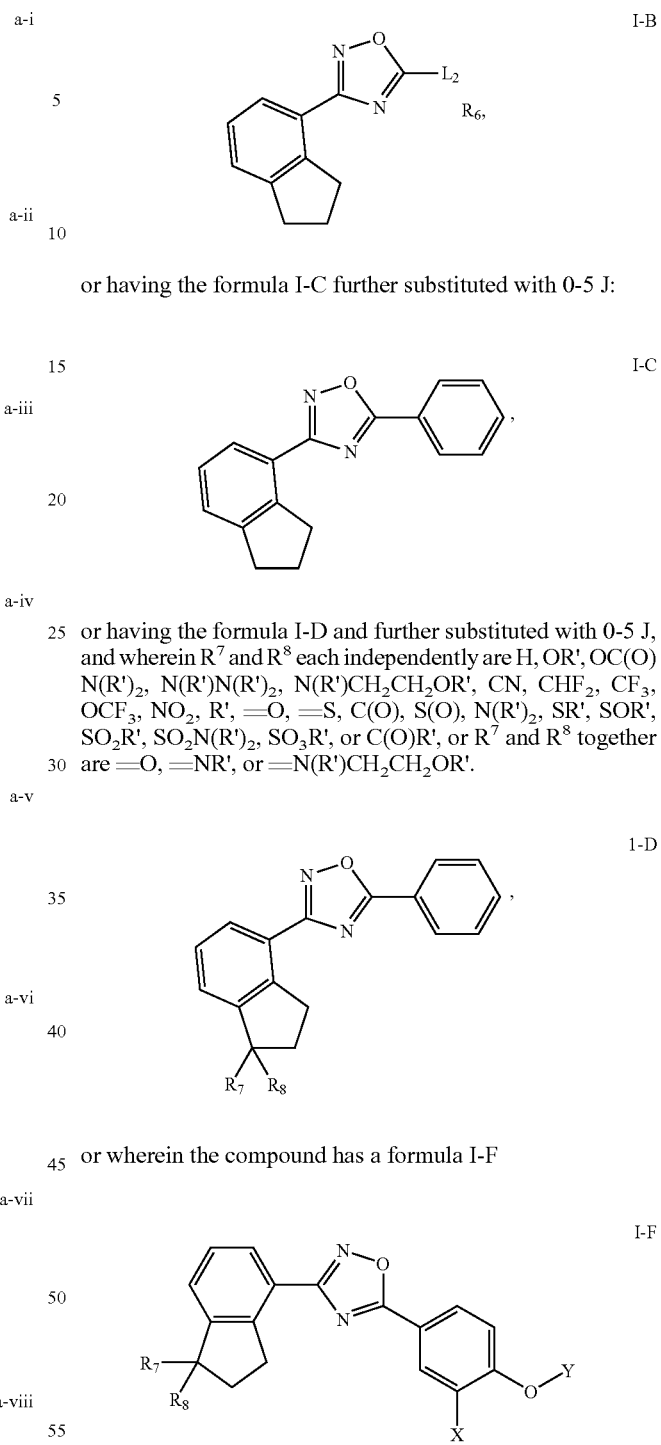

wherein any of the bicyclic ring moieties is substituted with 0-5 J.

In various embodiments, a method of the invention uses a compound having the formula I-B further substituted with 0-5 J:

or having the formula I-C further substituted with 0-5 J:

or having the formula I-D and further substituted with 0-5 J, and wherein $R^7$ and $R^8$ each independently are H, OR', OC(O)N(R')$_2$, N(R')N(R')$_2$, N(R')CH$_2$CH$_2$OR', CN, CHF$_2$, CF$_3$, OCF$_3$, NO$_2$, R', =O, =S, C(O), S(O), N(R')$_2$, SR', SOR', SO$_2$R', SO$_2$N(R')$_2$, SO$_3$R', or C(O)R', or $R^7$ and $R^8$ together are =O, =NR', or =N(R')CH$_2$CH$_2$OR'.

or wherein the compound has a formula I-F wherein $R^7$ and $R^8$ are each independently selected from H, OR', N(R'')$_2$, and SR'', wherein R'' is hydrogen or an alkyl, cycloalkyl, aryl, heterocyclyl, or heteroaryl, wherein any such alkyl, cycloalkyl, aryl, heterocyclyl or heteroaryl is substituted with 0-3 J; X is F, Cl, Br, I, CHF$_2$, CN, CF$_3$, NO$_2$, or OR'; Y is hydrogen or an alkyl, cycloalkyl, aryl, heterocyclyl, or heteroaryl, wherein any such alkyl, cycloalkyl, aryl, heterocyclyl or heteroaryl is substituted with 0-3 J.

In various embodiments, a method of the invention uses a compound wherein the compound is any of the following:

1
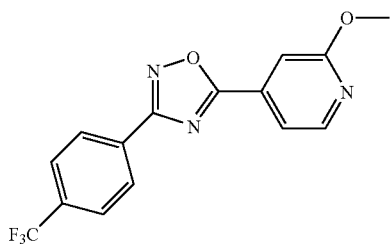
2
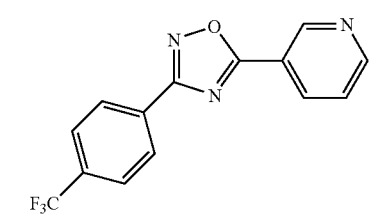
3
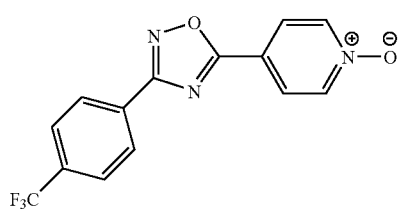
4
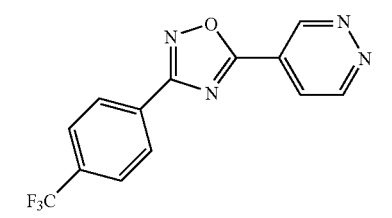
5
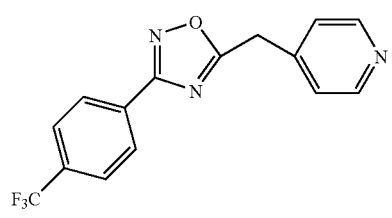
6
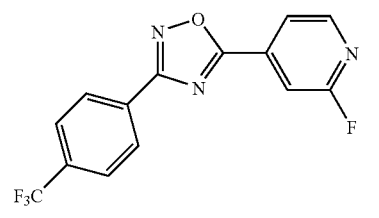
7
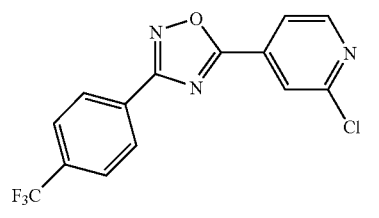
8
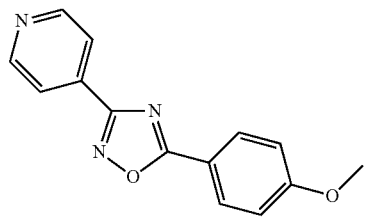
9
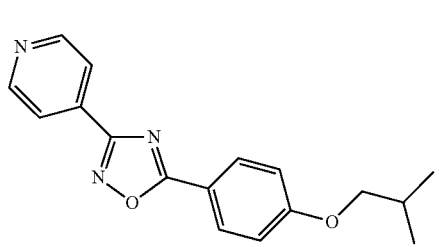
10
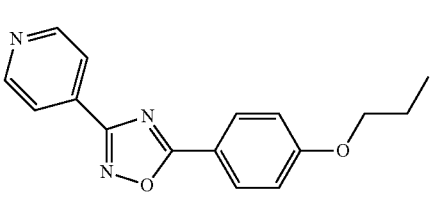
11
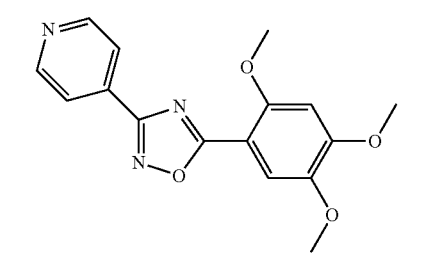
12
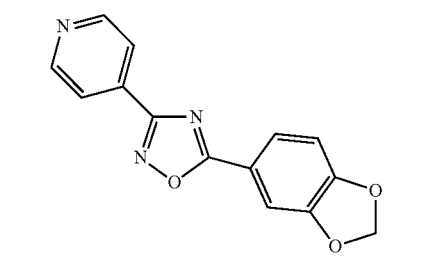
14
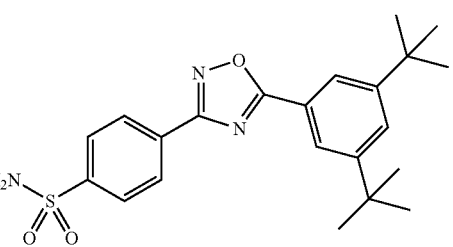

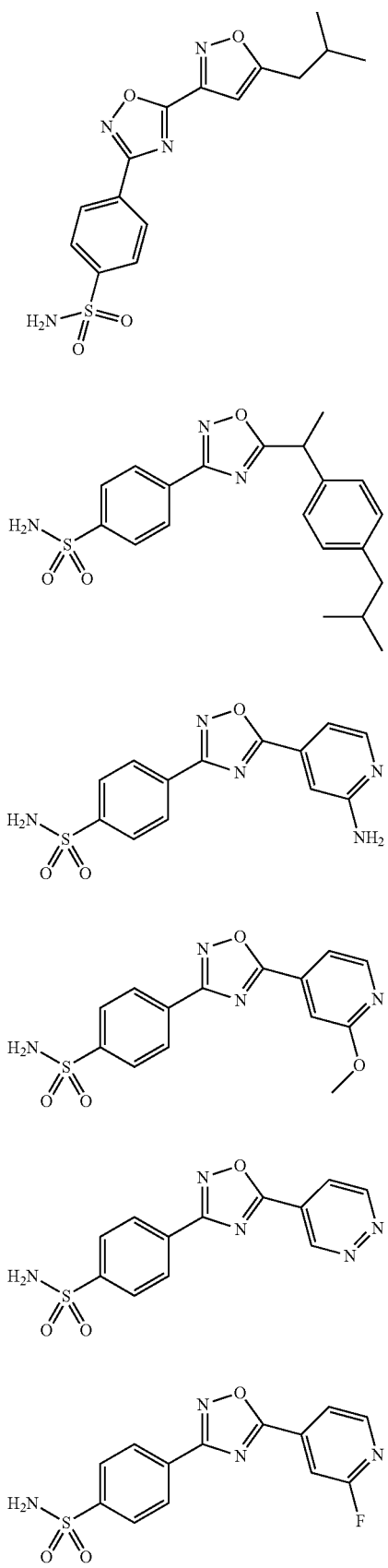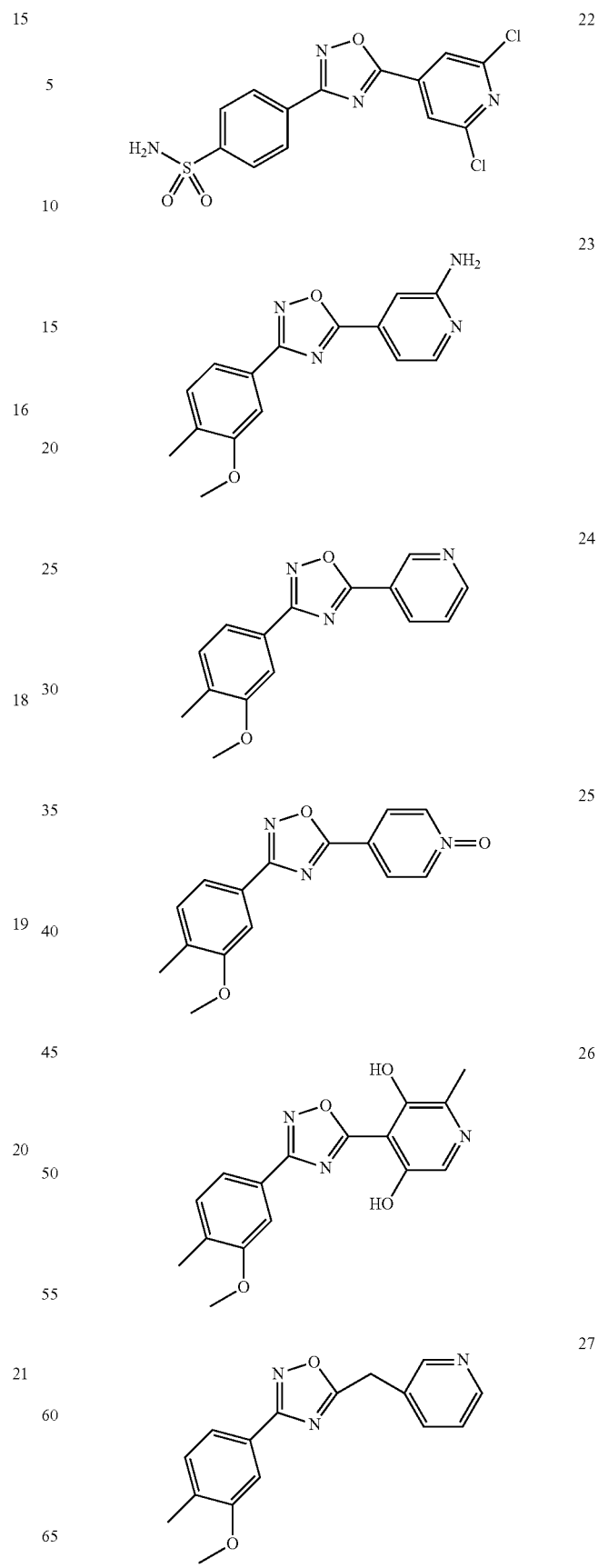

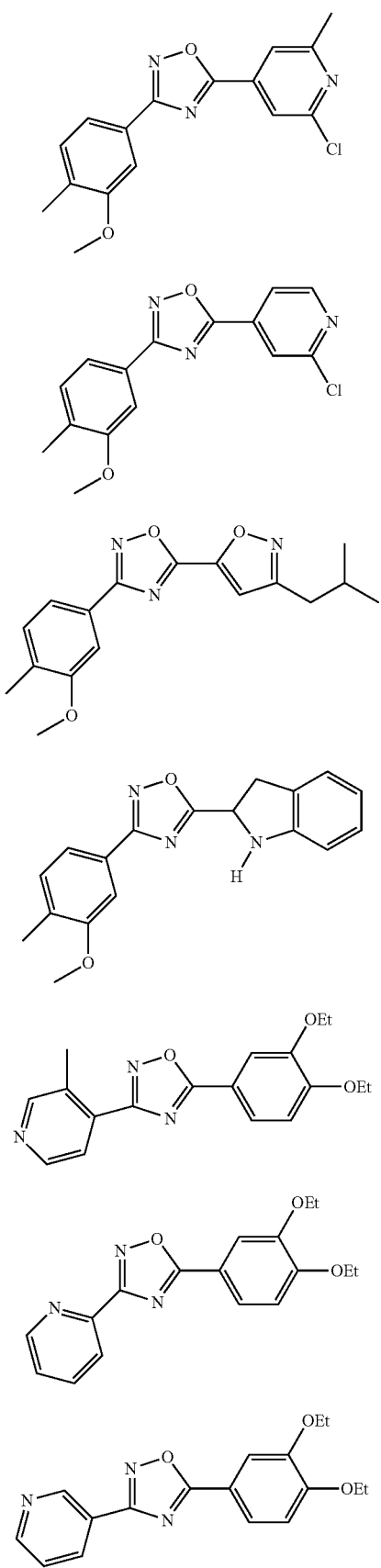
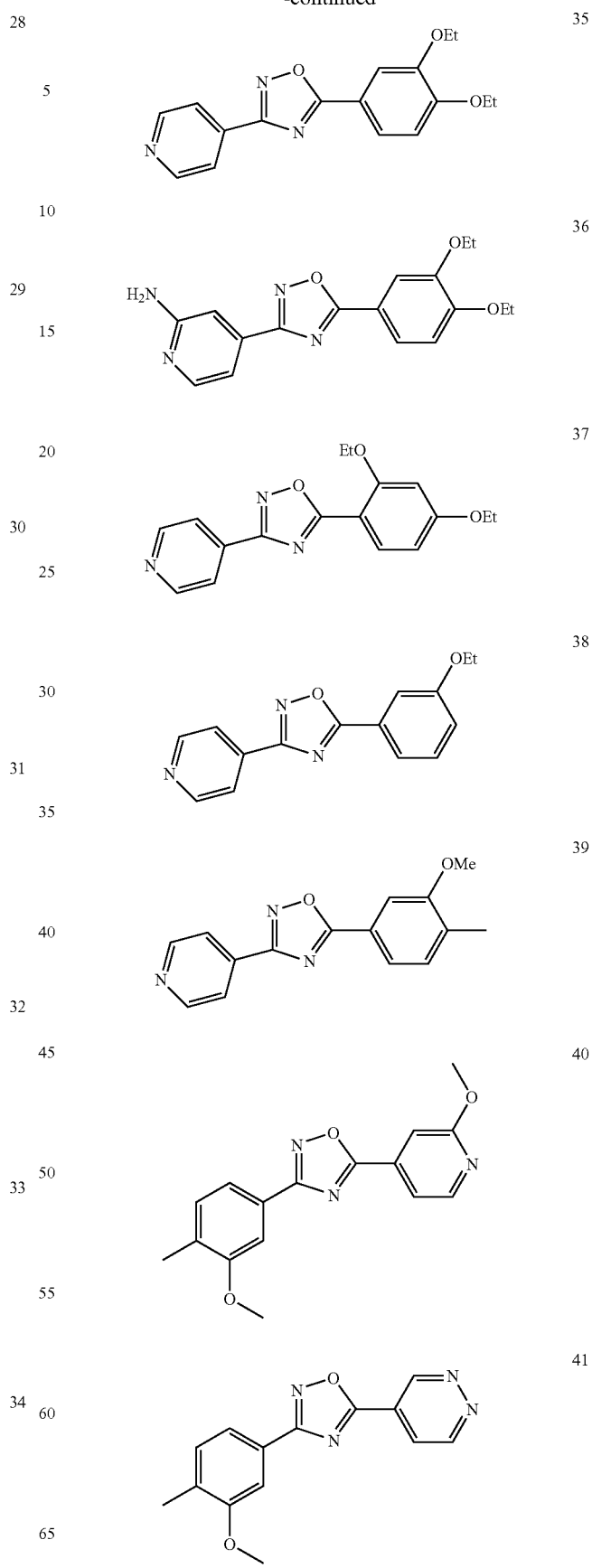

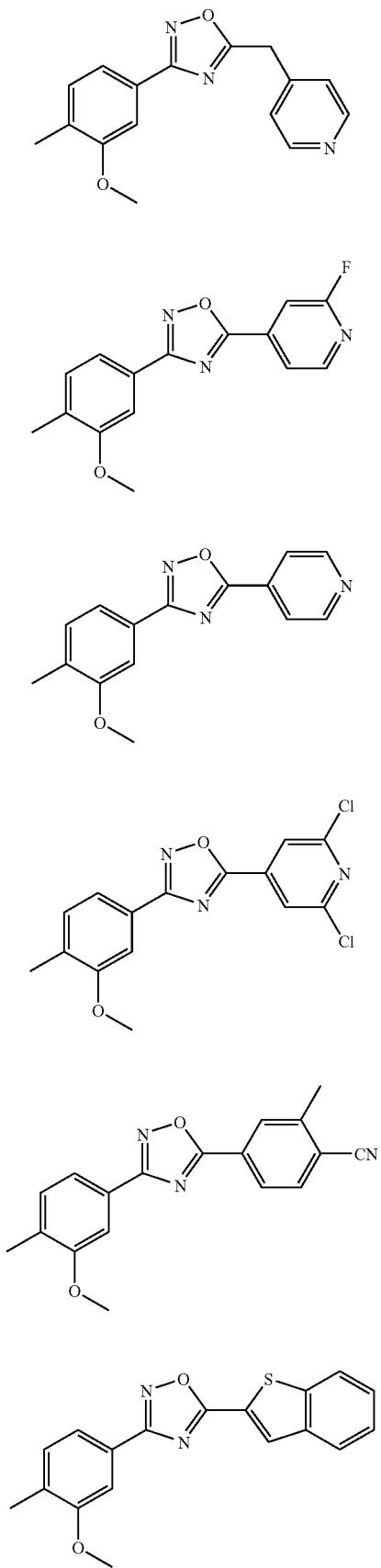
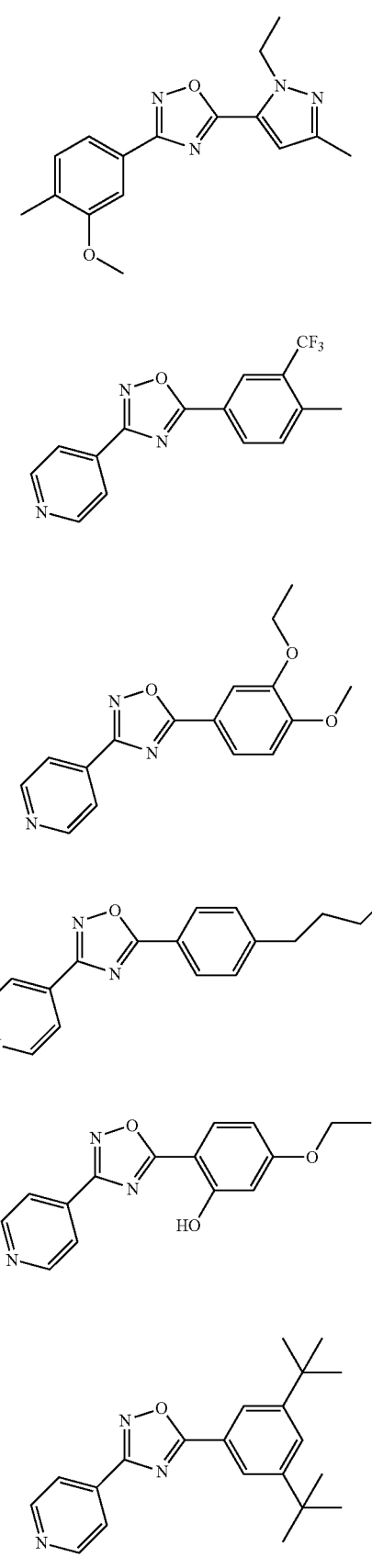

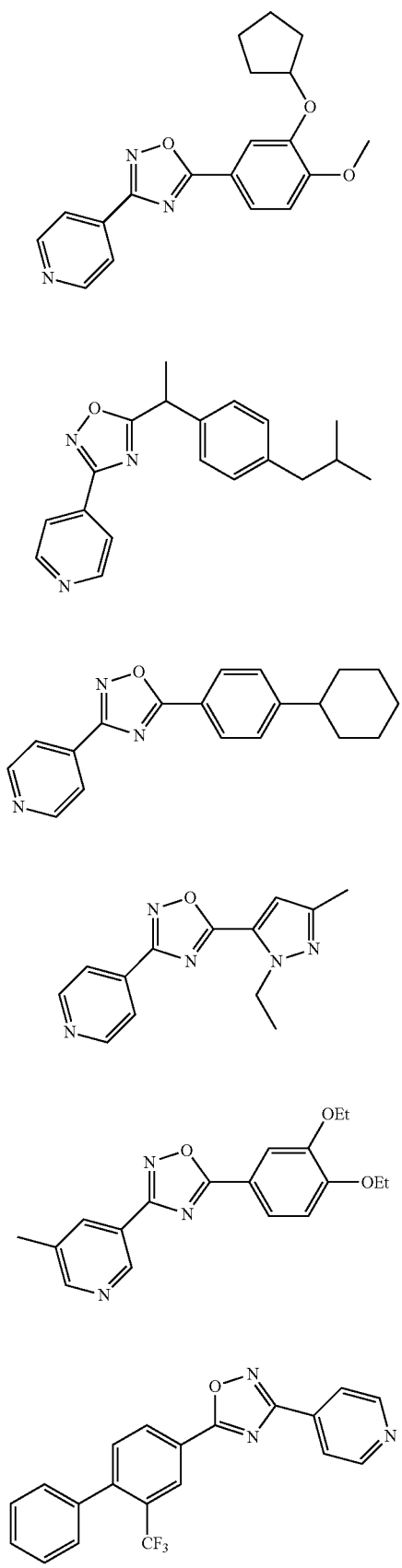
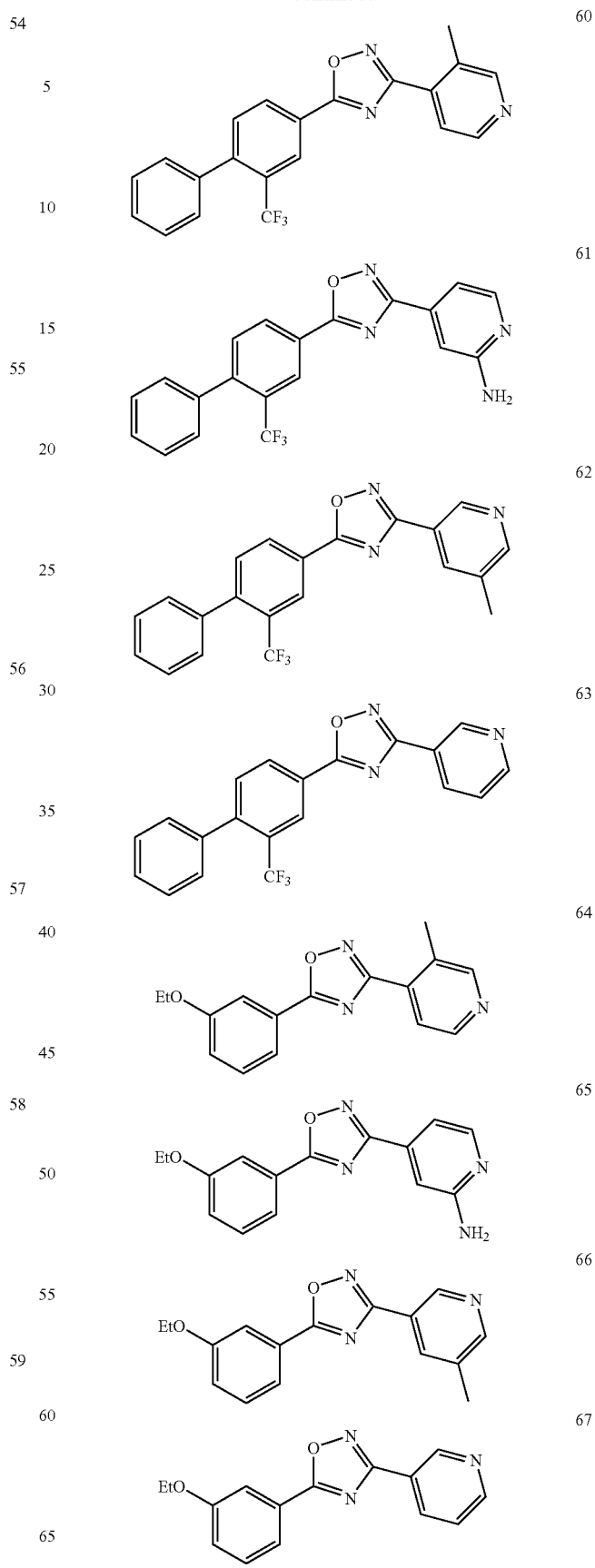

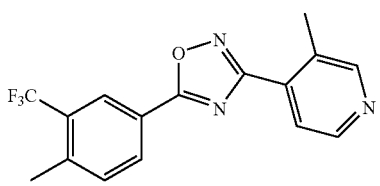
68
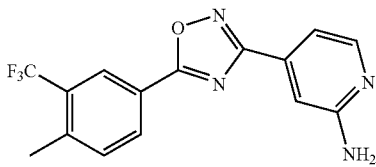
69
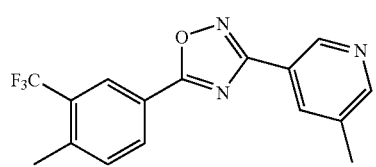
70
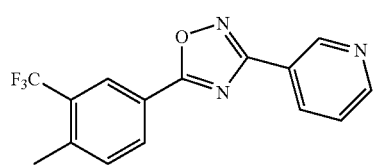
71
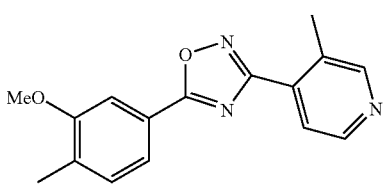
72
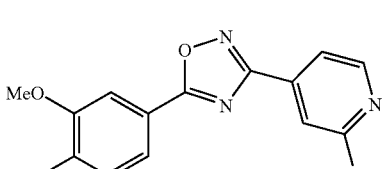
73
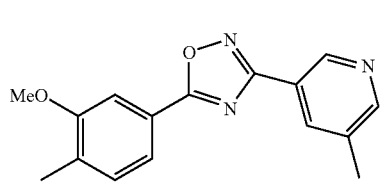
74
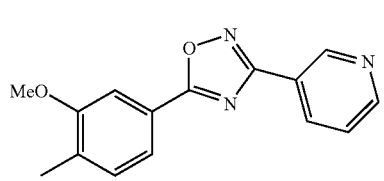
75
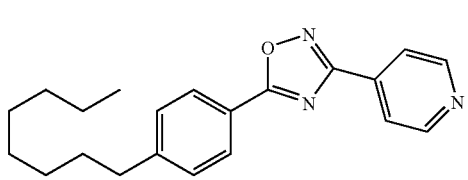
76
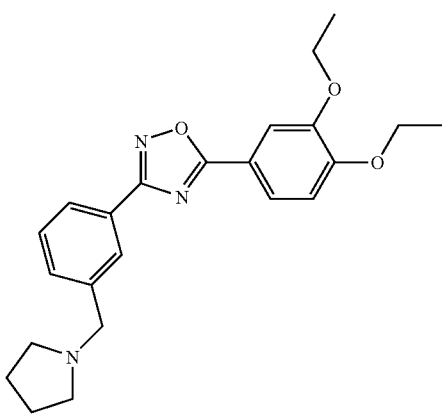
77
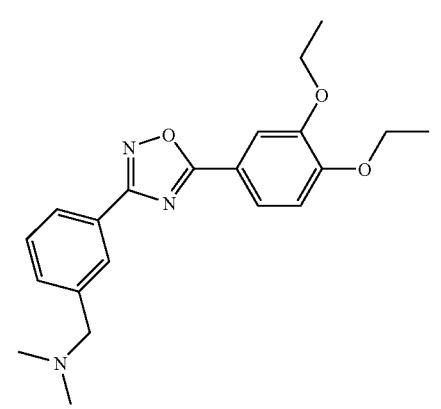
78
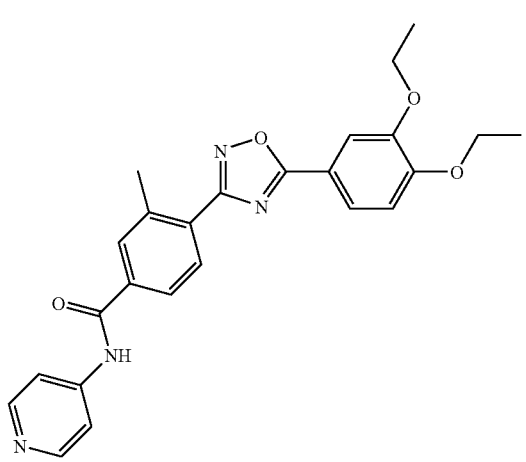
79
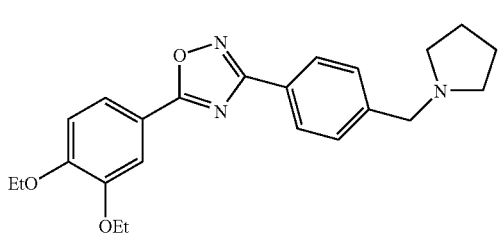
80

81
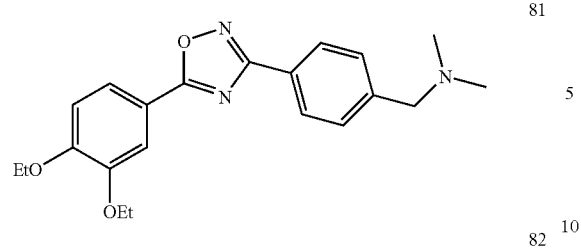
82
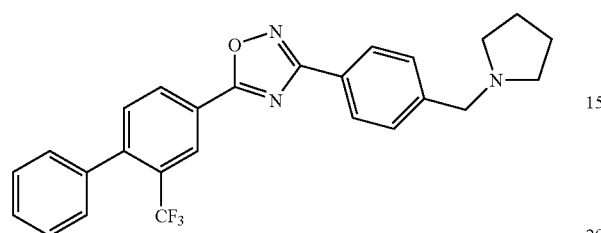
84
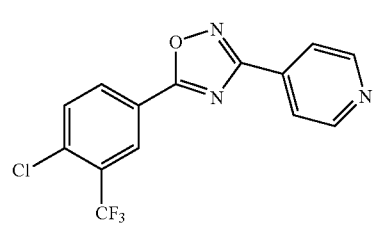
85
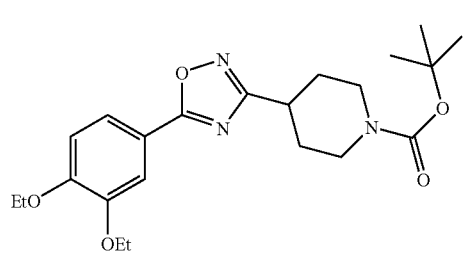
86
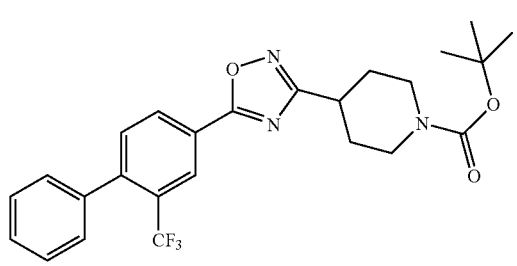
87
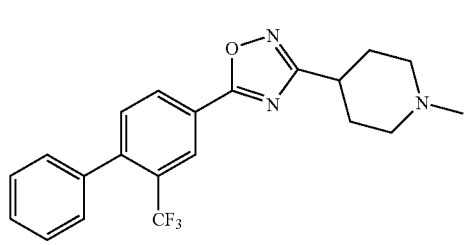
88
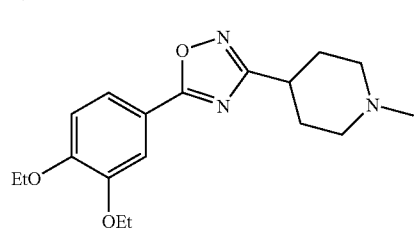
89
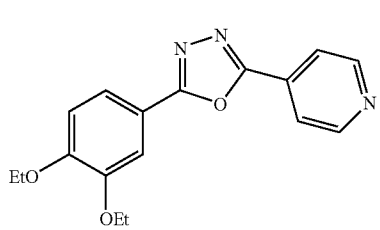
90
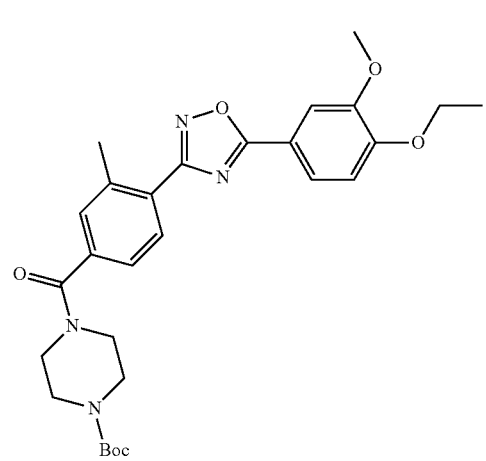
91
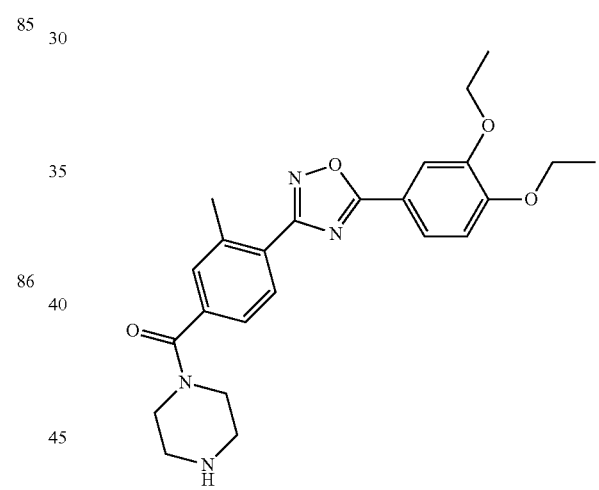
92
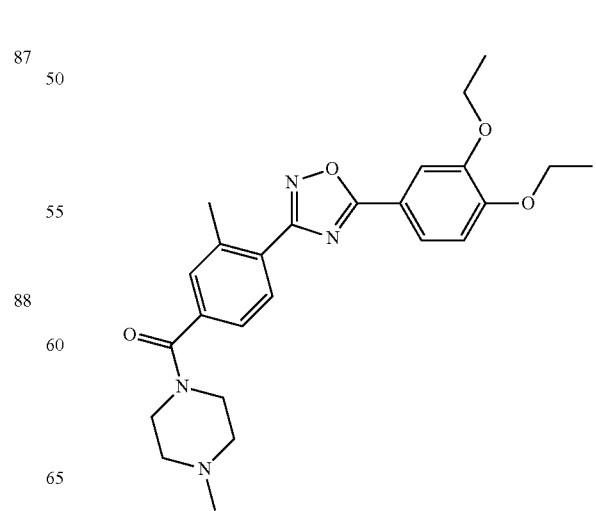

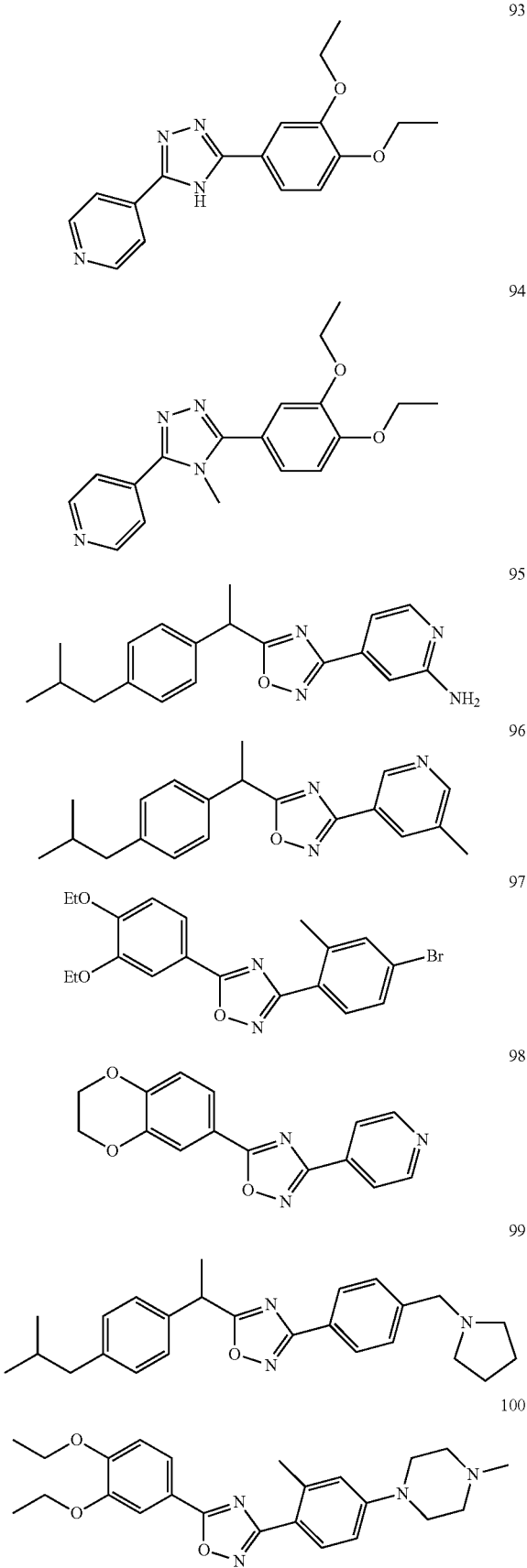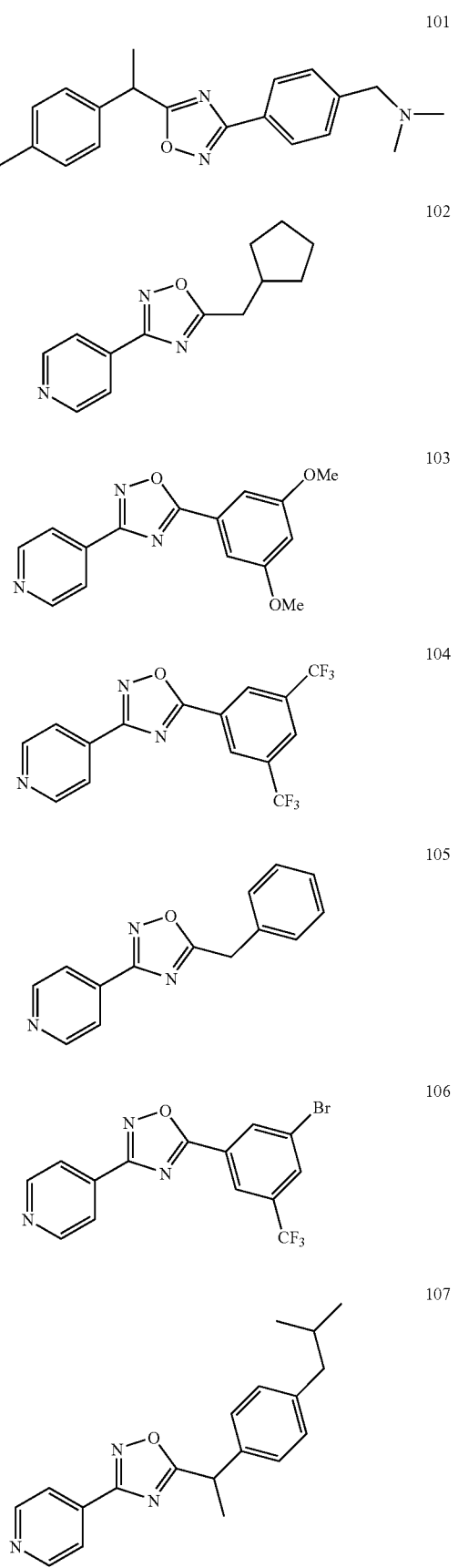

108
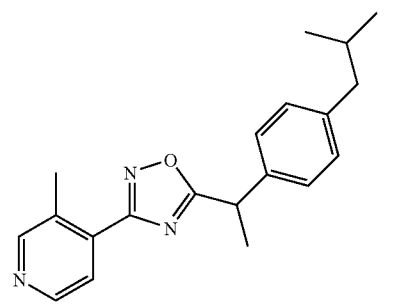
109
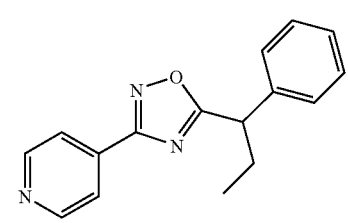
110
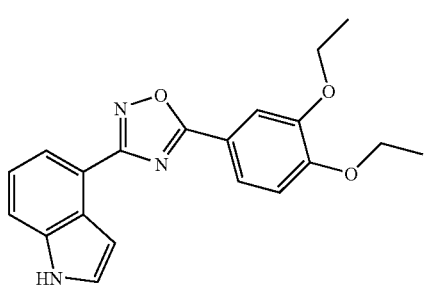
111
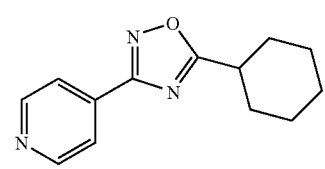
112
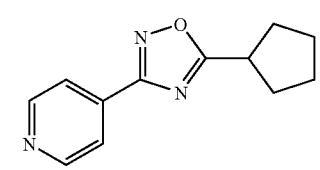
113
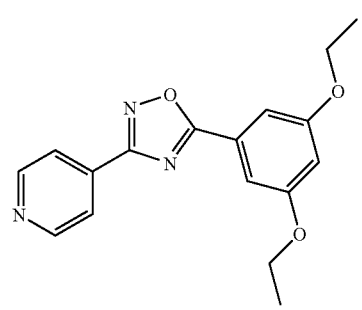
114
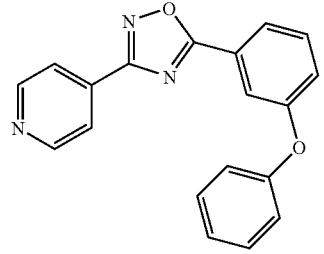
115
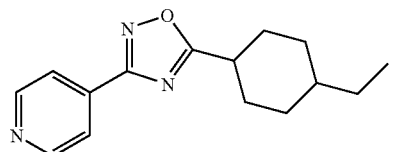
116
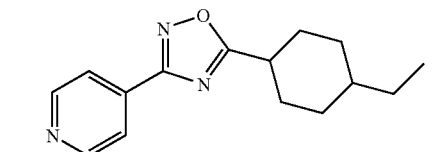
117
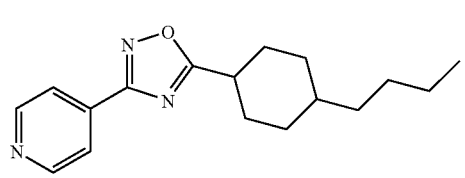
118
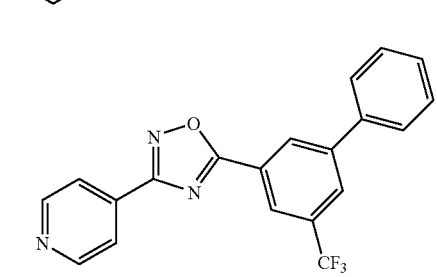
119
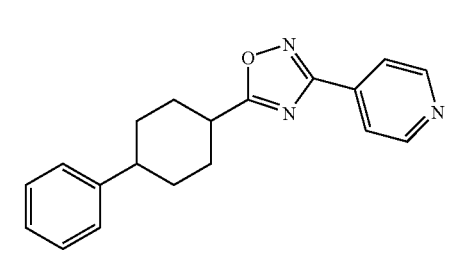
120
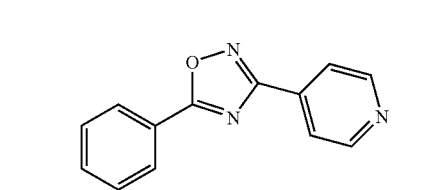

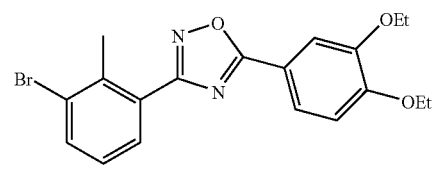 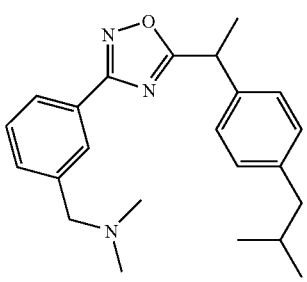 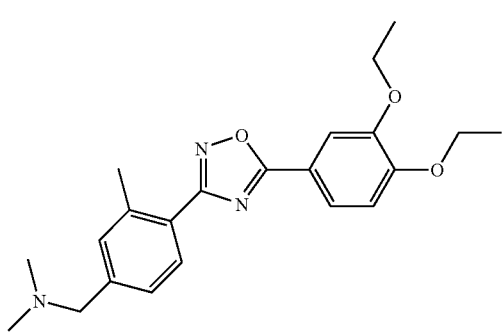 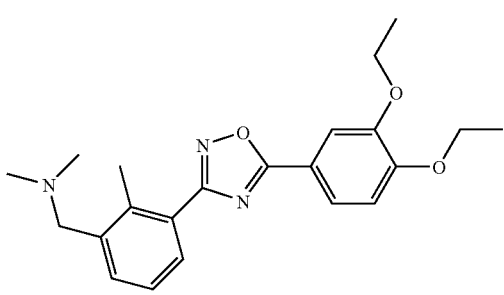 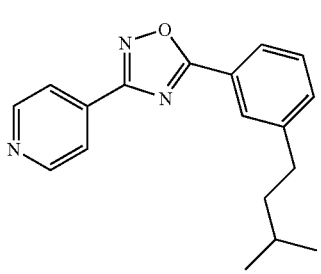 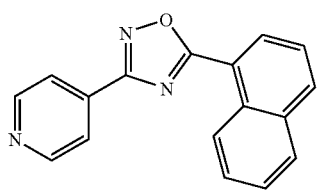 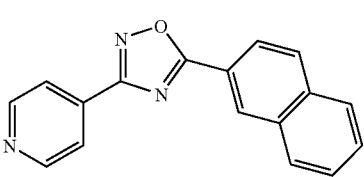

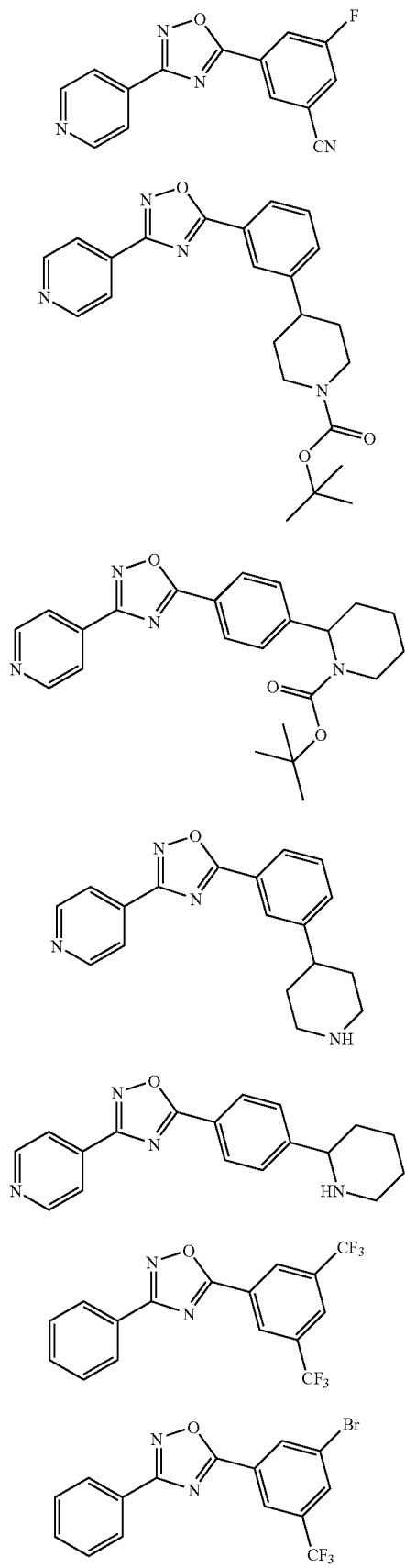
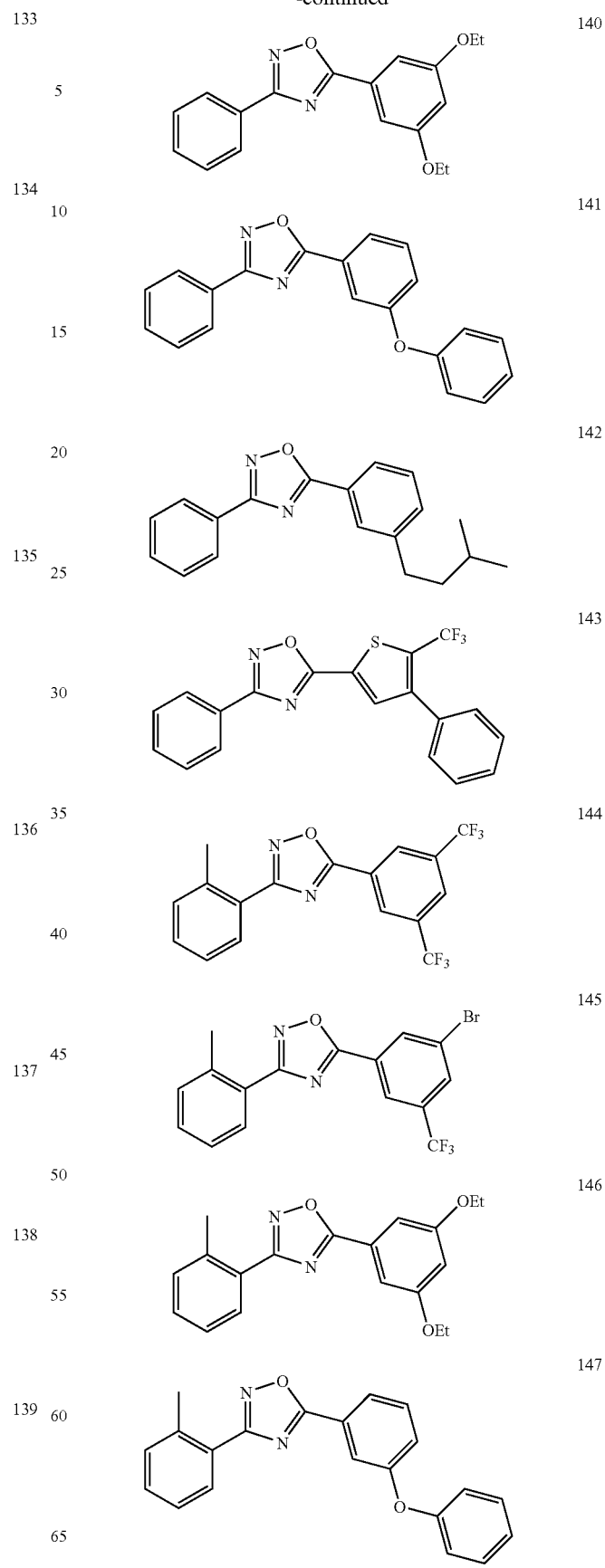

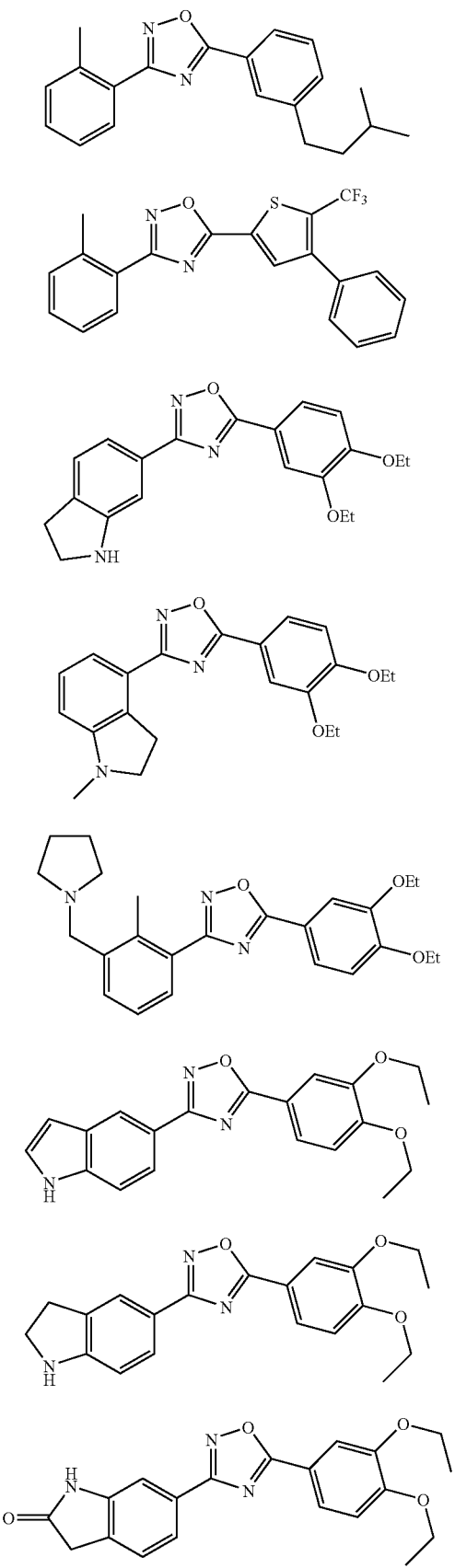
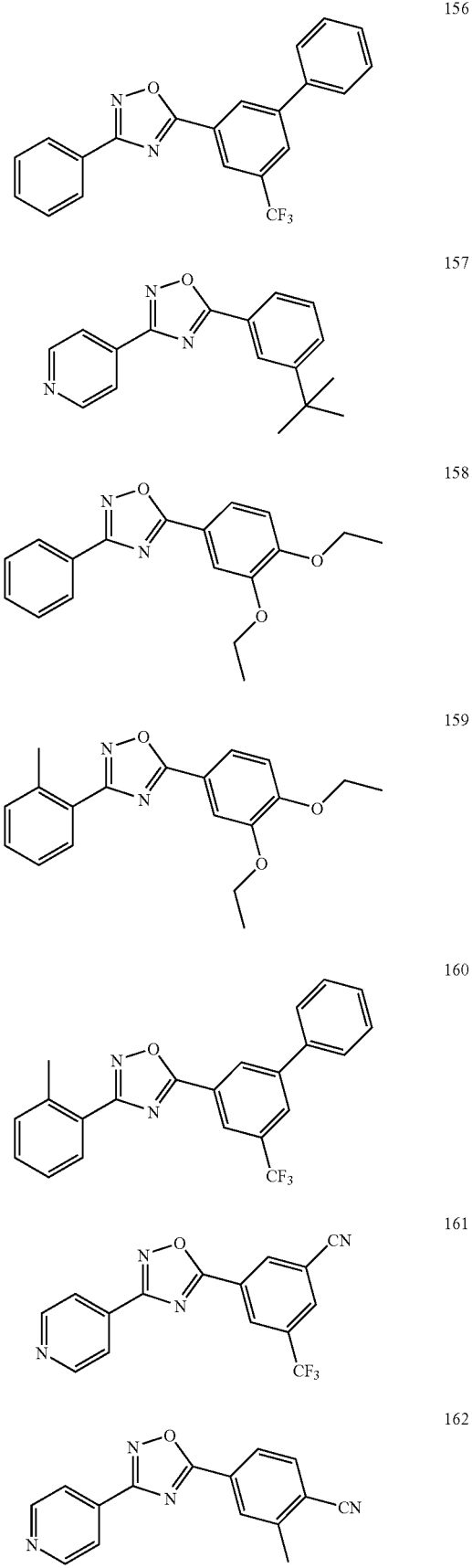

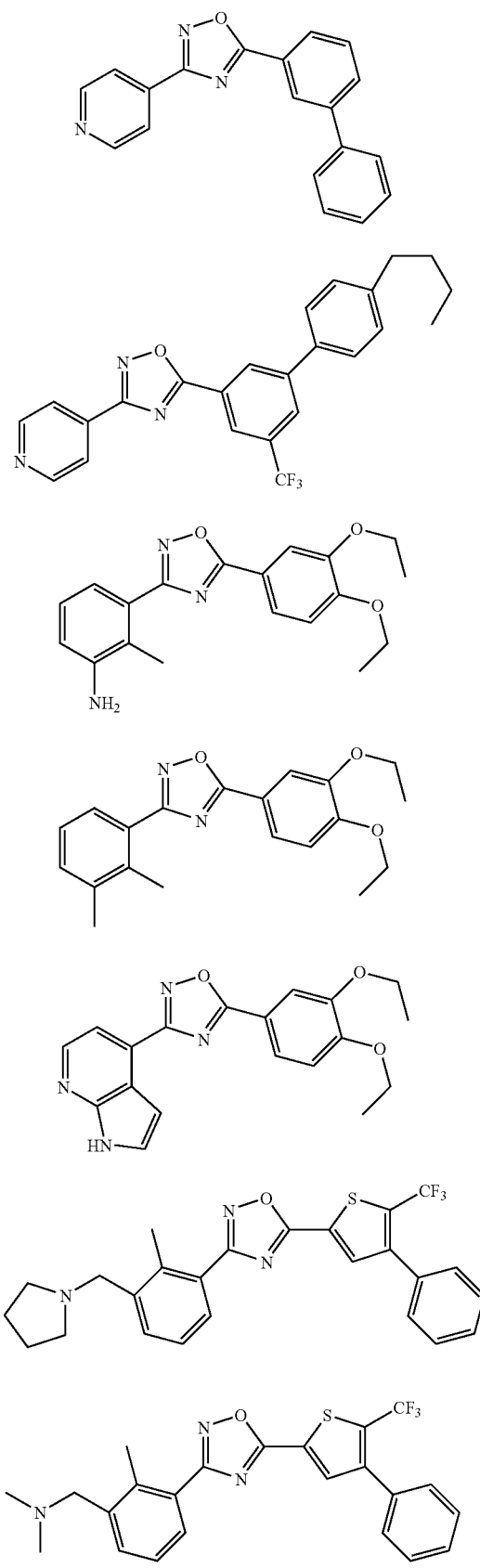
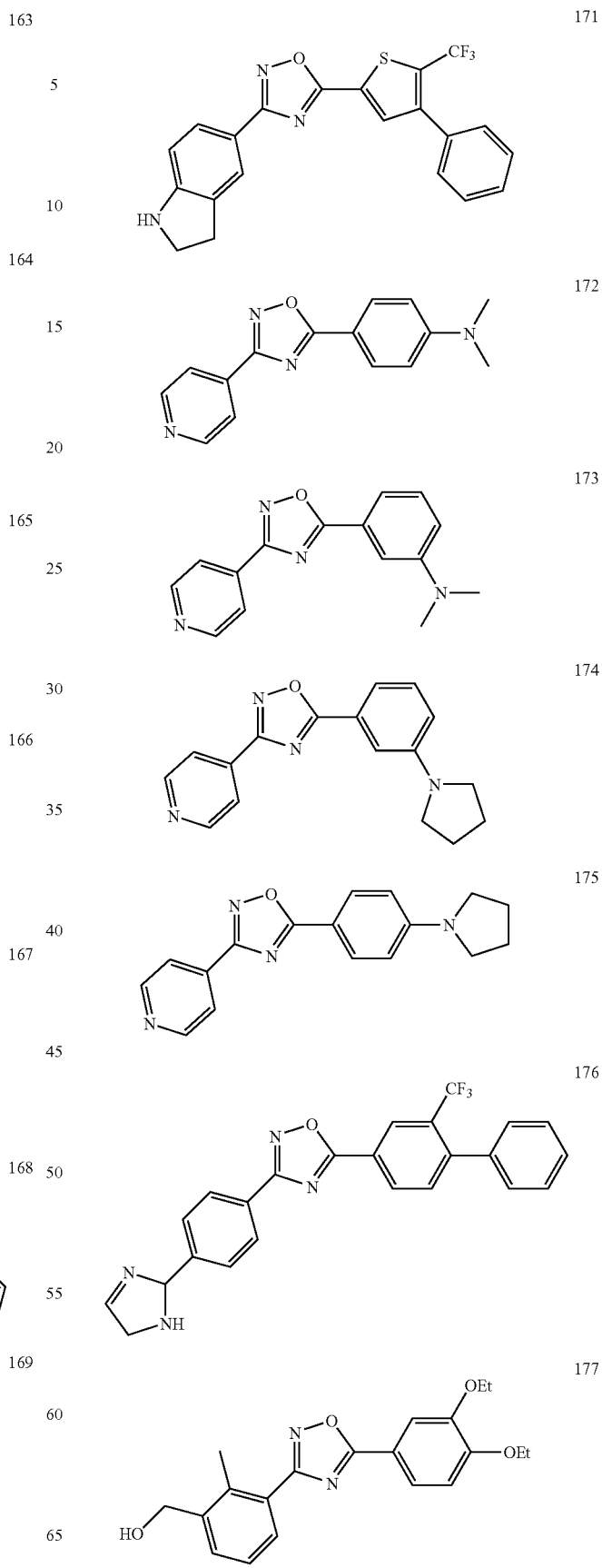

178 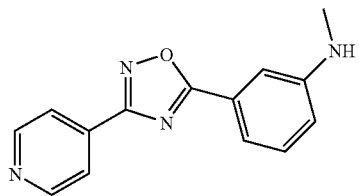
179 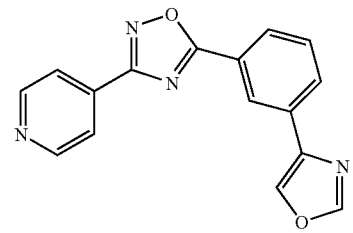
180 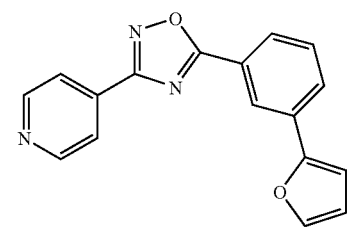
181 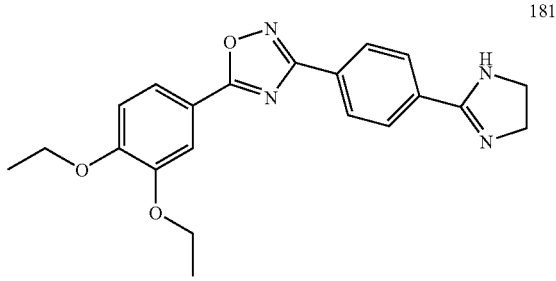
182 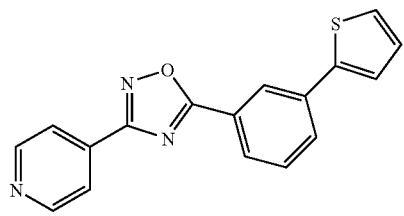
183 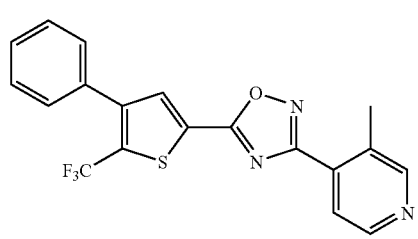
184 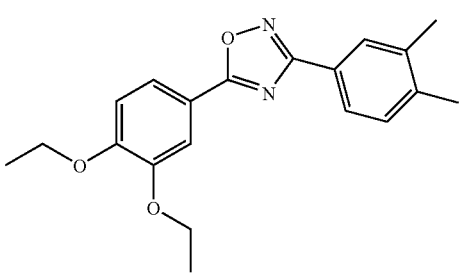
185 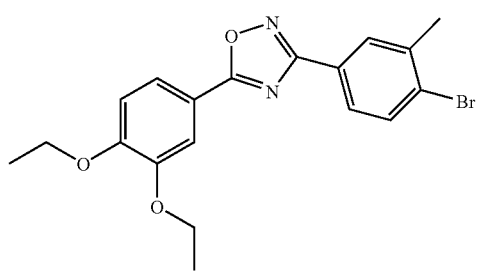
186 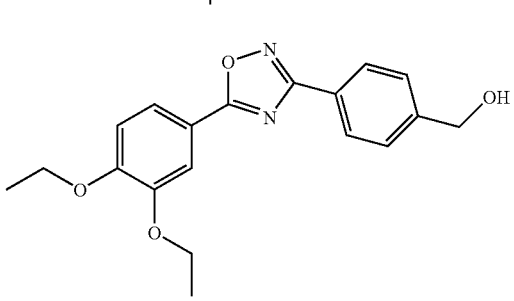
187 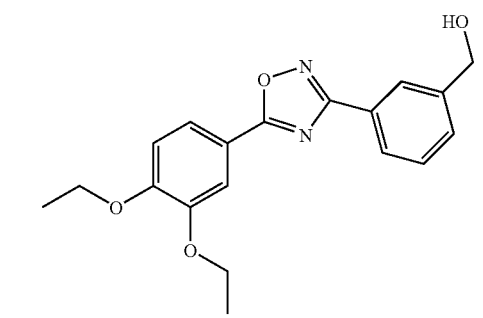
188 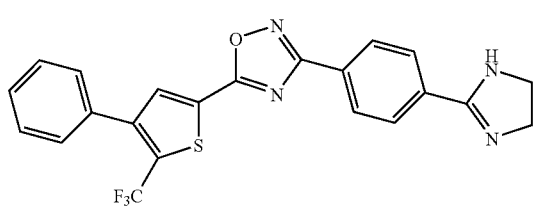
189 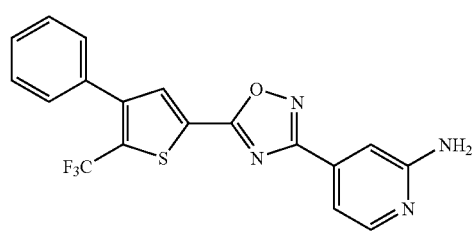

-continued
190
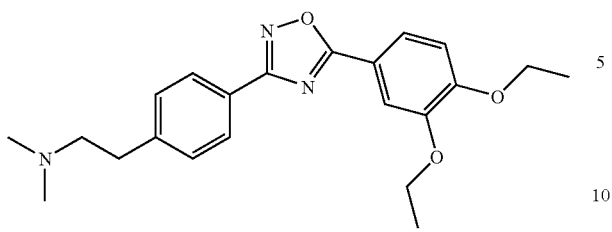
191
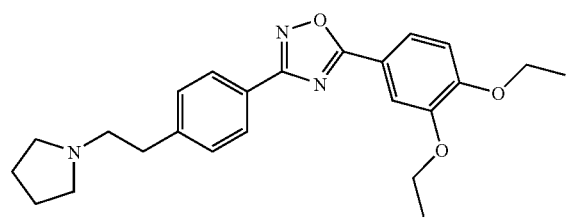
192
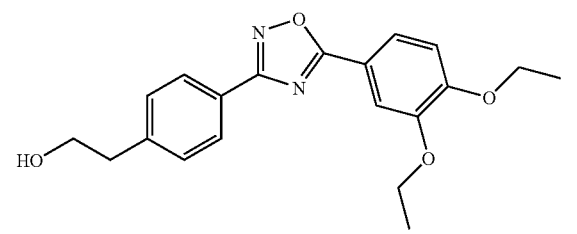
193
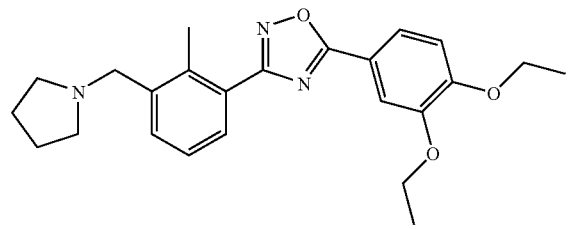
197
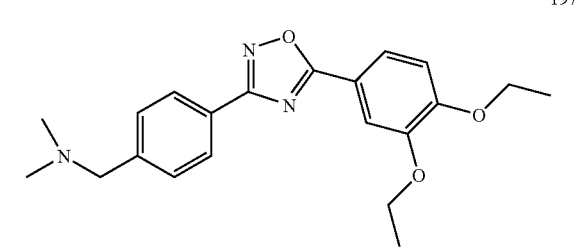
198
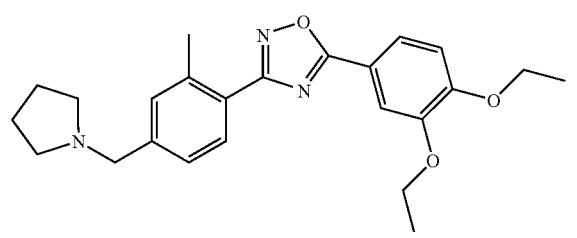
-continued
199
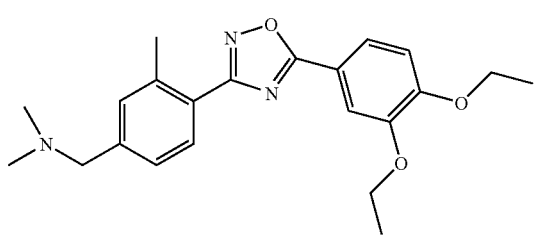
200
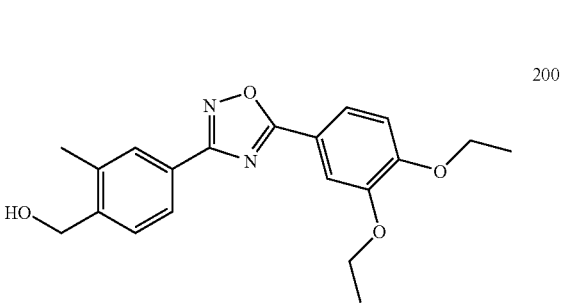
201
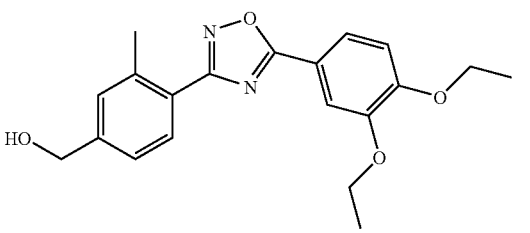
202
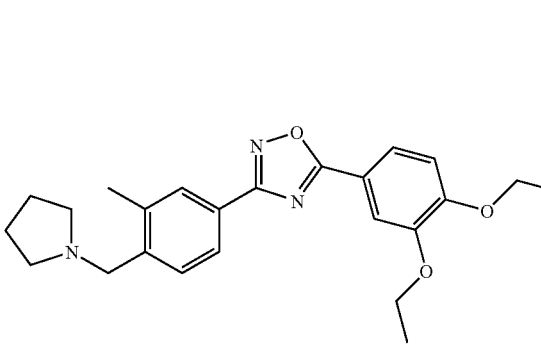
203
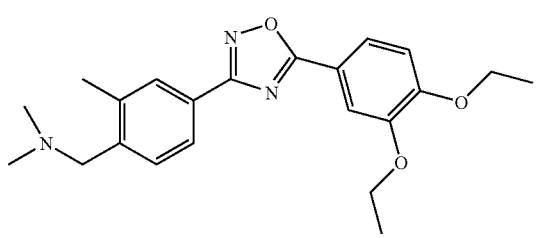

204 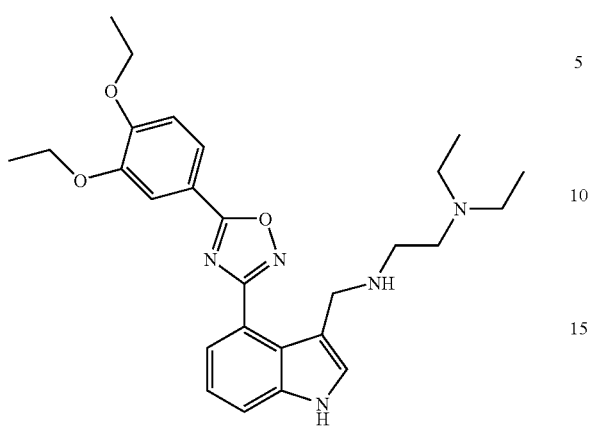
205 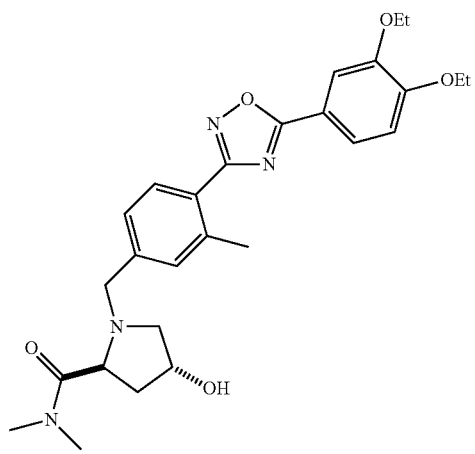
206
207
208 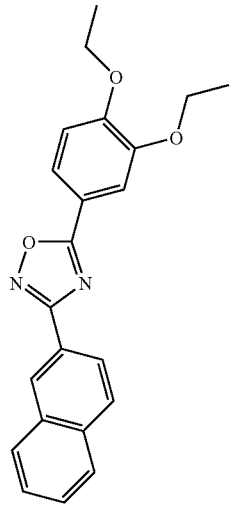
209 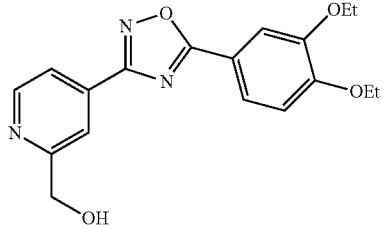
210
211 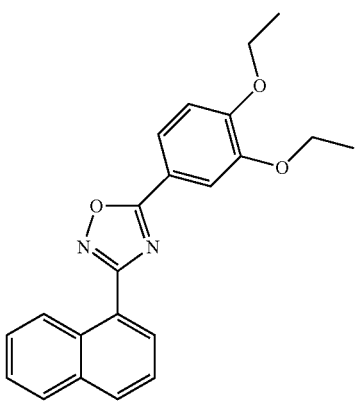
212

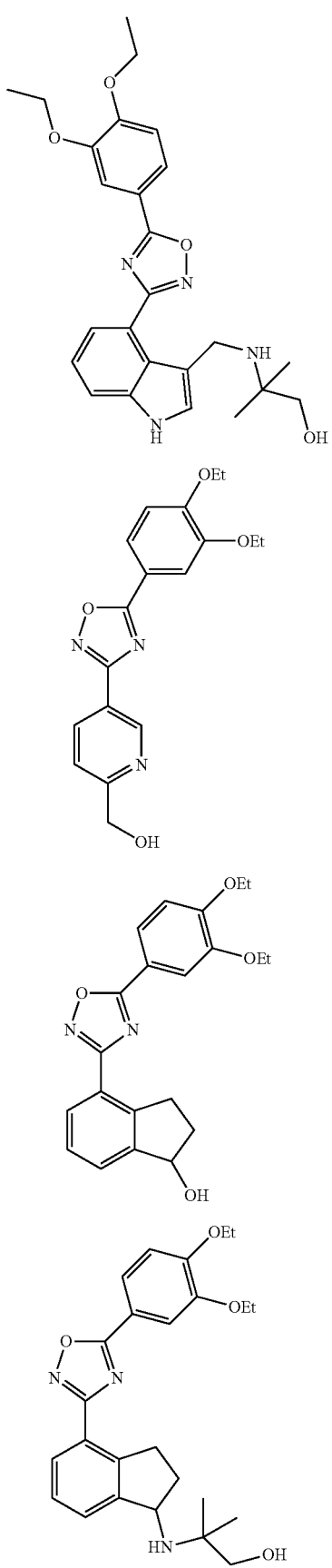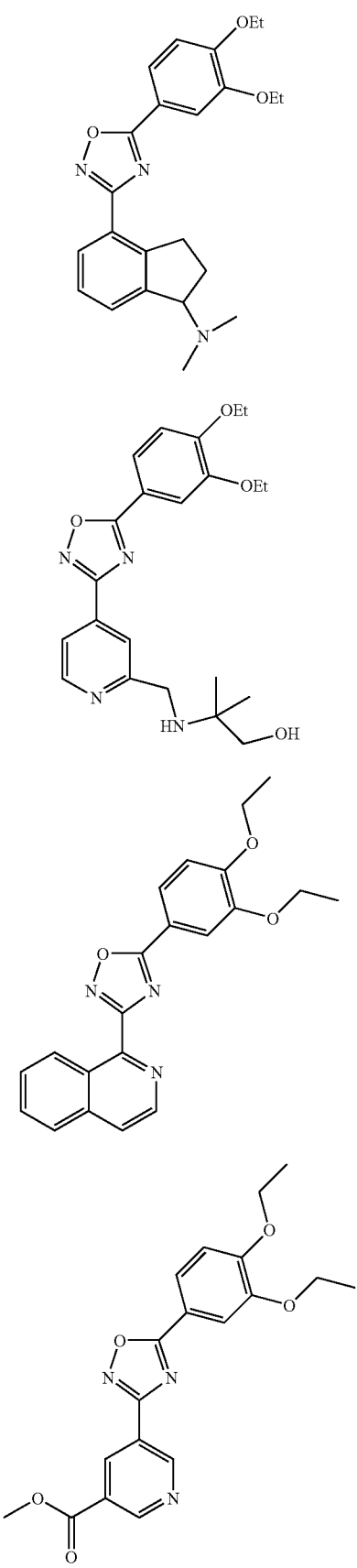

221 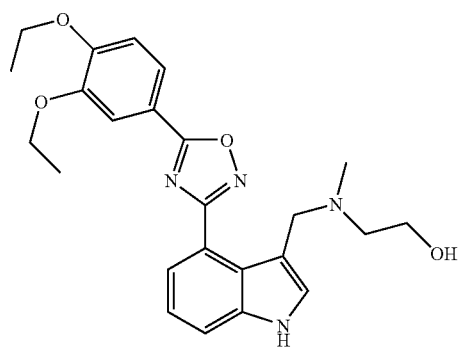
222 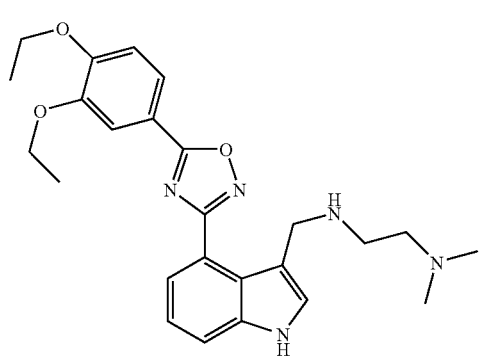
223 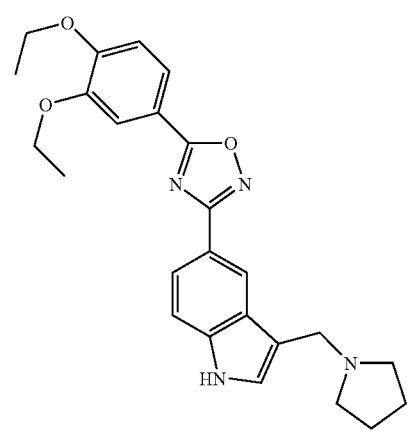
224 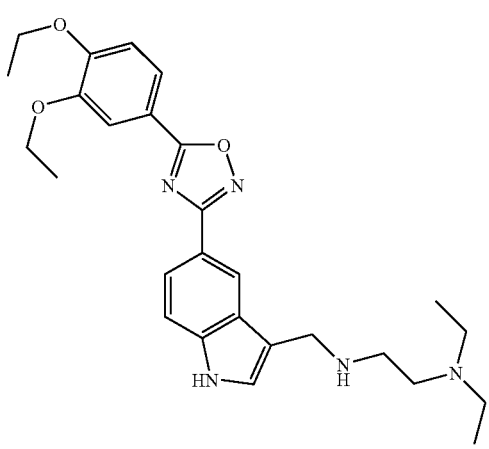
225 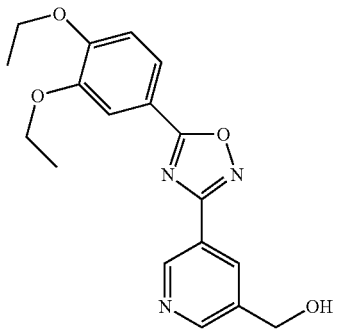
226 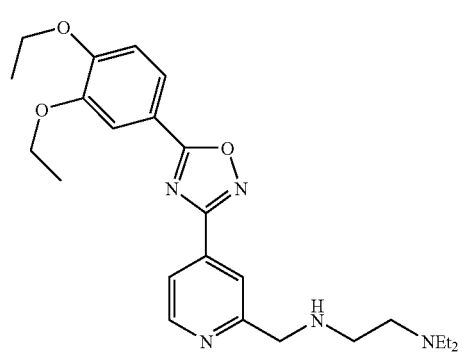
227 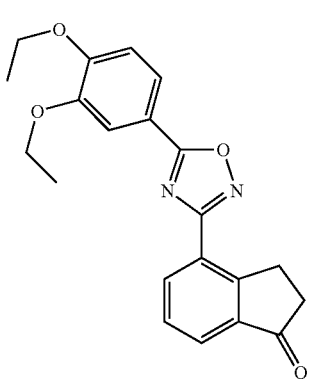
228 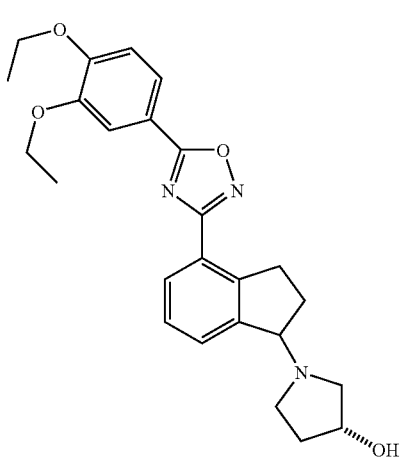

169 -continued
229
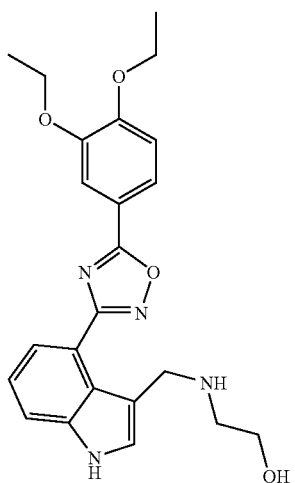
230
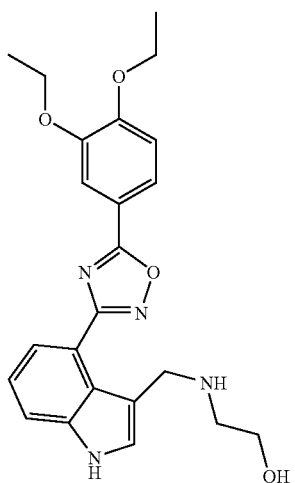
231
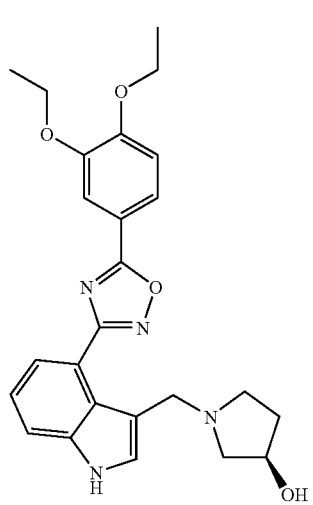
170 -continued
232
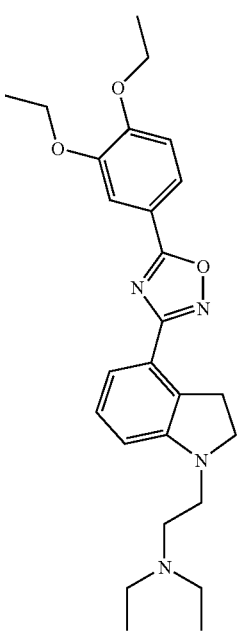
233
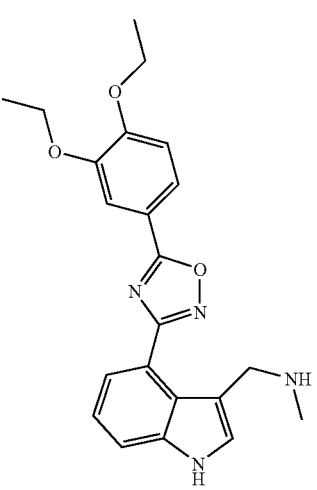
234
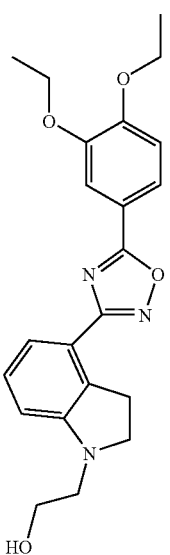

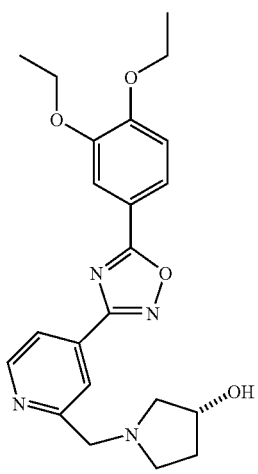
235
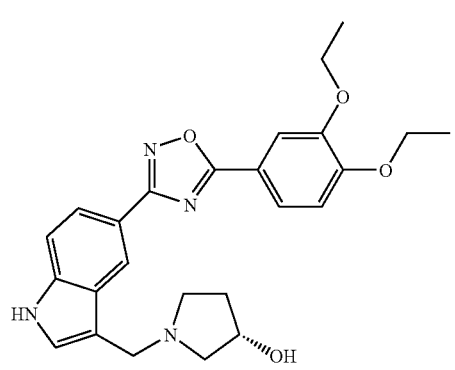
236
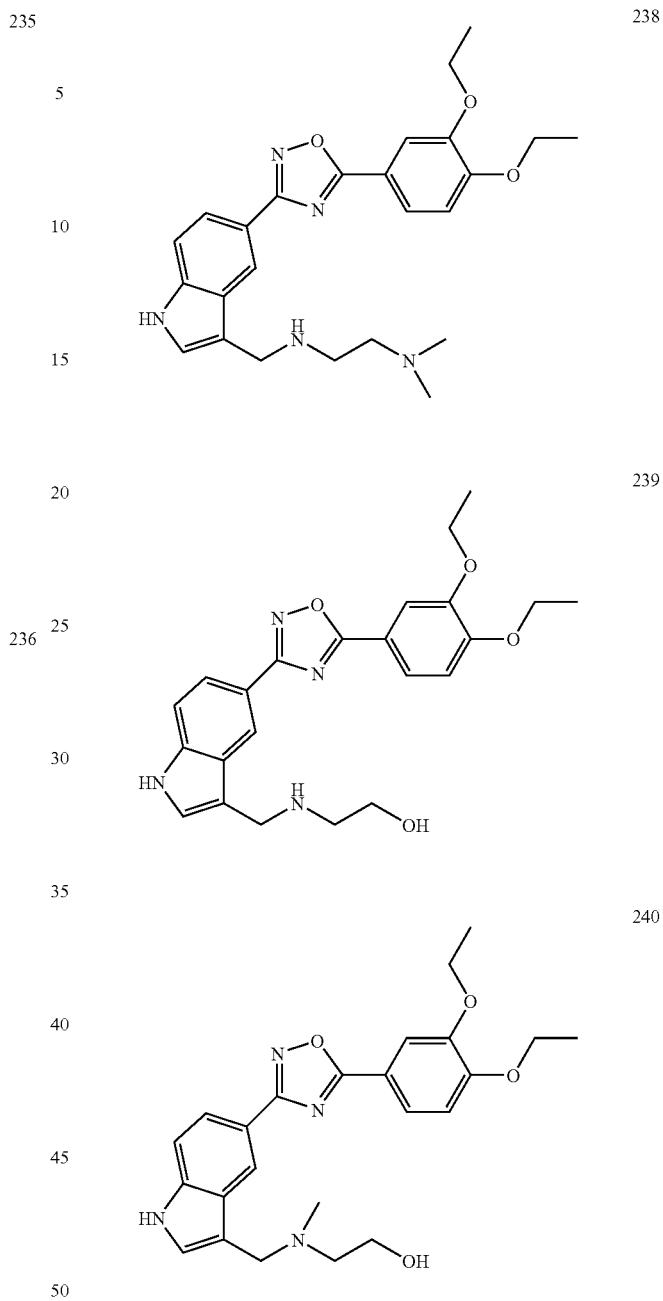
237
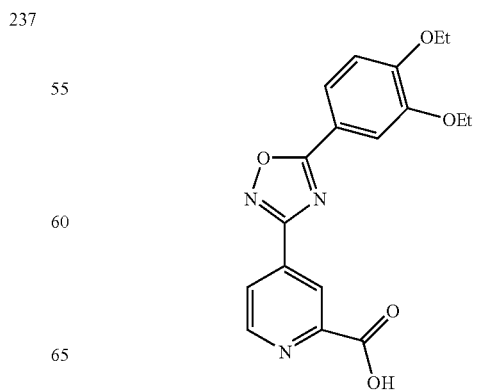

| 242 | 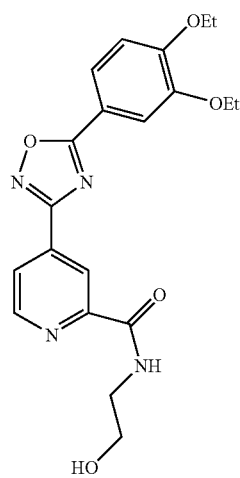 | 247 | 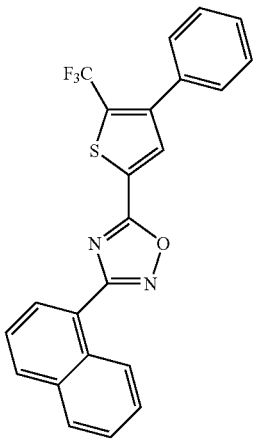 |
| 243 | | 248 | |
| 246 | 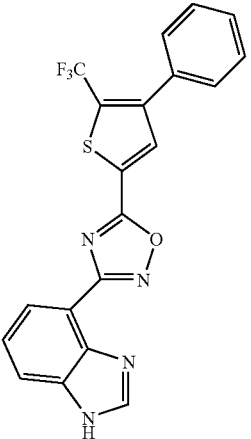 | 249 | |

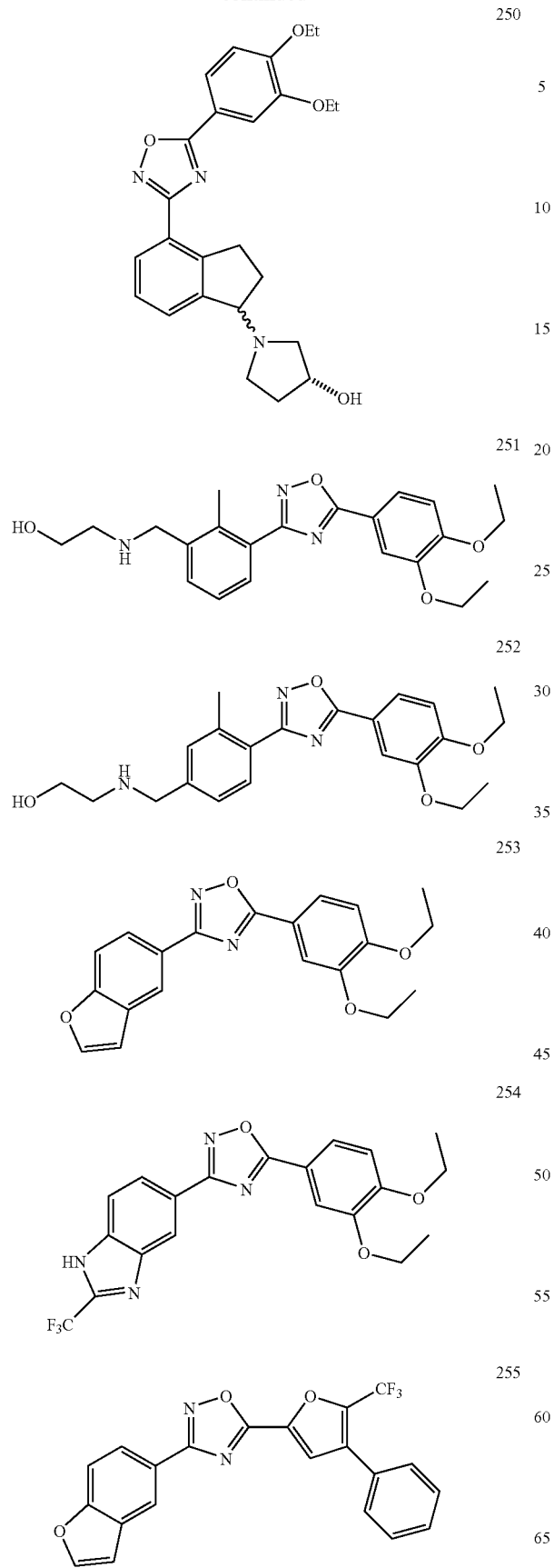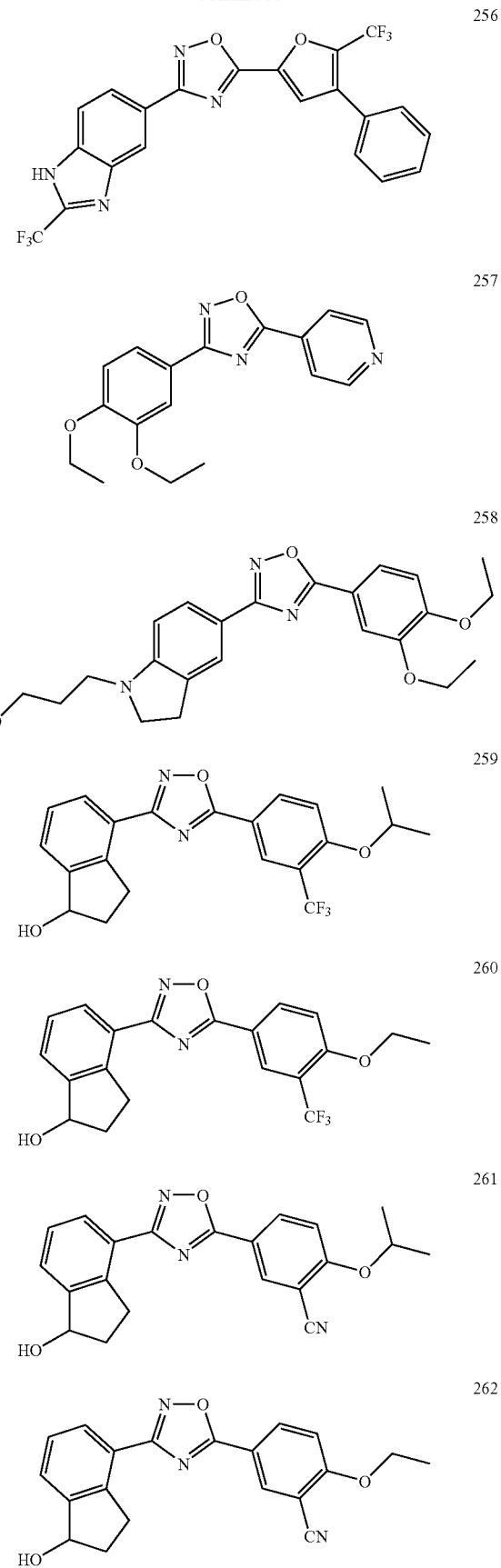

-continued

263
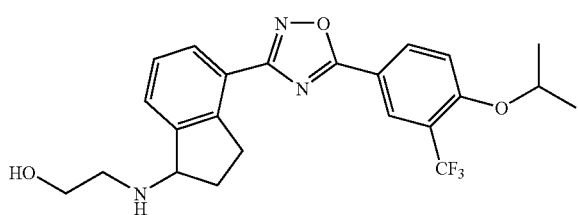

264
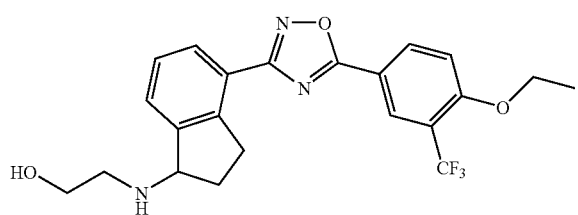

265
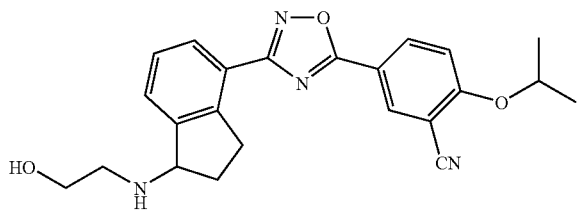

266
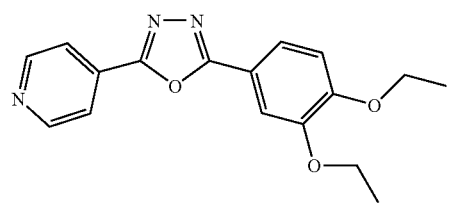

267
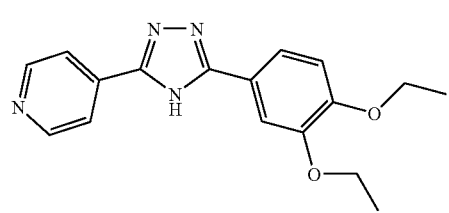

268
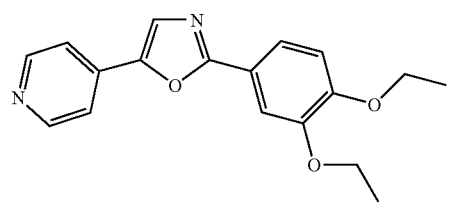

269
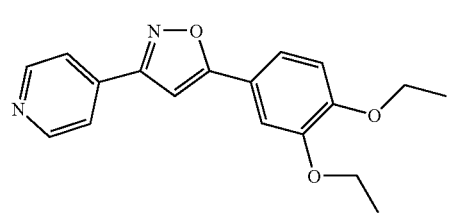

-continued

270
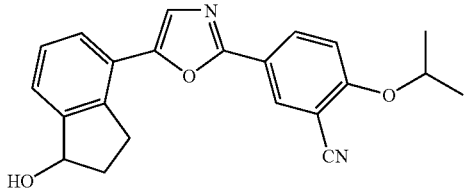

271
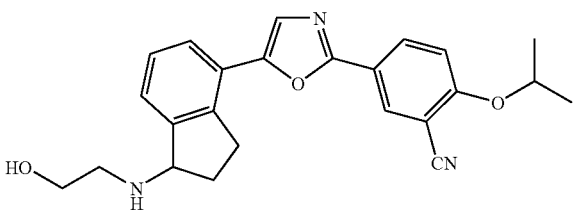

In various embodiments, a method of the invention uses a compound wherein the compound activates or agonizes the sphingosine-1-phosphate receptor subtype 1 to a greater extent than the compound activates or agonizes another subtype of sphingosine-1-phosphate receptor. For example, the other subtype of sphingosine-1-phosphate receptor can be subtype 3. In various embodiments, the sphingosine-1-phosphate receptor subtype 1 can be disposed within a living mammal.

In various embodiments, the invention provides a method of treatment of a malcondition in a patient for which activation, agonism, inhibition, or antagonism of an S1P1 receptor is medically indicated, comprising contacting the S1P1 receptor according to a method of the invention by administering the compound to the patient at a frequency and for a duration of time sufficient to provide a beneficial effect to the patient. For example, selective activation or agonism of an S1P subtype 1 receptor with respect to other subtypes of S1P receptor is medically indicated. More specifically, the malcondition can comprise multiple sclerosis, transplant rejection, or adult respiratory distress syndrome. The inventive method can further comprise administering an effective amount of a second medicament to the patient, such as wherein the second medicament is adapted for treatment of multiple sclerosis, transplant rejection, or adult respiratory distress syndrome.

Compositions and Combination Treatments

The S1P1 compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another S1P1 inhibitor or another type of therapeutic agent, or both. As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g. as described in Remington: *The Science and Practice of Pharmacy,* 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention which inhibits the enzymatic activity of the focal adhesion kinase to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tableted placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention which inhibits the enzymatic activity of the focal adhesion kinase, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| | | |
|---|---|---|
| Core: | Active compound (as free compound or salt thereof) | 250 mg |
| | Colloidal silicon dioxide (Aerosil) ® | 1.5 mg |
| | Cellulose, microcryst. (Avicel) ® | 70 mg |
| | Modified cellulose gum (Ac-Di-Sol) ® | 7.5 mg |
| | Magnesium stearate | Ad. |
| Coating: | HPMC approx. | 9 mg |
| | *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a human in need of such treatment, prevention, elimination, alleviation or amelioration of a malcondition that is mediated through the action of S1P1, for example, multiple sclerosis, transplant rejection, and adult respiratory distress syndrome.

The pharmaceutical compositions and compounds of the present invention can generally be administered in the form of a dosage unit (e.g. tablet, capsule, etc.) in an amount from about 1 µ/kg of body weight to about 1 g/kg of body weight, preferably from about 5 µ/kg of body weight to about 500 mg/kg of body weight, more preferably from about 10 µ/kg of body weight to about 250 mg/kg of body weight, most preferably from about 20 µ/kg of body weight to about 100 mg/kg of body weight. Those skilled in the art will recognize that the particular quantity of pharmaceutical composition and/or compounds of the present invention administered to an individual will depend upon a number of factors including, without limitation, the biological effect desired, the condition of the individual and the individual's tolerance for the compound.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge. S1P1 agonist bioactivity of the compounds of the invention can be determined by use of an in vitro assay system which measures the activation of S1P1, which can be expressed as $EC_{50}$ values, as are well known in the art inhibitors of the invention can be determined by the method described in the Examples.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other S1P1 inhibitors and/or ii) one or more other types of protein kinase inhibitors and/or one or more other types of therapeutic agents which can be administered orally in the same dosage form, in a separate oral dosage form (e.g., sequentially or non-sequentially) or by injection together or separately (e.g., sequentially or non-sequentially).

Accordingly, in another embodiment the invention provides combinations, comprising:
  a) a compound of the invention as described herein; and
  b) one or more compounds comprising:
   i) other compounds of the present invention,
   ii) other medicaments adapted for treatment of a malcondition for which
activation of S1P1 is medically indicated, for example multiple sclerosis, transplant rejection, or adult respiratory distress syndrome.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

Methods of Treatment

In various embodiments, the present invention provides a method for activating or agonizing (i.e., to have an agonic effect, to act as an agonist) a sphingosine-1-phosphate receptor subtype, such as S1P1, with a compound of the invention. The method involves contacting the receptor with a suitable concentration of an inventive compound to bring about activation of the receptor. The contacting can take place in vitro, for example in carrying out an assay to determine the S1P receptor activation activity of an inventive compound undergoing experimentation related to a submission for regulatory approval.

The method for activating an S1P receptor, such as S1P1, can also be carried out in vivo, that is, within the living body of a mammal, such as a human patient or a test animal. The inventive compound can be supplied to the living organism via one of the routes as described above, e.g., orally, or can be provided locally within the body tissues, for example by injection of a tumor within the organism. In the presence of the inventive compound, activation of the receptor takes place, and the effect thereof can be studied.

An embodiment of the present invention provides a method of treatment of a malcondition in a patient for which activation of an S1P receptor, such as S1P1, is medically indicated, wherein the patient is administered the inventive compound in a dosage, at a frequency, and for a duration to produce a beneficial effect on the patient. The inventive compound can be administered by any suitable means, examples of which are described above.

Experimental Procedures for Studying Agonist-Induced Internalization, Receptor Phosphorylation and Receptor Polyubiquitination in Stably Expressed $S1P_1$-GFP Cells
Materials.

S1P was obtained from Biomol. The S1P receptor agonist, AFD-R, was a gift from Dr. Brickman (Novartis Pharma). Anti-GFP antibodies (ab-1218 and ab-6556) were from Abcam, anti-ubiquitin P4D1 antibody from Santa Cruz, 4-12% Tris-Glycine Novex SDS-PAGE gels from Invitrogen, $P^{32}$ orthophosphate from Perkin-Elmer. Fetal bovine serum (FBS) and charcoal-stripped-FBS were from Hyclone, and other culture reagents were from the TSRI Supply Center (supplied by Invitrogen and Gibco BRL).
Cell Culture.

HEK-293 cells stably expressing the GFP-tagged human $S1P_1$ receptor ($S1P_1$-GFP) and 293-vector-GFP cells were a gift from Dr Timothy Hla (Connecticut Health Science Center). Cells were maintained in high-glucose modified Eagle's medium containing GlutaMAX, and supplemented with 10% FBS, 1% penicillin/streptomycin solution and selected with 500 ug/ml G418 (Gibco BRL).
Microscopy Imaging Studies for Ligand-Mediated $S1P_1$-GFP Internalization.

Single $S1P_1$-GFP cells grown in gelatin-coated coverslips were used to study ligand induced $S1P_1$-GFP internalization. Cells were incubated overnight in charcoal-stripped FBS (cs-FBS) medium before the start of the experiment, and all incubations thereafter were done in cs-FBS medium-containing 15 ug/ml cyclohexamide. Cells were incubated with agonists (or vehicle control for the indicated times and reactions were terminated by removal of medium, and washing with PBS. In experiments with the antagonist W146, antagonist or vehicle was added to the cells for 30-45 min prior to agonist incubation. Cells were fixed in 3.7% paraformaldehyde for 10 min and mounted on coverslips using GelMount mounting media. Cells were scanned with an Olympus BX61 scanning confocal fluorescence microscope. For detecting GFP, fluorescence was excited by using an argon laser at a wavelength of 488 nm, and the absorbed wavelength was detected for 510-520 nm for GFP. Photomicrographs of ligand vs. vehicle were obtained using Metamorph software and the images were assessed (in Photoshop) for the appearance or not of vesicular $S1P_1$-GFP pattern of internalization, a characteristic pattern adopted by most G protein-coupled receptors following ligand stimulation.
Immunoprecipitation and Immunoblotting for $S1P_1$-GFP and Ligand-Stimulated $S1P_1$ Polyubiquitination The effect of agonist-stimulated recruitment of poly-ubiquitin chains to $S1P_1$-GFP was analyzed by immunoprecipitation-immunoblotting experiments with anti-GFP antibodies. Cells were seeded in 35 mm dishes and grown to ~95% confluence using regular growth medium. The growth medium was replaced by cs-FBS medium and the cells were incubated overnight. Drugs or vehicle (both made in cs-FBS medium) were incubated for the indicated times. At the end of incubation, the monolayers were washed twice in ice-cold PBS and lysates were obtained by incubation in RIPA buffer (50 mM Tris-HCl, pH 7.5, 150 mM NaCl, 1 mM EDTA, 1% Nonidet P-40, 0.5% sodium deoxycholate, 0.1% SDS) plus protease inhibitors (Complete tablets, Roche), and 1 mM $NaVO_4$, 1 mM NaF and 0.5M B-glycerol-phosphate. Cellular lysates were cleared by centrifugation (10,000×g, 15 min) and the protein concentration of the lysate supernatants was determined by the BCA (Pierce) method. Equal amounts of lysates (0.5-1 mg) were incubated overnight at 4 C with a monoclonal GFP antibody (1 ug antibody per 400 ug protein), followed by incubation with protein-A sepharose beads (2 h, 4 C). The beads were recovered by centrifugation (10,000×g, 1 min) and washing: 3×RIPA buffer:PBS (1:1) without protease inhibitors and twice in PBS. The beads were suspended in 2× Laemli buffer containing 2-mercaptoethanol, boiled for 10 min and proteins in the beads separated by SDS-PAGE in Novex, 4-12% Tris-Glycine gels. Gels were subsequently transferred to PVDF membranes, and probed overnight (4 C) with a polyclonal GFP antibody (1:10,000) for detection of $S1P_1$-GFP expression or P4D1 (1:200-1:800) to detect the $S1P_1$-GFP-polyubiquitinated complex. Horseradish peroxidase-labeled antibodies were visualized by ECL chemiluminescence (Amersham Biosciences).
Agonists Stimulated Phosphorylation of $S1P_1$-GFP in HEK293 Cells.

Cells stably expressing the GFP-tagged human $S1P_1$ were metabolically labeled with $P^{32}$ orthophosphate (80 μCi/ml, Perkin Elmer) for 2 h and subsequently incubated with agonists at the indicated concentrations for the indicated times at 37° C. Incubations were terminated by agonist removal and PBS washing, and the receptor was immunoprecipitated with a GFP antibody from equal protein amounts of cellular lysates. The immunoprecipitated receptor was separated by SDS-PAGE, and incorporation of $P^{32}$ onto the agonist-stimulated receptor was assessed by autoradiography (−80 C, 24 h exposure).
Internalization, Ubiquination and Phosphorylation of S1P1-GFP During the course of the lead optimization studies, compounds SR-917, compound 32, and compound 236 were evaluated in depth in several biological studies. SR-917 is a known agonist of the S1P1 receptor, indexed in the NIH Molecular Libraries Small Molecule RepositoryMLMSR-Compound ID is 976135. It is commercially available from ChemBridge Screening Library.

Figure 1B:
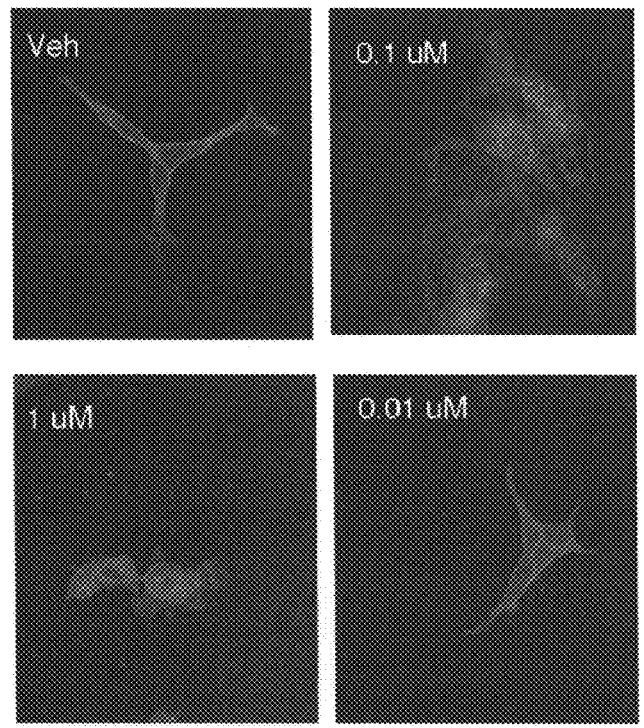
Figure 1C:
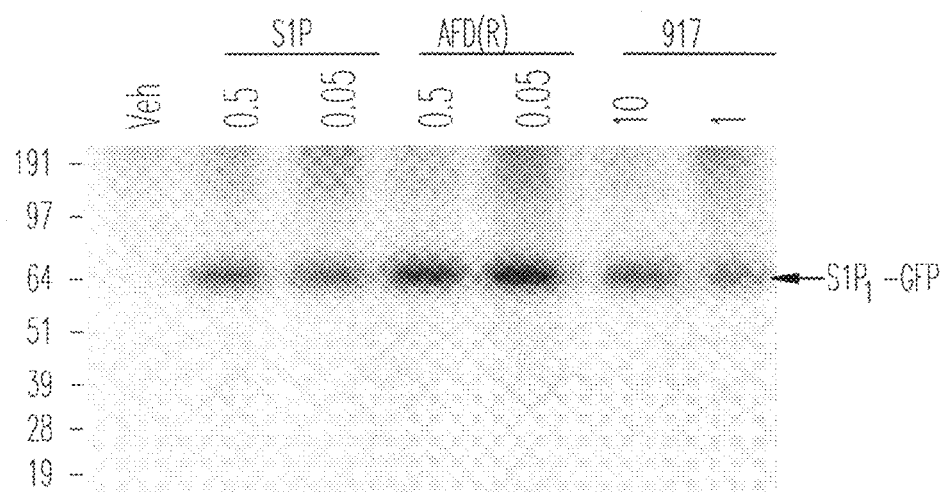

Agonistic stimulation of the S1P1 receptor is modulated by receptor degradation. Ligand stimulation induces receptor phosphorylation, internalization, polyubiquination and degradation (Gonzalez-Cabrera, Hla et al. 2007). Like AFD-R and S1P, stimulation with the synthetic compound identified by high throughput screening, SR-917, results in S1P1-GFP internalization, protein phosphorylation and polyubiquination; see FIG. 1.

Figure 2:
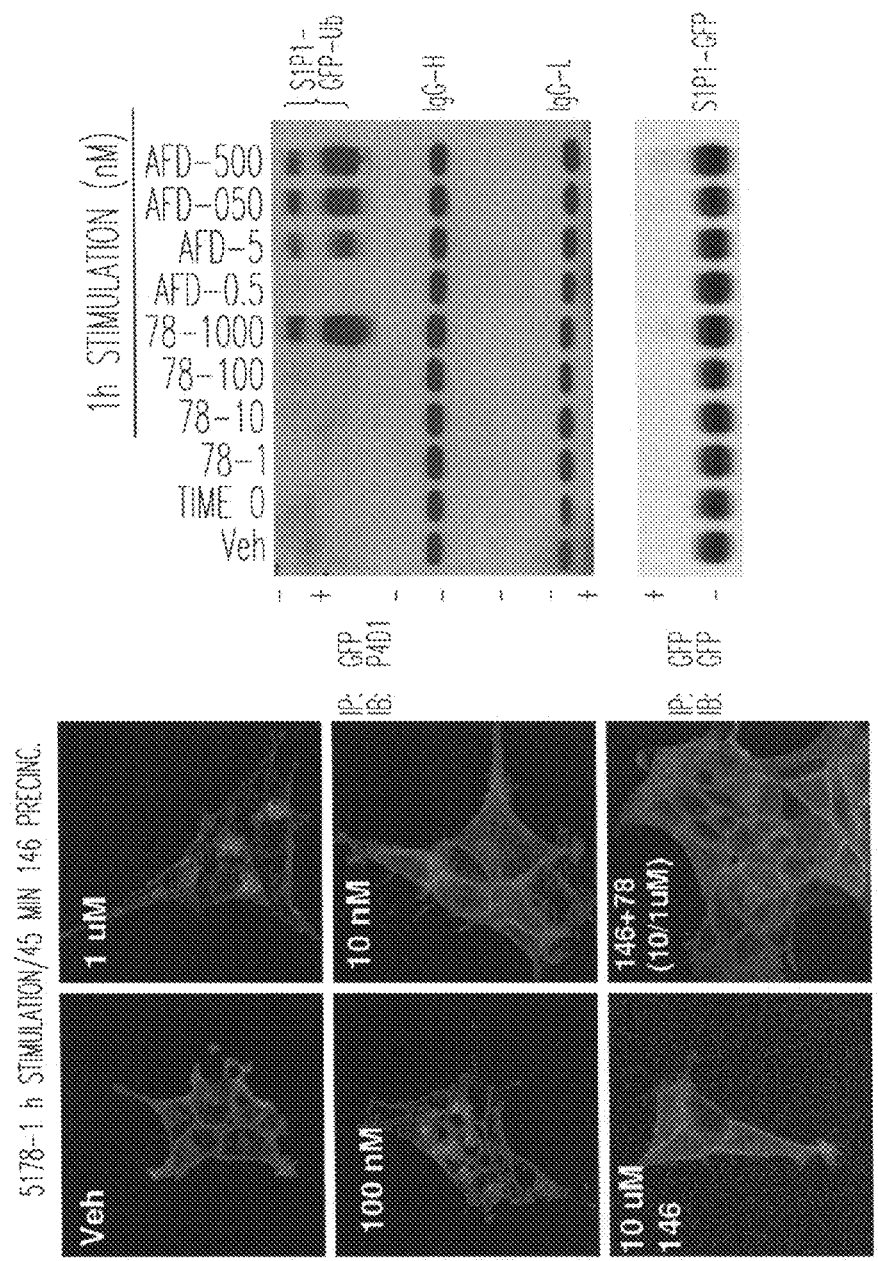
FIG. 2 shows compound 32 robustly induces internalization and polyubiquination, and these effects are blocked by the S1P1 antagonist, W146R.

Compound 32 robustly induces internalization and polyubiquination with 5178 and these effects are blocked by the S1P1 antagonist, W146R; see FIG. 2.

Figure 3:
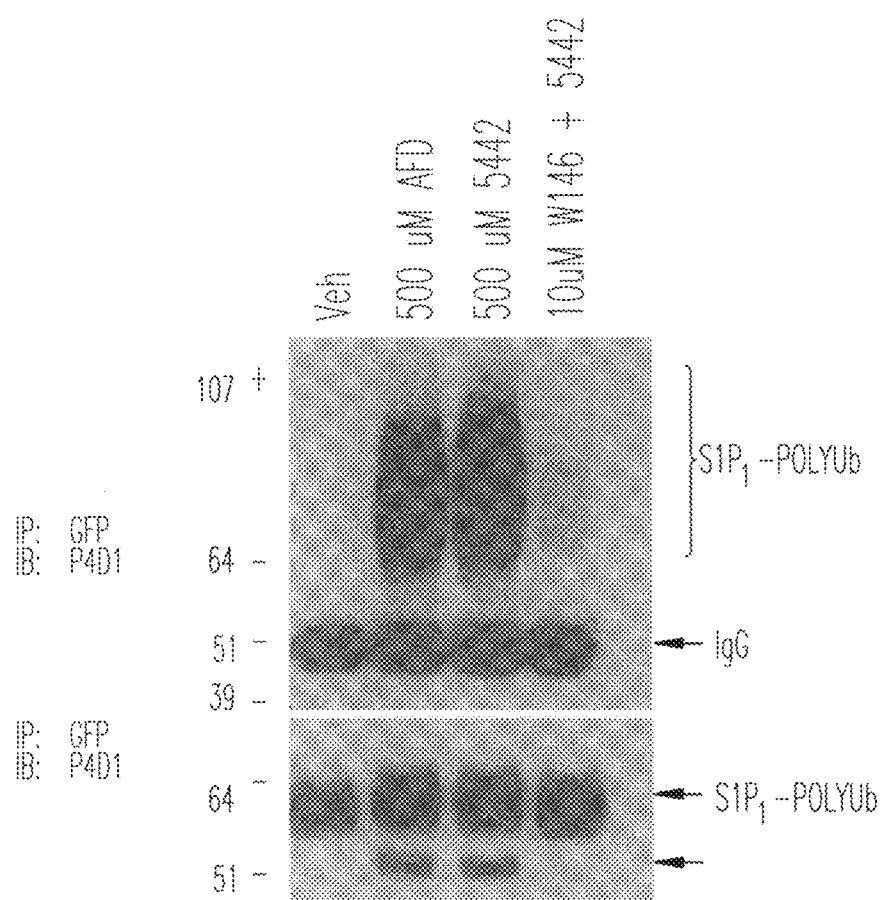
FIG. 3 shows that compound 236, like other compounds in the series, induces S1P1 polyubiquination.

Compound 236 like other compounds in the series, induces S1P1 polyubiquination; see FIG. 3.

Figure 4A:
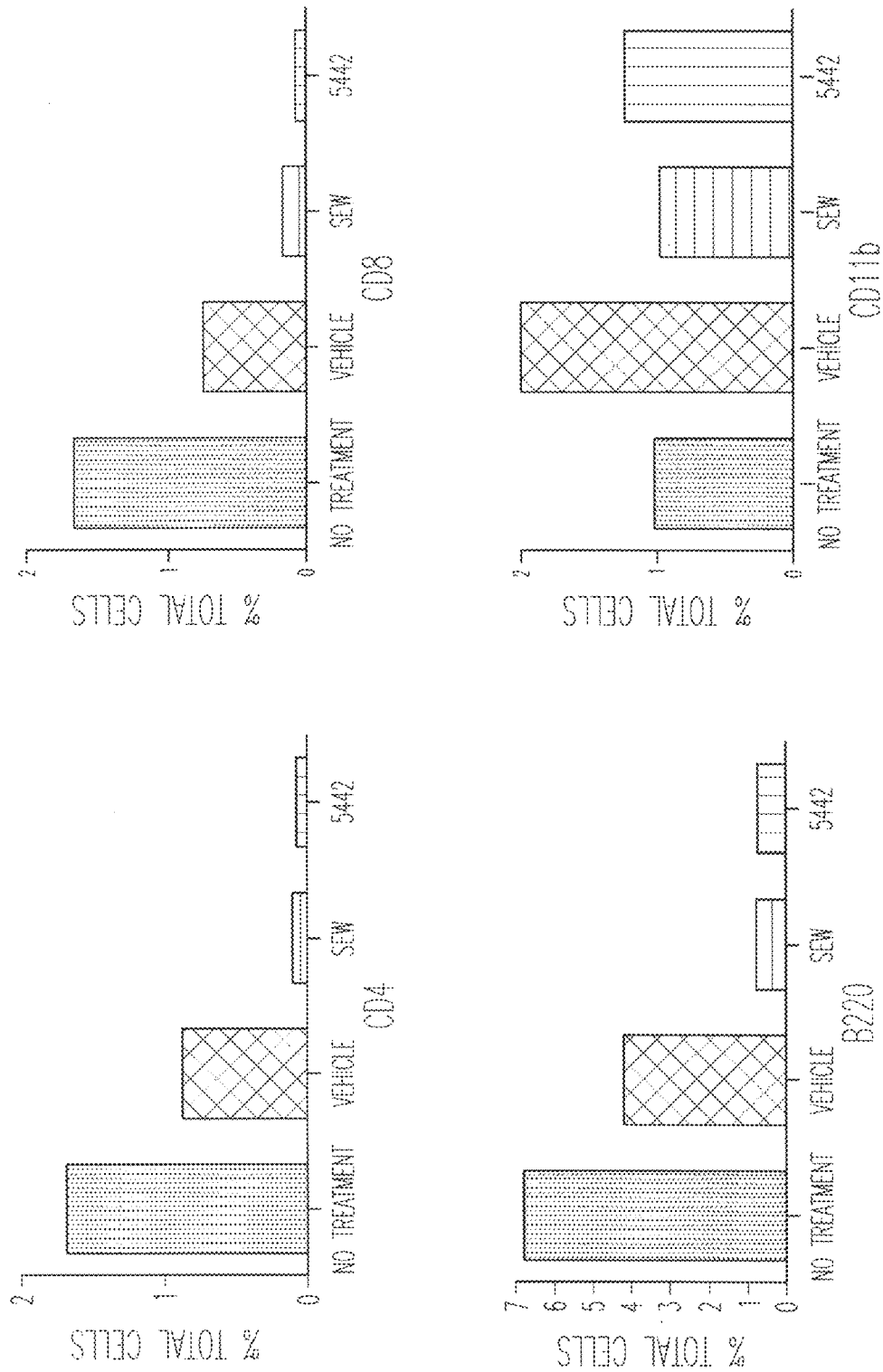
FIG. 4 shows compound 236 induces lymphopenia in mice. The compound was dissolved in 10% DMSO, Tween-20 and delivered by gavage.
Figure 4B:
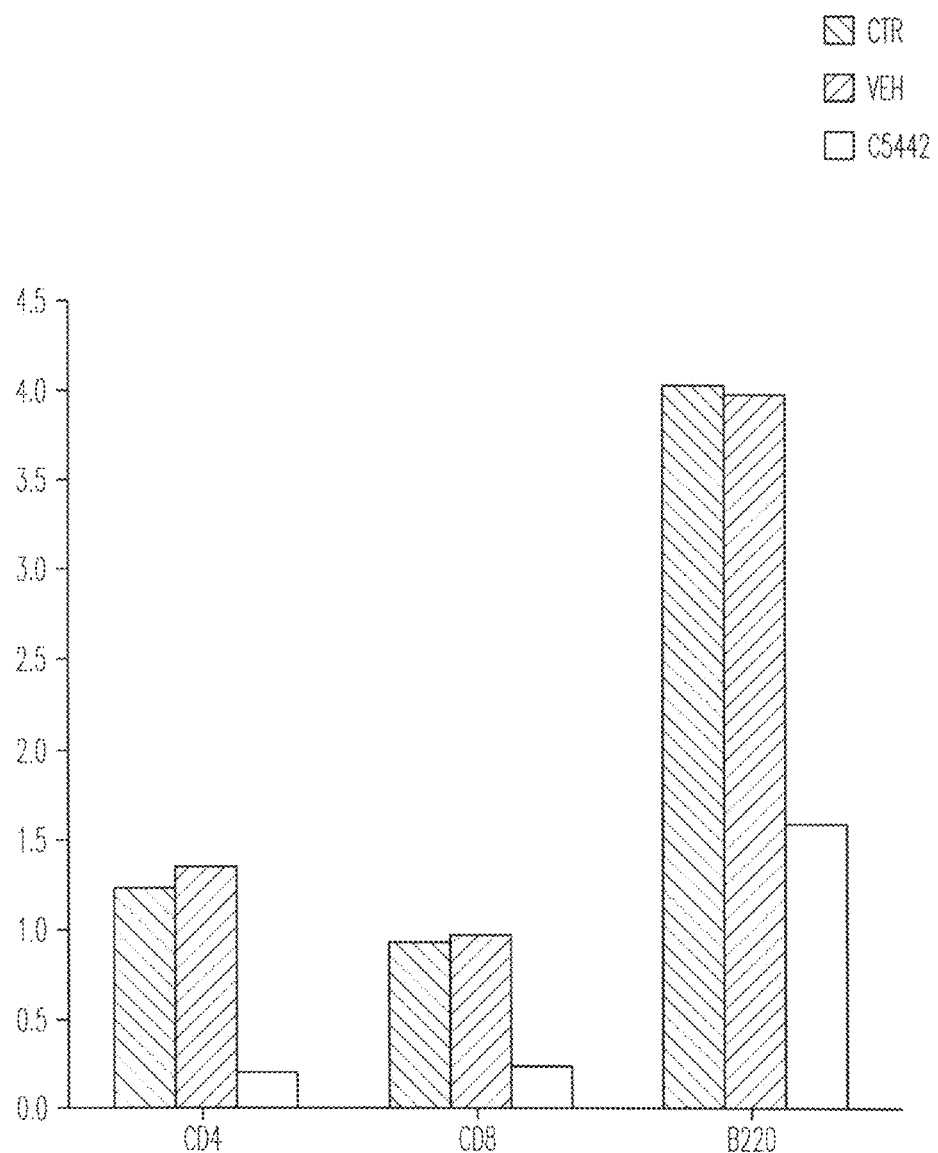

It was observed that S1P and the S1P1 specific agonist, SEW2897 induce lymphopenia (Wei, Rosen et al. 2005). SR-917 and compound 32, delivered by gavage, did not induce lymphopenia in mice. Compound 236, at 10 mgpk by gavage, induced lymphopenia; see FIG. 4. Compound 236 is soluble in water at 0.5 mg/mL and both i.v. and i.p. delivery induce lymphopenia (Sanna, Leaf).

Pharmacokinetics

Figure 5:
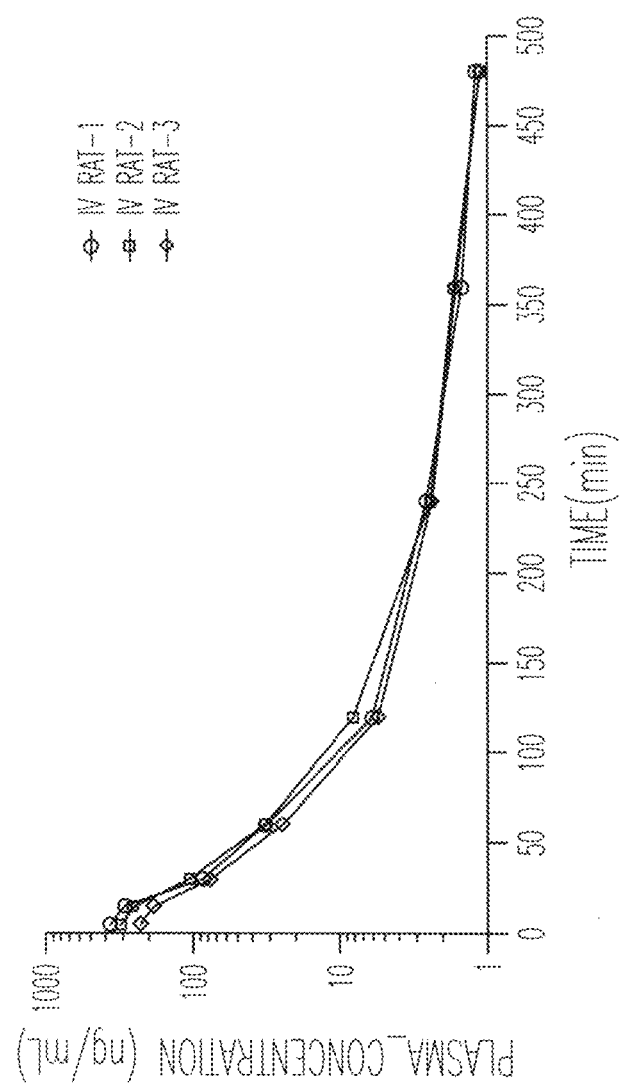
FIG. 5 shows a pharmacokinetic study of SR-917 1 mg/mL in 10/10/1980 DMSO/Tween/Water delivered 1 mg/kg i.v.

From the initial mouse efficacy studies (FIG. 5) plasma levels of Compound 236 at 5 hours were: 395/87.6 Mean/SD. Stability in hepatic microsomes for Compound 236 was species dependent. In human microsomes, the compound was very stable and moderately stable with rat. All were NADPH dependent. In the presence of 1.8 mg/ml hepatic microsomes the half lives (minutes) are human stable, Mouse 50, Rat 16.

Figure 6A:
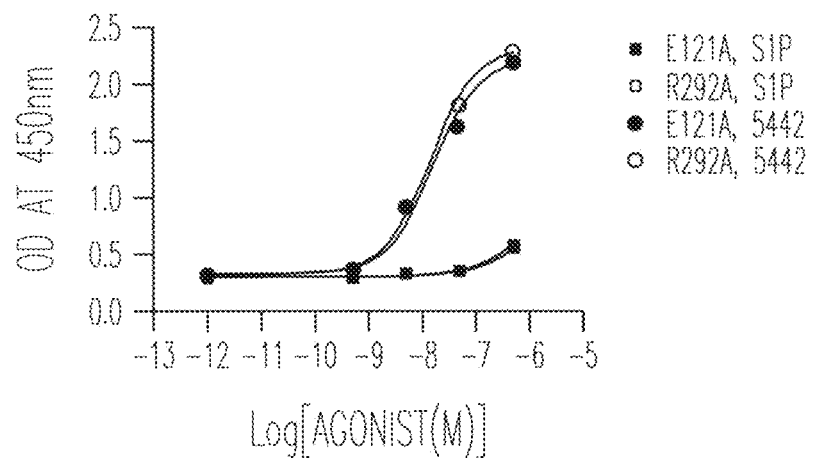
FIG. 6 shows S1P1 Polar Ligand Binding Pocket Mutations. CHO cells were transfected with S1P1 cDNA constructs. Cells were serum starved overnight and stimulated with 3-fold serial dilutions of S1P or CYM-5442. ERK1/2 phosphorylation was detected with the Phospho-ERK ELISA (Cell Signaling). A. S1P1 mutants E121A and R292A. B. wild type S1P1 (wt) and S1P1 mutants R120A.
Figure 6B:
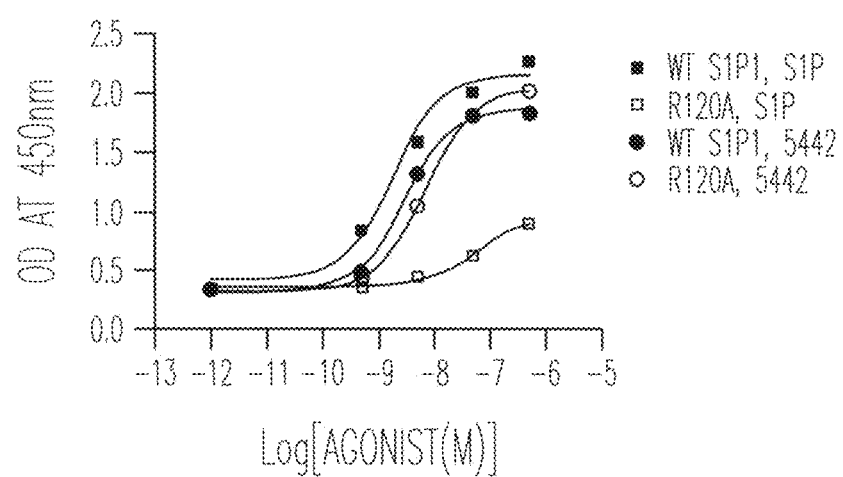

S1P1 polar amino acids essential for S1P mediated activation are not are required for S1P1 receptor activation by Compound 236. S1P requires several polar amino acids (R120, E121 and R292) that line the ligand binding pocket for complete activation (Jo, Sanna et al. 2005). The S1P1 polar side chains of residues R120, E121 and R29 forms saltbridges with the phosphate of S1P1 and the S1P can only minimally activate the R120A, E121A and R292A mutants. In contrast, wild-type S1P1 and R120A, E121A and R292A mutant S1P1 receptors are indistinguishably activated by Compound 236 (FIG. 6).

EXAMPLES

The following compounds were synthesized and evaluated in bioassays as described herein.

Synthetic Procedures

Solvents for extraction: ACS grade. Solvents for reaction: reagent grade. Reagents: unless otherwise noted, from Alfa Aesar, Fisher and Aldrich highest quality available. TLC: silica gel 60 $F_{254}$ aluminum plates, (whatman, type Al Sil G/UV, 250 μm layer); visualization by UV absorption. Flash chromatography was performed on silica gel 60 (0.40-0.63 mm, 230-440 mesh, EM Science). NMR: $^1$H: δ values in ppm (TMS as internal standard); $^{13}$C: δ values in ppm (TMS as internal standard)

Reactions were monitored by LC/MS.

General Procedure to Reduce Aldehyde:

To a stirred suspension of aldehyde (1.0 equiv, 0.4M) and silica gel (catalytic) in ethanol at 0° C. was added NaBH$_4$ (⅓ equiv). The reaction was allowed to warm up to room temperature and stirred for 2 h. The Solvent was removed under reduced pressure and the product purified by CC in hexane/EtOAc (7:3).

General Procedure to Synthesized Amidoximes:

To a stirred suspension of Hydroxylamine hydrochloride (1.1 equiv) and Na$_2$CO$_3$ (1.1 equiv) in ethanol was added, in one portion, the corresponding benzonitrile (1 equiv). The mixture was refluxed for 6 h followed by addition of NH$_2$OH.HCl (1.1 equiv) and Na$_2$CO$_3$ (1.1 equiv), the reaction was refluxed for additional 6 h. The suspension was cooled to room temperature and filtrated. The solid was washed with ethanol and the organic phase concentrated under reduced pressure. The amidoxime crude was recrystallized from EtOAc/Hexanes and used without further purification.

General Procedure to Synthesized Oxadiazoles:

To a stirring solution of 3,4-diethoxybenzoic acid (1 equiv, 0.2M) in DMF was added sequentially HOBt (1.3 equiv) and EDCI (1.3 equiv) at room temperature. The reaction was stirred for 20 min followed by addition, in a single portion, of the corresponding amidoxime (1.3 equiv, from previous step). The reaction was stirred for additional 30 min at room temperature and then heated to 90-95° C. for 8-14 h. The reaction was cooled to room temperature, diluted using a saturated solution of NaCl and extracted with EtOAc (3×). The organic phase was dried over Na$_2$SO$_4$ anhydrous and concentrated under reduced pressure. The product was purified by C.C. using CH$_2$Cl$_2$:MeOH (9:1) to offer the diaryloxadiazoles in moderated yields.

General Procedure to Synthesize Amines.

To a stirred solution of benzylalcohol (1 equiv) and pyridine (1.1 equiv) in CH$_2$Cl$_2$ at 0° C. was added drop wise SOCl$_2$ (1.1 equiv). The reaction was warmed up to room temperature, stirred for additional 1 h and concentrated under reduced pressure. To a stirred solution of crude chloride in CH$_2$Cl$_2$ at 0° C. was added dropwise a solution of pyrrolidine (3 equiv) in CH$_2$Cl$_2$. The reaction was allowed to warm up to room temperature and stirred for 2 h. The organic phase was washed with water and dried over Na$_2$SO$_4$ anhydrous. The crude was concentrated under reduced pressure and purified by column chromatography in DCM/MeOH to afford pyrrolidine derivatives in good yields.

Reduction of Indole-Derivatives.

To a stirred solution of Indole-core (1 equiv) in acetic acid at 13° C. was added slowly sodium cyanoborohydride (3 equiv). The reaction was stirred for 2 h at 13° C. and monitored by TLC. After completion of reaction the mixture was neutralize with 50% sodium hydroxide and the product extracted with ethyl acetate. The organic layer was dried over Na$_2$CO$_3$ and removed under reduced pressure. Indoline cores were purified by C.C. using CH$_2$Cl$_2$/MeOH (9:1) to offering quantitative yield.

Spectroscopic Data for Selected Compounds

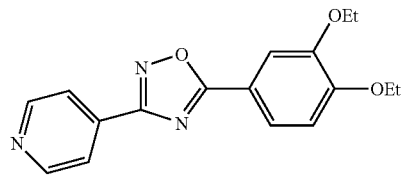 [SMILES: CCOc1ccc(-c2nc(-c3ccncc3)no2)cc1OCC]

$^1$H NMR (500 Hz, CDCl$_3$) δ: 8.80 (s, 2H), 8.03 (d, J=6.0 Hz, 2H), 7.80 (dd, J=8.5, 2.0 Hz, 1H), 7.67 (d, J=2.0 Hz, 1H), 6.99 (d, J=8.5 Hz, 1H), 4.23-4.16 (m, 4H), 1.53-1.44 (m, 6H). $^{13}$C NMR (125 Hz, CDCl$_3$) δ: 176.47, 167.23, 152.99, 150.48, 148.88, 134.68, 122.16, 121.38, 120.31, 116.08, 112.50, 112.25, 64.82, 64.60, 14.68, 14.60. MS. (M+1) 312.

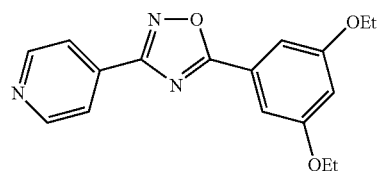 [SMILES: CCOc1cc(OCC)cc(-c2nc(-c3ccncc3)no2)c1]

$^1$H NMR (300 MHz, CDCl3) δ: 8.81 (brs, 2H), 8.06 (d, J=6.0 Hz, 2H), 7.32 (s, 1H), 7.31 (s, 1H), 6.68 (t, J=2.4 Hz, 1H), 4.10 (q, J=6.9 Hz, 4H), 1.45 (t, J=6.9 Hz, 6H); $^{13}$C NMR (75 MHz, CDCl3) δ: 176.68, 167.33, 160.64, 150.24, 134.96, 125.12, 121.62, 121.59, 106.64, 106.41, 64.06, 14.79. MS (M+1) 312

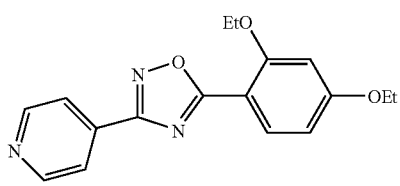 [SMILES: CCOc1ccc(-c2nc(-c3ccncc3)no2)c(OCC)c1]

¹H NMR (500 Hz, CDCl₃) δ: 8.80 (s, 2H), 8.05 (d, J=5.0 Hz, 2H), 7.65 (d, J=3.0 Hz, 1H), 7.11-7.09 (dd, J=9.0, 3.0 Hz, 1H), 7.02 (d, J=9.0 Hz, 1H), 4.18 (q, J=7.0 Hz, 2H), 4.08 (q, J=7.0 Hz, 2H), 1.52 (t, J=7.0 Hz, 3H), 1.44 (t, J=7.0 Hz, 3H). ¹³C NMR (125 Hz, CDCl₃) δ: 175.92, 166.66, 152.78, 152.44, 150.48, 134.73, 121.53, 116.36, 115.86, 115.40, 113.89, 113.82, 113.69, 65.62, 64.30, 14.84, 14.80. MS. (M+1) 312.

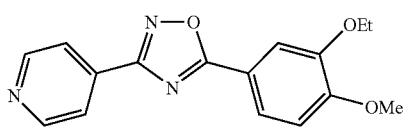 [SMILES: CCOc1cc(-c2nc(-c3ccncc3)no2)ccc1OC]

¹H NMR (300 Hz, CDCl₃) δ: 8.81 (s, 2H), 8.04 (d, J=4.5 Hz, 2H), 7.82 (dd, J=8.4, 2.0 Hz, 1H), 7.66 (d, J=2.0 Hz, 1H), 7.00 (d, J=8.4 Hz, 1H), 4.22 (q, J=7.0 Hz, 2H), 3.97 (s, 3H), 1.53 (t, J=7.0 Hz). ¹³C NMR (125 Hz, CDCl₃) δ: 176.53, 167.28, 153.48, 150.41, 148.75, 134.89, 122.18, 116.30, 111.62, 111.36, 64.72, 56.20, 14.75. MS. (M+1) 298.

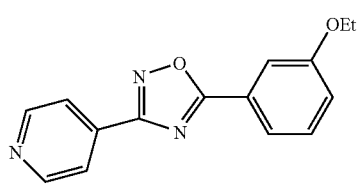 [SMILES: CCOc1cccc(-c2nc(-c3ccncc3)no2)c1]

¹H NMR (500 Hz, CDCl₃) δ: 8.81 (s, 2H), 8.04 (d, J=6.0 Hz, 2H), 7.80 (d, J=7.5 Hz, 1H), 7.71-7.70 (m, 1H), 7.47 (t, J=8.5 Hz, 1H), 7.16 (d, J=8.5 Hz, 1H), 4.16 (q, J=7.0 Hz, 2H), 1.48 (t, J=7.0 Hz, 3H). ¹³C NMR (125 Hz, CDCl₃) δ: 176.48, 167.38, 159.39, 150.53, 134.50, 130.32, 129.40, 124.82, 121.39, 120.46, 120.03, 115.92, 113.32, 63.88, 14.70. MS. (M+1) 268.

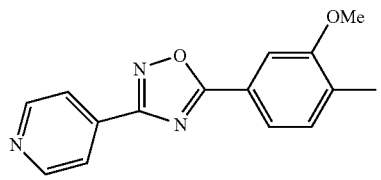 [SMILES: COc1cc(-c2nc(-c3ccncc3)no2)ccc1C]

¹H NMR (500 Hz, CDCl₃) δ: 8.81 (s, 2H), 8.05 (d, J=4.5 Hz, 2H), 7.73 (d, J=8.0 Hz, 1H), 7.60 (s, 1H), 7.31 (d, J=7.5 Hz, 1H), 3.96 (s, 3H), 2.31 (s, 3H). ¹³C NMR (125 Hz, CDCl₃) δ: 176.71, 167.31, 158.13, 150.51, 134.60, 133.06, 131.24, 130.10, 122.33, 121.41, 120.56, 118.84, 108.90, 55.58, 16.62. MS. (M+1) 268.

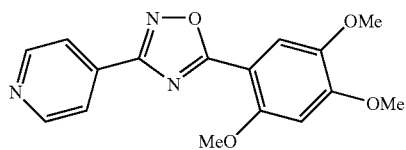 [SMILES: COc1cc(OC)c(-c2nc(-c3ccncc3)no2)cc1OC]

¹H NMR (300 MHz, CDCl₃) δ: 8.84 (bs, 2H), 8.35 (d, J=4.5 Hz, 2H), 7.64 (s, 1H), 6.63 (s, 1H), 4.03 (s, 3H), 4.01 (s, 3H), 3.96 (s, 3H). MS (M+1) 314.

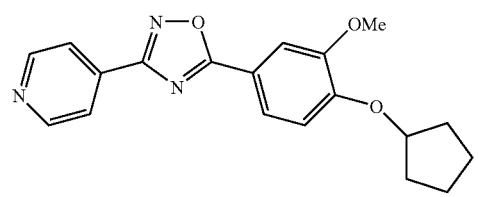 [SMILES: COc1cc(-c2nc(-c3ccncc3)no2)ccc1OC1CCCC1]

¹H NMR (300 MHz, CDCl₃) δ: 8.80 (bs, 2H), 8.04 (bs, 2H), 7.78 (dd, J=8.4, 2.1 Hz, 1H), 7.65 (d, J=9.3 Hz, 1H), 6.97 (d, J=5.1 Hz, 1H), 4.92-4.88 (m, 1H), 3.93 (s, 3H), 2.03-1.82 (m, 6H), 1.66-1.61 (m, 2H); ¹³C NMR (75 MHz, CDCl₃) δ: 176.31, 167.01, 153.95, 150.20, 147.79, 134.61, 121.75, 119.99, 115.94, 113.98, 113.96, 113.32, 111.35, 110.87, 80.91, 55.91, 32.59, 23.93. MS (M+1) 338.

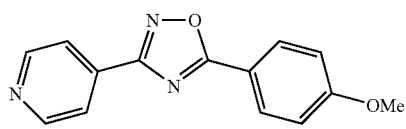 [SMILES: COc1ccc(-c2nc(-c3ccncc3)no2)cc1]

¹H NMR (300 MHz, CDCl₃) δ: 8.83 (d, J=5 Hz, 2H), 8.24 (d, J=5 Hz, 2H), 8.15 (d, J=8.7 Hz, 2H), 7.05 (d, J=8.7 Hz, 2H), 3.91 (s, 3H). MS (M+1) 254.

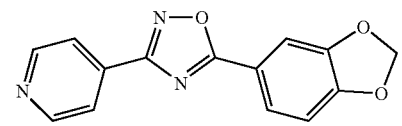 [SMILES: c1cc(-c2noc(-c3ccc4c(c3)OCO4)n2)ccn1]

¹H NMR (300 MHz, CDCl₃) δ: 8.86 (bs, 2H), 8.34 (bs, 2H), 7.82 (dd, J=8.1, 1.7 Hz, 1H), 7.63 (d, J=1.7 Hz, 1H), 6.99 (d, J=8.1 Hz, 1H), 6.12 (s, 2H). MS (M+1) 268.

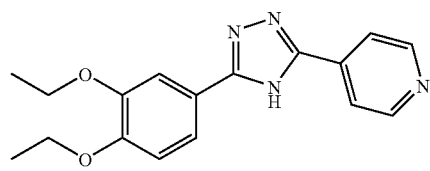 [SMILES: CCOc1ccc(-c2nnc(-c3ccncc3)[nH]2)cc1OCC]

4-(5-(3,4-diethoxyphenyl)-4H-1,2,4-triazol-3-yl)pyridine

Cold 4M HCl in dioxane (31.5 mmol, 8.87 mL) was added to a stirred solution of 3,4-diethoxybenzonitrile (7.84 mmol, 1.5 g) in anhydrous MeOH (23.53 mmol, 954 µl) and anhydrous ether (4 mL). The reaction was stirred at 0° C. for 1 h and then placed in the refrigerator (0-5° C.) for 48 h. To the mixture was bubbles N₂ to eliminate HCl and concentrated under reduced pressure. To the crude was added ether anhydrous and the methyl 3,4-diethoxybenzimidate precipitate as pale orange solid in 63% yield (1.3 g). The product was used without further purification.

To a stirred solution of the imidine (0.5 mmol, 130 mg) (freshly liberated using a solution 1M of Na₂CO₃ and extracted with ether) in acetonitrile was added pyridine-4-carbohydrazide (0.55 mmol, 75.5 mg) and the reaction was reflux for 2 h. The mixture was concentrated under reduced pressure and the crude was heated at 180° C. for 2 h. The product was purified by C.C. using CH₂Cl₂:MeOH (9:1) to offer the product as a with solid in 65% yield.

¹H NMR (400 MHz, CDCl₃) δ: 8.71 (bs, 2H), 8.11 (d, J=5.2 Hz, 2H), 7.60 (s, 1H), 7.57 (d, J=8.4 Hz, 1H), 6.90 (d, J=8.4, 1H), 4.11 (q, J=6.8 Hz, 2H), 4.07 (q, J=6.8 Hz, 2H), 1.45 (t, J=7.0 Hz, 3H), 1.40 (t, J=7.0 Hz, 3H). ¹³C NMR (CDCl₃): 157.73, 150.89, 149.42, 149.14, 139.66, 121.29, 120.56, 120.06, 119.68, 113.00, 111.53, 64.82, 64.72, 14.90, 14.86. MS (M+1) 311

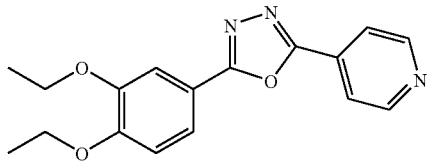

2-(3,4-diethoxyphenyl)-5-(pyridin-4-yl)-1,3,4-oxadiazole (25)

To a stirred solution of 3,4-diethoxybenzoic acid (0.71 mmol, 150 mg) in CH₂Cl₂ was added SOCl₂ at room temperature and the reaction was refluxed for 1.5 h. The mixture was concentrated under reduced pressure.

To a stirred suspension of Na₂CO₃ (1.42 mmol, 150.52 mg) and pyridine-4-carbohydrazide (0.71 mmol, 97 mg) in NMP (0.8 mL) was added a solution of 3,4-diethoxybenzoylchloride (prepare above) in NMP (0.8 mL). The reaction was stirred for 12 h at room temperature, poured to 20 mL of cold H₂O and filtered. The precipitated intermediate was dried in vacuo. The solid was added to POCl₃ (5 mL) and heated to 70-72° C. for 6 h. The solution was poured in an ice-water container and neutralized with a solution of NaOH (2M). The precipitated product was filtered and purified by C.C. using CH₂Cl₂:MeOH (9:1) to yield the product in 67% yield (150 mg).

¹H NMR (400 MHz, CDCl₃) δ: 8.84 (bs, 2H), 7.99 (d, J=4.4 Hz, 2H), 7.67 (dd, J=2.0, 8.4 Hz, 1H), 7.64 (d, J=2.0 Hz, 1H), 6.98 (d, J=8.4 Hz, 1H), 4.20 (q, J=7.2 Hz, 2H), 4.18 (q, J=7.2 Hz, 2H), 1.51 (t, J=7.2 Hz, 3H), 1.50 (t, J=7.2 Hz, 3H). ¹³C NMR (CDCl₃) δ: 165.81, 162.46, 152.51, 150.84, 149.20, 131.52, 128.05, 120.97, 115.77, 112.78, 111.58, 65.05, 64.80, 14.92, 14.85. MS (M+1)

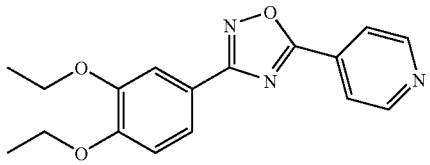 [SMILES: CCOc1ccc(-c2noc(-c3ccncc3)n2)cc1OCC]

3-(3,4-diethoxyphenyl)-5-(pyridin-4-yl)-1,2,4-oxadiazole

To a stirred solution of triethylamine (2 equiv) and NH₂OH.HCl (2 equiv) in ethanol was added 3,4-diethoxybenzonitrile (1 equiv) and the reaction was reflux overnight. The reaction was concentrated under reduced pressure. The crude was dissolved in AcOEt and extracted with water. The organic portion was dried over Na₂SO₄ anhydrous and concentrated under reduced pressure. The crude was used without further purification.

To a stirred solution of isonicotinic acid (1 equiv) in DMF (in a microwave vial) was added EDCI (1.3 equiv) and HOBt (1.3 equiv), the reaction was stirred for 5 min at room temperature followed by addition of the amidoxime (1.3 equiv) prepare above. The reaction was stirred for additional 10 min, at room temperature then heated at 170° C. for 5 min in the microwave. The reaction was diluted using a saturated solution of NaCl and extracted with EtOAc (3×). The organic phase was dried over Na₂SO₄ anhydrous and concentrated under reduced pressure. The product was purified by C.C. using CH₂Cl₂:MeOH (9:1) to yield the oxadiazole in % yield.

¹H NMR (300 MHz, CDCl3) δ: 8.85 (d, J=5.4 Hz, 2H), 8.02 (d, J=6.0 Hz, 2H), 7.71 (dd, J=8.1, 1.8 Hz, 1H), 7.62 (d, J=2.1 Hz, 1H), 6.95 (d, J=8.4 Hz, 1H), 4.19 (q, J=6.9 Hz, 2H), 4.14 (q, J=6.9 Hz, 2H), 1.50 (t, J=3.0 Hz, 3H), 1.46 (t, J=3.3 Hz, 3H); ¹³C NMR (75 MHz, CDCl₃) δ: 173.54, 16928, 151.64, 151.07, 148.91, 131.37, 121.48, 121.15, 118.75, 112.74, 111.82, 64.78, 64.59, 14.87, 14.81; MS (M+1) 312.

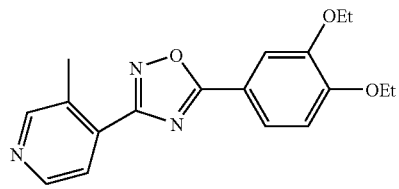 [SMILES: CCOc1ccc(-c2nc(-c3ccncc3C)no2)cc1OCC]

¹H NMR (500 Hz, CDCl₃) δ: 8.63-8.61 (m, 1H), 7.99 (d, J=5 Hz, 1H), 7.80 (dd, J=8.5, 2.0 Hz, 1H), 7.67 (d, J=1.5 Hz, 1H), 7.00 (d, J=8.5 Hz, 1H), 4.23-4.17 (m, 4H), 2.68 (s, 3H), 1.52-1.49 (m, 6H). ¹³C NMR (125 Hz, CDCl₃) δ: 175.43, 167.82, 152.93, 152.24, 148.88, 147.62, 133.73, 132.32, 123.10, 122.14, 116.13, 112.52, 112.29, 64.81, 64.60, 19.00, 14.69, 14.61. MS. (M+1) 326.

191

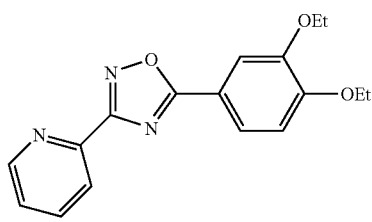 [SMILES: CCOc1ccc(-c2nc(-c3ccccn3)no2)cc1OCC]

¹H NMR (500 Hz, CDCl₃) δ: 8.84 (dt, J=3.0, 1.0 Hz, 1H), 8.76 (dd, J=7.5, 1.0 Hz, 1H), 7.85-7.84 (m, 1H), 7.75 (d, J=2.0 Hz, 1H), 7.45-7.42 (m, 1H), 6.98 (d, J=8.5 Hz, 1H), 4.22-4.16 (m, 4H), 1.51 (t, J=7.0 Hz, 6H). ¹³C NMR (125 Hz) δ: 176.50, 168.61, 152.79, 150.35, 148.80, 146.62, 136.99, 125.36, 123.20, 122.21, 116.33, 112.40, 64.81, 64.55, 14.70, 14.60. MS. (M+1) 312.

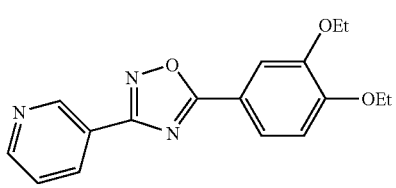 [SMILES: CCOc1ccc(-c2nc(-c3cccnc3)no2)cc1OCC]

¹H NMR (500 Hz, CDCl₃) δ: 9.40 (s, 1H), 8.76 (d, J=3.0 Hz, 1H), 8.45 (d, J=8.0 Hz, 1H), 7.82 (dd, J=8.5, 2.0 Hz, 1H), 7.69 (d, J=2.0 Hz, 1H), 7.47-7.44 (m, 1H), 7.00 (d, J=8.5 Hz, 1H), 4.24-4.17 (m, 4H), 1.53-1.50 (m, 6H). ¹³C NMR (125 Hz, CDCl₃) δ: 176.19, 166.82, 152.92, 151.68, 148.89, 148.56, 134.90, 122.67, 122.15, 120.32, 116.23, 112.52, 112.29, 64.84, 64.61, 14.70, 14.62. MS. (M+1) 312.

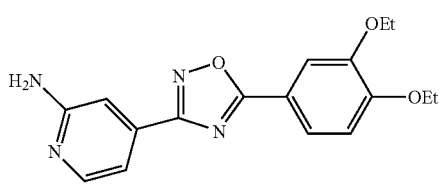 [SMILES: CCOc1ccc(-c2nc(-c3ccnc(N)c3)no2)cc1OCC]

¹H NMR (500 Hz, CDCl₃) δ: 8.22 (d, J=4.5 Hz, 2H), 7.79 (dd, J=8.5, 2.0 Hz, 1H), 7.66 (d, J=2.0 Hz, 1H), 7.37 (d, J=5.0 Hz, 1H), 7.26 (s, 1H), 6.99 (d, J=8.5 Hz, 1H), 4.77-4.71 (m, 2H), 4.23-4.17 (m, 4H), 1.52-1.49 (m, 6H). ¹³C NMR (125 Hz, CDCl₃) δ: 176.20, 167.51, 158.85, 152.90, 148.86, 148.78, 136.32, 122.11, 116.22, 112.50, 112.25, 111.76, 106.58, 64.82, 64.61, 14.70, 14.61. MS. (M+1) 327.

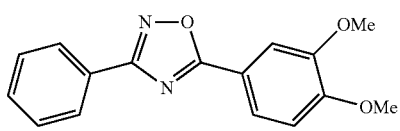 [SMILES: COc1ccc(-c2nc(-c3ccccc3)no2)cc1OC]

¹H NMR (300 Hz, CDCl₃) δ: 8.18-8.15 (m, 2H), 7.80 (dd, J1=1.8 Hz, J2=8.4 Hz, 1H), 7.69 (d, J=3.1 Hz, 1H), 7.53-7.48 (m, 3H), 6.99 (d, J=8.4 Hz, 1H), 4.23 (q, J=7.2 Hz, 2H), 4.19 (q, J=4.8 Hz, 2H), 1.53 (t, J=2.7 Hz, 3H), 1.49 (t, J=4.2 Hz, 3H); MS (M+1) 311.

192

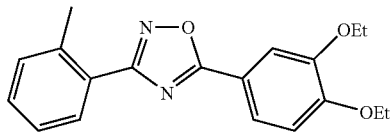 [SMILES: CCOc1ccc(-c2nc(-c3ccccc3C)no2)cc1OCC]

¹H NMR (300 MHz, CDCl₃) δ: 8.06 (dd, J=2.1, 8.7 Hz, 1H), 7.81 (dd, J=1.8, 8.4 Hz, 1H), 7.70 (d, J=2.1 Hz, 1H), 7.43-7.30 (m, 3H), 6.69 (d, J=8.7 Hz), 4.21 (q, J=6.9 Hz, 2H), 4.19 (q, J=6.9 Hz, 2H), 2.67 (s, 3H), 1.51 (t, J=7.2 Hz, 6H); ¹³C NMR (75 MHz, CDCl3) δ: 174.76, 169.45, 152.59, 148.80, 138.22, 131.33, 130.53, 130.49, 130.12, 126.45, 125.98, 122.01, 116.69, 112.48, 112.25, 64.79, 64.09, 22.08, 14.75; MS 325 (M+1)

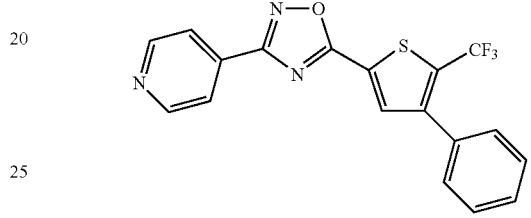

¹H NMR (300 MHz, CDCl₃) δ: 8.82 (bs, 2H), 8.02 (d, J=2.7, 2H), 7.93 (q, J=1.5 Hz, 1H), 7.47 (s, 5H); ¹³C NMR (75 MHz, CDCl₃) δ: 171.12, 167.81, 150.86, 145.70, 135.09, 134.12, 133.14, 123.32, 129.04, 126.35, 126.33, 121.67, 120.21, 105.04; MS 374 (M+1).

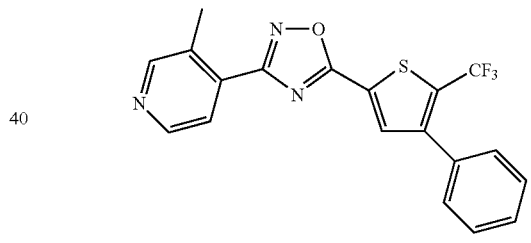

¹H NMR (300 MHz, CDCl₃) δ: 8.63 (brs, 2H), 7.95 (d, J=5.1 Hz, 1H), 7.912 (t, J=1.5 Hz, 1H), 7.462 (s, 5H), 2.67 (s, 3H); ¹³C NMR (75 MHz, CDCl₃) δ: 170.06, 168.32, 152.51, 147.88, 145.63, 145.60, 134.93, 133.13, 132.69, 129.26, 128.85, 126.40, 120.18, 105.01, 19.38; MS 388 (M+1)

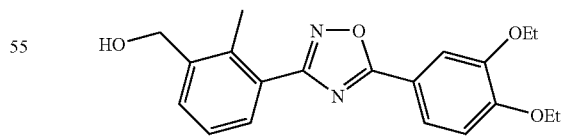

H¹ NMR (400 MHz, CDCl₃) δ: 7.83 (d, J=7.6 Hz, 1H), 7.79 (dd, J=2, 8.4 Hz, 1H), 7.68 (d, J=2 Hz, 1H), 7.32 (t, J=8 Hz, 1H), 6.98 (d, J=8.0 Hz, 1H), 4.78 (s, 2H) 4.18 (q, J=7.2 Hz, 4H), 2.55 (s, 3H), 1.50 (t, J=6.8 Hz, 6H). ¹³C NMR (CDCl₃) δ: 175.2, 169.8, 152.9, 149.0, 140.2, 136.3, 130.0, 129.9, 127.6, 126.1, 122.2, 116.7, 112.7, 112.4, 65.0, 64.8, 63.8, 16.4, 14.9. MI (M+1)

193

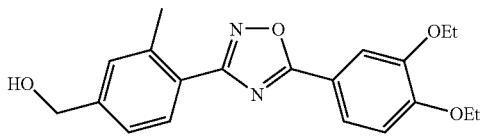 [SMILES: CCOc1ccc(-c2nc(-c3ccc(CO)cc3C)no2)cc1OCC]

¹H NMR (500 MHz, CDCl₃) δ: 8.05 (d, J=7.5 Hz, 1H), 7.80 (dd, J=8.0 Hz, 2.0 Hz, 1H), 7.68 (d, J=2.0 Hz, 1H), 7.31-7.29 (m, 2H), 6.99 (d, J=8.5 Hz, 1H), 4.73 (s, 2H), 4.21-4.18 (m, 4H), 2.66 (s, 3H), 1.52 (dt, J=7.0 Hz, 1 Hz, 6H). ¹³C NMR (125 MHz, CDCl₃) δ: 174.70, 169.17, 152.59, 148.78, 143.23, 138.45, 130.34, 129.57, 125.56, 124.18, 121.18, 121.99, 116.60, 112.51, 112.32, 64.78, 64.57, 22.07, 14.69, 14.61. MS. (M+1) 355.

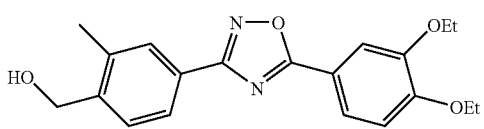 [SMILES: CCOc1ccc(-c2nc(-c3ccc(CO)c(C)c3)no2)cc1OCC]

¹H NMR (500 MHz, CDCl₃) δ: 7.968-7.94 (m, 2H), 7.79 (dd, J=8.5 Hz, 1.5 Hz, 1H), 7.68 (d, J=2.0 Hz, 1H), 7.50 (d, J=8.0 Hz, 1H), 6.98 (d, J=8.0 Hz, 1H), 4.75 (s, 2H), 4.23-4.16 (m, 4H), 2.40 (s, 3H), 1.52 (dt, J=7.0 Hz, 1 Hz, 6H). ¹³C NMR (125 MHz, CDCl₃) δ: 175.62, 168.61, 164.61, 152.61, 148.77, 141.82, 136.39, 129.06, 127.47, 126.14, 125.20, 122.0, 116.59, 112.47, 112.28, 64.78, 64.56, 63.05, 18.57, 14.69, 14.61. MS. (M+1) 355.

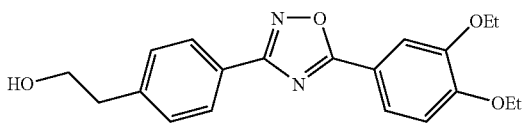 [SMILES: CCOc1ccc(-c2nc(-c3ccc(CCO)cc3)no2)cc1OCC]

1H NMR (300 MHz, CDCl₃) δ: 8.06 (d, J=8.1 Hz, 2H), 7.76 (dd, J=1.5, 9.9 Hz, 1H), 7.66 (d, J=1.8 Hz, 1H), 7.34 (d, J=8.1 Hz, 2H), 6.96 (d, J=8.4 Hz, 1H), 4.21 (q, J=7.2 Hz, 2H), 4.16 (q, J=6.9 Hz, 2H), 3.88 (t, J=6.6 Hz, 2H), 2.91 (t, J=6.6 Hz, 2H), 1.51 (t, J=1.5, 3H), 1.48 (t, J=1.2 Hz, 3H); ¹³C NMR (75 MHz, CDCl₃) δ: 175.54, 168.52, 152.49, 148.64, 141.98, 132.14, 129.72, 127.59, 125.17, 121.93, 116.46, 112.31, 112.07, 64.68, 64.47, 63.25, 39.07, 14.64. MS 355 (M+1)

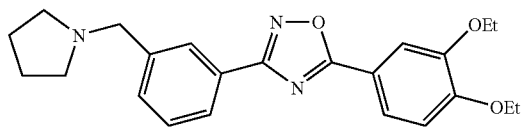 [SMILES: CCOc1ccc(-c2nc(-c3cccc(CN4CCCC4)c3)no2)cc1OCC]

H¹ NMR (400 MHz, CDCl₃) δ: 8.11 (s, 1H), 8.05 (d, J=7.6 Hz, 1H), 7.79 (dd, J=2.0, 8.4 Hz, 1H), 7.55 (d, J=7.6 Hz, 1H), 7.46 (t, J=7.6 Hz, 1H), 6.98 (d, J=8.4 Hz, 1H), 4.22 (q, J=7.2 Hz, 2H), 4.18 (q, J=7.2 Hz, 2H), 3.74 (s, 2H), 2.60 (s, 4H), 1.82 (s, 4H), 1.52 (t, J=7.0 Hz, 3H), 1.50 (t, J=7.0 Hz, 3H). ¹³C NMR (CDCl₃) δ: 175.87, 169.02, 152.80, 148.98, 132.02, 129.09, 128.21, 127.27, 126.51, 122.20, 116.85, 112.64, 112.44, 64.99, 64.77, 60.47, 54.31, 23.69, 14.93, 14.85. MI (M+1) 394.

194

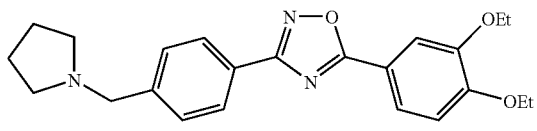

¹H NMR (400 MHz, CDCl₃) δ: 8.07 (d, J=8.4 Hz, 2H), 7.74 (dd, J=1.6, 8.4 Hz, 1H), 1.64 (d, J=1.6 Hz, 1H), 7.44 (d, J=8.0 Hz, 2H), 6.92 (d, J=8.4 Hz, 1H), 4.17 (q, J=7.2 Hz, 2H), 4.12 (q, J=7.2 Hz, 2H), 3.68 (s, 2H), 2.54 (s, 4H), 1.77 (s, 4H), 1.47 (t, J=7.0 Hz, 3H), 1.45 (t, J=7.0 Hz, 3H). ¹³C NMR (CDCl₃) δ: 175.68, 168.72, 152.65, 148.82, 142.13, 129.42, 127.54, 125.95, 122.05, 116.67, 112.50, 112.27, 64.82, 64.61, 60.31, 54.14, 23.51, 14.79, 14.71. MI (M+1) 394.

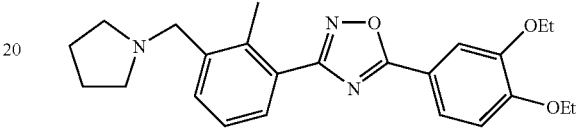

H¹ NMR (400 MHz, CDCl₃) δ: 7.79 (dd, J=2.0, 8.4 Hz, 1H), 7.77 (d, J=7.6 Hz, 1H), 7.68 (d, J=2.0 Hz, 1H), 7.50 (d, J=7.6 Hz, 1H), 7.28 (t, J=7.6 Hz, 1H), 6.98 (d, J=8.4 Hz, 1H), 4.20 (q, J=7.0 Hz, 2H), 4.19 (q, J=7.0 Hz, 2H), 3.72 (s, 2H), 2.59 (s, 4H), 1.80 (s, 4H), 1.50 (t, J=7.0 Hz, 6H). ¹³C NMR (CDCl₃) δ: 175.06, 170.12, 152.77, 148.98, 137.18, 131.98, 129.40, 127.50, 125.75, 122.17, 116.84, 112.66, 112.40, 64.95, 64.77, 58.51, 54.42, 23.74, 16.80, 14.91, 14.84.

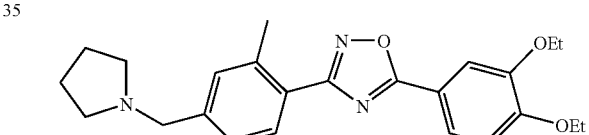

¹H NMR (500 Hz, CDCl₃) δ: 8.01 (d, J=7.5 Hz, 1H), 7.81 (dd, J=8.5 Hz, 2 Hz, 1H), 7.69 (d, J=2 Hz, 1H), 7.32-7.31 (m, 2H), 6.99 (d, J=8.5 Hz, 1H), 4.23-4.17 (m, 4H), 3.67 (s, 2H), 2.65 (s, 3H), 2.56 (s, 4H), 1.83-1.80 (m, 4H), 1.52-1.49 (m, 6H). ¹³C NMR (125 Hz, CDCl₃) δ: 174.63, 169.33, 152.56, 148.80, 138.15, 131.78, 131.07, 126.46, 125.11, 121.96, 116.72, 112.54, 112.35, 64.78, 64.7, 60.32, 54.17, 23.46, 22.00, 14.70, 14.63. MS. (M+1) 408.

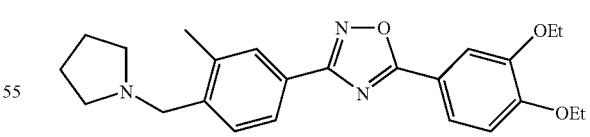

¹H NMR (500 MHz, CDCl₃) δ: 7.94-7.93 (m, 2H), 7.80 (dd, J=8.5 Hz, 2.0 Hz, 1H), 7.69 (d, J=2.0 Hz, 1H), 7.47 (d, J=8.0 Hz, 1H), 6.98 (d, J=8.5 Hz, 1H), 4.24-4.15 (m, 4H), 3.65 (s, 2H), 2.56-2.54 (m, 4H), 2.44 (s, 3H), 1.80-1.78 (m, 4H), 1.52 (q, J=7.0 Hz, 6H). ¹³C NMR (125 MHz, CDCl₃) δ: 175.49, 168.80, 152.54, 148.76, 140.88, 137.34, 129.51, 128.95, 125.39, 124.82, 121.94, 116.71, 112.46, 112.29, 64.76, 64.53, 57.82, 54.29, 23.55, 19.14, 14.68, 14.60. MS. (M+1) 408.

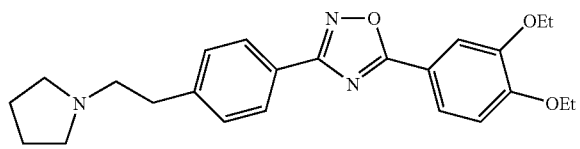 [SMILES: CCOc1ccc(-c2nc(-c3ccc(CCN4CCCC4)cc3)no2)cc1OCC]

¹H NMR (300 MHz, CDCl3) δ: 8.06 (d, J=8.0 Hz, 2H), 7.72 (dd, J=8.4, 2.0, 1H), 7.61 (d, J=2.0 Hz, 1H), 7.33 (d, J=8.4, 2H), 6.92 (d, J=8.4, 1H), 4.16 (q, J=6.8, 2H), 4.11 (q, J=6.8, 2H), 3.30-3.22 (m, 4H), 2.74-2.69 (m, 2H), 2.21-2.19 (m, 2H), 2.02 (m, 2H), 1.47 (t, J=10 Hz, 3H), 1.43 (t, J=3.6, 3H); MS 408 (M+1).

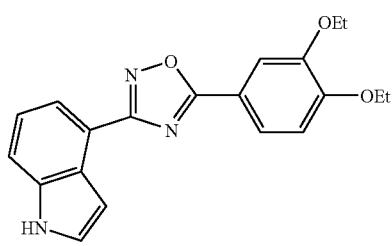 [SMILES: CCOc1ccc(-c2nc(-c3cccc4[nH]ccc34)no2)cc1OCC]

H¹ NMR (400 MHz, CDCl₃) δ: 8.01 (d, J=7.2 Hz, 1H), 7.81 (dd, J=8.4, 2.0 Hz, 1H), 7.52 (s, 1H), 7.52 (d, J=8.0 Hz, 1H), 7.34 (s, 1H), 7.28 (t, J=8.0 Hz, 1H), 7.23 (s, 1H), 6.96 (d, J=8.4 Hz, 1H), 4.18 (q, J=6.8 Hz, 2H), 4.16 (q, J=6.8 Hz, 2H), 1.47 (t, J=6.8 Hz, 3H), 1.46 (t, J=6.8 Hz, 3H). ¹³C NMR (CDCl₃) δ: 175.0, 169.5, 152.6, 148.9 (2), 125.7, 122.2, 121.8, 121.7, 121.3, 121.2, 117.0, 114.4, 114.3, 112.7, 112.5; MI (M+1) 350.

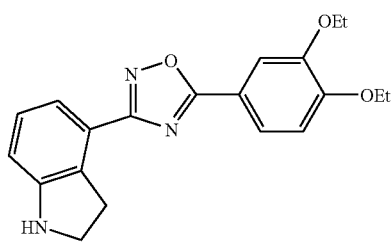 [SMILES: CCOc1ccc(-c2nc(-c3cccc4c3CCN4)no2)cc1OCC]

¹H NMR (300 MHz, CDCl₃) δ: 7.78 (dd, J=8.4, 2.1 Hz, 1H), 7.68 (d, J=1.8 Hz, 1H), 7.55 (d, J=7.8 Hz, 1H), 7.16 (t, J=7.5 Hz, 1H), 6.97 (d, J=7.5 Hz, 1H), 6.76 (d, J=7.5 Hz, 1H), 4.21 (q, J=6.9 Hz, 2H), 4.16 (q, J=6.9 Hz, 2H), 3.65 (brs, 2H), 3.46 (t, J=8.1 Hz, 2H), 1.52 (t, J=3.1 Hz, 3H), 1.48 (t, J=3.3 Hz, 3H); ¹³C NMR (75 MHz, CDCl3) δ: 175.05, 169.06, 152.62, 148.84, 127.84, 123.67, 122.09, 118.90, 116.83, 112.53, 112.32, 111.60, 64.86, 64.67, 47.29, 31.41, 14.85, 14.78. MS 352 (M+1)

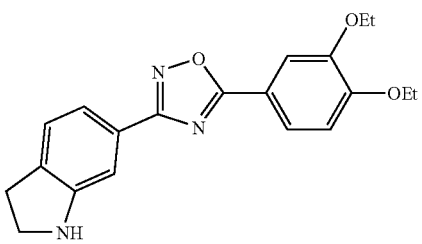 [SMILES: CCOc1ccc(-c2nc(-c3ccc4c(c3)NCC4)no2)cc1OCC]

¹H NMR (500 MHz, CDCl₃) δ: 7.80 (dd, J=8.5, 2 Hz, 1H), 7.69 (d, J=2.0 Hz, 1H), 7.45 (d, J=7.5 Hz, 1H), 7.14 (d, J=8.0 Hz, 2H), 6.97 (d, J=8.0 Hz, 1H), 4.24-4.15 (m, 4H), 3.98-3.95 (m, 1H), 3.43 (t, J=8.5 Hz, 2H), 3.01 (t, J=8.5 Hz, 2H), 1.52 (q, J=7.0 Hz, 6H), 1.20 (d, J=6.5 Hz, 6H). ¹³C NMR (125 MHz, CDCl₃) δ: 175.24, 169.48, 152.4, 148.74, 133.96, 126.11, 124.39, 121.93, 116.92, 112.46, 112.35, 105.03, 64.77, 64.52, 4.42, 28.42, 28.10, 18.18, 14.69, 14.60. MS. (M+1) 352.

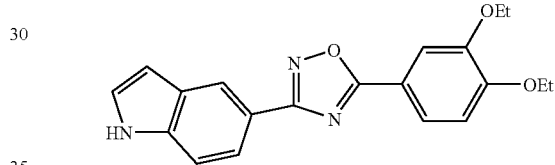

¹H NMR (500 MHz, CDCl₃) δ: 8.56 (s, 1H), 8.51 (s, 1H), 8.01 (dd, J=8.5 Hz, 1.5 Hz, 1H), 7.83 (dd, J=8.5 Hz, 2.0 Hz, 1H), 7.73 (d, J=1.5 Hz, 1H), 7.45 (d, J=8.5 Hz, 1H), 7.27-7.26 (m, 1H), 7.00 (d, J=8.5 Hz, 1H), 6.66-6.65 (m, 1H), 4.24-4.17 (m, 4H), 1.52-1.48 (m, 6H). ¹³C NMR (125 MHz, CDCl₃) δ: 175.26, 169.79, 152.44, 148.75, 137.33, 127.93, 125.27, 121.94, 121.27, 120.94, 118.77, 116.96, 112.51, 112.34, 111.43, 103.56, 64.78, 64.56, 14.70, 14.62. MS. (M+1) 350.

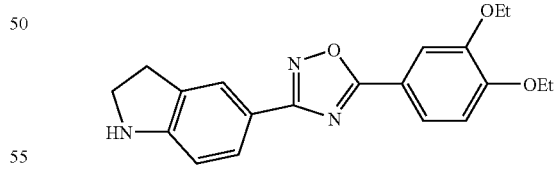

¹H NMR (500 MHz, CDCl₃) δ: 7.86-7.82 (m, 2H), 7.78 (dd, J=8.0 Hz, 2 Hz, 1H), 7.68 (d, J=2.0 Hz, 1H), 6.98 (d, J=8.5 Hz, 1H), 6.69 (d, J=8.0 Hz, 1H), 4.23-4.16 (m, 5H), 3.67 (t, J=8.5 Hz, 2H), 3.18 (t, J=8.0 Hz, 2H), 1.52-1.48 (m, 6H). ¹³C NMR (125 MHz, CDCl₃) δ: 175.00, 169.08, 154.04, 152.40, 148.73, 129.62, 127.89, 123.85, 121.87, 117.04, 116.98, 112.48, 112.32, 105.92, 64.76, 64.54, 47.28, 29.23, 14.71, 14.63. MS. (M+1) 352

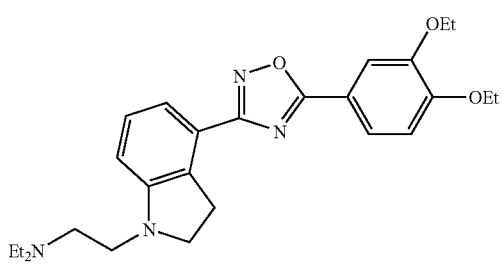

¹H NMR (300 MHz, CDCl₃) δ: 7.78 (dd, J=8.4, 2.1 Hz, 1H), 7.68 (d, J=2.1, 1H), 7.46 (d, J=7.8 Hz, 1H), 7.20 (t, J=9.6 Hz, 1H), 6.96 (d, J=8.4 Hz, 1H), 6.60 (d, J=7.8 Hz, 1H), 4.20 (q, J=7.2 Hz, 2H), 4.17 (q, J=7.2 Hz, 2H), 3.55 (t, J=1.8 Hz, 2H), 3.40 (t, J=7.2 Hz, 2H), 3.29 (t, J=7.2 Hz, 2H), 2.73 (t, J=7.8 Hz, 2H), 2.60 (q, J=7.2 Hz, 4H), 1.51 (t, J=2.1 Hz, 3H), 1.49 (t, J=1.8 Hz, 3H), 1.09 (t, J=7.2 Hz, 6H). ¹³C NMR (CDCl3) δ: 174.30, 168.39, 152.52, 151.93, 148.17, 129.32, 127.33, 122.70, 121.40, 116.75, 116.21, 111.87, 107.94, 104.24, 64.15, 52.82, 49.53, 46.92, 29.54, 14.15, 11.03; MS 451 (M+1).

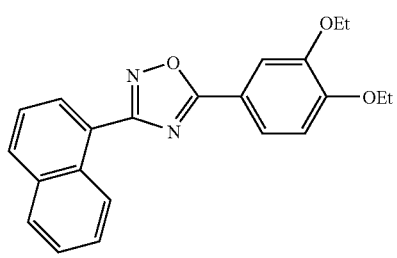 [SMILES: CCOc1ccc(-c2nc(-c3cccc4ccccc34)no2)cc1OCC]

¹H NMR (300 MHz, CDCl₃) δ: 8.95 (d, J=8.4 Hz, 1H), 8.33 (d, J=7.2 Hz, 1H), 8.02 (d, J=8.4 Hz, 1H), 7.94 (d, J=8.1 Hz, 1H), 7.86 (d, J=8.4 Hz, 1H), 7.74 (s, 1H), 7.65-7.54 (m, 3H), 7.0 (d, J=8.4 Hz, 1H), 4.23 (q, J=6.9 Hz, 2H), 4.20 (q, J=7.2 Hz, 2H), 1.52 (t, J=7.2 Hz, 6H); ¹³C NMR (75 MHz, CDCl₃) δ: 174.23, 168.57, 152.00, 148.15, 133.22, 131.00, 130.08, 128.65, 127.94, 126.82, 125.64, 124.44. 123.51, 121.44, 115.92, 111.81, 111.61, 64.13, 14.07. MS (M+23) 383.

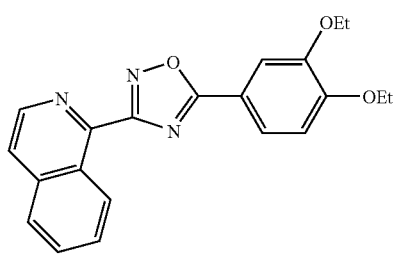 [SMILES: CCOc1ccc(-c2nc(-c3nccc4ccccc34)no2)cc1OCC]

¹H NMR (500 MHz, CDCl₃) δ: 9.03 (d, J=8.5 Hz, 1H), 8.80 (d, J=5.5 Hz, 1H), 7.94-7.90 (m, 2H), 7.84-7.71 (m, 4H), 7.01 (d, J=8.5 Hz, 1H), 4.23-4.17 (m, 4H), 1.52-1.49 (m, 6H). ¹³C NMR (125 Hz, CDCl₃) δ: 175.95, 168.38, 152.91, 148.84, 146.36, 142.37, 136.93, 130.70, 128.68, 127.20, 127.08, 123.04, 122.38, 122.37, 116.22, 112.62, 112.45, 64.86, 64.58, 14.72, 14.62. MS. (M+1) 362.

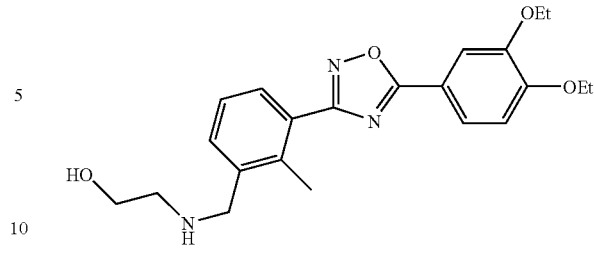

¹H NMR (500 MHz, CDCl₃) δ: 7.83 (d, J=7.5 Hz, 1H), 7.80 (dd, J=8.5 Hz, 2.0 Hz, 1H), 7.68 (d, J=2.0 Hz, 1H), 7.50 (d, J=7.0 Hz, 1H), 7.33 (t, J=7.5 Hz, 1H), 6.99 (d, J=8.5 Hz, 1H), 4.22-4.17 (m, 4H), 3.95 (s, 2H), 3.73-3.70 (m, 2H), 2.92-2.90 (m, 2H), 2.60 (s, 3H), 2.47 (s, 2H), 1.52-1.49 (m, 6H). ¹³C NMR (125 MHz, CDCl₃) δ: 174.95, 169.69, 152.68, 148.84, 137.99, 136.65, 132.75, 131.30, 129.76, 127.70, 125.93, 122.02, 116.58, 112.32, 64.80, 64.59, 60.51, 51.27, 50.68, 14.70, 14.63. MS. (M+1) 398.

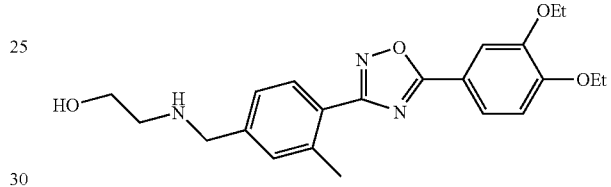

¹H NMR (500 MHz, CDCl₃) δ: 8.05 (d, J=8.0 Hz, 1H), 7.80 (dd, J=5.0 Hz, 2.0 Hz, 1H), 7.68 (d, J=2.0 Hz, 1H), 7.32-7.23 (m, 2H), 6.99 (d, J=8.5 Hz, 1H), 4.28-4.17 (m, 4H), 3.89-3.84 (m, 2H), 3.72-3.69 (m, 2H), 2.86 (s, 2H), 2.66 (s, 3H), 2.54-2.48 (m, 3H), 1.52 (dt, J=7.0 Hz, 1 Hz, 6H). ¹³C NMR (125 MHz, CDCl₃) δ: 174.72, 169.16, 152.63, 148.82, 138.52, 132.63, 131.27, 130.41, 129.78, 125.85, 125.61, 121.99, 116.65, 112.56, 112.37, 64.80, 64.59, 22.06, 14.71, 14.63. MS. (M+1) 398.

1-hydroxy-2,3-dihydro-1H-indene-4-carbonitrile

To a stirred suspension of 1-oxo-2,3-dihydro-1H-indene-4-carbonitrile (1.0 equiv, 0.4M) and silica gel (catalytic) in ethanol at 0° C. was added NaBH₄ (⅓ equiv). The reaction was allowed to warm up to room temperature and stirred for 2 h. The Solvent was removed under reduced pressure and the product purified by CC in hexane/EtOAc (5:5) to offer 1-hydroxy-2,3-dihydro-1H-indene-4-carbonitrile in 80% yield.

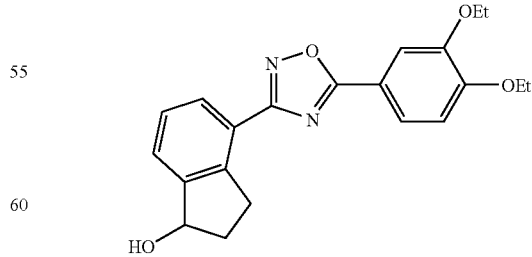

¹H NMR (400 MHz, CDCl₃) δ: 8.10 (d, J=7.6, 1H), 7.78 (dd, J=1.6, 8 Hz, 1H), 7.67 (d, J=1.6 Hz, 1H), 7.56 (d, J=7.6 Hz, 1H), 7.39 (t, J=7.6, 1H), 6.97 (d, J=8.0 Hz, 1H), 5.29 (t, J=6.4 Hz, 1H), 4.19 (q, J=7.2, 2H), 4.18 (q, J=7.2, 2H), 3.51-4.43 (m, 1H), 3.22-3.14 (m, 1H), 2.59-2.51 (m, 1H), 2.04-1.97 (m, 1H), 1.5 (t, J=7.2, 3H), 1.49 (t, J=7.2, 3H): $^{13}$C NMR (CDCl$_3$) δ: 175.2, 168.9, 152.8, 148.9, 146.6, 143.3, 128.9, 127.4, 127.0, 123.8, 122.2, 116.7, 112.7, 112.4, 76.2, 64.9, 64.8, 35.7, 31.5, 14.9, 14.8: MI (M+1) 367

4-(5-(3,4-diethoxyphenyl)-1,2,4-oxadiazol-3-yl)-2,3-dihydro-1H-inden-1-one

To a suspension of PCC (1.5 equiv.) and powdered molecular sieves (3 Å, one-half the weight of PCC) in dry CH$_2$Cl$_2$ was added the benzylic alcohol (1 equiv. prepared in previous step) at 0° C. The reaction mixture was stirred overnight at room temperature and concentrated under reduced pressure. To the residue was added Et$_2$O-EtOAc (1:1) and the slurry was stirred and filtered through a pad of Celite. The residue was washed 4 times with Et$_2$O-EtOAc (1:1). The filtrate was concentrated under reduced pressure and the product purified by CC offering the ketone in 70% yield.

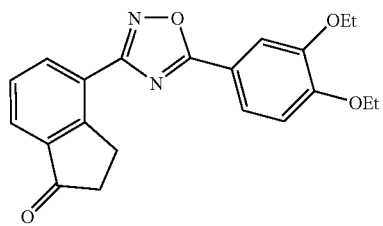 [SMILES: CCOc1ccc(-c2nc(-c3cccc4c3CCC4=O)no2)cc1OCC]

$^1$H NMR (500 MHz, CDCl$_3$) δ: 8.48 (dd, J=8.0 Hz, 1.5 Hz, 1H), 7.91 (d, J=7.5 Hz, 1H), 7.81 (dd, J=8.5 Hz, 2.0 Hz, 1H), 7.68 (d, J=2.0 Hz, 1H), 7.56 (t, J=7.5 Hz, 1H), 6.99 (d, J=8.5 Hz, 1H), 4.24-4.17 (m, 4H), 3.55-3.53 (m, 2H), 2.79-2.77 (m, 2H), 1.53-1.49 (m, 6H). $^{13}$C NMR (125 MHz, CDCl$_3$) δ: 206.62, 175.32, 167.79, 154.40, 152.86, 148.86, 138.22, 134.63, 127.72, 126.00, 125.55, 122.10, 116.32, 112.55, 112.36, 64.82, 64.60, 36.25, 27.61, 14.70, 14.61. MS. (M+1) 365.

Amination Procedure.

A solution of alcohol (1 equiv), at 0° C., was treated with SOCl$_2$ (1.1 equiv) and pyridine (1.1 equiv) in CH$_2$Cl$_2$. The reaction was stirred at room temperature for 2 h. The reaction was diluted with CH$_2$Cl$_2$ and washed with NaHCO$_3$ (2×). The organic phase was dried over sodium sulfate and concentrated under reduced pressure. The crude was dissolved in DMF and treated with the corresponding amine (2 equiv) and DIPEA (2.0 equiv). The reaction was stirred at 50° C. for 48 h. The reaction was diluted with H$_2$O and the product extracted with EtOAc (3×). The product was purified by C.C. using CH$_2$Cl$_2$/MeOH (9:1) to offer amino-diaryloxadiazoles in moderated yields.

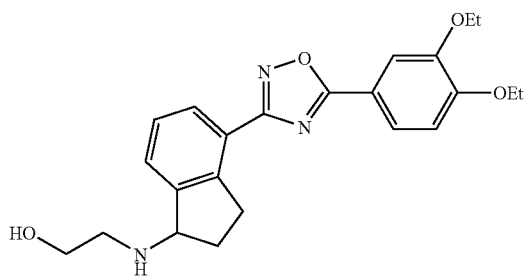 [SMILES: CCOc1ccc(-c2nc(-c3cccc4c3CCC4NCCO)no2)cc1OCC]

$^1$H NMR (500 MHz, CDCl$_3$) δ: 8.12 (d, J=7.5 Hz, 1H), 7.79 (dd, J=8.5, 2.0 Hz, 1H), 7.68 (d, J=2.0 Hz, 1H), 7.63 (d, J=7.5 Hz, 1H), 7.40-7.37 (m, 1H), 4.49-4.47 (m, 1H), 4.23-4.16 (m, 4H), 3.78-3.70 (m, 1H), 3.53-3.46 (m, 1H), 3.29-3.22 (m, 1H), 2.96-2.94 (m, 4H), 2.56-2.50 (m, 1H), 2.09-2.03 (m, 1H), 1.52-1.49 (m, 6H). $^{13}$C NMR (125 Hz): 175.03, 168.66, 152.71, 148.87, 143.76, 128.71, 127.11, 123.89, 122.04, 116.67, 112.63, 112.49, 64.84, 64.61, 62.70, 60.34, 47.98, 31.90, 29.69, 14.72, 14.64. MS. (M+1) 410.

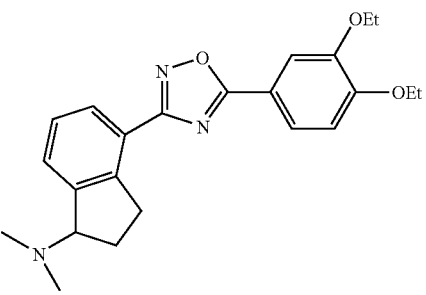 [SMILES: CCOc1ccc(-c2nc(-c3cccc4c3CCC4N(C)C)no2)cc1OCC]

$^1$H NMR (400 MHz, CDCl$_3$) δ: 8.10 (d, J=7.6 Hz, 1H), 7.79 (dd, J=8.5, 2.0 Hz, 1H), 7.69 (d, J=2.0 Hz, 1H), 7.55 (d, J=7.6 Hz, 1H), 7.38 (t, J=7.6 Hz, 1H), 6.99 (d, J=8.4 Hz, 1H), 4.44 (t, J=6.8 Hz, 1H), 4.24-4.16 (m, 4H), 3.42-3.34 (m, 1H), 3.27-3.19 (m, 1H), 3.28 (s, 6H), 2.19-2.12 (m, 4H), 1.53-1.48 (m, 6H). $^{13}$C NMR (75 MHz, CDCl$_3$): 174.09, 168.87, 152.58, 148.77, 143.88, 128.27, 127.91, 126.79, 123.47, 121.98, 116.67, 114.84, 112.49, 112.31, 69.67, 64.77, 64.56, 40.66, 32.40, 23.05, 14.70, 14.62. MS. (M+1) 394.

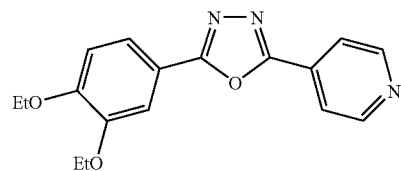 [SMILES: CCOc1ccc(-c2nnc(-c3ccncc3)o2)cc1OCC]

2-(3,4-diethoxyphenyl)-5-(pyridin-4-yl)-1,3,4-oxadiazole

To a stirred solution of 3,4-diethoxybenzoic acid (0.71 mmol, 150 mg) in CH$_2$Cl$_2$ was added SOCl$_2$ at room temperature; the reaction was refluxed for 1.5 h and the mixture concentrated under reduced pressure to yield 3,4-diethoxybenzoylchloride quantitatively. To a stirred suspension of Na$_2$CO$_3$ (1.42 mmol, 150.52 mg) and pyridine-4-carbohydrazide (0.71 mmol, 97 mg) in NMP (0.8 mL) was added a solution of the 3,4-diethoxybenzoylchloride in NMP (0.8 mL) and the reaction was stirred for 12 h at room temperature. The mixture was poured into 20 mL of cold H$_2$O and filtered. The precipitated intermediate was dried in vacuum. The solid was added to POCl$_3$ (5 mL) and heated to 70-72° C. for 6 h. The solution was poured into an ice-water container and neutralized with a solution of NaOH (2M). The precipitated product was filtered and purified by column chromatography using CH$_2$Cl$_2$:MeOH (9:1) to yield the product as white solid in 67% yield (150 mg). $^1$H NMR (400 MHz, CDCl$_3$): δ 8.84 (bs, 2H), 7.99 (d, J=4.4 Hz, 2H), 7.67 (dd, J1=2.0, J2=8.4 Hz, 1H), 7.64 (d, J=2.0 Hz, 1H), 6.98 (d, J=8.4 Hz, 1H), 4.20 (q, J=7.2 Hz, 2H), 4.18 (q, J=7.2 Hz, 2H), 1.51 (t, J=7.2 Hz, 3H), 1.50 (t, J=7.2 Hz, 3H); $^{13}$C NMR (100 MHz, CDCl$_3$):

δ 165.81, 162.46, 152.51, 150.84, 149.20, 131.52, 128.05, 120.97, 115.77, 112.78, 111.58, 65.05, 64.80, 14.92, 14.85. MS (EI) m/z: 312 (M+), HRMS (EI) for $C_{17}H_{17}N_3O_3$ (M+): calcd 312.1343, found 312.1350.

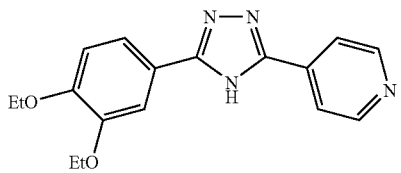 [SMILES: CCOc1ccc(-c2nnc(-c3ccncc3)[nH]2)cc1OCC]

4-(5-(3,4-diethoxyphenyl)-4H-1,2,4-triazol-3-yl)pyridine

Cold 4M HCl in dioxane (31.5 mmol, 8.87 mL) was added to a stirred solution of 3,4-diethoxybenzonitrile (7.84 mmol, 1.5 g) in anhydrous MeOH (23.53 mmol, 954 μl) and anhydrous ether (4 mL). The reaction was stirred at 0° C. for 1 h and then placed in the refrigerator (0-5° C.) for 48 h. The mixture was bubbled with $N_2$ to eliminate HCl and concentrated under reduced pressure. To the crude was added anhydrous ether and the methyl 3,4-diethoxybenzimidate salt precipitated as pale orange solid in 63% yield (1.3 g). The product was used without further purification. To a stirred solution of the imidine (0.5 mmol, 130 mg) (freshly liberated from the imidate salt using a solution IM of $Na_2CO_3$ and extracted with ether) in acetonitrile was added pyridine-4-carbohydrazide (0.55 mmol, 75.5 mg) and the reaction was refluxed for 2 h. The mixture was concentrated under reduced pressure and the crude was heated at 180° C. for 2 h. The product was purified by column chromatography using $CH_2Cl_2$:MeOH (9:1) to offer the product as a white solid in 65% yield (100 mg, 0.32 mmol). $^1$H NMR (400 MHz, CDCl$_3$): δ 8.71 (bs, 2H), 8.11 (d, J=5.2 Hz, 2H), 7.60 (s, 1H), 7.57 (d, J=8.4 Hz, 1H), 6.90 (d, J=8.4, 1H), 4.11 (q, J=6.8 Hz, 2H), 4.07 (q, J=6.8 Hz, 2H), 1.45 (t, J=7.0 Hz, 3H), 1.40 (t, J=7.0 Hz, 3H); $^{13}$C NMR (100 MHz, CDCl$_3$): δ 157.73, 150.89, 149.42, 149.14, 139.66, 121.29, 120.56, 120.06, 119.68, 113.00, 111.53, 64.82, 64.72, 14.90, 14.86. MS (EI) m/z: 311 (M+), HRMS (EI) for $C_{17}H_{18}N_4O_2$ (M+): calcd 311.1502, found 311.1506.

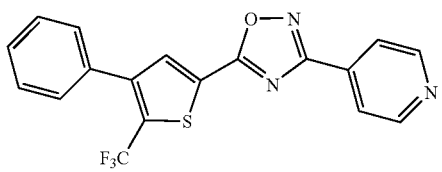 [SMILES: FC(F)(F)c1sc(-c2nc(-c3ccncc3)no2)cc1-c1ccccc1]

4-[5-(4-Phenyl-5-trifluoromethyl-thiophen-2-yl)-[1,2,4]oxadiazol-3-yl]-pyridine

In a round bottom flask, a stirring solution of 3,4-diethoxybenzoic acid (100 mg, 0.3673 mmol) in DMF (1.8 mL) was treated sequentially with HOBt (64 mg, 0.48 mmol)) and EDCI (91 mg, 0.48 mmol) at room temperature. The reaction was stirred for 20 min followed by addition, in a single portion of N'-hydroxyisonicotinimidamide (66 mg, 0.48 mmol). The reaction was stirred for additional 30 min at room temperature and then heated to 90-95° C. for 10 h. The reaction was cooled to room temperature, diluted with a saturated solution of NaCl and extracted with EtOAc (3×50 mL). The organic phase was dried over $Na_2SO_4$ anhydrous and concentrated under reduced pressure. The product was purified by column chromatography using $CH_2Cl_2$:MeOH (9:1) to offer the product as a pale yellow solid in 56% yield (78 mg). $^1$H NMR (300 MHz, CDCl$_3$): δ 8.82 (bs, 2H), 8.02 (d, J=2.7, 2H), 7.93 (q, J=1.5 Hz, 1H), 7.47 (s, 5H); $^{13}$C NMR (75 MHz, CDCl$_3$): δ 171.12, 167.81, 150.86, 145.70, 135.09, 134.12, 133.14, 123.32, 129.04, 126.35, 126.33, 121.67, 120.21, 105.04. MS (EI) m/z: 374 (M+), HRMS (EI) for $C_{18}H_{10}F_3N_3SO$ (M+): calcd 374.0569, found 374.0579.

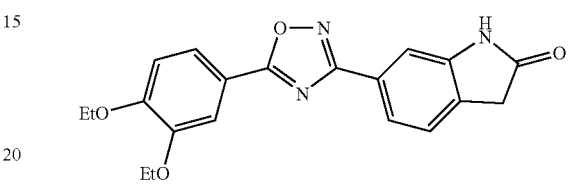

6-(5-(3,4-diethoxyphenyl)-1,2,4-oxadiazol-3-yl)indolin-2-one

To a solution of 2-oxoindoline-4-carbonitrile (500 mg, 3.16 mmol) in ethanol were added cautiously hydroxylamine hydrochloride (286 mg, 4.11 mmol) and potassium bicarbonate (411 mg, 4.11 mmol). The reaction mixture was refluxed for 20 h under nitrogen atmosphere. The mixture was cooled to room temperature and the solid was filtered. The organic solvent was concentrated under reduced pressure and the N'-hydroxyimidamide was used in the next step without further purification.

To a stirred solution of 3,4-diethoxybenzoic acid (73 mg, 0.35 mmol) in 1,4-dioxane was added EDCI (87 mg, 0.45 mmol) and HOBt (62 mg, 0.45 mmol), the reaction was stirred 20 min at room temperature. To the reaction was added the N'-hydroxyimidamide (87 mg, 0.45 mmol) and the mixture was stirred for 30 min at room temperature followed by 16 h at 95° C. The reaction was concentrated under reduced pressure, diluted with EtOAc (80 ml) and washed with brine (2×30 ml). The organic layer was dried over $Na_2SO_4$ and concentrated under reduced pressure. The crude was purified by column chromatography using $CH_2Cl_2$:MeOH (9:1) to offer the product as a pale yellow solid 50% yield (64 mg, 0.175 mmol). MS (E1) m/z: 366 (M+)

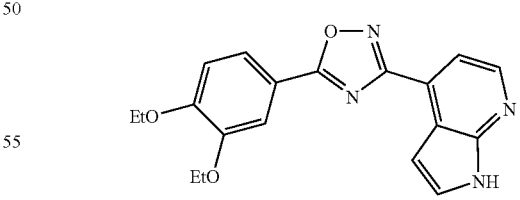

5-(3,4-diethoxyphenyl)-3-(1H-pyrrolo[2,3-b]pyridin-4-yl)-1,2,4-oxadiazole

To a solution of 4-cyano-7-azaindole (1 g, 7 mmol) in methanol (30 mL) were added cautiously hydroxylamine hydrochloride (632 mg, 9.1 mmol) and sodium carbonate (964 mg, 9.1 mmol). The reaction mixture was reflux for 6 h under nitrogen atmosphere and hydroxylamine hydrochloride (632 mg, 9.1 mmol) and sodium carbonate (964 mg, 9.1 mmol) were added, the reaction was reflux for additional 14 h. The mixture was cooled to room temperature and the solid was filtered. The organic solvent was concentrated under reduced pressure and the crude was recrystallized from ethanol to yield 200 mg of N'-hydroxyimidamide.

To a stirred solution of 3,4-diethoxybenzoic acid (50 mg, 0.24 mmol) in DMF was added EDCI (59 mg, 0.31 mmol) and HOBt (41 mg, 0.31 mmol), the reaction was stirred 20 min at room temperature. To the reaction was added the N'-hydroxyimidamide (54 mg, 0.31 mmol) and the mixture was stirred for 30 min at room temperature followed by 16 h at 95° C. The reaction was concentrated under reduced pressure, diluted with EtOAc (80 ml) and washed with a saturated solution of NaHCO$_3$ (2×30 ml) and brine (50 ml). The organic layer was dried over Na$_2$SO$_4$ and concentrated under reduced pressure. The crude was purified by column chromatography using CH$_2$Cl$_2$:MeOH (9:1) to offer the product as a brown solid in 5% yield (4 mg, 0.01 mmol). MS (EI) m/z: 351 (M$^+$)

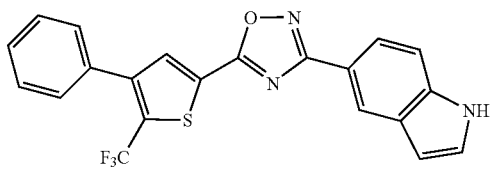 [SMILES: FC(F)(F)c1sc(-c2nc(-c3ccc4[nH]ccc4c3)no2)cc1-c1ccccc1]

3-(1H-indol-5-yl)-5-(4-phenyl-5-(trifluoromethyl)thiophen-2-yl)-1,2,4-oxadiazole To a solution of 1H-indole-5-carbonitrile (2 g, 14.06 mmol) in ethanol under reflux were added, in three equal portions, hydroxylamine hydrochloride (4.88 g, 70.3 mmol) and potassium bicarbonate (7.04 g, 70.3 mmol), the reaction was reflux for 16 h. The mixture was cooled to room temperature and the solid was filtered. The organic solvent was concentrated under reduced pressure and the N'-hydroxyimidamide was used in the next step without further purification.

To a solution of 4-phenyl-5-(trifluoromethyl)-2-thiophenecarboxylic acid in 1,4-dioxane were added under nitrogen atmosphere EDCI (125 mg, 0.65 mmol) and HOBt (88 mg, 0.65 mmol). The reaction was stirred at room temperature for 30 min followed by addition of N'-hydroxyimidamide (114 mg, 0.65 mmol), the reaction was stirred for 30 additional minutes at room temperature followed by 16 h at 95° C. The reaction was concentrated under reduced pressure. The crude was diluted with EtOAc (80 mL) and washed with a saturated solution of NaHCO$_3$ (2×50 ml). The organic phase was dried over Na$_2$SO$_4$ anhydrous and concentrated under reduced pressure. The product was purified by column chromatography using CH$_2$Cl$_2$:MeOH (9:1) to yield 91 mg (46.7%) of the product. MS (EI) m/z: 412 (M$^+$).

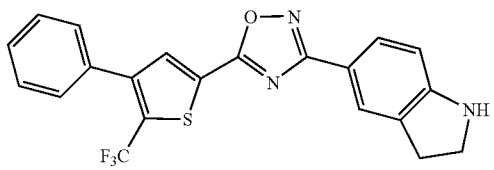 [SMILES: FC(F)(F)c1sc(-c2nc(-c3ccc4c(c3)CCN4)no2)cc1-c1ccccc1]

3-(indolin-5-yl)-5-(4-phenyl-5-(trifluoromethyl)thiophen-2-yl)-1,2,4-oxadiazole

To a stirred solution of 3-(1H-indol-5-yl)-5-(4-phenyl-5-(trifluoromethyl)thiophen-2-yl)-1,2,4-oxadiazole (40 mg, 0.097 mmol) in acetic acid at 12-14° C. was added slowly sodium cyanoborohydride (19 mg, 0.29 mmol). At the end of the addition the reaction was allowed to warm to 18-20° C. and was stirred for 2 h. After completion the reaction mixture was neutralized with 50% sodium hydroxide and extracted with ethyl acetate (50 ml×2). The organic layers were combined and dried over Na$_2$SO$_4$ and removed under reduced pressure. The crude indoline compound was purified by column chromatography using CH$_2$Cl$_2$/MeOH (9:1) to offer the product in 84.3% yield (33.8 mg, 0.082 mmol). MS (EI) m/z: 414 (M$^+$)

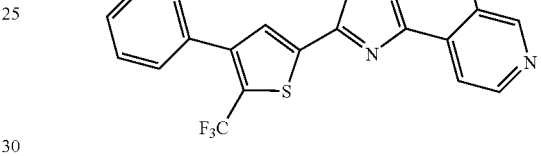

3-(3-methylpyridin-4-yl)-5-(4-phenyl-5-(trifluoromethyl)thiophen-2-yl)-1,2,4-oxadiazole Hydroxylamine hydrochloride (23.53 g, 339 mmol) was dissolved in water (120 ml) and potassium bicarbonate (33.9 g, 3339 mmol) was added cautiously. The mixture was stirred slowly until complete solution. The mixture was added to a solution of 3-methyl isonicotinonitrile (2 g, 16.9 mmol) in THF (30 mL) at −25° C. (ice methanol bath) and the reaction was stirred at room temperature for 16 h. The reaction mixture was extracted with EtOAc (3×100 mL) and the combined organic phases were washed with brine (80 ml). The organic phase was dried over Na$_2$SO$_4$ and concentrated under reduced pressure. The product was purified by column chromatography using hexanes/EtOAc (1:1) to yield N'-hydroxyimidamide in 47% yield (1.2 g).

To a solution of 4-phenyl-5-(trifluoromethyl)-2-thiophenecarboxylic acid (200 mg, 0.735 mmol) in DMF were added under nitrogen atmosphere EDCI (183 mg, 0.95 mmol) and HOBt (129 mg, 0.95 mmol). The reaction was stirred at room temperature for 30 min followed by addition of N'-hydroxyimidamide (143 mg, 0.95 mmol), the reaction was stirred for 30 min at room temperature followed by 16 h at 95° C. The reaction was concentrated under reduced pressure. The crude was diluted with EtOAc (80 mL) and washed with a saturated solution of NaHCO$_3$ (2×50 ml). The organic phase was dried over Na$_2$SO$_4$ and concentrated under reduced pressure. The product was purified by column chromatography using CH$_2$Cl$_2$:MeOH (9:1) to yield 161 mg (56.6%) of the product. MS (EI) m/z: 412 (M$^+$)

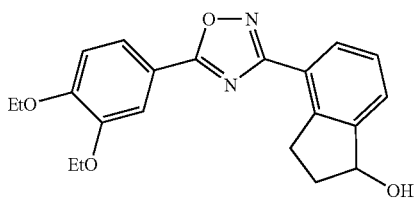 [SMILES: CCOc1ccc(-c2nc(-c3cccc4c3CCC4O)no2)cc1OCC]

4-(5-(3,4-diethoxyphenyl)-1,2,4-oxadiazol-3-yl)-2,3-dihydro-1H-inden-1-ol

To a stirred suspension of 1-oxo-2,3-dihydro-1H-indene-4-carbonitrile (5 g, 31.8 mmol) and silica gel (100 mg) in ethanol (30 mL) at 0° C. was added NaBH$_4$ (400 mg, 10.6 mmol). The reaction was allowed to warm up to room temperature and stirred for 2 h. The solvent was removed under reduced pressure and the product purified by column chromatography in hexane/EtOAc (5:5) to offer 1-hydroxy-2,3-dihydro-1H-indene-4-carbonitrile as white solid in 80% yield (4.04 g, 25.4 mmol). $^1$H NMR (300 MHz, CDCl$_3$): δ 7.62 (d, J=7.5 Hz, 1H), 7.54 (d, J=7.8 Hz, 1H), 7.33 (t, J=7.8 Hz, 1H), 5.28 (t, J=6.3 Hz, 1H), 3.28-3.18 (m, 1H), 3.02-2.92 (m, 1H), 2.63-2.52 (m, 1H), 2.06-1.99 (m, 1H).

To a stirred solution of 1-hydroxy-2,3-dihydro-1H-indene-4-carbonitrile (3 g, 18.86 mmol) in ethanol (100 mL) were added cautiously over a period of 16 h under refluxing conditions hydroxylamine hydrochloride (6.55 g, 94.3 mmol) and potassium carbonate (13.03 g, 94.3 mmol) in equal portions. The mixture was cooled to room temperature and the solid was filtered. The organic solvent was concentrated under reduced pressure and the crude was recrystallized from ethanol to yield 2.5 g (69%) of amidoxime.

In a microwave vial, a stirring solution of 3,4-diethoxybenzoic acid (200 mg, 0.95 mmol) in DMF was treated with HOBt (168 mg, 1.24 mmol) and EDCI (237 mg, 1.24 mmol) at room temperature. The reaction was stirred for 20 min followed by addition, in a single portion, of amidoxime (238 mg, 1.24 mmol). The reaction was stirred for additional 30 min at room temperature and then heated to 130° C. for 35 min in the initiator. The reaction was diluted using a saturated solution of NaCl and extracted with EtOAc (3×80 ml). The organic phase was dried over Na$_2$SO$_4$ anhydrous and concentrated under reduced pressure. The product was purified by column chromatography using CH$_2$Cl$_2$:MeOH (9:1) to offer the product as a white solid in 69% yield (208 mg). $^1$H NMR (400 MHz, CDCl$_3$): δ 8.10 (d, J=7.6, 1H), 7.78 (dd, J1=1.6 Hz, J2=8 Hz, 1H), 7.67 (d, J=1.6 Hz, 1H), 7.56 (d, J=7.6 Hz, 1H), 7.39 (t, J=7.6 Hz, 1H), 6.97 (d, J=8.0 Hz, 1H), 5.29 (t, J=6.4 Hz, 1H), 4.19 (q, J=7.2 Hz, 2H), 4.18 (q, J=7.2 Hz, 2H), 3.51-4.43 (m, 1H), 3.22-3.14 (m, 1H), 2.59-2.51 (m, 1H), 2.04-1.97 (m, 1H), 1.5 (t, J=7.2 Hz, 3H), 1.49 (t, J=7.2 Hz, 3H); $^{13}$C NMR (100 MHz, CDCl$_3$): δ 175.2, 168.9, 152.8, 148.9, 146.6, 143.3, 128.9, 127.4, 127.0, 123.8, 122.2, 116.7, 112.7, 112.4, 76.2, 64.9, 64.8, 35.7, 31.5, 14.9, 14.8. MS (EI) m/z 367 (M$^+$), HRMS (EI) for C$_{21}$H$_{22}$N$_2$O$_4$ (M$^+$): calcd 367.1652, found 367.1653.

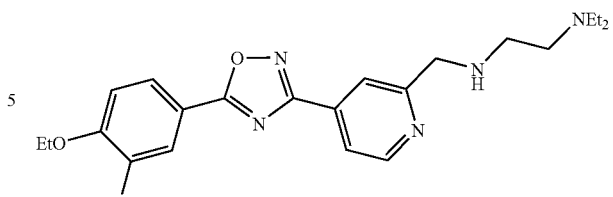

N1-((4-(5-(3,4-diethoxyphenyl)-1,2,4-oxadiazol-3-yl)pyridin-2-yl)methyl)-N2,N2-diethylethane-1,2-diamine To a stirred solution of 2-(hydroxymethyl)isonicotinonitrile (570 mg, 4.25 mmol) in ethanol (40 mL) were added cautiously over a period of 16 h under refluxing conditions hydroxylamine hydrochloride (1.37 g, 21.25 mmol) and sodium carbonate (2.25 g, 21.25 mmol)—in equal portions—. The mixture was cooled to room temperature and the solid was filtered. The organic solvent was concentrated under reduced pressure and the crude was recrystallized from ethanol to yield 600 mg (3.59 mmol, 84%) of amidoxime.

In a microwave vial, a stirring solution of 3,4-diethoxybenzoic acid (300 mg, 1.43 mmol) in DMF was treated with HOBt (250 mg, 1.85 mmol) and EDCI (354 mg, 1.85 mmol) at room temperature. The reaction was stirred for 20 min followed by addition, in a single portion, of amidoxime (309 mg, 1.85 mmol). The reaction was stirred for additional 30 min at room temperature and then heated to 130° C. for 35 min in the initiator. The reaction was diluted using a saturated solution of NaCl and extracted with EtOAc (3×80 ml). The organic phase was dried over Na$_2$SO$_4$ anhydrous and concentrated under reduced pressure. The product was purified by column chromatography using CH$_2$Cl$_2$:MeOH (9:1) to offer (4-(5-(3,4-diethoxyphenyl)-1,2,4-oxadiazol-3-yl)pyridin-2-yl)methanol as brown solid in 71% yield (350 mg). $^1$H NMR (400 MHz, CDCl$_3$): δ 8.65 (d, J=4.8 Hz, 1H), 8.00 (s, 1H), 7.86 (d, J=4.8 Hz, 1H), 7.70 (dd, J1=2.0 Hz, J2=8.8 Hz, 1H), 7.59 (d, J=2.0, 1H), 6.91 (d, J=8.8 Hz, 1H), 4.85 (s, 2H), 4.16 (q, J=7.2 Hz, 2H), 4.13 (q, J=7.2 Hz, 2H), 1.49 (t, J=6.8 Hz, 3H), 1.46 (t, J=6.8 Hz, 3H); $^{13}$C NMR (100 MHz CDCl$_3$): δ 176.54, 167.22, 153.03, 149.36, 148.91, 135.50, 122.23, 120.11, 118.48, 116.05, 112.48, 112.17, 64.90, 64.50, 14.82, 14.73. MS (EI) m/z: 342 (M$^+$), HRMS (EI) for C$_{18}$H$_{19}$N$_3$O4

To a stirred solution of pyridinol (20 mg, 0.059 mmol) in DMSO (1 ml) were added sequentially N,N'-dicyclohexylcarbodiimide (36.3 mg, 0.176 mmol) and 1.0M anhydrous H$_3$PO$_4$ in DMSO (30 μL, 0.03 mmol) and the reaction mixture was stirred 2 h at room temperature. Precipitated dicyclohexylurea was filtered off and washed with ether (10 ml) and water (10 ml). The aqueous layer was extracted with ether (3×20 ml) and the organic layer was dried over sodium sulfate and concentrated under reduced pressure. The residue was purified by column chromatography using CH$_2$Cl$_2$:MeOH (95:5) to yield 15 mg (75%) of pyridinecarboxaldehyde. MS (EI) m/z 340 (M$^+$).

To a stirred solution of pyridinecarboxaldehyde (15 mg, 0.044 mmol) in dichloroethane were added N$^1$,N$^1$-diethylethane-1,2-diamine (19 μl, 0.13 mmol) and sodium triacetoxyborohydride (11 mg, 0.05 mmol), the reaction was stirred for 4 h at room temperature. The mixture was poured un silica gel and was purified by column chromatography using CH$_2$Cl$_2$:MeOH:Et$_3$N (90:9.8:0.2) to yield 8 mg (42%) of the product as a brown solid. MS (EI) m/z 440 (M$^+$).

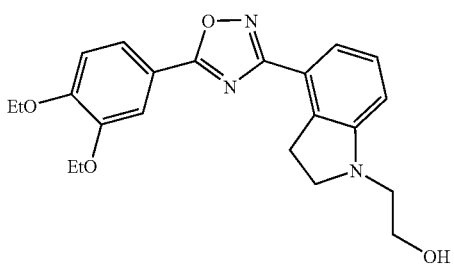 [SMILES: CCOc1ccc(-c2nc(-c3cccc4c3CCN4CCO)no2)cc1OCC]

2-(4-(5-(3,4-diethoxyphenyl)-1,2,4-oxadiazol-3-yl)indolin-1-yl)ethanol

To a stirred solution of 3,4-diethoxybenzoic acid (400 mg, 1.9 mmol) in DMF were added sequentially HOBt (330 mg, 2.5 mmol) and EDCI (474 mg, 2.5 mmol) at room temperature. The reaction was stirred for 20 min followed by addition, in a single portion, of the N-hydroxy-1H-indole-4-carboximidamide (666 mg, 3.8 mmol). The reaction was stirred for additional 30 min at room temperature then heated at 90-95° C. for 14 h. The reaction was cooled to room temperature, diluted using a saturated solution of $Na_2CO_3$ and extracted with EtOAc (100 ml×3). The organic phase was dried over $Na_2SO_4$ anhydrous and concentrated under reduced pressure. The product was purified by column chromatography using $CH_2Cl_2$:MeOH (9:1) to afford compound 110 in 50% yield (331 mg). $H^1$ NMR (400 MHz, $CDCl_3$): δ8.01 (d, J=7.2 Hz, 1H), 7.81 (dd, J1=2.0 Hz, J2=8.4 Hz, 1H), 7.52 (s, 1H), 7.52 (d, J=8.0 Hz, 1H), 7.34 (s, 1H), 7.28 (t, J=8.0 Hz, 1H), 7.23 (s, 1H), 6.96 (d, J=8.4 Hz, 1H), 4.18 (q, J=6.8 Hz, 2H), 4.16 (q, J=6.8 Hz, 2H), 1.47 (t, J=6.8 Hz, 3H), 1.46 (t, J=6.8 Hz, 3H); $^{13}C$ NMR (100 MHz, $CDCl_3$): δ 175.0, 169.5, 152.6, 148.9 (2), 125.7, 122.2, 121.8, 121.7, 121.3, 121.2, 117.0, 114.4, 114.3, 112.7, 112.5, 64.97, 64.76, 14.86, 14.78. MS (EI) m/z 350 (M+), HRMS (EI) for $C_{20}H_{19}N_3O_3$ (M+): calcd 350.1499, found 350.1504.

To a stirred solution of the previous product 110 (260 mg, 0.74 mmol) in acetic acid at 10-15° C. was added slowly sodium cyanoborohydride (140 mg, 2.25 mmol). The reaction was allowed to warm to 18-20° C. and was stirred for 2 h. After completion the reaction mixture was neutralized with 50% sodium hydroxide and extracted with ethyl acetate (100 ml×2). The organic layers were combined, dried over $Na_2SO_4$ and removed under reduced pressure. The crude indoline compound was purified by column chromatography using $CH_2Cl_2$/MeOH (9:1) to provide the dihydro compound in 80.5% yield (211 mg, 0.60 mmol). $^1H$ NMR (300 MHz, $CDCl_3$): δ 7.78 (dd, J1=2.1 Hz, J2=8.4 Hz, 1H), 7.68 (d, J=1.8 Hz, 1H), 7.55 (d, J=7.8 Hz, 1H), 7.16 (t, J=7.5 Hz, 1H), 6.97 (d, J=7.5 Hz, 1H), 6.76 (d, J=7.5 Hz, 1H), 4.21 (q, J=6.9 Hz, 2H), 4.16 (q, J=6.9 Hz, 2H), 3.65 (bs, 2H), 3.46 (t, J=8.1 Hz, 2H), 1.52 (t, J=3.1 Hz, 3H), 1.48 (t, J=3.3 Hz, 3H); $^{13}C$ NMR (75 MHz, $CDCl_3$): δ 175.05, 169.06, 152.62, 148.84, 127.84, 123.67, 122.09, 118.90, 116.83, 112.53, 112.32, 111.60, 64.86, 64.67, 47.29, 31.41, 14.85, 14.78. MS (EI) m/z 352 (M+), HRMS (EI) for $C_{20}H_{21}N_3O_3$ (M+): calcd 352.1656, found 352.1660.

To a stirred solution of the previous dihydro product (50 mg, 0.14 mmol) in DMF (3 ml) was added potassium carbonate (118 mg, 0.85 mmol) and 2-bromoethanol (20 μl, 0.28 mmol). The reaction was stirred at 60° C. for 48 h. At the end of the reaction the solution was poured into water (50 ml) and the mixture was extracted with EtOAc (3×50 ml). The organic phases were combined, washed with water, dried over sodium sulfate and concentrated under reduced pressure. The product was purified by column chromatography using $CH_2Cl_2$:MeOH (9:1) to yield 35 mg (63%) of the product as a brown solid. $^1H$ NMR (300 MHz, $CDCl_3$) δ: 7.74 (dd, J1=1.8 Hz, J2=8.4 Hz, 1H), 7.61 (d, J=2.1 Hz, 1H), 7.33 (dd, J1=0.6 Hz, J2=7.8 Hz, 1H), 7.20 (t, J=5.1 Hz, 1H), 7.17 (d, J=1.8 Hz, 1H), 6.70 (d, J=8.1 Hz, 1H), 4.14 (q, J=7.2 Hz, 4H), 3.62 (t, J=6.0 Hz, 2H), 3.55 (t, J=8.7 Hz, 2H), 3.28 (t, J=8.1 Hz, 2H), 3.21 (t, J=6.0 Hz, 2H), 1.39 (t, J=1.8 Hz, 3H), 1.35 (t, J=1.5 Hz, 3H); $^{13}C$ NMR (75 MHz, $CDCl_3$): δ 168.67, 158.97, 158.46, 153.35, 152.73, 148.72, 129.76, 128.39, 122.19, 117.36, 115.89, 113.54, 113.38, 111.94, 64.48, 64.43, 58.90, 53.20, 51.46, 29.99, 15.00, 14.90. MS (EI) m/z 396 (M+), HRMS (EI) for $C_{22}H_{25}N_3O_4$ (M+): calcd 396.1918, found 396.1918.

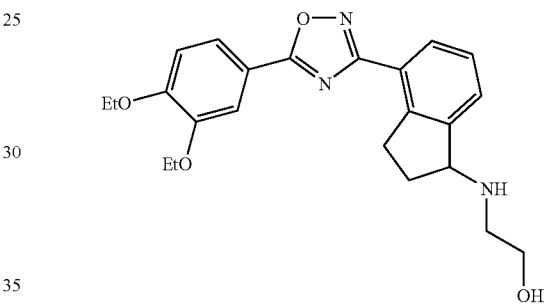

2-(4-(5-(3,4-diethoxyphenyl)-1,2,4-oxadiazol-3-yl)-2,3-dihydro-1H-inden-1-ylamino)ethanol To a stirred solution of compound 215 (400 mg, 1.09 mmol) in $CH_2Cl_2$ were added at 0° C. pyridine (89 μl, 1.1 mmol) and thionyl chloride (81 μl, 1.1 mmol), the reaction was stirred 1 h at room temperature and the mixture was concentrated under reduced pressure. The crude was diluted in DMF (10 ml) and were added potassium carbonate (290 mg, 2.1 mmol) and ethanolamine (128 μl, 2.1 mmol), the reaction was stirred overnight at 60° C. The reaction mixture was poured into water (100 ml) and extracted with EtOAc (100 ml×3). The organic phase was dried over $Na_2SO_4$ and concentrated under reduced pressure. The crude was purified by column chromatography using $CH_2Cl_2$:MeOH (9:1) to yield 312 mg (70% yield) of the product as a white solid. $^1H$ NMR (500 MHz, $CDCl_3$): δ8.12 (d, J=7.5 Hz, 1H), 7.79 (dd, J1=2.0 Hz J2=8.5 Hz, 1H), 7.68 (d, J=2.0 Hz, 1H), 7.63 (d, J=7.5 Hz, 1H), 7.40-7.37 (m, 1H), 4.49-4.47 (m, 1H), 4.23-4.16 (m, 4H), 3.78-3.70 (m, 1H), 3.53-3.46 (m, 1H), 3.29-3.22 (m, 1H), 2.96-2.94 (m, 4H), 2.56-2.50 (m, 1H), 2.09-2.03 (m, 1H), 1.52-1.49 (m, 6H); $^{13}C$ NMR (125 MHz, $CDCl_3$): δ175.03, 168.66, 152.71, 148.87, 143.76, 128.71, 127.11, 123.89, 122.04, 116.67, 112.63, 112.49, 104.66, 64.84, 64.61, 62.70, 60.34, 47.98, 31.90, 29.69, 14.72, 14.64. MS (EI) m/z 410 (M+), HRMS (EI) for $C_{23}H_{27}N_3O_4$ (M+): calcd 410.2074, found 410.2077.

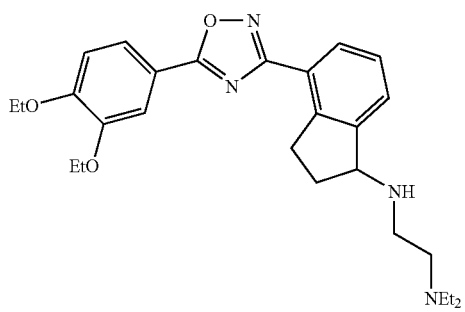

N1-(4-(5-(3,4-diethoxyphenyl)-1,2,4-oxadiazol-3-yl)-2,3-dihydro-1H-inden-1-yl)-N2,N2-diethyl-ethane-1,2-diamine To a stirred solution of compound 215 (40 mg, 0.109 mmol) in CH$_2$Cl$_2$ were added at 0° C. pyridine (9 μl, 1.1 mmol) and thionyl chloride (8 μl, 1.1 mmol), the reaction was stirred 1 h at room temperature and concentrated under reduced pressure. The crude was diluted in DMF (1 ml) and were added potassium carbonate (29 mg, 0.21 mmol) and N,N-diethylethylenediamine (30 μl, 0.21 mmol). The reaction was stirred overnight at 60° C. The reaction mixture was poured into water (100 ml) and extracted with EtOAc (20 ml×3). The organic phase was dried over Na$_2$CO$_3$ and concentrated under reduced pressure. The crude was purified by column chromatography using CH$_2$Cl$_2$:MeOH (9:1) to yield 65% (33 mg) of the product as a brown solid. MS (EI) m/z 465 (M$^+$).

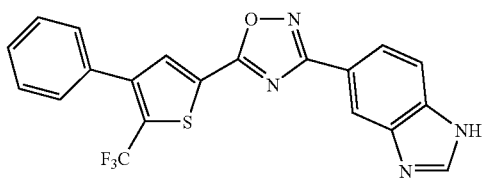 [SMILES: FC(F)(F)c1sc(-c2nc(-c3ccc4[nH]cnc4c3)no2)cc1-c1ccccc1]

3-(1H-benzo[d]imidazol-5-yl)-5-(4-phenyl-5-(trifluoromethyl)thiophen-2-yl)-1,2,4-oxadiazole In a microwave vial, a stirring solution of 3,4-diethoxybenzoic acid (100 mg, 0.367 mmol) in DMF was treated with HOBt (64 mg, 0.48 mmol) and EDCI (92 mg, 0.48 mmol) at room temperature. The reaction was stirred for 20 min followed by addition, in a single portion, of N'-hydroxy-1H-benzo[d]imidazole-4-carboximidamide (68 mg, 0.367 mmol). The reaction was stirred for additional 30 min at room temperature and then heated to 130° C. for 35 min in the initiator. The reaction was diluted using a saturated solution of NaHCO$_3$ and extracted with EtOAc (3×80 ml). The organic phase was dried over Na$_2$SO$_4$ anhydrous and concentrated under reduced pressure. The crude was purified by column chromatography using CH$_2$Cl$_2$:MeOH (9:1) to provide a 40% yield (61 mg) of the product as brown solid. MS (EI) m/z 413 (M$^+$).

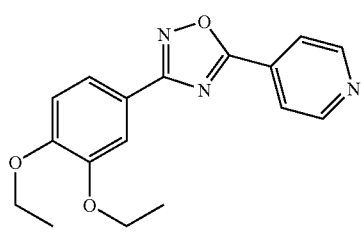 [SMILES: CCOc1ccc(-c2noc(-c3ccncc3)n2)cc1OCC]

3-(3,4-diethoxyphenyl)-5-(pyridin-4-yl)-1,2,4-oxadiazole

In a microwave vial, a stirring solution of isonicotinic acid (200 mg, 1.62 mmol) in DMF was treated with HOBt (319 mg, 2.43 mmol) and EDCI (467 mg, 2.43 mmol) at room temperature. The reaction was stirred for 20 min followed by addition, in a single portion, of (Z)-3,4-diethoxy-N'-hydroxybenzimidamide (436 mg, 1.94 mmol). The reaction was stirred for additional 30 min at room temperature and then heated to 130° C. for 35 min in the initiator. The reaction was diluted using a saturated solution of NaHCO$_3$ and extracted with EtOAc (80 ml×3). The organic phase was dried over Na$_2$SO$_4$ anhydrous and concentrated under reduced pressure. The product was purified by column chromatography using CH$_2$Cl$_2$:MeOH (95:5) to offer the product in 26% yield (131 mg) as pale brown solid. $^1$H NMR (300 MHz, CDCl$_3$): δ 8.85 (d, J=5.4 Hz, 2H), 8.02 (d, J=6.0 Hz, 2H), 7.71 (dd, J1=1.8 Hz, J2=8.1 Hz, 1H), 7.62 (d, J=2.1 Hz, 1H), 6.95 (d, J=8.4 Hz, 1H), 4.19 (q, J=6.9 Hz, 2H), 4.14 (q, J=6.9 Hz, 2H), 1.50 (t, J=3.0 Hz, 3H), 1.46 (t, J=3.3 Hz, 3H); $^{13}$C NMR (75 MHz, CDCl$_3$): δ 173.54, 16928, 151.64, 151.07, 148.91, 131.37, 121.48, 121.15, 118.75, 112.74, 111.82, 64.78, 64.59, 14.87, 14.81. MS (EI) m/z: 312 (M$^+$), HRMS (EI) for C$_{17}$H$_{17}$N$_3$O$_3$ (M$^+$): calcd 312.1343, found 312.1348.

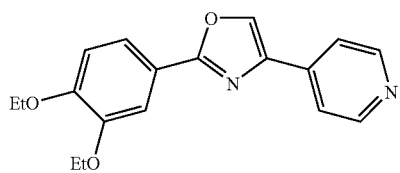 [SMILES: CCOc1ccc(-c2nc(-c3ccncc3)co2)cc1OCC]

2-(3,4-diethoxyphenyl)-4-(pyridin-4-yl)oxazole

In a microwave vial were dissolved 2-bromo-1-(pyridin-4-yl)ethanone hydrobromide (134 mg, 0.478 mmol) and 3,4-diethoxybenzamide (100 mg, 0.478 mmol) in DMF (5 ml) and the reaction was heated at 170° C. for 40 min. The reaction mixture was poured in a saturated solution of NaHCO$_3$ and extracted with EtOAc (50 ml×3). The combined organic phases were washed with a saturated solution of NaCl (2×30 ml) and concentrated under reduced pressure. The product was purified by column chromatography using CH$_2$Cl$_2$:MeOH (95:5) to yield 4 mg (2.7%) of the product. MS (EI) m/z: 311 (M$^+$).

211

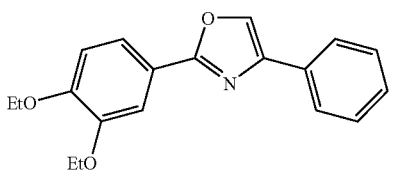 [SMILES: CCOc1ccc(-c2nc(-c3ccccc3)co2)cc1OCC]

2-(3,4-diethoxyphenyl)-4-phenyloxazole

In a microwave vial were dissolved 2-bromo-1-phenylethanone (95 mg, 0.478 mmol) and 3,4-diethoxybenzamide (100 mg, 0.478 mmol) in DMF (5 ml) and the reaction was heated at 170° C. for 40 min. The reaction mixture was poured in a saturated solution of $NaHCO_3$ and extracted with EtOAc (50 ml×3). The combined organic phases were washed with a saturated solution of NaCl (30 ml×2) and concentrated under reduced pressure. The product was purified by column chromatography using $CH_2Cl_2$:MeOH (95:5) to yield 25 mg (17%) of the product. MS (EI) m/z: 310 ($M^+$)

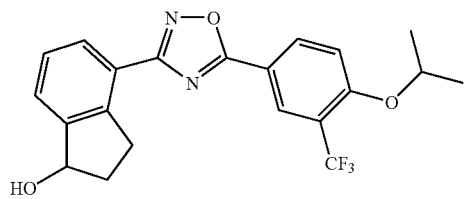 [SMILES: CC(C)Oc1ccc(-c2nc(-c3cccc4c3CCC4O)no2)cc1C(F)(F)F]

4-(5-(4-isopropoxy-3-(trifluoromethyl)phenyl)-1,2,4-oxadiazol-3-yl)-2,3-dihydro-1H-inden-1-ol In a microwave vial, a stirring solution of 4-isopropoxy-3-(trifluoromethyl)benzoic acid (700 mg, 2.82 mmol) in DMF was treated with HOBt (495 mg, 3.67 mmol) and EDCI (702 mg, 3.67 mmol) at room temperature. The reaction was stirred for 20 min followed by addition, in a single portion, of N',1-dihydroxy-2,3-dihydro-1H-indene-4-carboximidamide (650 mg, 3.38 mmol). The reaction was stirred for additional 30 min at room temperature and then heated to 130° C. for 35 min in the initiator. The reaction was diluted using a saturated solution of NaCl and extracted with EtOAc (100 ml×3). The organic phase was dried over $Na_2SO_4$ anhydrous and concentrated under reduced pressure. The product was purified by column chromatography using $CH_2Cl_2$:MeOH (9:1) to offer the product as white solid in 68% yield (780 mg). $^1$H NMR (300 MHz, $CDCl_3$—$CH_3OD$): δ 8.38 (d, J=1.8 Hz, 1H), 8.28 (dd, J1=2.4 Hz, J2=8.7 Hz, 1H), 8.06 (d, J=7.8 Hz, 1H), 7.55 (d, J=7.51H), 7.7.37 (t, J=7.5 Hz, 1H), 7.11 (dd, J1=2.4 Hz, J2=9.0 Hz, 1H), 5.24 (t, J=6.3 Hz, 1H), 4.20 (q, J=6.9 Hz, 1H), 3.48-3.40 (m, 1H), 3.19-3.09 (m, 1H), 2.57-2.46 (m, 1H), 2.04-1.92 (m, 1H), 1.46 (t, J=6.9 Hz, 3H), 1.39 (d, J=6.0 Hz, 3H); $^{13}$C NMR (75 MHz, $CDCl_3$—$CH_3OD$): δ 169.05, 158.85, 146.82, 143.33, 133.55, 128.79, 127.41, 127.22, 116.23, 113.38, 104.88, 65.27, 35.55, 31.44, 21.87, 14.55. MS (E1) m/z 405 ($M^+$), HRMS (EI) for $C_{21}H_{19}N_2O_3$ ($M^+$): calcd 405.1420, found 405.1424.

212

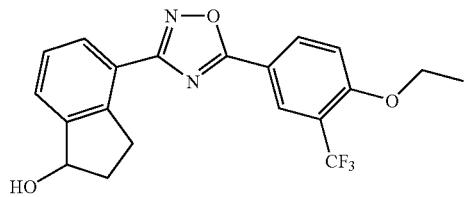

4-(5-(4-ethoxy-3-(trifluoromethyl)phenyl)-1,2,4-oxadiazol-3-yl)-2,3-dihydro-1H-inden-1-ol In a microwave vial, a stirring solution of 4-ethoxy-3-(trifluoromethyl)benzoic acid (200 mg, 0.85 mmol) in DMF was treated with HOBt (151 mg, 1.11 mmol) and EDCI (212 mg, 1.11 mmol) at room temperature. The reaction was stirred for 20 min followed by addition, in a single portion, of N',1-dihydroxy-2,3-dihydro-1H-indene-4-carboximidamide (213 mg, 1.11 mmol). The reaction was stirred for additional 30 min at room temperature and then heated to 130° C. for 35 min in the initiator. The reaction was diluted using a saturated solution of NaCl and extracted with EtOAc (80 ml×3). The organic phase was dried over $Na_2SO_4$ anhydrous and concentrated under reduced pressure. The product was purified by column chromatography using $CH_2Cl_2$:MeOH (9:1) to offer the product as white solid in 51% yield (200 mg).
$^1$H NMR (300 MHz, $CDCl_3$—$CH_3OD$): δ 8.27 (d, J=1.8 Hz, 1H), 8.21 (dd, J1=2.1 Hz, J2=8.7 Hz, 1H), 7.94 (d, J=7.5 Hz, 1H), 7.44 (d, J=7.8 Hz, 1H), 7.26 (q, J=9.9 Hz, 1H), 7.05 (d, J=8.7 Hz, 1H), 5.13 (t, J=6.3 Hz, 1H), 4.11 (q, J=6.9 Hz, 2H), 3.38-3.28 (m, 1H), 3.08-2.97 (m, 1H), 2.44-2.34 (m, 1H), 1.91-1.84 (m, 1H), 1.35 (t, J=6.9 Hz, 3H); $^{13}$C NMR (75 MHz, $CDCl_3$—$CH_3OD$): δ 150.90, 147.26, 143.96, 137.60, 137.59, 132.62, 132.59, 131.31, 131.27, 131.24, 127.21, 120.11, 117.48, 104.99, 79.55, 69.27, 39.27, 35.35, 18.39. MS (EI) m/z 391 ($M^+$), HRMS (EI) for $C_{20}H_{17}F_3N_2O_3$ ($M^+$): calcd 391.1264, found 391.1261.

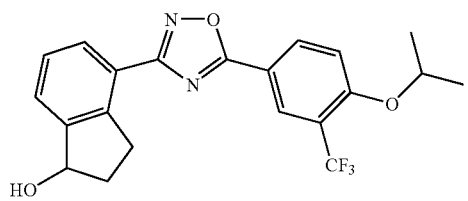 [SMILES: CC(C)Oc1ccc(-c2nc(-c3cccc4c3CCC4O)no2)cc1C(F)(F)F]

4-(5-(4-isopropoxy-3-(trifluoromethyl)phenyl)-1,2,4-oxadiazol-3-yl)-2,3-dihydro-1H-inden-1-ol In a microwave vial, a stirring solution of 4-ethoxy-3-(trifluoromethyl)benzoic acid (200 mg, 0.97 mmol) in DMF was treated with HOBt (172 mg, 1.26 mmol) and EDCI (242 mg, 1.26 mmol) at room temperature. The reaction was stirred for 20 min followed by addition, in a single portion, of N',1-dihydroxy-2,3-dihydro-1H-indene-4-carboximidamide (243 mg, 1.26 mmol). The reaction was stirred for additional 30 min at room temperature and then heated to 130° C. for 35 min in the initiator. The reaction was diluted using a saturated solution of NaCl and extracted with EtOAc (80 ml×3). The organic phase was dried over $Na_2SO_4$ anhydrous and concentrated under reduced pressure. The product was purified by column chromatography using $CH_2Cl_2$:MeOH (9:1) to offer the product as pale yellow solid in 63% yield (229 mg).

$^1$H NMR (300 MHz, $CDCl_3$—$CH_3OD$): δ 8.36 (d, J=2.1 Hz, 1H), 8.29 (dd, J1=2.4 Hz, J2=9.0 Hz, 1H), 8.06 (d, J=7.8 Hz, 1H), 7.55 (d, J=7.5 Hz, 1H), 7.37 (t, J=7.5 Hz, 1H), 7.10 (d, J=9.0 Hz, 1H), 5.26 (t, J=6.3 Hz, 1H), 4.81-4.73 (m, 1H), 3.48-3.38 (m, 1H), 3.19-3.08 (m, 1H), 2.56-2.49 (m, 1H), 2.04-1.95 (m, 1H), 1.45 (d, J=6.3 Hz, 6H); $^{13}$C NMR (75 MHz, $CDCl_3$—$CH_3OD$): δ 173.11, 168.95, 162.82, 146.70, 143.26, 134.15, 134.041, 128.27, 127.30, 127.18, 123.18, 116.85, 115.41, 113.66, 103.86, 72.85, 35.57, 31.42, 21.82. MS (EI) m/z 362 (M$^+$), HRMS (EI) for $C_{21}H_{19}N_3O_3$ (M$^+$): calcd 362.1499, found 362.1494.

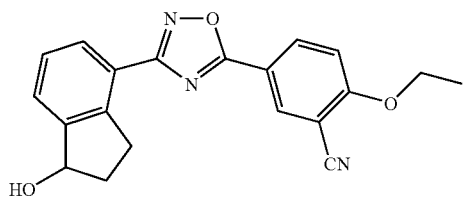 [SMILES: CCOc1ccc(-c2nc(-c3cccc4c3CCC4O)no2)cc1C#N]

2-ethoxy-5-(3-(1-hydroxy-2,3-dihydro-1H-inden-4-yl)-1,2,4-oxadiazol-5-yl)benzonitrile In a microwave vial, a stirring solution of 3-cyano-4-ethoxybenzoic acid (200 mg, 1.05 mmol) in DMF was treated with HOBt (185 mg, 1.36 mmol) and EDCI (260 mg, 1.36 mmol) at room temperature. The reaction was stirred for 20 min followed by addition, in a single portion, of N',1-dihydroxy-2,3-dihydro-1H-indene-4-carboximidamide (261 mg, 1.36 mmol). The reaction was stirred for additional 30 min at room temperature and then heated to 130° C. for 35 min in the initiator. The reaction was diluted using a saturated solution of NaCl and extracted with EtOAc (80 ml×3). The organic phase was dried over $Na_2SO_4$ anhydrous and concentrated under reduced pressure. The product was purified by column chromatography using $CH_2Cl_2$:MeOH (9:1) to offer the product as pale yellow solid in 79% yield (274 mg).

$^1$H NMR (300 MHz, $CDCl_3$—$CH_3OD$): δ 8.31 (d, J=2.1 Hz, 1H), 8.25 (dd, J1=2.1 Hz, J2=8.7 Hz, 1H), 7.96 (d, J=7.5 Hz, 1H), 7.46 (d, J=7.5 Hz, 1H), 7.29 (t, J=7.8 Hz, 1H), 7.06 (d, J=9.0 Hz, 1H), 5.16 (t, J=6.0 Hz, 11H), 4.18 (q, J=6.9 Hz, 2H), 3.40-3.30 (m, 1H), 3.10-2.93 (m, 1H), 2.46-2.39 (m, 1H), 1.94-1.87 (m, 1H), 1.43 (t, J=6.9 Hz, 3H); $^{13}$C NMR (75 MHz, $CDCl_3$—$CH_3OD$): δ 172.91, 167.05, 161.92, 145.72, 142.08, 133.24, 132.83, 127.38, 126.16, 126.10, 121.85, 115.98, 111.76, 101.85, 74.36, 64.55, 34.08, 30.18, 13.20. MS (EI) m/z 348 (M$^+$), HRMS (EI) for $C_{23}H_{27}N_3O_3$ (M$^+$): calcd 348.1343, found 348.1345.

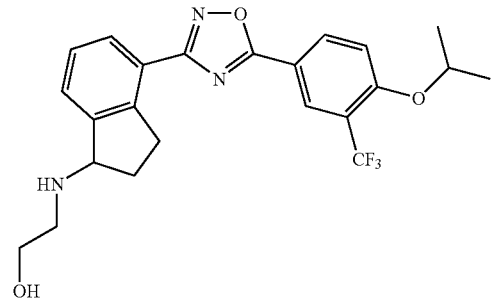 [SMILES: CC(C)Oc1ccc(-c2nc(-c3cccc4c3CCC4NCCO)no2)cc1C(F)(F)F]

2-(4-(5-(4-isopropoxy-3-(trifluoromethyl)phenyl)-1,2,4-oxadiazol-3-yl)-2,3-dihydro-1H-inden-1-ylamino)ethanol To a stirred solution of compound 259 (75 mg, 0.185 mmol) in $CH_2Cl_2$ were added at 0° C. pyridine (15 μl, 0.195 mmol) and thionyl chloride (14 μl, 0.195 mmol), the reaction was stirred 1 h at room temperature and concentrated under reduced pressure. The crude was diluted in DMF (1 ml) and were added DIPEA (161 μl, 0.927 mmol) and ethanolamine (56 μl, 0.927 mmol) at 0° C. The reaction was stirred overnight at 60° C. The reaction mixture was poured into water (100 ml) and extracted with ethyl acetate (20 ml×3). The organic phase was dried over sodium sulfate and concentrated under reduced pressure. The crude was purified by column chromatography using $CH_2Cl_2$:MeOH (9:1) to yield 40% (18 mg) of the product as a brown solid.

$^1$H NMR (300 MHz, $CDCl_3$—$CH_3OD$): δ 8.37 (s, 1H), 8.28-8.24 (m, 1H), 8.06 (t, J=4.8 Hz, 1H), 7.51 (d, J=6.9 Hz, 1H), 7.35 (t, J=7.5 Hz, 1H), 7.11 (d, J=8.4 Hz, 1H), 4.36-4.32 (m, 1H), 4.19 (d, J=6.9 Hz, 1H), 3.67-3.59 (m, 3H), 3.39-3.34 (m, 2H), 3.23-3.12 (m, 1H), 2.49-2.43 (m, 1H), 1.97-1.90 (m, 1H), 1.45 (t, J=6.9 Hz, 3H), 1.38 (d, J=4.2 Hz, 3H); $^{13}$C NMR (75 MHz, $CDCl_3$—$CH_3OD$): δ 169.63, 146.26, 144.53, 134.30, 128.97, 127.76, 127.64, 124.09, 116.72, 115.25, 114.30, 103.98, 72.86, 65.91, 63.32, 61.30, 32.74, 32.59, 22.08, 14.76. MS (EI) m/z 448 (M$^+$), HRMS (EI) for $C_{23}H_{24}F_3N_3O_3$ (M$^+$): calcd 448.1842, found 448.1849.

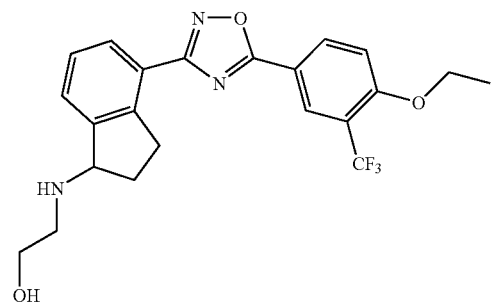 [SMILES: CCOc1ccc(-c2nc(-c3cccc4c3CCC4NCCO)no2)cc1C(F)(F)F]

2-(4-(5-(4-ethoxy-3-(trifluoromethyl)phenyl)-1,2,4-oxadiazol-3-yl)-2,3-dihydro-1H-inden-1-ylamino)ethanol To a stirred solution of compound 260 (154 mg, 0.394 mmol) in $CH_2Cl_2$ were added at 0° C. pyridine (33 μl, 0.414 mmol) and thionyl chloride (30 μl, 0.414 mmol), the reaction was stirred 1 h at room temperature and concentrated under reduced pressure. The crude was diluted in DMF (2 ml) and were added DIPEA (360 µl, 2.07 mmol) and ethanolamine (125 µl, 2.07 mmol) at 0° C. The reaction was stirred overnight at 60° C. The reaction mixture was poured into water (100 ml) and extracted with ethyl acetate (20 ml×3). The organic phase was dried over sodium sulfate and concentrated under reduced pressure. The crude was purified by column chromatography using $CH_2Cl_2$:MeOH (9:1) to yield 18% (31 mg) of the product as a brown solid.

$^1$H NMR (300 MHz, $CDCl_3$—$CH_3OD$): δ 8.31 (s, 1H), 8.23 (d, J=8.7 Hz, 1H), 7.99 (d, J=7.5 Hz, 1H), 7.48 (d, J=7.2 Hz, 1H), 7.30 (t, J=7.5 Hz, 1H), 7.07 (d, J=8.7 Hz, 1H), 4.33 (t, J=6.0 Hz, 1H), 4.15 (q, J=6.9 Hz, 3H), 3.64 (t, J=4.5 Hz, 2H), 3.41-3.33 (m, 1H), 3.19-3.08 (m, 1H), 2.78 (t, J=4.8 Hz, 2H), 2.45 (m, 1H), 2.18 (bs, 1H, —NH), 1.96-1.87 (m, 1H), 1.40 (t, J=7.2 Hz, 3H); $^{13}$C NMR (75 MHz, $CDCl_3$—$CH_3OD$): δ 168.45, 159.91, 144.62, 143.36, 133.04, 128.04, 127.17, 126.73, 126.57, 122.99, 119.63, 115.59, 112.89, 100.08, 64.73, 62.19, 60.09, 48.89, 48.32, 31.63, 31.46, 13.93. MS (EI) m/z 434 (M$^+$), HRMS (EI) for $C_{22}H_{22}F_3N_3O_3$ (M$^+$): calcd 434.1686, found 434.1692.

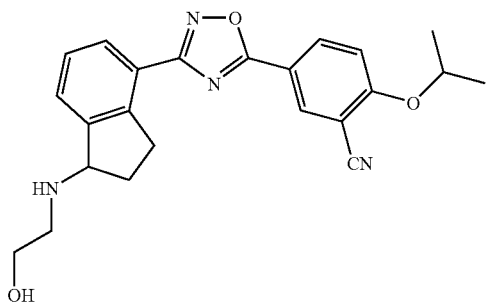 [SMILES: CC(C)Oc1ccc(-c2nc(-c3cccc4c3CCC4NCCO)no2)cc1C#N]

5-(3-(1-(2-hydroxyethylamino)-2,3-dihydro-1H-inden-4-yl)-1,2,4-oxadiazol-5-yl)-2-isopropoxybenzonitrile To a stirred solution of compound 261 (130 mg, 0.360 mmol) in $CH_2Cl_2$ were added at 0° C. pyridine (30 µl, 0.378 mmol) and thionyl chloride (27 µl, 0.378 mmol), the reaction was stirred 1 h at room temperature and concentrated under reduced pressure. The crude was diluted in DMF (2 ml) and were added DIPEA (328 µl, 1.889 mmol) and ethanolamine (114 µl, 1.889 mmol) at 0° C. The reaction was stirred overnight at 60° C. The reaction mixture was poured into water (100 ml) and extracted with ethyl acetate (20 ml×3). The organic phase was dried over sodium sulfate and concentrated under reduced pressure. The crude was purified by column chromatography using $CH_2Cl_2$:MeOH (9:1) to yield 23% (34 mg) of the product as a pale brown solid.

$^1$H NMR (300 MHz, $CDCl_3$—$CH_3OD$): δ 8.33 (d, J=2.1 Hz, 1H), 8.26 (dd, J1=2.4 Hz, J2=9.0 Hz, 1H), 7.99 (d, J=7.5 Hz, 1H), 7.47 (d, J=7.5 Hz, 1H), 7.33 (t, J=7.5 Hz, 1H), 7.07 (d, J=9.0 Hz, 1H), 4.74 (t, J=6.0 Hz, 1H), 4.27 (t, J=6.6 Hz, 1H), 3.62 (q, J=6.0 Hz, 2H), 3.37-3.32 (m, 1H), 3.18-3.10 (m, 1H), 2.79 (t, 5.1 Hz, 2H), 2.48-2.37 (m, 1H), 1.92-1.85 (m, 1H), 1.40 (d, J=6.0 Hz, 6H); $^{13}$C NMR (75 MHz, $CDCl_3$—$CH_3OD$): δ 172.73, 168.58, 162.49, 145.45, 143.33, 133.74, 133.71, 127.85, 126.69, 126.58, 122.81, 116.40, 115.00, 113.31, 103.33, 72.46, 62.30, 60.54, 32.15, 31.51, 21.35. MS (EI) m/z 405 (M$^+$), HRMS (EI) for $C_{23}H_{24}N_4O_3$ (M$^+$): calcd 405.1921, found 405.1920.

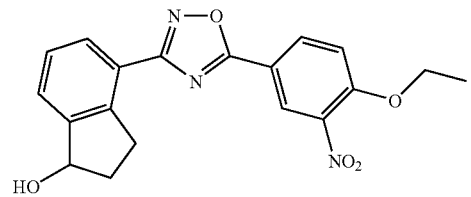 [SMILES: CCOc1ccc(-c2nc(-c3cccc4c3CCC4O)no2)cc1[N+](=O)[O-]]

4-(5-(4-ethoxy-3-nitrophenyl)-1,2,4-oxadiazol-3-yl)-2,3-dihydro-1H-inden-1-ol

In a microwave vial, a stirring solution of 4-ethoxy-3-nitrobenzoic acid (200 mg, 0.947 mmol) in DMF was treated with HOBt (167 mg, 1.231 mmol) and EDCI (236 mg, 1.23 mmol) at room temperature. The reaction was stirred for 20 min followed by addition, in a single portion, of N',1-dihydroxy-2,3-dihydro-1H-indene-4-carboximidamide (200 mg, 1.04 mmol). The reaction was stirred for additional 30 min at room temperature and then heated to 130° C. for 35 min in the initiator. The reaction was diluted using a saturated solution of NaCl and extracted with EtOAc (80 ml×3). The organic phase was dried over $Na_2SO_4$ anhydrous and concentrated under reduced pressure. The product was purified by column chromatography using $CH_2Cl_2$:MeOH (9:1) to offer the product as pale yellow solid in 40% yield (150 mg).

$^1$H NMR (300 MHz, $CDCl_3$—$CH_3OD$): δ 8.03 (d, J=1.2 Hz, 1H), 7.73 (dd, J1=1.5 Hz, J2=8.7 Hz, 1H), 7.46 (d, J=7.5 Hz, 1H), 6.97 (d, J=7.2 Hz, 1H), 6.79 (t, J=7.5 Hz, 1H), 6.67 (d, J=8.7 Hz, 1H), 4.65 (t, J=6.0 Hz, 1H), 3.70 (q, J=6.9 Hz, 2H), 2.87-2.79 (m, 1H), 2.60-2.49 (m, 1H), 1.96-1.90 (m, 1H), 1.43-1.36 (m, 1H), 0.91 (t, J=6.9 Hz, 3H); $^{13}$C NMR (75 MHz, $CDCl_3$—$CH_3OD$): δ 177.85, 168.55, 156.35, 154.87, 146.33, 142.70, 139.50, 133.09, 128.02, 126.86, 125.14, 122.43, 115.87, 114.54, 74.97, 65.63, 34.68, 30.80, 13.82. MS (EI) m/z 368 (M$^+$), HRMS (EI) for $C_{19}H_{17}N_3O_5$ (M$^+$): calcd 368.1241, found 368.1242.

Additional exemplary compounds shown as specific embodiments throughout bearing compound numbers 1-271 have been prepared and evaluated as shown below.

TABLE 1

Biological Data for Selected Compounds

| Compound Number | tPSA | ClogP | Ec$_{50}$ (S1P$_1$Ag) (nM) | Ec$_{50}$ (S1P$_3$Ag) (nM) |
|---|---|---|---|---|
| 1 | 55.5 | 3.99 | 466 µM | NA |
| 2 | 46.3 | 3.17 | 6.5 µM | NA |
| 3 | 68.7 | 1.59 | 5.9 µM | NA |
| 4 | 58.7 | 1.86 | 7.8 µM | NA |
| 5 | 46.3 | 2.82 | 4.1 µM | 5100 |
| 6 | 46.3 | 3.35 | 4.1 µM | NA |
| 7 | 46.3 | 3.92 | 270 nM | 782 |
| 8 | 55.5 | 2.33 | 73 µM | NA |
| 9 | 55.5 | 3.78 | 68.4 µM | NA |
| 10 | 55.5 | 3.10 | 246 nM | 3330 |
| 11 | 74 | 1.50 | 6500 | NA |
| 12 | 64.8 | 2.34 | NA | NA |
| 14 | 94.1 | 5.72 | 12.3 µM | NA |
| 15 | 115.7 | 2.13 | 19.7 µM | NA |
| 16 | 94.1 | 4.39 | 3.3 | 1201 |
| 18 | 132.5 | 0.42 | 397 | NA |
| 19 | 115.7 | 1.47 | 12 µM | NA |
| 20 | 118.8 | −0.65 | NA | NA |
| 21 | 106.5 | 0.84 | NA | NA |
| 22 | 106.5 | 2.13 | 1028 | NA |
| 23 | 51.1 | 6.06 | 3300 | 3500 |
| 24 | 55.5 | 2.82 | 1800 | NA |

TABLE 1-continued

Biological Data for Selected Compounds

| Compound Number | tPSA | ClogP | Ec50 (S1P1Ag) (nM) | Ec50 (S1P3Ag) (nM) |
| --- | --- | --- | --- | --- |
| 25 | 71.9 | 1.24 | NA | NA |
| 26 | 96 | 3.03 | NA | NA |
| 27 | 55.5 | 2.47 | NA | NA |
| 28 | 55.5 | 4.07 | 477 | NA |
| 29 | 55.5 | 3.58 | 576 | NA |
| 30 | 64.8 | 4.30 | 1390 | NA |
| 31 | 55.2 | 3.21 | NA | NA |
| 32 | 64.8 | 3.29 | 0.15 | 397 |
| 33 | 64.8 | 3.30 | 116 | NA |
| 34 | 64.8 | 3.09 | 8.8 | 5370 |
| 35 | 64.8 | 3.09 | 3.7 | 661 |
| 36 | 90.8 | 2.85 | 1.7 | 387 |
| 37 | 64.8 | 2.88 | NA | NA |
| 38 | 55.5 | 2.86 | 938 | NA |
| 39 | 55.5 | 2.86 | 418 | NA |
| 40 | 64.8 | 3.64 | 621 | NA |
| 41 | 67.9 | 1.51 | 7700 | NA |
| 42 | 55.5 | 2.47 | 909 | NA |
| 43 | 55.5 | 3.01 | 1180 | NA |
| 44 | 55.5 | 2.83 | 731 | NA |
| 45 | 55.5 | 4.30 | 1480 | NA |
| 46 | 66.9 | 4.31 | 544 | NA |
| 47 | 43.2 | 298.34 | 31.8 μM | NA |
| 48 | 58.8 | 3.44 | 295 | NA |
| 49 | 46.3 | 3.67 | 487 | NA |
| 50 | 64.8 | 2.57 | 64 | 2700 |
| 51 | 46.3 | 4.37 | 847 | NA |
| 52 | 75.8 | 2.17 | NA | NA |
| 53 | 46.3 | 5.94 | 156 | 327 |
| 54 | 64.8 | 3.51 | 71.6 | 322 |
| 55 | 46.3 | 4.61 | 113 | 448 |
| 56 | 46.3 | 4.91 | 83.4 | NA |
| 57 | 61.9 | 1.49 | 290 | NA |
| 58 | 64.8 | 3.59 | 11.7 | 3400 |
| 59 | 46.3 | 5.06 | 10.8 | 5600 |
| 60 | 46.3 | 5.26 | 1 | 803 |
| 61 | 72.3 | 4.82 | 0.78 | 1319 |
| 62 | 46.3 | 5.56 | 5.0 | 24 μM |
| 63 | 46.3 | 5.06 | 129 | NA |
| 64 | 55.5 | 3.05 | 228 | NA |
| 65 | 81.6 | 2.61 | 319 | NA |
| 66 | 55.5 | 3.35 | 1990 | NA |
| 67 | 55.5 | 2.86 | 95.5 μM | NA |
| 68 | 46.3 | 3.87 | 37.7 | NA |
| 69 | 72.3 | 3.43 | 197 | NA |
| 70 | 46.3 | 4.17 | 7.08 μM | NA |
| 71 | 46.3 | 3.67 | 491.8 | NA |
| 72 | 55.5 | 3.02 | 84.8 | NA |
| 73 | 81.6 | 2.58 | 249 | NA |
| 74 | 55.5 | 3.32 | 601 | NA |
| 75 | 55.5 | 2.83 | 274 | NA |
| 76 | 46.3 | 6.49 | | |
| 77 | 55.6 | 4.97 | 450 | NA |
| 78 | 55.6 | 4.33 | 45.2 | NA |
| 79 | 93.9 | 4.60 | 14.9 | NA |
| 80 | 55.6 | 4.97 | 86.5 | NA |
| 81 | 55.6 | 4.33 | 123 | NA |
| 82 | 37.2 | 6.94 | 48 | NA |
| 86 | 63.5 | 6.27 | NA | NA |
| 87 | 37.2 | 4.79 | NA | NA |
| 88 | 55.6 | 2.65 | NA | NA |
| 89 | 64.8 | 3.09 | 224 | NA |
| 93 | 67.6 | 2.71 | 2800 | NA |
| 100 | 58.9 | 4.05 | 86.3 | NA |
| 103 | 64.8 | 2.39 | 4400 | NA |
| 104 | 46.3 | 4.05 | 264 | 3500 |
| 105 | 46.3 | 2.26 | 8400 | NA |
| 106 | 46.3 | 4.03 | 63 | 8000 |
| 109 | 46.3 | 3.18 | 1500 | NA |
| 110 | 64.4 | 4.48 | 0.52 | 823 |
| 121 | 52.4 | 5.56 | 639 | NA |
| 122 | 76.2 | 4.14 | 5.0 | NA |
| 123 | 64.4 | 4.39 | 0.2 | 529 |
| 124 | 64.4 | 4.49 | 3.0 | NA |
| 125 | 55.6 | 5.16 | 171 | NA |
| 128 | 55.6 | 4.53 | 19.1 | NA |
| 129 | 55.6 | 4.48 | 4.1 | 5200 |
| 150 | 64.4 | 4.39 | 4.2 | NA |
| 151 | 55.6 | 5.06 | 5.9 | 2400 |
| 152 | 55.6 | 5.11 | 6.0 | 2100 |
| 153 | 64.4 | 4.49 | 6.9 | 2000 |
| 154 | 64.4 | 4.39 | 3.1 | 1800 |
| 155 | 81.5 | 3.28 | 1.7 | NA |
| 165 | 78.4 | 3.66 | 29.4 | NA |
| 166 | 52.4 | 5.14 | 12.5 | NA |
| 167 | 76.8 | 3.62 | 2.2 | 2200 |
| 177 | 72.6 | 3.61 | 0.8 | 774 |
| 181 | 76.8 | 5.0 | 733 | NA |
| 184 | 52.4 | 5.45 | 11.7 | 2000 |
| 185 | 52.4 | 5.86 | 245 | NA |
| 186 | 72.6 | 3.46 | 4.2 | 606 |
| 187 | 72.6 | 3.46 | 7 | 1500 |
| 191 | 55.6 | 5.27 | 53.8 | NA |
| 192 | 72.6 | 3.69 | 1.1 | 691 |
| 200 | 72.6 | 3.66 | 104 | NA |
| 201 | 72.6 | 3.66 | 0.5 | 716 |
| 202 | 55.6 | 5.41 | 35.8 | NA |
| 203 | 55.6 | 4.78 | 12.2 | 10 uM |
| 204 | 79.7 | 5.29 | 32.2 | NA |
| 205 | 61.6 | 5.65 | 10 uM | NA |
| 206 | 67.7 | 4.96 | >5000 | NA |
| 208 | 64.8 | 4.48 | 153.7 | NA |
| 209 | 85 | 2.0 | 0.14 | 938 |
| 210 | 96.2 | 3.44 | 163.6 | NA |
| 211 | 52.4 | 5.67 | 27.2 | 13.5 uM |
| 212 | 52.4 | 5.67 | 341 | NA |
| 213 | 96.7 | 3.97 | 636 | NA |
| 214 | 85 | 2.06 | 15.9 | 13.5 uM |
| 215 | 72.6 | 4.6 | 0.1 | NA |
| 216 | 84.7 | 4.40 | 91.5 | NA |
| 217 | 55.6 | 4.75 | 24.6 | 13.5 |
| 218 | 97.0 | 2.58 | 132 | NA |
| 219 | 64.8 | 4.48 | 13 | NA |
| 220 | 91.1 | 3.17 | 28 | NA |
| 221 | 87.9 | 3.80 | 1400 | NA |
| 222 | 79.7 | 4.23 | 284 | NA |
| 223 | 67.7 | 4.99 | 10 uM | NA |
| 224 | 79.7 | 5.29 | 485 | NA |
| 225 | 85 | 2.05 | 24.5 | NA |
| 226 | 80.0 | 3.90 | 2.7 | NA |
| 227 | 69.5 | 4.14 | 21.3 | NA |
| 228 | 75.9 | 4.03 | 17.8 | 2900 |
| 229 | 96.7 | 3.26 | 648 | NA |
| 230 | 87.9 | 3.70 | 300 | NA |
| 231 | 87.9 | 3.70 | 120 | NA |
| 232 | 58.9 | 6.24 | 93.9 | NA |
| 233 | 76.5 | 3.85 | 581 | NA |
| 234 | 75.9 | 4.24 | <0.5 | NA |
| 235 | 88.2 | 2.3 | 82.1 | NA |
| 236 | 84.7 | 3.7 | 1.1 | NA |
| 237 | 87.9 | 3.70 | 1200 | NA |
| 238 | 79.7 | 5.29 | 686 | NA |
| 239 | 96.7 | 3.26 | 867 | NA |
| 240 | 87.9 | 3.80 | 3100 | NA |
| 241 | 102.1 | 3.65 | 95.6 | NA |
| 242 | 114.1 | 2.36 | 26.5 | NA |
| 243 | 67.7 | 5.72 | 0.7 | NA |
| 248 | 76.8 | 3.92 | 1.5 | 2300 |
| 250 | 75.9 | 4.03 | 6.1 | NA |
| 251 | 84.7 | 3.42 | 3.4 | 692 |
| 252 | 84.7 | 3.42 | 10.1 | NA |
| 253 | 61.6 | 5.05 | 26.6 | NA |
| 254 | 76.8 | 5.15 | 15.4 | NA |
| 257 | 64.8 | 3.09 | 7.3 | |
| 258 | 75.9 | 4.55 | 1 | NA |
| 259 | 63.4 | 4.96 | <0.5 | NA |
| 260 | 63.4 | 4.69 | <0.5 | NA |
| 261 | 87.2 | 3.63 | <0.5 | NA |
| 262 | 87.2 | 3.32 | <0.5 | NA |
| 263 | 75.4 | 4.81 | 10 | NA |

TABLE 1-continued

Biological Data for Selected Compounds

| Compound Number | tPSA | ClogP | Ec$_{50}$ (S1P$_1$Ag) (nM) | Ec$_{50}$ (S1P$_3$Ag) (nM) |
|---|---|---|---|---|
| 264 | 75.4 | 4.50 | 8 | NA |
| 265 | 99.2 | 3.44 | <0.5 | NA |
| 266 | 64.8 | 2.33 | 224 | NA |
| 267 | 67.6 | 2.86 | 2800 | NA |
| 268 | 52.4 | 3.42 | 10.7 | NA |
| 269 | 53.4 | 3.77 | 112 | NA |
| 270 | 74.8 | 3.95 | 2.5 | NA |
| 271 | 86.9 | 3.77 | <0.5 | NA |

Using the synthetic procedures provided herein, it is within ordinary skill to prepare any compounds of the invention. Using the knowledge of the person of ordinary skill combined with the above cited references and methods for evaluation of S1P1 inhibitory bioactivity, the person of ordinary skill in the art can evaluate any compound so prepared for its effectiveness in inhibiting S1P1, for inhibiting S1P1 selectively in the presence of other receptor subtypes such as S1P3, and for effectiveness in cell-based bioassays indicative of S1P1 inhibition in vivo. Accordingly, the full scope of the claims provided below are enabled by the disclosure herein.

REFERENCES

1. Matloublan, M.; Lo, C. G; Cinamon, G.; Lesneski, M. J.; Xu, Y.; Brinkmann, V.; Allende, M. L.; Proia, R. L.; Cyster, J. G. *Nature* 2004, 427, 355. (b) Allande, M. L.; Dreier, J. L.; Mandala, S.; Proia, R. L. *J. Biol. Chem.* 2004, 279, 15396.
2. Germana, S. M.; Liao, J.; Jo, E.; Alfonso, C.; Ahn, M.-Y.; Peterson, M. S.; Webb, B.; Lefebvre, S.; Chun, J.; Gray, N.; Rosen, H. *J. Biol. Chem.* 2004, 279, 13839.
3. (a) Budde, K.; Schmouder, R. L.; Nashan, B.; Brunkhorst, R.; Lucker, P. W.; Mayer, T.; Brookman, L.; Nedelman, J.; Skerjanec, A.; Bohler, T.; Neumayer, H.-H. *Am. J. Transplant.* 2003, 3, 846-854. (b) Budde, K.; Schmouder, R. L.; Brunkhorst, R.; Nashan, B.; Lucker, P. W.; Mayer, T.; Choudhury, S.; Skerjanec, A.; Kraus, G.; Neumayer, H. H. *J. Am. Soc. Nephrol.* 2002, 13, 1073-1083. (c) Kahan, B. D.; Karlix, J. L.; Ferguson, R. M.; Leichtman, A. B.; Mulgaonkar, S.; Gonwa, T. A.; Skerjanec, A.; Schmouder, R. L.; Chodoff, L. *Transplantation* 2003, 7, 1079-1084.
4. Yan L.; Huo P.; Hale J.; Mills S. G.; Hajdu R.; Keohane C. A.; Rosenbach M. J.; Milligan J. A.; Shei G.; Chrebet G.; Bergstrom J.; Card D.; Mandala S. M. *Bioorg Med Chem Lett* 2006, 16, 3684-3687.
5. Li Z.; Chen W.; Hale J.; Lynch C. L.; Mills S. G.; Hajdu R.; Keohane C. A.; Rosenbach M. J.; Milligan J. A.; Shei G.; Chrebet G.; Parent S. A.; Bergstrom J.; Card D.; Forrest M.; Quackenbush E. J.; Wickham L. A.; Vargas H.; Evans R. M.; Rosen H.; Mandala S. *J Med Chem* 2005, 48, 6169-6173.
6. Hale J. J.; Lynch C. L.; Neway W.; Mills S. G.; Hajdu R.; Keohane C. A.; Rosenbach M. J.; Milligan J. A.; Shei G.; Parent S. A.; Chrebet G.; Bergstrom J.; Card D.; Ferrer M.; Hodder P.; Strulovici B.; Rosen H.; Mandala S. *J Med Chem* 2004, 47, 6662-5.
7. Gonzalez-Cabrera, P. J., T. Hla, et al. (2007). "Mapping pathways downstream of sphingosine 1-phosphate subtype 1 by differential chemical perturbation and proteomics." J Biol Chem 282 (10): 7254-64.
8. Jo, E., M. G. Sanna, et al. (2005). "S1P1-selective in vivo-active agonists from high-throughput screening: off-the-shelf chemical probes of receptor interactions, signaling, and fate." Chem Biol 12 (6): 703-15.
9. Wei, S. H., H. Rosen, et al. (2005). "Sphingosine 1-phosphate type 1 receptor agonism inhibits transendothelial migration of medullary T cells to lymphatic sinuses." Nat Immunol 6 (12): 1228-35.

What is claimed is:

1. A compound of formula (I) or a pharmaceutically acceptable salt, tautomer, or stereoisomer, thereof:

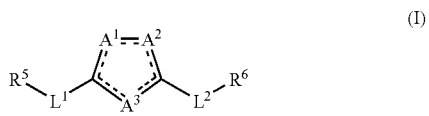

(I)

wherein a dashed line signifies that a single bond or a double bond can be present, provided that there are two double bonds and three single bonds in the ring comprising $A^1$, $A^2$, and $A^3$;

$A^1$ and $A^3$ are N and $A^2$ is O;

$L^1$ and $L^2$ are each independently a bond; or (CHR')$_n$ wherein R' is H or ($C_1$-$C_6$)alkyl and n is 1, 2, or 3;

J independently at each occurrence is F, Cl, Br, I, OR', OC(O)N(R')$_2$, CN, CF$_3$, OCF$_3$, CHF$_2$, NO$_2$, methylenedioxy, ethylenedioxy, N(R')$_2$, N(R')CH$_2$CH$_2$OR', SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')N(R'), N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J;

$R^5$ a group of formula a-i

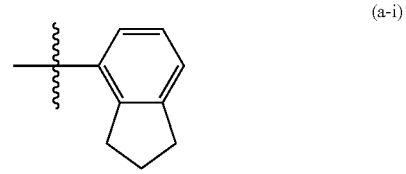 [SMILES: *c1cccc2c1CCC2]

(a-i)

substituted with 0-5 J, wherein a wavy line indicates a point of attachment;

$R^6$ is cycloalkyl, aryl, heterocyclyl, or heteroaryl, wherein any cycloalkyl, aryl, heterocyclyl, or heteroaryl is mono- or pluri-substituted with J.

2. The compound of claim 1 wherein $L^2$ is bond.

3. A compound of formula I-C further substituted with 0-5 J:

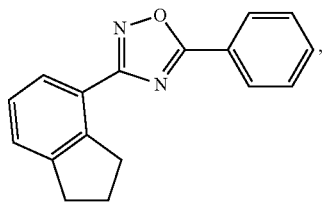

I-C wherein J independently at each occurrence is F, Cl, Br, I, OR', OC(O)N(R')$_2$, CN, CF$_3$, OCF$_3$, CHF$_2$, NO$_2$, methylenedioxy, ethylenedioxy, N(R')$_2$, N(R')CH$_2$CH$_2$OR', SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')N(R'), N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J.

4. A compound of formula I-D further substituted with 0-3 J, and wherein R$^7$ and R$^8$ each independently are H, OR', OC(O)N(R')$_2$, N(R')N(R')$_2$, N(R')CH$_2$CH$_2$OR', CN, CHF$_2$, CF$_3$, OCF$_3$, NO$_2$, N(R')$_2$, SR', SORT, SO$_2$R', SO$_2$N(R')$_2$, SO$_3$R', or C(O)R'

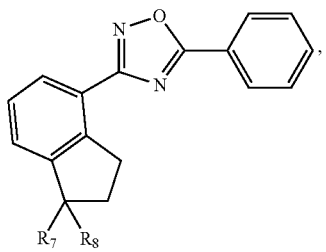

I-D wherein J independently at each occurrence is F, Cl, Br, I, OR', OC(O)N(R')$_2$, CN, CF$_3$, OCF$_3$, CHF$_2$, NO$_2$, methylenedioxy, ethylenedioxy, N(R')$_2$, N(R')CH$_2$CH$_2$OR', SR', SORT, SO$_2$R', SO$_2$N(R')$_2$, SO$_3$R', C(O)R', C(O)C(O)R', C(O)CH$_2$C(O)R', C(S)R', C(O)OR', OC(O)R', OC(O)OR', C(O)N(R')$_2$, OC(O)N(R')$_2$, C(S)N(R')$_2$, (CH$_2$)$_{0-2}$NHC(O)R', (CH$_2$)$_{0-2}$N(R')$_2$, (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')N(R'), N(R')C(S)R', N(R')C(O)N(R')$_2$, N(R')C(S)N(R')$_2$, N(COR')COR', N(ORT)R', C(=NH)N(R')$_2$, C(O)N(ORT)R', or C(=NOR')R', wherein two J groups together can form a ring; wherein R' is independently at each occurrence hydrogen or an alkyl, cycloalkyl, aryl, heterocyclyl, or heteroaryl wherein any alkyl, cycloalkyl, aryl, heterocyclyl or heteroaryl is substituted with 0-3 J.

5. The compound according to claim 1 wherein the compound of formula (I) is of formula I-F

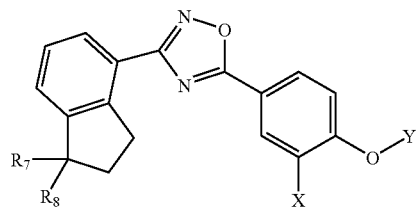

I-F wherein

R$^7$ and R$^8$ are each independently selected from H, OR'', N(R'')$_2$, and SR'', wherein R'' is independently at each occurrence hydrogen or an alkyl, cycloalkyl, aryl, heterocyclyl, or heteroaryl, wherein any such alkyl, cycloalkyl, aryl, heterocyclyl or heteroaryl is substituted with 0-3 J;

X is F, Cl, Br, I, CHF$_2$, CN, CF$_3$, NO$_2$, or OR';

Y is hydrogen or an alkyl, cycloalkyl, aryl, heterocyclyl, or heteroaryl, wherein any such alkyl, cycloalkyl, aryl, heterocyclyl or heteroaryl is substituted with 0-3 J.

6. The compound according to claim 1, wherein the compound of formula (I) is any of:

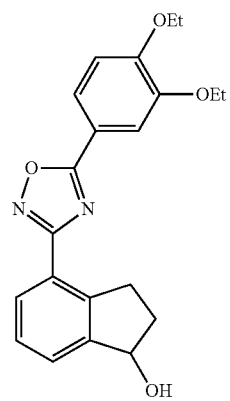

215

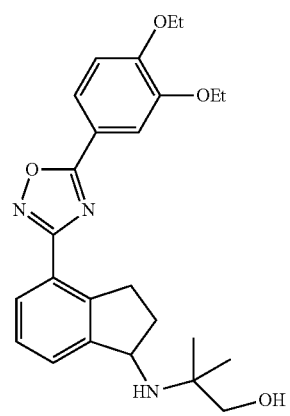

216

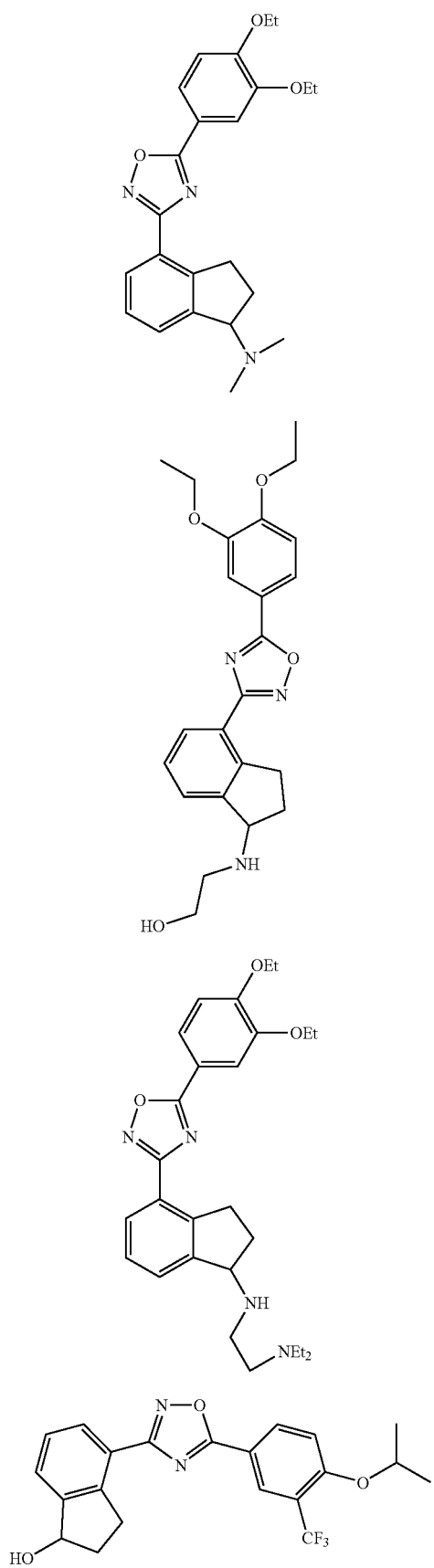
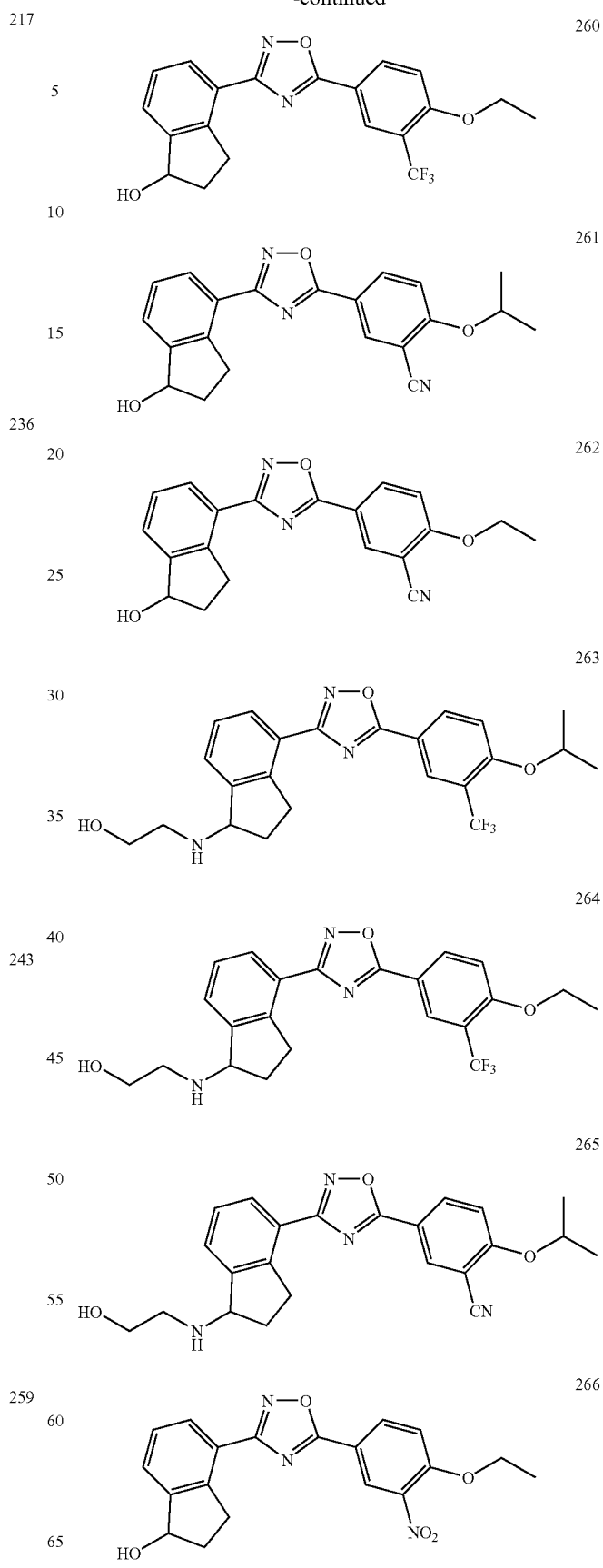

267

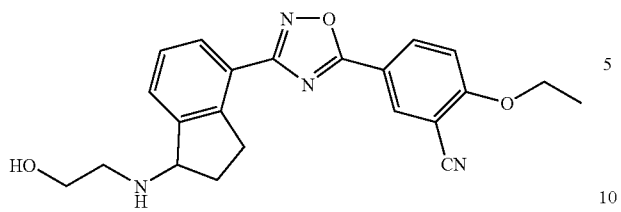

or any pharmaceutically acceptable salt, tautomer, or stereoisomer, thereof.

7. A pharmaceutical composition comprising a compound of claim 1 and a suitable excipient.

8. A pharmaceutical combination comprising the compound of claim 1 and a medicament.

9. The combination of claim 8 wherein the medicament is medically indicated for alleviation of symptoms of multiple sclerosis, transplant rejection, or adult respiratory distress syndrome.

* * * * *

UNITED STATES PATENT AND TRADEMARK OFFICE
CERTIFICATE OF CORRECTION

PATENT NO. : 8,796,318 B2
APPLICATION NO. : 12/465767
DATED : August 5, 2014
INVENTOR(S) : Roberts et al.

It is certified that error appears in the above-identified patent and that said Letters Patent is hereby corrected as shown below:

On the Title page, item (54), and in the Specification, in column 1, line 1, in "Title", before "MODULATORS", insert --NOVEL--, therefor On Title page 2, in column 1, item 56 under "Other Publications", line 55, delete "filedd" and insert --filed--, therefor On Title page 2, in column 2, item 56 under "Other Publications", line 28, delete "097628267" and insert --09762826.7--, therefor In the Specification In column 19, line 19, delete "contro" and insert --control--, therefor In column 24, line 33, delete "SW" and insert --SR'--, therefor In column 24, line 34, delete "SOW" and insert --SOR'--, therefor In column 49, line 16, delete "OR'" and insert --OR"--, therefor In column 179, line 59, after "tableted", insert --,--, therefor In column 179, line 67, after "agent", insert --.--, therefor In column 182, line 36, after "which", delete "¶", therefor In column 185, line 37, after "standard)", insert --.--, therefor In column 186, line 67 (Approx.), after "312", insert --.--, therefor Signed and Sealed this
Twenty-ninth Day of September, 2015

Michelle K. Lee
*Director of the United States Patent and Trademark Office*

CERTIFICATE OF CORRECTION (continued)
U.S. Pat. No. 8,796,318 B2

In column 189, line 25, after "311", insert --.--, therefor

In column 189, line 67, after "(M+1)", insert --.--, therefor

In column 192, line 16, after "(M+1)", insert --.--, therefor

In column 192, line 51, after "(M+1)", insert --.--, therefor

In column 192, line 67, after "(M+1)", insert --.--, therefor

In column 193, line 50, after "(M+1)", insert --.--, therefor

In column 195, line 67, after "(M+1)", insert --.--, therefor

In column 196, line 67, after "352", insert --.--, therefor

In column 199, line 5, after "367", insert --.--, therefor

In column 202, line 48, after "(M$^+$)", insert --.--, therefor

In column 203, line 20, after "(M$^+$)", insert --.--, therefor

In column 204, line 18, after "(M$^+$)", insert --.--, therefor

In column 204, line 67, after "(M$^+$)", insert --.--, therefor

In column 206, line 65, delete "un" and insert --on--, therefor

In column 211, line 24, after "(M$^+$)", insert --.--, therefor

In the Claims

In column 221, line 34, in Claim 4, delete "SORT" and insert --SOR'--, therefor

In column 221, line 53, in Claim 4, delete "SORT" and insert --SOR'--, therefor

In column 221, line 60, in Claim 4, delete "N(ORT)R'" and insert --N(OR')R'--, therefor In column 221, line 61, in Claim 4, delete "C(O)N(ORT)R'" and insert --C(O)N(OR')R'--, therefor